US012753242B2

(12) United States Patent
Chang et al.

(10) Patent No.: US 12,753,242 B2
(45) Date of Patent: Oct. 6, 2026

(54) ANTIBODY CONJUGATES AND USES THEREOF

(71) Applicant: GlycoNex Inc., New Taipei City (TW)

(72) Inventors: Tong-Hsuan Chang, New Taipei City (TW); Mei-Chun Yang, New Taipei City (TW); Liahng-Yirn Liu, New Taipei City (TW); Jerry Ting, New Taipei City (TW); Shu-Yen Chang, New Taipei City (TW); Yen-Ying Chen, New Taipei City (TW); Yu-Yu Lin, New Taipei City (TW); Shu-Lun Tang, New Taipei City (TW)

(73) Assignee: GlycoNex Inc., New Taipei City (TW)

( * ) Notice: Subject to any disclaimer, the term of this patent is extended or adjusted under 35 U.S.C. 154(b) by 0 days.

(21) Appl. No.: 18/175,905

(22) Filed: Feb. 28, 2023

(65) Prior Publication Data

US 2024/0067746 A1 Feb. 29, 2024

Related U.S. Application Data

(62) Division of application No. 17/815,117, filed on Jul. 26, 2022, now Pat. No. 11,643,471, which is a division of application No. 16/427,146, filed on May 30, 2019, now Pat. No. 11,440,967.

(60) Provisional application No. 62/678,890, filed on May 31, 2018.

(51) Int. Cl.

| | |
|---|---|
| ***C07K 16/28*** | (2006.01) |
| ***A61K 47/65*** | (2017.01) |
| ***A61K 47/68*** | (2017.01) |
| ***A61K 49/00*** | (2006.01) |
| ***A61K 51/10*** | (2006.01) |
| ***C12N 15/85*** | (2006.01) |

(52) U.S. Cl.

CPC .......... *C07K 16/2896* (2013.01); *A61K 47/65* (2017.08); *A61K 47/6801* (2017.08); *A61K 49/0058* (2013.01); *A61K 51/1048* (2013.01); *C12N 15/85* (2013.01); *C07K 2317/565* (2013.01); *C12N 2015/8518* (2013.01)

(58) Field of Classification Search

None

See application file for complete search history.

(56) References Cited

U.S. PATENT DOCUMENTS

| | | | |
|---|---|---|---|
| 4,237,224 | A | 12/1980 | Cohen et al. |
| 4,751,180 | A | 6/1988 | Cousens et al. |
| 4,816,567 | A | 3/1989 | Cabilly et al. |
| 4,935,233 | A | 6/1990 | Bell et al. |
| 5,151,510 | A | 9/1992 | Stec et al. |
| 5,530,101 | A | 6/1996 | Queen et al. |
| 5,641,870 | A | 6/1997 | Rinderknecht et al. |
| 5,770,429 | A | 6/1998 | Lonberg et al. |
| 5,837,458 | A | 11/1998 | Minshull et al. |
| 6,323,039 | B1 | 11/2001 | Dykens et al. |
| 6,596,541 | B2 | 7/2003 | Murphy et al. |
| 7,049,426 | B2 | 5/2006 | Green et al. |
| 7,498,415 | B2 | 3/2009 | Shitara et al. |
| 9,574,000 | B2 | 2/2017 | Langermann et al. |
| 11,440,967 | B2 * | 9/2022 | Chang ................ A61K 51/1048 |
| 11,643,471 | B2 * | 5/2023 | Chang .................... A61K 47/65 424/133.1 |
| 2008/0057063 | A1 | 3/2008 | Rinkenberger et al. |
| 2010/0040620 | A1 | 2/2010 | Durrant et al. |

FOREIGN PATENT DOCUMENTS

| | | | |
|---|---|---|---|
| CN | 101547937 | A | 9/2009 |
| CN | 101578296 | A | 11/2009 |
| EP | 0404097 | A2 | 12/1990 |
| EP | 3802604 | A1 | 4/2021 |
| JP | 06000093 | A | 1/1994 |
| JP | 2004529181 | A | 9/2004 |
| JP | 2010504289 | A | 2/2010 |
| JP | 2021525719 | A | 9/2021 |
| WO | WO 9311161 | A1 | 6/1993 |
| WO | 9614339 | A1 | 5/1996 |
| WO | WO 020-92126 | A1 | 11/2002 |
| WO | 2005018572 | A2 | 3/2005 |
| WO | 2006034488 | A2 | 3/2006 |
| WO | 2006074397 | A2 | 7/2006 |
| WO | WO 2008034181 | A1 | 3/2008 |

(Continued)

OTHER PUBLICATIONS

Strop et al., Chemistry and Biology 20: 161-167 (Year: 2013).*
Paul, Fundamental Immunology, 3rd Edition, pp. 292-295 (Year: 1993).*
Khongorzul et al., Molecular Cancer Research 18(1): 3-19 (Year: 2020).*
Lund et al., The Journal of Immunology 157:4963-4969 (Year: 1996).*
Moore et al., mAbs 2(2): 181-189 (Year: 2010).*
Nejadmoghaddam et al., Avicenna Journal of Medical Biotechnology 2(1): 3-23 (Year: 2019).*
Altschul et al., "Basic Local Alignment Search Tool," *Journal of Molecular Biology* 215:403-410, Oct. 1990. (8 pages).

(Continued)

*Primary Examiner* — Phuong Huynh
(74) *Attorney, Agent, or Firm* — Seed Intellectual Property Law Group LLP

(57) ABSTRACT

Disclosed herein are humanized antibodies, antigen-binding fragments thereof, and antibody conjugates, that are capable of specifically binding to certain biantennary Lewis antigens, which antigens are expressed in a variety of cancers. The presently disclosed antibodies are useful to target antigen-expressing cells for treatment or detection of disease, including various cancers. Also provided are polynucleotides, vectors, and host cells for producing the disclosed antibodies and antigen-binding fragments thereof. Pharmaceutical compositions, methods of treatment and detection, and uses of the antibodies, antigen-binding fragments, antibody conjugates, and compositions are also provided.

26 Claims, 58 Drawing Sheets

Specification includes a Sequence Listing.

(56) References Cited

FOREIGN PATENT DOCUMENTS

| | | | |
|---|---|---|---|
| WO | 2008070593 | A2 | 6/2008 |
| WO | 2009092011 | A1 | 7/2009 |
| WO | WO 2010084158 | A1 | 7/2010 |
| WO | 2011156328 | A1 | 12/2011 |
| WO | WO 2012032181 | A2 | 3/2012 |
| WO | WO 2013025779 | A1 | 2/2013 |
| WO | 2013093809 | A1 | 6/2013 |
| WO | 2015157592 | A1 | 10/2015 |
| WO | WO 2016040724 | A1 | 3/2016 |
| WO | WO 2016054638 | A1 | 4/2016 |
| WO | WO 2016134333 | A1 | 8/2016 |
| WO | WO 2017021526 | A1 | 2/2017 |
| WO | WO 2019232246 | A1 | 12/2019 |

OTHER PUBLICATIONS

Altschul et al., "Gapped BLAST and PSI-BLAST: a new generation of protein database search programs," *Nucleic Acids Research* 25(17):3389-3402, Sep. 1, 1997. (14 pages).
Androulla N. Miliotou et al., "CAR T-cell Therapy: A New Era in Cancer Immunotherapy," Current Pharmaceutical Biotechnology 19:5-18, 2018. (14 pages).
Aziz et al., "Current trends in inflammatory and immunomodulatory mediators in sepsis," *Journal of Leukocyte Biology* 93:329-342, Mar. 2013. (14 pages).
Becker et al., "Fucose: biosynthesis and biological function in mammals," *Glycobiology* 13(7):41R-53R, Jul. 1, 2003. (13 pages).
Beyrau et al., "Neutrophil heterogeneity in health and disease: a revitalized avenue in inflammation and immunity," *Open Biology* 2:120134, Nov. 1, 2012. (10 pages).
Bird et al., "Single-Chain Antigen-Binding Proteins," *Science* 242:423-426, Oct. 21, 1988. (5 pages).
Blanas et al., "Fucosylated Antigens in Cancer: An Alliance toward Tumor Progression, Metastasis, and Resistance to Chemotherapy," *Frontiers in Oncology* 8:39, Feb. 23, 2018. (14 pages).
Bobrovnik, "Determination of antibody affinity by ELISA. Theory," *Journal of Biochemical and Biophysical Methods* 57:213-236, Sep. 30, 2003. (24 pages).
Bonini et al., "Adoptive T-cell therapy for cancer: The era of engineered T cells," *European Journal of Immunology* 45:2457-2469, Jul. 22, 2015. (13 pages).
Bradley et al., "Toward High-Resolution de Novo Structure Prediction for Small Proteins," *Science* 309:1868-1871, Sep. 16, 2005. (5 pages).
Brinkmann et al., "The making of bispecific antibodies," mAbs 9(2): 182-212, Jan. 10, 2017. (31 pages).
Brodin et al., "A Monoclonal Antibody that Recognizes both $Le^b$ and Y ($Le^y$) Antigens," *Glycoconjugate Journal* 4:399-406, Dec. 1987. (8 pages).
Brooks et al., "CHARMM: A Program for Macromolecular Energy, Minimization, and Dynamics Calculations," *Journal of Computational Chemistry* 4(2):187-217, 1983. (31 pages).
Bunn, "Worldwide Overview of the Current Status of Lung Cancer Diagnosis and Treatment," *Archives of Pathology & Laboratory Medicine* 136:1478-1481, Dec. 1, 2012. (4 pages).
Cavallo et al., "2011: the immune hallmarks of cancer," *Cancer Immunology, Immunotherapy* 60:319-326, Jan. 26, 2011. (8 pages).
Chaudhary et al., "A rapid method of cloning functional variable-region antibody genes in *Escherichia coli* as single-chain immunotoxins," *Proceedings of the National Academy of Sciences* 87:1066-1070, Feb. 1990. (6 pages).
Cheever et al., "The Prioritization of Cancer Antigens: A National Cancer Institute Pilot Project for the Acceleration of Translation Research," *Clinical Cancer Research* 15(17):5323- 5337, Sep. 1, 2009. (16 pages).
Chothia et al., "Canonical Structures for the Hypervariable Regions of Immunoglobulins," *Journal of Molecular Biology* 196:901-917, Aug. 20, 1987. (17 pages).
Chu et al., "SV40 DNA transfection of cells in suspension: analysis of the efficiency of transcription and translation of T-antigen," *Gene* 13:197-202, Mar. 1981. (8 pages).
Clackson et al., "Making antibody fragments using phage display libraries," *Nature* 352:624-628, Aug. 15, 1991. (5 pages).
Cochran et al., "Domain-level antibody epitope mapping through yeast surface display of epidermal growth factor receptor fragments," *Journal of Immunological Methods* 287:147-158, Apr. 2004. (12 pages).
Dakour et al., "Detection and Isolation of Oligosaccharides with $Le^a$ and $Le^b$ Blood Group Activities by Affinity Chromatography Using Monoclonal Antibodies," *Archives of Biochemistry and Biophysics* 264(1):203-213, Jul. 1988. (11 pages).
Dam et al., "Isothermal Titration Calorimetry Reveals Differential Binding Thermodynamics of Variable Region-Identical Antibodies Differing in Constant Region for a Univalent Ligand," *The Journal of Biological Chemistry* 283(46):31366-31370, Nov. 14, 2008. (6 pages).
Dangaj et al., "Novel Recombinant Human B7-H4 Antibodies Overcome Tumoral Immune Escape to Potentiate T-Cell Antitumor Responses," *Cancer Research* 73(15):4820-4829, Aug. 1, 2013 [Published online May 30, 2013]. (11 pages).
Dayhoff et al., "Chapter 22: A Model of Evolutionary Change in Proteins," *Atlas of Protein Sequence and Structure,* vol. 5, pp. 345-352, 1978. (8 pages).
De Vries et al., "Fucosyltransferases: structure/function studies," *Glycobiology* 11(10):119R-128R, Nov. 2001. (11 pages).
Dietz et al., "Protein structure by mechanical triangulation," *PNAS* 103(5):1244-1247, Jan. 31, 2006. (4 pages).
Dingjan et al., "Structural biology of antibody recognition of carbohydrates epitopes and potential uses for targeted cancer immunotherapies," *Molecular Immunology* 67:75-88, Mar. 7, 2015. (14 pages).
Dodson, "Protein predictions," *Nature* 450:176-177, Nov. 8, 2007. (2 pages).
Donate et al., "Molecular evolution and domain structure of plasminogen-related growth factors (HGF/SF and HGFI/MSP)," *Protein Science* 3:2378-2394, Dec. 1994. (17 pages).
Faix, "Biomarkers of sepsis," *Critical Reviews in Clinical Laboratory Sciences* 50(1):23-36, Mar. 1, 2013. (14 pages).
Fan et al., "Production of multivalent protein binders using a self-trimerizing collagen-like peptide scaffold," *The FASEB Journal* 22:3795-3804, Nov. 2008. (10 pages).
Floros et al., "Anticancer Cytokines: Biology and Clinical Effects of IFN-a2, IL-2, IL-15, IL-21, and IL-12," *Semin. Oneal.* 42(4):539-548, Aug. 2015 (HHS Public Access Author Manuscript, available in PMC Aug. 1, 2016). (17 pages).
Freise et al., "In vivo Imaging with Antibodies and Engineered Fragments," *Mol. Immunol.* 67(200): 142-152, Oct. 2015 (HHS Public Access Author Manuscript, available in PMC Oct. 1, 2016). (26 pages).
Gao et al., "Making artificial antibodies: A format for phage display of combinatorial heterodimeric arrays," *Proc. Natl. Acad. Sci. USA* 96:6025-6030, May 1999. (6 pages).
Graham et al., "A New Technique for the Assay of Infectivity of Human Adenovirus 5 DNA," *Virology* 52:456-467, 1973. (12 pages).
Haji-Ghassemi et al., "Antibody recognition of carbohydrate epitopes," *Glycobiology* 25(9):920-952, Jun. 1, 2015. (33 pages).
Hanahan et al., "Hallmarks of Cancer: The Next Generation," *Cell* 144:646-674, Mar. 4, 2011. (29 pages).
Harris et al., "Adoptive T Cell Therapies: A Comparison of T Cell Receptors and Chimeric Antigen Receptors," *Trends Pharmacol. Sci.* 37(3):220-230, Mar. 2016 (HHS Public Access Author Manuscript, available in PMC Mar. 1, 2017). (21 pages).
Hein, "Unified Approach to Alignment and Phylogenies," *Methods in Enzymology* 183:626-645, 1990. (20 pages).
Hellström et al., "Highly Tumor-reactive, Internalizing, Mouse Monoclonal Antibodies to $Le^y$-related Cell Surface Antigens," *Cancer Research* 50:2183-2190, Apr. 1, 1990. (9 pages).
Henikoff et al., "Amino acid substitution matrices from protein blocks," *Proc. Natl. Acad. Sci. USA* 89:10915-10919, Nov. 1992. (5 pages).

(56) References Cited

OTHER PUBLICATIONS

Higgins et al., "Fast and sensitive multiple sequence alignments on a microcomputer," *CABIOS Communications* 5(2):151-153, Apr. 1989. (3 pages).
Holliger et al., "'Diabodies': Small bivalent and bispecific antibody fragments," *Proc. Natl. Acad. Sci. USA* 90:6444-6448, Jul. 1993. (5 pages).
Hotchkiss et al., "Sepsis-induced immunosuppression: from cellular dysfunctions to immunotherapy," *Nat. Rev. Immunol.* 13(12):862-874, Dec. 2013 (NIH Public Access Author Manuscript, available in PMC Dec. 1, 2014). (31 pages).
International Search Report and Written Opinion, dated Jul. 29, 2019, for International Application No. PCT/US2019/034708. (14 pages).
Ito et al., "Specificity and Immunobiological Properties of Monoclonal Antibody IMH2, Established after Immunization with $Le^b$/$Le^a$ Glycosphingolipid, a Novel Extended Type 1 Chain Antigen," *Cancer Research* 52:3739-3745, Jul. 1, 1992. (8 pages).
Jones et al., "Replacing the complementarity-determining regions in a human antibody with those from a mouse," *Nature* 321:522-525, May 29, 1986. (4 pages).
Kellum et al., "Understanding the Inflammatory Cytokine Response in Pneumonia and Sepsis: Results of the Genetic and Inflammatory Markers of Sepsis (GenIMS) Study," *Arch. Intern. Med.* 167(15):1655-1663, Aug. 13, 2007 (HHS Public Access Author Manuscript, available in PMC Jul. 8, 2015). (21 pages).
Kyrgidis et al., "Melanoma: Stem cells, sun exposure and hallmarks for carcinogenesis, molecular concepts and future clinical implications," *Journal of Carcinogenesis* 9:3, Apr. 1, 2010. (26 pages).
Köhler et al., "Continuous cultures of fused cells secreting antibody of predefined specificity," *Nature* 256:495-497, Aug. 7, 1975. (3 pages).
Laplanche et al., "Phosphorothioate-modified oligodeoxyribonucleotides. Iii. NMR and UV spectroscopic studies of the $R_p$-$R_p$, $S_p$-$S_p$, and $R_p$-$S_p$ duplexes[d($GG_SAATTCC$)]$_2$, derived from diastereomeric O-ethvl phosphorothioates," *Nucleic Acids Research* 14(22):9081-9093, Nov. 25, 1986. (13 pages).
Layke et al., "Gastric Cancer: Diagnosis and Treatment Options," *American Family Physician* 69(5):1133-1140, Mar. 1, 2004. (8 pages).
Lim et al., "Disulfide Trapping of Protein Complexes on the Yeast Surface," *Biotechnology and Bioengineering* 106(1):27-41, May 1, 2010. (15 pages).
Liu et al., "Selective inhibition of IDO1 effectively regulates mediators of antitumor immunity," *Blood* 115(17):3520-3530, Apr. 29, 2010. (12 pages).
Luo et al., "Expression of a fusion protein of scFv-biotin mimetic peptide for immunoassay," *Journal of Biotechnology* 65:225-228, Oct. 27, 1998. (4 pages).
Mabry et al., "A dual-targeting PDGFRβ/VEGF-A molecule assembled from stable antibody fragments demonstrates anti-angiogenic activity in vitro and in vivo," *mAbs* 2(1):20-34, Jan./Feb. 2010. (15 pages).
Maloy et al., "Induction of mucosal and systemic immune responses by immunization with ovalbumin entrapped in poly(lactide-co-glycolide) microparticles," *Immunology* 81:661-667, Apr. 1994. (7 pages).
Manne et al., "Keynote review: Recent advances in biomarkers for cancer diagnosis and treatment," *DDT* 10(14):965-976, Jul. 2005. (12 pages).
Marcos et al., "Principles for designing proteins with cavities formed by curved βsheets," *Science* 355:201-206, Jan. 13, 2017. (7 pages).
Marks et al., "By-passing Immunization. Human Antibodies from V-gene libraries displayed on phage," *J. Mol. Biol.* 222:581-597, Dec. 5, 1991. (17 pages).
Mehta et al., "Chimeric Antigen Receptor Expressing Natural Killer Cells for the Immunotherapy of Cancer," *Frontiers in Immunology* 9(283), Feb. 15, 2018. (12 pages).
Meyer et al., "Click Chemistry and Radiochemistry: The First 10 Years," *Bioconjug. Chem.* 27(12):2791-2807, Dec. 21, 2016. (40 pages).
Moek et al., "Theranostics Using Antibodies and Antibody-Related Therapeutics," *J. Nucl. Med.* 58(9—Suppl. 2):83S-90S, Sep. 2017. (9 pages).
Mohr et al., "Reversible chemical reactions as the basis for optical sensors used to detect amines, alcohols, and humidity," *J. Mater. Chem.* 9:2259-2264, 1999. (6 pages).
Morrison et al., "Chimeric human antibody molecules: Mouse antigen-binding domains with human constant region domains," *Proc. Natl. Acad. Sci. USA* 81:6851-6855, Nov. 1984. (5 pages).
Murphy et al., "Genetic construction, expression, and melanoma-selective cytotoxicity of a diphtheria toxin-related α-melanocyte-stimulating hormone fusion protein," *Proc. Natl. Acad. Sci. USA* 83:8258-8262, Nov. 1986. (5 pages).
Myers et al., "Optimal alignments in linear space," *CABIOS* 4(1):11-17, Mar. 1988. (7 pages).
Nareshkumar Jain et al., "Current ADC Linker Chemistry," *Pharm. Res.* 32:3526-3540, Mar. 11, 2015. (15 pages).
Needleman et al., "A General Method Applicable to the Search for Similarities in the Amino Acid Sequence of Two Proteins," *J. Mol. Biol.* 48:443-453, Mar. 1970. (11 pages).
Park et al., "Cancer Stem Cell-Directed Therapies: Recent Data From the Laboratory and Clinic," *Molecular Therapy* 17(2):219-230, Feb. 2009. (12 pages).
Parslow et al., "Antibody-Drug Conjugates for Cancer Therapy," *Biomedicines* 4(14), Jul. 11, 2016. (17 pages).
Pearson et al., "Improved tools for biological sequence comparison," *Proc. Natl. Acad. Sci. USA* 85:2444-2448, Apr. 1988. (5 pages).
Pedersen, "Conformational Properties of Molecules by ab Initio Quantum Mechanical Energy Minimization," *Environmental Health Perspectives* 61:185-190, Sep. 1985. (6 pages).
Plückthun, "Antibody Engineering: Advances from the Use of *Escherichia coli* Expression Systems," *Bio/Technology* 9:545-551, Jun. 1991. (7 pages).
Qian et al., "High resolution protein structure prediction and the crystallographic phase problem," *Nature* 450(7167):259-264, Nov. 8, 2007. (23 pages).
Raman et al., "NMR Structure Determination for Larger Proteins Using Backbone-Only Data," *Science* 327: 1014-1018, Feb. 19, 2010. (6 pages).
Reff, "High-level production ofrecombinant immunoglobulins in mammalian cells," Current Opinion in Biotechnology 4:573-576, Oct. 1993. (4 pages).
Reiter et al., "Engineering interchain disulfide bonds into conserved framework regions of Fv fragments: improved biochemical characteristics of recombinant immunotoxins containing disulfide-stabilized Fv," *Protein Engineering* 7(5):697-704, May 1994. (8 pages).
Remick, "Biological Perspectives: Pathophysiology of Sepsis," *The American Journal of Pathology* 170(5): 1435-1444, May 2007. (10 pages).
Ren et al., "Advancing chimeric antigen receptor T cell therapy with CRISPR/Cas9," *Protein Cell* 8(9):634-643, Sep. 2017. (10 pages).
Riechmann et al., "Reshaping human antibodies for therapy," *Nature* 332:323-327, Mar. 24, 1988. (5 pages).
Robinson, "Comparison of Labeled Trees with Valency Three," *Journal of Combinatorial Theory* 11:105-119, Oct. 1971. (15 pages).
Sadelain et al., "The basic principles of chimeric antigen receptor (CAR) design," *Cancer Discov.* 3(4):388-398, Apr. 2013 (NIH Public Access Author Manuscript, available in PMC Apr. 2, 2014). (21 pages).
Saitou et al., "The Neighbor-joining Method: A New Method for Reconstructing Phylogenetic Trees," *Mol. Biol. Evol.* 4(4):406-425, Jul. 1987. (20 pages).
Scatchard, "The Attractions of Proteins for Small Molecules and Ions," *Annals New York Academy of Sciences* 51(4):660-672, May 1949. (13 pages).
Schueler-Furman et al., "Progress in Modeling of Protein Structures and Interactions," *Science* 310:638-642, Oct. 28, 2005. (5 pages).

(56) References Cited

OTHER PUBLICATIONS

Smith, "Comparison of Biosequences," *Advances in Applied Mathematics* 2:482-489, 1981. (8 pages).
Sneath et al., "Numerical taxonomy: the principles and practice of numerical classification," *LS. V.* 30(1), Jan. 5, 1987. (1 page).
Spiess et al., "Alternative molecular formats and therapeutic applications for bispecific antibodies," *Molecular Immunology* 67:95-106, Jan. 27, 2015. (12 pages).
Stein et al., "Physicochemical properties of phosphorothioate oligodeoxynucleotides," *Nucleic Acids Research* 16(8):3209-3221, Apr. 25, 1988. (13 pages).
Stone et al., "A novel T cell receptor single-chain signaling complex mediates antigen-specific T cell activity and tumor control," *Cancer Immunol. Immunother.* 63(11 ): 1163-1176, Nov. 2014 (NIH Public Access Author Manuscript, available in PMC Nov. 1, 2015). (23 pages).
Suslick et al., "Colorimetric sensor arrays for molecular recognition," *Tetrahedron* 60:11133-11138, Oct. 1, 2004. (6 pages).
Topalian et al., "Cancer Immunotherapy Comes of Age," *Journal of Clinical Oncology* 29(36):4828-4836, Dec. 20, 2011. (9 pages).
Verhoeyen et al., "Reshaping Human Antibodies: Grafting an Antilysozyme Activity," *Science* 239: 1534-1536, Mar. 25, 1988. (4 pages).
Wiersinga et al., "Host innate immune responses to sepsis," *Virulence* 5(1):36-44, Jan. 1, 2014. (9 pages).
Wilbur et al., "Rapid similarity searches of nucleic acid and protein data banks," *Proc. Natl. Acad. Sci. USA* 80:726-730, Feb. 1983. (5 pages).
Wu et al., "Universal phosphatase-coupled glycosyltransferase assay," *Glycobiology* 21(6):727-733, 2011 [Advance Access publication on Nov. 15, 2010]. (7 pages).
Xu et al., "The development of CAR design for tumor CAR-T cell therapy," *Oncotarget* 9(17):13991-14004, Jan. 12, 2018. (14 pages).
Younson et al., "A Human Domain Antibody and Lewis[b] Glycoconjugate That Inhibit Binding of Helicobacter pylori to Lewis[b] Receptor and Adhesion to Human Gastric Epithelium," *JID* 200:1574-1582, Nov. 15, 2009. (9 pages).
Zhu et al., "Remodeling domain interfaces to enhance heterodimer formation," *Protein Science* 6:781-788, Apr. 1997. (8 pages).
Wang et al., "Structural characterization of the maytansinoid- monoclonal antibody immunoconjugate, huN901-DM1, by mass spectrometry," Protein Science 14:2436-2446, Sep. 2005. (11 pages).
Decision on Appeal Before the Appeals Review Panel of the Patent Trial and Appeal Board of the United States Patent and Trademark Office for U.S. Appl. No. 16/803,690, filed May 21, 2024. (42 pages).
Declaration Under 37 C.F.R. § 1.132 for U.S. Appl. No. 16/427,146, Mar. 7, 2022. (12 pages).
Deonarain et al., "Small-Format Drug Conjugates: A Viable Alternative to ADCs for Solid Tumours?" Antibodies 7(16), Mar. 30, 2018. (19 pages).
McDonagh et al., "Engineered anti-CD70 antibody-drug conjugate with increased therapeutic index," Mol Cancer Ther 7(9):2913-2923, Sep. 2008. (11 pages).

* cited by examiner

```
BBC           DVQLQESGPDLVKPSQSLSLTCTVTGYSITSG-YTWHWIRQF
1             -VQLQEWGPGLVKPSQTLSLTCTVSGGSIYNFGHYWSWIRHY
2             QVQLQESGPGLVKPSQTLSLTCTVSGDSINSSGFYWTWIRQH
3(acceptor)   QVQLQESGPGLVKPSQTLSLTCTVSGGSISSGAYYWSWIRQH
4             QVQLQESGPGLVKPSETLSLTCTVSGDSISSGGTHWSWIRQL
5             QVQLQESGPGLVKPSQTLSLTCTVSGTSISTGGYHWTWIRQQ
6             QLQLQESGPRLVKPSQTLSLTCSVSGGSISG-AYHWSWIRQL
7             ---LEQSGPSLVKPSQTLSLTCSVTGDSITSG-Y-WNWIRKF
8             EVQLQESGPSLVKPSQTLSLTCSVTGDSITNG-F-WIWIRKF

BBC           PGNTLEWLGYIHYSGNTKYSPSLKSRLSVTRDTSKNQFFLQLNSVTTEDTATYYCGREAL
1             PGKGLEWIGYIYYSGSTYYNPSLKSRLTISADTSKNQFSLELNSMTAADTAVYYCARAGG
2             PGKGLEWIGSMFYGGSPYNNPSLKSRLTISVDTSKNQFSLYLNSVTAADTAVYYCARAFD
3(acceptor)   PGKGLEWIGYIYYSGTTYYNPSLKSRLSMSRDTSKNOFSLKLSSVTAADTAVYYCARGPY
4             PGQGLEWLGYLYNSRSTYYNPSLESRLTISADTSKNQFSLNLSTVTAADTAVYYCARKSG
5             PGKGLEWLGYIYHSGSSYYNPSLKSRLTISVDTSKNQFSLNLNSVTAADTAVYYCARNSG
6             PGKGLEWVGYIYYTGNTYFNPSLKSRISISVDTSKNQFSLKMNSVTVADTAMYYCARDPI
7             PGNKLEYMGYISYSGSTYYNLSLRSRISITRDTSKNQYYLQLNSVTTEDTATYYCALITT
8             PGNKLEYMGYISYSGSTYYNPSLKSRISITRDTSQNQFYLQLNSVTTEDTGTYYCACRSY

BBC           RGYDHG---FWFTYWGQGTLVTV
1             SAAGTHD---AFDIWGPGTMVTV
2             YSASGSF---YFGSWGQGTLVTV
3(acceptor)   YDSPRP------FDPWGQGTLVTV
4             F---------REFDLWGQGTLVTV
5             ----------ADFDYWGQGTLVTV
6             ALPGRG----VFDYWGQGTLVTV
7             ----TT---YAMDYWGQGTTVTV
8             G--RTP---YYFDFWGQGTTLTV
```

FIG. 1

| | |
|---|---|
| BBC | DIQMTQSSSSFSVSLGDRVTITCTASEDIYNRLTWYQQKPGNVPRLLISGATSLDTGVPS |
| hBBC.8 | DIQMTQSPSSLSASVGDRVTITCTASEDIYNRLTWYQQKPGKVPRLLISGATSLDTGVPS |
| hBBC.9 | DIQMTQSPSSLSASVGDRVTITCTASEDIYNRLTWYQQKPGKVPRLLISGATSLDTGVPS |
| hBBC.10 | DIQMTQSPSSLSASVGDRVTITCTASEDIYNRLTWYQQKPGKVPRLLISGATSLDTGVPS |
| human | DIQMTQSPSSLSASVGDRVTITCRASQGISNYLAWYQQKPGKVPKLLIYAASTLQSGVPS |

| | |
|---|---|
| BBC | RFSGSRSGKDYALSITSLQTEDVATYYCQQYWTTPWTFGGGTRLEIK |
| hBBC.8 | RFSGSRSGTDFTLTISSLQPEDVATYYCQQYWTTPWTFGQGTKLEIK |
| hBBC.9 | RFSGSRSGTDYTLTISSLQPEDVATYYCQQYWTTPWTFGQGTKLEIK |
| hBBC.10 | RFSGSGSGTDYTLTISSLQPEDVATYYCQQYWTTPWTFGQGTKLEIK |
| human | RFSGSGSGTDFTLTISSLQPEDVATYYCQKYNSAPYTFGQGTKLEIK |

FIG. 2A

| | |
|---|---|
| hBBC.10.1 | RLSISRDTSKNQFFLKLSSVTTEDTAVYYCGR |
| hBBC.10.1FQ | RLSISRDTSKNTFYLQMNSLTTEDTAVYYCGR |
| reference 1 | RFTISRDDSKNTFYLQMNSLRAEDTAVYYCAR |
| reference 2 | RFTISADTSKNTAYLQMNSLRAEDTAVYYCSR |

FIG. 3

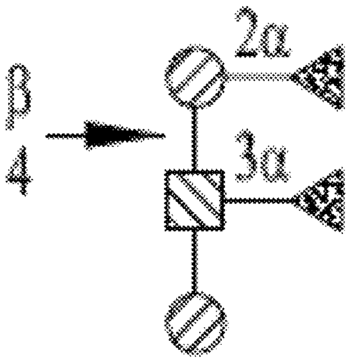
FIG. 25A
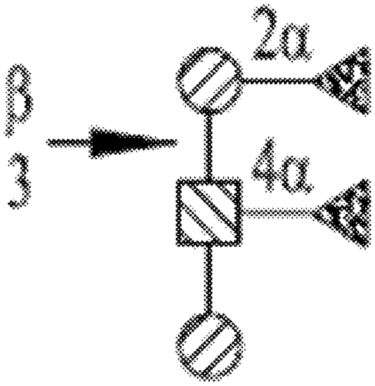
FIG. 25B
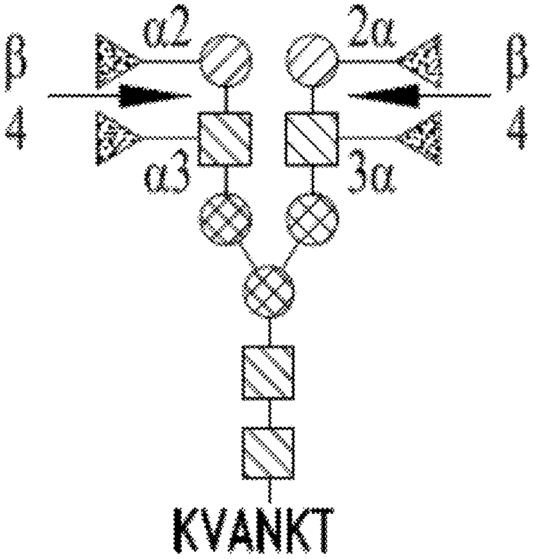
FIG. 25C
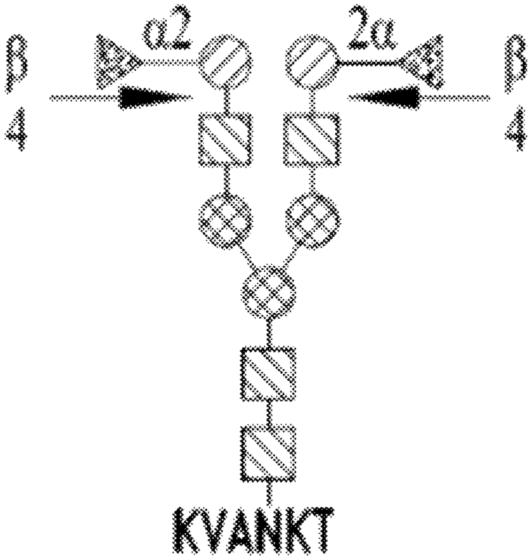
FIG. 25D

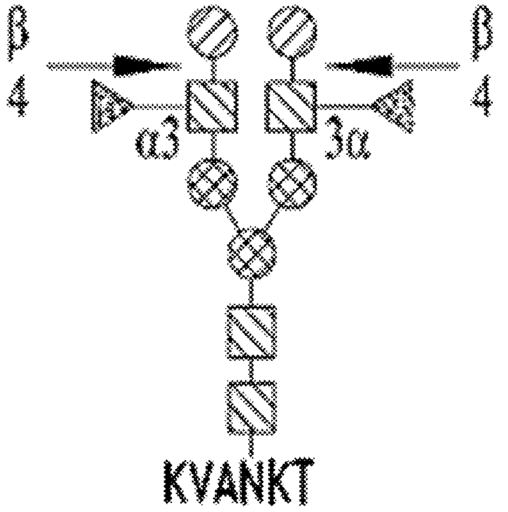
FIG. 25E
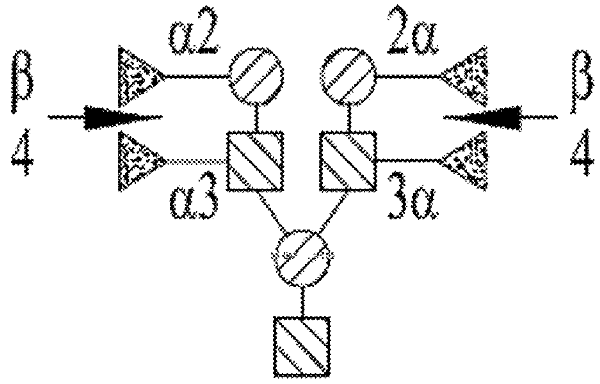
FIG. 25F
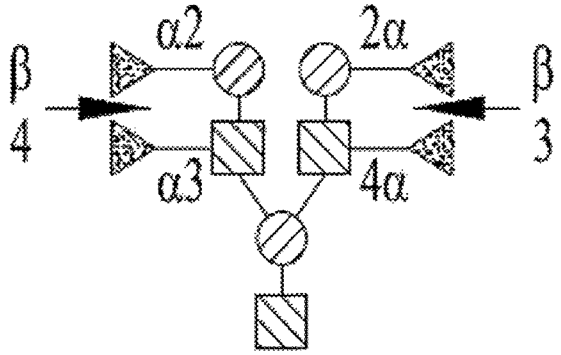
FIG. 25G
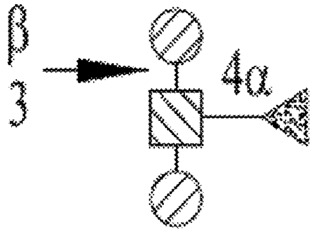
FIG. 25H

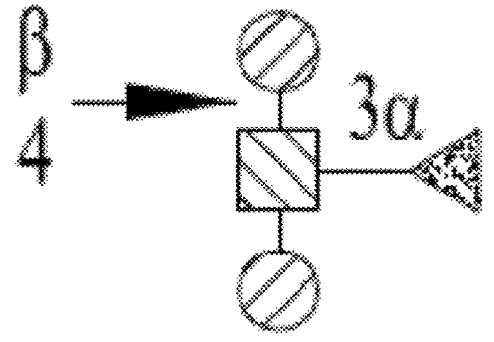
FIG. 25I
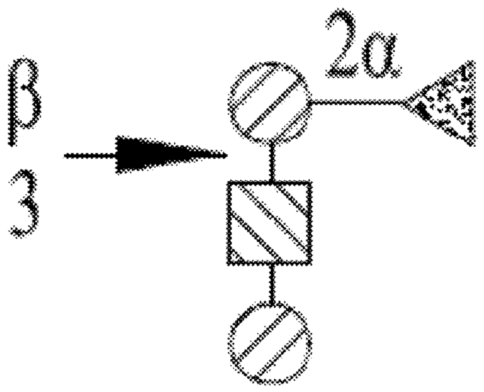
FIG. 25J
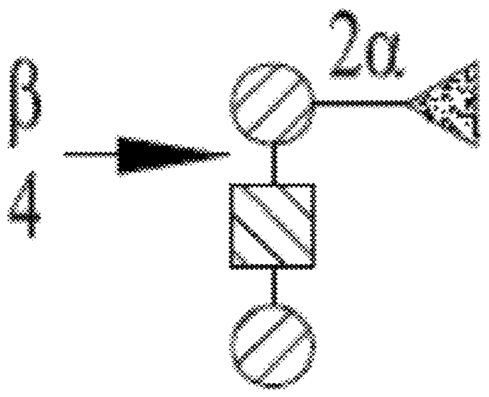
FIG. 25K

= Gal = GlcNAc = Fuc = Man

⊘ = Gal ⧅ = GlcNAc ◁ = Fuc ⊗ = Man

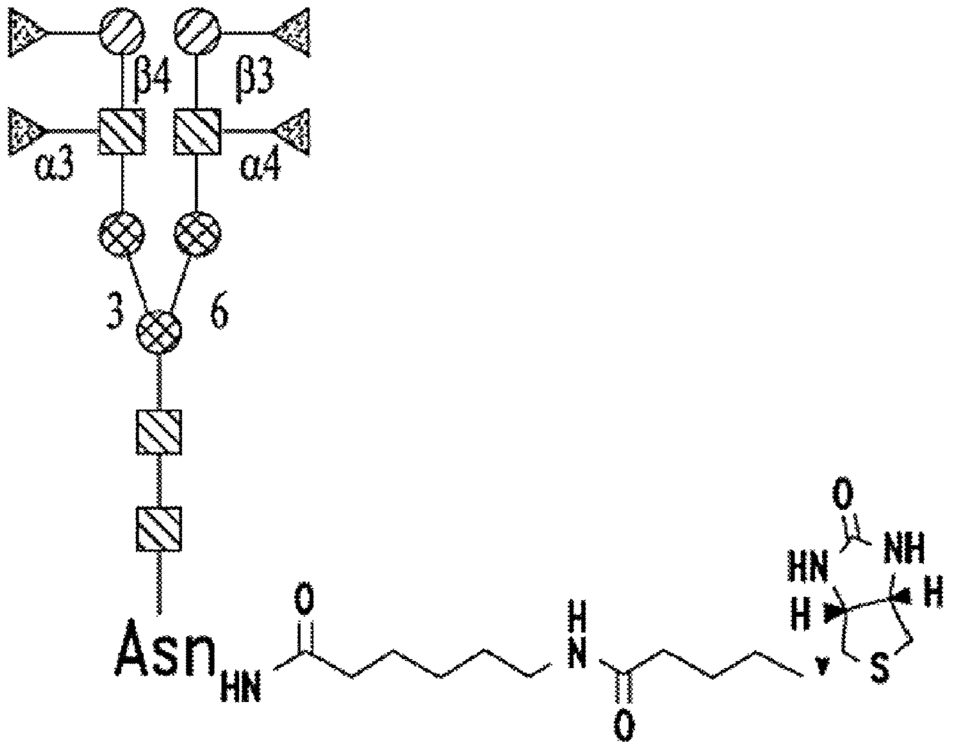
FIG. 26E
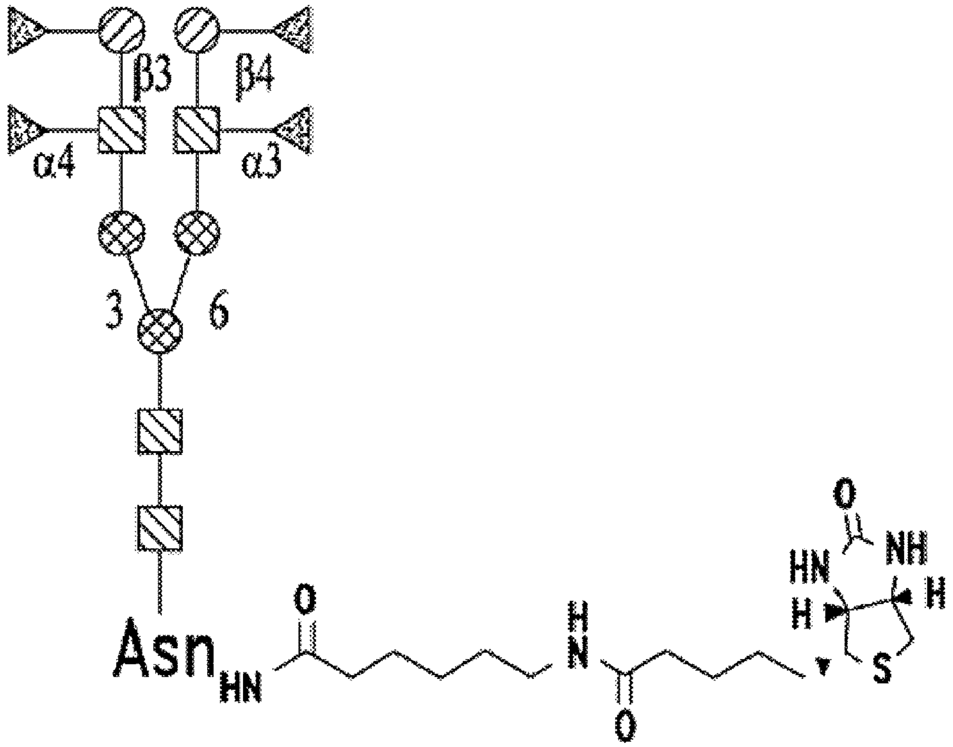
FIG. 26F

ANTIBODY CONJUGATES AND USES THEREOF

CROSS-REFERENCES TO RELATED APPLICATIONS

This application is a divisional of U.S. application Ser. No. 17/815,117, filed on Jul. 26, 2022, now U.S. Pat. No. 11,643,471, which is a divisional of U.S. application Ser. No. 16/427,146, filed May 30, 2019, now U.S. Pat. No. 11,440,967, which claims benefit of provisional application 62/678,890, filed May 31, 2018.

REFERENCE TO AN ELECTRONIC SEQUENCE LISTING

The contents of the electronic sequence listing (400100_401C1_SEQUENCE_LISTING.xml; Size: 77,174 bytes; and Date of Creation: Feb. 24, 2023) is herein incorporated by reference in its entirety.

TECHNICAL FIELD

Embodiments of the present disclosure relate generally to antibodies, and antigen-binding fragments thereof, that are capable of specifically binding to certain Lewis antigens, and to methods of making and using the same. Also provided are compositions, polynucleotides, vectors, fusion proteins, and host cells related to the herein disclosed antibodies and antigen-binding fragments. In certain embodiments, presently disclosed antibodies and antigen-binding fragments thereof are capable of binding specifically to biantennary $Le^B/Le^B$, $Le^Y/Le^Y$, $Le^B/Le^Y$, and $Le^Y/Le^B$ antigens, and are useful in treating or detecting diseases characterized by expression of such antigens, such as cancer.

BACKGROUND

Immunotherapies are an emerging modality for treating a variety of diseases, including various cancers. For example, clinical efficacy of monoclonal antibodies (mAbs) with antitumor activity has been demonstrated since the late 1990s (see, e.g., Topalian et al., *J. Clin. Oncol.* 29(36):4828-4836 (2011)), and several blockbuster cancer drugs are mAbs (e.g., rituximab, trastuzumab, and bevacizumab).

Antibody-based therapies can specifically target antigen-expressing cells, such as tumor cells, and can, for example, effect cytotoxic activity through a number of means, including by eliciting antibody-dependent cellular cytotoxicity (ADCC), complement-mediated cytotoxicity (CDC), and T-cell mediated cytotoxicity. Other approaches involve using antibodies as carrier vehicles to selectively deliver, e.g., cytotoxic or antiproliferative agents to kill target cells and/or to inhibit growth and metastatic spread of such cells.

Relevant criteria for monoclonal antibody therapies include, for example, the ability of the antibody to specifically recognize and bind to the desired antigen, rather than promiscuously binding to one or more other potential epitopes, e.g., proteins or glycans that are expressed on healthy cells. Also, the antibody should not be immunogenic to the patient. In this regard, antibodies specific for human disease antigens are often generated in non-human hosts, such as mice and rabbits, and may possess, for example, host-species amino acid sequences and/or carbohydrate motifs that may be immunogenic in a human patient. Accordingly, a preferred antibody for use in therapy lacks or has minimal potentially immunogenic properties. Features of the target antigen must also be considered. Preferably, the antigen is selectively expressed, or is highly over-expressed, in the particular disease state (for example, cancer), such that the antibody-mediated therapy will not have unwanted deleterious "on-target, off-tumor" effects against healthy tissue.

Aberrant glycosylation (e.g., over-expression or mis-expression of glycoproteins and glycolipids) is a feature common to numerous cancers (see, e.g., Blanas et al., *Front. Oncol.* 8:39 (2018). Without wishing to be bound by theory, aberrant glycosylation may affect a number of cell processes that lead to cancer progression and metastasis (e.g., cellular growth and metabolism, angiogenesis, cell-matrix interactions, and cell-cell adhesion). Exemplary carbohydrate antigens that are aberrantly expressed in cancers include Type I and Type II Lewis antigens, which are terminally (at the non-reducing terminus) fucosylated carbohydrate epitopes of the Lewis antigen system. Type I and Type II Lewis antigens include the structurally related H1, H2, and Lewis A, B, X, and Y antigens, all of which share three monosaccharide units: a (reducing) terminal acetylglucosamine (GlcNac); galactose (Gal); and Fucose (Fuc). Type I Lewis antigens differ from Type II by virtue of the nature of the glycosidic bonds in their lactosamine core chains (Galβ1→3GlcNac: Type I; Galβ1→4GlcNac: Type II), and exist in a variety of structures (e.g., linear or branched, with one, two, or more antennae comprising antigen motifs). Lewis antigens have moderate expression levels in healthy adult tissues (e.g., digestive and reproductive epithelia), but are overexpressed on the cell surface in a number of solid cancers, including, for example, cancers of the lung, breast, liver, kidney, bladder, pancreas, and prostate, and are also associated with acute myeloid leukemia, acute lymphoblastic leukemia, and Non-Hodgkin's lymphoma.

Some therapies targeting Lewis antigens to treat cancer are known, including the discontinued Seattle Genetics/Bristol Meyers Squibb antibody-drug conjugate "cBR96-Dox", which delivers doxorubicin to $Le^Y$ antigen-expressing tumor cells using the BR96 monoclonal antibody (Hellstrom et al., *Cancer Res.* 50(7):2183-2190 (1990)) as a carrier molecule. Clearly, there remains a need in the art for additional therapies to treat cancers, such as cancers that express Lewis antigens as tumor-associated antigens or tumor specific antigens. Presently disclosed embodiments address this need and provide other related advantages.

BRIEF SUMMARY

According to certain presently disclosed embodiments, there is provided an isolated antibody comprising an immunoglobulin heavy chain having the amino acid sequence set forth in SEQ ID NO: 10 and an immunoglobulin light chain having the amino acid sequence set forth in SEQ ID NO: 11.

In certain embodiments, there is provided an isolated antibody or antigen-binding fragment thereof, comprising: an immunoglobulin heavy chain variable region that comprises the amino acid sequence set forth in SEQ ID NO: 35; and an immunoglobulin light chain variable region that comprises the amino acid sequence set forth in SEQ ID NO: 5, wherein the antibody or antigen-binding fragment thereof is capable of binding specifically:

to a biantennary $Le^B/Le^B$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II], to a biantennary $Le^Y/Le^Y$ antigen comprising $Fuc_4(Gal\beta1\rightarrow4GlcNAc)_2$ [III] or [Fucα1-2Galβ1-4(Fucα1-3)GlcNAc]2 [IV], to a biantennary $Le^B/Le^Y$ antigen comprising $Fuc_2$(Galβ1→3GlcNAc)[$Fuc_2$(Galβ1→4GlcNAc)] [V], or [Fucα1-2Galβ1-3(Fucα1-4)GlcNAc][Fucα1-2Galβ1-4(Fucα1-3)GlcNAc] [VI], and to a biantennary $Le^Y/Le^B$ antigen comprising $Fuc_2$(Galβ1-4GlcNAc)[$Fuc_2$(Galβ1-3GlcNAc)] [VII] or [Fucα1-2Galβ1-4(Fucα1-3)GlcNAc][Fucα1-2Galβ1-3(Fucα1-4)GlcNAc] [VIII], and wherein the antibody or antigen-binding fragment thereof does not bind specifically to a monoantennary $Le^X$ antigen that comprises Galβ1→4(Fucα1→3)GlcNAc [IX], or to a biantennary $Le^X$ antigen that comprises [Galβ1→4(Fucα1→3)GlcNAc]$_2$ [X], or to a monoantennary $Le^A$ antigen that comprises Galβ1-3(Fucα1-4)GlcNAc [XI], or to a monoantennary H antigen type 2 that comprises Fucα1-2Galβ1-4GlcNAc [XII], or to a biantennary H antigen type 2 that comprises (Fucα1-2Galβ1-4GlcNAc)$_2$ [XIII] or to a monoantennary H antigen type 1 that comprises Fucα1-2Galβ1-3GlcNAc [XIV].

In certain embodiments, an isolated antibody or antigen-binding fragment thereof is provided, comprising: (a) an immunoglobulin heavy chain variable region that comprises a heavy chain complementarity determining region 1 (VH CDR1) comprising the amino acid sequence set forth in SEQ ID NO: 2; a heavy chain complementarity determining region 2 (VH CDR2) comprising the amino acid sequence set forth in SEQ ID NO: 3; a heavy chain complementarity determining region 3 (VH CDR3) comprising the amino acid sequence set forth in SEQ ID NO: 4; and (b) an immunoglobulin light chain variable region that comprises a light chain complementarity determining region 1 (VL CDR1) comprising the amino acid sequence set forth in SEQ ID NO: 6; a light chain complementarity determining region 2 (VL CDR2) comprising the amino acid sequence set forth in SEQ ID NO: 7; and a light chain complementarity determining region 3 (VL CDR3) comprising the amino acid sequence set forth in SEQ ID NO: 8; wherein the antibody or antigen-binding fragment thereof is capable of binding specifically:

to a biantennary $Le^B/Le^B$ antigen comprising $Fuc_4$(Galβ1→3GlcNAc)$_2$ [I] or [Fucα1-2Galβ1-3(Fucα1-4)GlcNAc]$_2$ [II], to a biantennary $Le^Y/Le^Y$ antigen comprising $Fuc_4$(Galβ1→4GlcNAc)$_2$ [III] or [Fucα1-2Galβ1-4(Fucα1-3)GlcNAc]$_2$ [IV], to a biantennary $Le^B/Le^Y$ antigen comprising $Fuc_2$(Galβ1→3GlcNAc)[$Fuc_2$(Galβ1→4GlcNAc)] [V], or [Fucα1-2Galβ1-3(Fucα1-4)GlcNAc][Fucα1-2Galβ1-4(Fucα1-3)GlcNAc] [VI], and to a biantennary $Le^Y/Le^B$ antigen comprising $Fuc_2$(Galβ1-4GlcNAc)[$Fuc_2$(Galβ1-3GlcNAc)] [VII] or [Fucα1-2Galβ1-4(Fucα1-3)GlcNAc][Fucα1-2Galβ1-3(Fucα1-4)GlcNAc] [VIII], and wherein the antibody or antigen-binding fragment thereof does not bind specifically to a monoantennary $Le^x$ antigen that comprises Galβ1→4(Fucα1→3)GlcNAc [IX], or to a biantennary $Le^x$ antigen that comprises [Galβ1→4(Fucα1→3)GlcNAc]$_2$ [X], or to a monoantennary $Le^A$ antigen that comprises Galβ1-3(Fucα1-4)GlcNAc [XI], or to a monoantennary H antigen type 2 that comprises Fucα1-2Galβ1-4GlcNAc [XII], or to a biantennary H antigen type 2 that comprises (Fucα1-2Galβ1-4GlcNAc)$_2$ [XIII] or to a monoantennary H antigen type 1 that comprises Fucα1-2Galβ1-3GlcNAc [XIV].

In certain of the herein described embodiments, an isolated antibody may be a monoclonal antibody. In certain embodiments, an isolated antibody or antigen-binding fragment thereof is a humanized antibody. In certain embodiments, an isolated antibody or antigen-binding fragment thereof is selected from a Fab fragment, a F(ab')2 fragment, a Fv fragment, a single chain Fv (scFv) antibody, and a diabody.

Also provided herein are embodiments wherein an isolated antibody or an antigen-binding fragment thereof comprises an immunoglobulin heavy chain variable region that comprises an amino acid sequence that has at least 90, 91, 92, 93, 94, 95, 96, 97, 98 or 99 percent identity to the amino acid sequence set forth in SEQ ID NO: 35; and an immunoglobulin light chain variable region that comprises an amino acid sequence that has at least 90, 91, 92, 93, 94, 95, 96, 97, 98 or 99 percent identity to the amino acid sequence set forth in SEQ ID NO: 5, wherein the antibody or antigen-binding fragment thereof is capable of binding specifically:

to a biantennary $Le^B/Le^B$ antigen comprising $Fuc_4$(Galβ1→3GlcNAc)$_2$ [I] or [Fucα1-2Galβ1-3(Fucα1-4)GlcNAc]$_2$ [II], to a biantennary $Le^Y/Le^Y$ antigen comprising $Fuc_4$(Galβ1→4GlcNAc)$_2$ [III] or [Fucα1-2Galβ1-4(Fucα1-3)GlcNAc]$_2$ [IV], to a biantennary $Le^B/Le^Y$ antigen comprising $Fuc_2$(Galβ1→3GlcNAc)[$Fuc_2$(Galβ1→4GlcNAc)] [V], or [Fucα1-2Galβ1-3(Fucα1-4)GlcNAc][Fucα1-2Galβ1-4(Fucα1-3)GlcNAc] [VI], and to a biantennary $Le^Y/Le^B$ antigen comprising $Fuc_2$(Galβ1-4GlcNAc)[$Fuc_2$(Galβ1-3GlcNAc)] [VII] or [Fucα1-2Galβ1-4(Fucα1-3)GlcNAc][Fucα1-2Galβ1-3(Fucα1-4)GlcNAc] [VIII], and wherein the antibody or antigen-binding fragment thereof does not bind specifically to a monoantennary $Le^x$ antigen that comprises Galβ1→4(Fucα1→3)GlcNAc [IX], or to a biantennary $Le^x$ antigen that comprises [Galβ1→4(Fucα1→3)GlcNAc]$_2$ [X], or to a monoantennary $Le^A$ antigen that comprises Galβ1-3(Fucα1-4)GlcNAc [XI], or to a monoantennary H antigen type 2 that comprises Fucα1-2Galβ1-4GlcNAc [XII], or to a biantennary H antigen type 2 that comprises (Fucα1-2Galβ1-4GlcNAc)$_2$ [XIII] or to a monoantennary H antigen type 1 that comprises Fucα1-2Galβ1-3GlcNAc [XIV].

In certain embodiments, the present disclosure provides an isolated antibody or an antigen-binding fragment thereof, comprising (a) an immunoglobulin heavy chain variable region that comprises a heavy chain complementarity determining region 1 (VH CDR1) comprising the amino acid sequence set forth in SEQ ID NO: 2 or an amino acid sequence that has at least 90, 91, 92, 93, 94, 95, 96, 97, 98 or 99 percent identity to the amino acid sequence set forth in SEQ ID NO:2; a heavy chain complementarity determining region 2 (VH CDR2) comprising the amino acid sequence set forth in SEQ ID NO: 3 or an amino acid sequence that has at least 90, 91, 92, 93, 94, 95, 96, 97, 98 or 99 percent identity to the amino acid sequence set forth in SEQ ID NO:3; a heavy chain complementarity determining region 3 (VH CDR3) comprising the amino acid sequence set forth in SEQ ID NO: 4 or an amino acid sequence that has at least 90, 91, 92, 93, 94, 95, 96, 97, 98 or 99 percent identity to the amino acid sequence set forth in SEQ ID NO:4; and (b) an immunoglobulin light chain variable region that comprises a light chain complementarity determining region 1 (VL CDR1) comprising the amino acid sequence set forth in SEQ ID NO: 6 or an amino acid sequence that has at least 90, 91, 92, 93, 94, 95, 96, 97, 98 or 99 percent identity to the amino acid sequence set forth in SEQ ID NO:6; a light chain complementarity determining region 2 (VL CDR2) comprising the amino acid sequence set forth in SEQ ID NO: 7 or an amino acid sequence that has at least 90, 91, 92, 93, 94, 95, 96, 97, 98 or 99 percent identity to the amino acid sequence set forth in SEQ ID NO: 7; and a light chain complementarity determining region 3 (VL CDR3) comprising the amino acid sequence set forth in SEQ ID NO: 8 or an amino acid sequence that has at least 90, 91, 92, 93, 94, 95, 96, 97, 98 or 99 percent identity to the amino acid sequence set forth in SEQ ID NO: 8.

In certain further embodiments, there is provided an isolated antibody or an antigen-binding fragment thereof according to the present disclosure, comprising (i), (ii), (iii), (iv), (v), or (vi) as follows, or any combination thereof: (i) a VH CDR1 comprising a variant of the amino acid sequence set forth in SEQ ID NO: 2, wherein the variation consists of a Y→A substitution at position 33 according to Kabat numbering; (ii) a VH CDR3 comprising a variant of the amino acid sequence set forth in set forth in SEQ ID NO: 4, wherein the variation consists of a Y→A substitution at position 104 according to Kabat numbering; (iii) a VH CDR3 comprising a variant of the amino acid sequence set forth in set forth in SEQ ID NO: 4, wherein the variation consists of a H→A substitution at position 106 according to Kabat numbering; (iv) a VL CDR1 comprising a variant of the amino acid sequence set forth in SEQ ID NO: 6, wherein the variation consists of a Y→A substitution at position 30 according to Kabat numbering; (v) a VL CDR2 comprising a variant of the amino acid sequence set forth in SEQ ID NO: 7, wherein the variant consists of a G→A substitution at position 50 according to Kabat numbering; or (vi) a VL CDR3 comprising a variant of the amino acid sequence set forth in SEQ ID NO: 8, wherein the variation consists of a T→S substitution at position 93 according to Kabat numbering.

In certain further embodiments, an isolated antibody or antigen-binding fragment is provided that comprises complementarity determining regions (CDRs) as described herein (i.e., CDRs having at least 90% identity to SEQ ID NOs:2, 3, 4, 6, 7, and 8, respectively, including those CDR variants with the herein described amino acid substitutions), and comprises an immunoglobulin heavy chain variable region comprising or consisting of an amino acid sequence that has at least 90, 91, 92, 93, 94, 95, 96, 97, 98 or 99 percent identity to the amino acid sequence set forth in SEQ ID NO: 35; and an immunoglobulin light chain variable region that comprises or consists of an amino acid sequence that has at least 90, 91, 92, 93, 94, 95, 96, 97, 98 or 99 percent identity to the amino acid sequence set forth in SEQ ID NO:5.

In any of the herein described embodiments, an isolated antibody or an antigen-binding fragment thereof, or an antibody-drug conjugate comprising an antibody or antigen-binding fragment of the present disclosure, may exhibit reduced (e.g., decreased in a statistically significant manner as determined using an art-accepted methodology) binding (including, in certain embodiments, no binding) to a monoantennary Lewis B or a monoantennary Lewis Y antigen as compared to a "BBC" antibody which, as disclosed herein, comprises a VL domain having the amino acid sequence set forth in SEQ ID NO: 27 and a VH domain having the amino acid sequence set forth in SEQ ID NO: 28. Monovalent Lewis B is a blood group antigen that is expressed in normal human tissues; accordingly, presently disclosed antibodies, antigen-binding fragments, and antibody drug conjugates have improved specificity for a cancer antigen, and reduced binding to a monoantennary Lewis B antigen that is expressed in normal human tissues, as compared to BBC antibody. In certain embodiments, a herein disclosed antibody, antigen-binding fragment, or antibody drug conjugate has a 1-fold, 2-fold, 3-fold, 5-fold, 6-fold, 7-fold, 8-fold, or greater increase in binding to a cell surface-expressed antigen according to any one or more of Formulas [I]-[VIII] herein as compared to binding to a monoantennary Lewis B antigen.

In certain embodiments, an antibody, antigen-binding fragment, or antibody drug conjugate binds to a monoantennary Lewis B antigen with 1/10, 1/9, 1/8, 1/7, 1/6, 1/5, 1/4, 1/3, or 1/2 the affinity of BR96, e.g., as measured in an ELISA binding assay.

In any of the herein described embodiments, an isolated antibody or an antigen-binding fragment thereof, or an antibody-drug conjugate comprising an antibody or antigen-binding fragment of the present disclosure, binds antigens that are distinct from the monoantennary $Le^Y$ antigen recognized by antibody BR96 and may according to non-limiting theory allow for safer and more specific targeting of cancer cells in therapeutic applications, as compared to BR96. In any of the herein described embodiments, an isolated antibody or an antigen-binding fragment thereof, or an antibody-drug conjugate comprising an antibody or antigen-binding fragment of the present disclosure, binds to antigen-expressing cancer cells, efficiently and stably internalizes into lysosomes of such cells, and is safely tolerated at therapeutic doses in a non-human primate model.

In another aspect, the present disclosure provides isolated polynucleotides that encode the herein disclosed antibodies or antigen-binding fragments thereof. In certain embodiments, the polynucleotide is codon-optimized for expression in a host cell. In certain related embodiments, recombinant vectors are provided that comprise a polynucleotide that encodes a herein disclosed antibody or antigen-binding fragment thereof. In certain embodiments, a recombinant vector comprises an expression control sequence operably linked to the polynucleotide encoding the antibody or antigen-binding fragment thereof. In particular embodiments, a recombinant vector is an expression vector in which the expression control sequence comprises a promoter.

In another embodiment, there are provided host cells which comprise a recombinant and/or expression vector of the present disclosure. In certain other embodiments there are provided related methods of producing a herein disclosed antibody or an antigen-binding fragment thereof that is capable of binding specifically:

- to a biantennary $Le^B/Le^B$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II],
- to a biantennary $Le^Y/Le^Y$ antigen comprising $Fuc_4(Gal\beta1\rightarrow4GlcNAc)_2$ [III] or $[Fuc\alpha1\text{-}2Gal\beta1\text{-}4(Fuc\alpha1\text{-}3)GlcNAc]_2$ [IV],
- to a biantennary $Le^B/Le^Y$ antigen comprising $Fuc_2(Gal\beta1\rightarrow3GlcNAc)[Fuc_2(Gal\beta1\rightarrow4GlcNAc)]$ [V], or $[Fuc\alpha1\text{-}2Gal\beta1\text{-}3(Fuc\alpha1\text{-}4)GlcNAc][Fuc\alpha1\text{-}2Gal\beta1\text{-}4(Fuc\alpha1\text{-}3)GcNAc]$ [VI],
- and to a biantennary $Le^Y/Le^B$ antigen comprising $Fuc_2(Gal\beta1\text{-}4GlcNAc)[Fuc_2(Gal\beta1\text{-}3GlcNAc)]$ [VII] or $[Fuc\alpha1\text{-}2Gal\beta1\text{-}4(Fuc\alpha1\text{-}3)GlcNAc][Fuc\alpha1\text{-}2Gal\beta\text{-}3(Fuc\alpha1\text{-}4)GlcNAc]$ [VIII],
- and wherein the antibody or antigen-binding fragment thereof does not bind specifically to a monoantennary $Le^x$ antigen that comprises $Gal\beta1\rightarrow4(Fuc\alpha1\rightarrow3)$ GlcNAc [IX], or to a biantennary $Le^x$ antigen that comprises [Galβ1→4(Fucα1→3)GlcNAc]$_2$ [X], or to a monoantennary $Le^A$ antigen that comprises Galβ1-3 (Fucα1-4)GlcNAc [XI], or to a monoantennary H antigen type 2 that comprises Fucα1-2Galβ1-4GlcNAc [XII], or to a biantennary H antigen type 2 that comprises (Fucα1-2Galβ1-4GlcNAc)$_2$ [XIII] or to a monoantennary H antigen type 1 that comprises Fucα1-2Galβ1-3GlcNAc [XIV], wherein the methods comprise: culturing a host cell as described herein under conditions and for a time sufficient for expression by the host cell of the polynucleotide encoding the antibody or antigen-binding fragment thereof, thereby to obtain a culture comprising the antibody or antigen-binding fragment thereof; and recovering the antibody or antigen-binding fragment thereof from the culture.

In another embodiment, antibody conjugates are provided that comprise an isolated antibody or an antigen-binding fragment thereof of the present disclosure; and a payload molecule linked thereto. In certain embodiments, a payload molecule is covalently linked by a linker to the antibody or antigen-binding fragment thereof. In certain embodiments the linker is selected from a cleavable linker and a non-cleavable linker. In certain embodiments the cleavable linker is a protease-sensitive linker, a pH-sensitive linker, or a glutathione-sensitive linker. In certain embodiments, the cleavable linker is a protease-sensitive linker comprising a valine-citrulline dipeptide. In some embodiments, the linker comprises a maleimide group. In certain embodiments, the herein disclosed antibody or antigen-binding fragment thereof comprises a reduced disulfide bridge in a hinge region and the reduced disulfide bridge is coupled to the maleimide group. Also provided herein are embodiments in which the linker further comprises a self-demolishing group, such as, for example, para-amino benzyl alcohol (PABC). In certain embodiments, an antibody conjugate comprises a herein disclosed antibody or antigen-binding fragment and a payload molecule that is selected from a therapeutic agent and a detectable indicator. In certain embodiments, the payload molecule is a therapeutic agent selected from a tubulin-targeting antimitotic agent, a peptide-based toxin, a pyrrolobenzodiazepine (PBD) dimer, an antibiotic, a pyrimidine synthesis inhibitor, an anti-metabolite, a DNA alkylating agent, and a topoisomerase inhibitor. In certain embodiments, the payload molecule is selected from a maytansinoid, an auristatin, doxorubicin, calicheamicin, a PBD dimer, monomethylauristatin E (MMAE), and monomethylauristatin F (MMAF). In certain other embodiments, the payload molecule is a detectable indicator. In certain further embodiments, the detectable indicator is selected from a radionuclide, a dye, a radiometal, a fluorescent moiety, an MRI contrast agent, a microbubble, a carbon nanotube, a gold particle, fluorodeoxyglucose, an enzyme, a chromophore, and a radioopaque marker. In particular embodiments, the detectable indicator is a radionuclide selected from $^{68}$Ga, $^{64}$Cu, $^{86}$Y, $^{89}$Zr, $^{124}$I, $^{99m}$Tc, $^{123}$I, $^{111}$In, $^{177}$Lu, $^{131}$I, $^{76}$Br, $^{78}$Zr, $^{18}$F, and $^{124}$T. In certain embodiments, the antibody conjugate comprises a radionuclide chelator selected from maleimide-labeled DOTA, N-hydroxysuccinimide-DOTA, and desferrioxamine (DFO).

Pharmaceutical compositions are also provided herein and, in some embodiments, comprise an isolated herein-disclosed antibody, antigen-binding fragment, or antibody conjugate; and a pharmaceutical carrier.

The present disclosure also provides, in certain embodiments, therapeutic or detection methods comprising use of the presently disclosed antibodies, antigen-binding fragments, and/or antibody conjugates. In some embodiments, methods of treating or detecting cancer are provided, wherein the methods comprise administering a pharmaceutical composition as disclosed herein to a subject in need thereof. In certain embodiments, the subject has or is suspected of having a cancer that is selected from gastric cancer, colon cancer, breast cancer, lung cancer, lymphatic cancer, liver cancer, ovarian cancer, pancreatic prostate cancer, uterine cancer, and squamous cell carcinoma. In certain embodiments, the cancer is selected from a stomach adenocarcinoma, a mucinous stomach adenocarcinoma, an undifferentiated stomach adenocarcinoma, a signet-ring cell stomach carcinoma, a colon adenocarcinoma, an invasive breast ductal carcinoma, a hepatocellular carcinoma, a lung adenocarcinoma, a squamous cell carcinoma, a metastatic lymph node adenocarcinoma, a mucinous ovarian adenocarcinoma, a pancreatic ductal adenocarcinoma, a pancreatic papillary adenocarcinoma, a prostate adenocarcinoma, and an endometrioid carcinoma. In certain embodiments, there is provided a method that comprises administering to a subject a presently disclosed composition (e.g., comprising a herein disclosed antibody or antigen-binding fragment thereof) by a route that is selected from intravenous, parenteral, intragastric, intrapleural, intrapulmonary, intrarectal, intradermal, intraperitoneal, intratumoral, subcutaneous, oral, topical, transdermal, intracisternal, intrathecal, intranasal, and intramuscular. In certain further embodiments of the presently disclosed methods for detecting or treating cancer, the subject is receiving or has previously received: (a) an immunosuppressive therapy; (b) a stimulatory immune checkpoint molecule; (c) a radiation therapy; (d) a chemotherapy; (e) a cell immunotherapy; or (f) any combination of (a)-(e).

These and other aspects and embodiments of the present disclosure will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWINGS

FIG. 1 shows multiple amino acid sequence alignments of the presently disclosed "BBC" antibody heavy chain variable region (SEQ ID NO:28) to selected candidate human acceptor amino acid sequences (1-8; corresponding to SEQ ID NOs:44-51, respectively). Row 3 (boxed with broken line) shows the human acceptor sequence that was selected for CDR grafting. In the middle portion of the Figure, the single boxed amino acid (V/I/M) is a rare methionine in the human acceptor sequence; this residue was substituted for the more common isoleucine during humanization.

FIG. 2A shows amino acid sequence alignments of light chain (LC) variable region sequences of IMH2/BBC antibody (SEQ ID NO: 27) and humanized variants: hBBC.8 (SEQ ID NO: 31); hBBC.9 and hBBC.9.1 (SEQ ID NO: 33); and hBBC.10, hBBC.10.1, and hBBC.10.1FQ (SEQ ID NO: 5). hBBC CDR sequences are shown in boxes (broken lines), and human acceptor CDR sequences are underlined. In the bottom portion of the Figure, the two single boxed amino acid residues (R/G and Y/F) show differences in framework region sequence.

FIG. 3 provides sequence alignments of hBBC.10.1 antibody (SEQ ID NO:38), hBBC.10.1FQ antibody (SEQ ID NO:39), and two FDA-approved humanized therapeutic antibodies (reference 1 and reference 2) (SEQ ID NOs:40 and 41, respectively) within the heavy chain framework 3 region.

In FIGS. 4A-7B, glycans are depicted as follows: open circles=Gal; filled circles=Glc; filled squares=GlcNac; closed triangles=Fuc. The same conventions are used in FIGS. 8A-8B with the difference that filed circles=Man.

FIGS. 7A and 7B provide MALDI-MSMS sequencing of $Fuc_4(LacNAc)_3Lac$ and $Fuc_6(LacNAc)_5Lac$ of NCI-N87 GSL cells at m/z 2970 (7A) and m/z 3767 (7B) in BBC-bound (eluted) fraction.

FIG. 25A illustrates the structure of antigen $Le^Y$-Gal.

FIG. 25B illustrates the structure of antigen $Le^B$-Gal.

FIG. 25C illustrates the structure of antigen $Le^Y/Le^Y$-ASGP.

FIG. 25D illustrates the structure of antigen H-ASGP.

FIG. 25E illustrates the structure of antigen $Le^X/Le^X$-ASGP.

FIG. 25F illustrates the structure of antigen $Le^Y/Le^Y$-I.

FIG. 25G illustrates the structure of antigen $Le^Y/Le^B$-I.

FIG. 25H illustrates the structure of antigen $Le^A$-Gal.

FIG. 25I illustrates the structure of antigen $Le^X$-Gal.

FIG. 25J illustrates the structure of antigen H antigen type 1.

FIG. 25K illustrates the structure of antigen H antigen type II.

FIG. 26E illustrates the structure of antigen 3-$Le^Y$/6-$Le^B$-ASGA-biotin.

FIG. 26F illustrates the structure of antigen 3-$Le^B$/6-$Le^Y$-ASGA-biotin.

BRIEF DESCRIPTION OF THE SEQUENCES

Figure 2B:
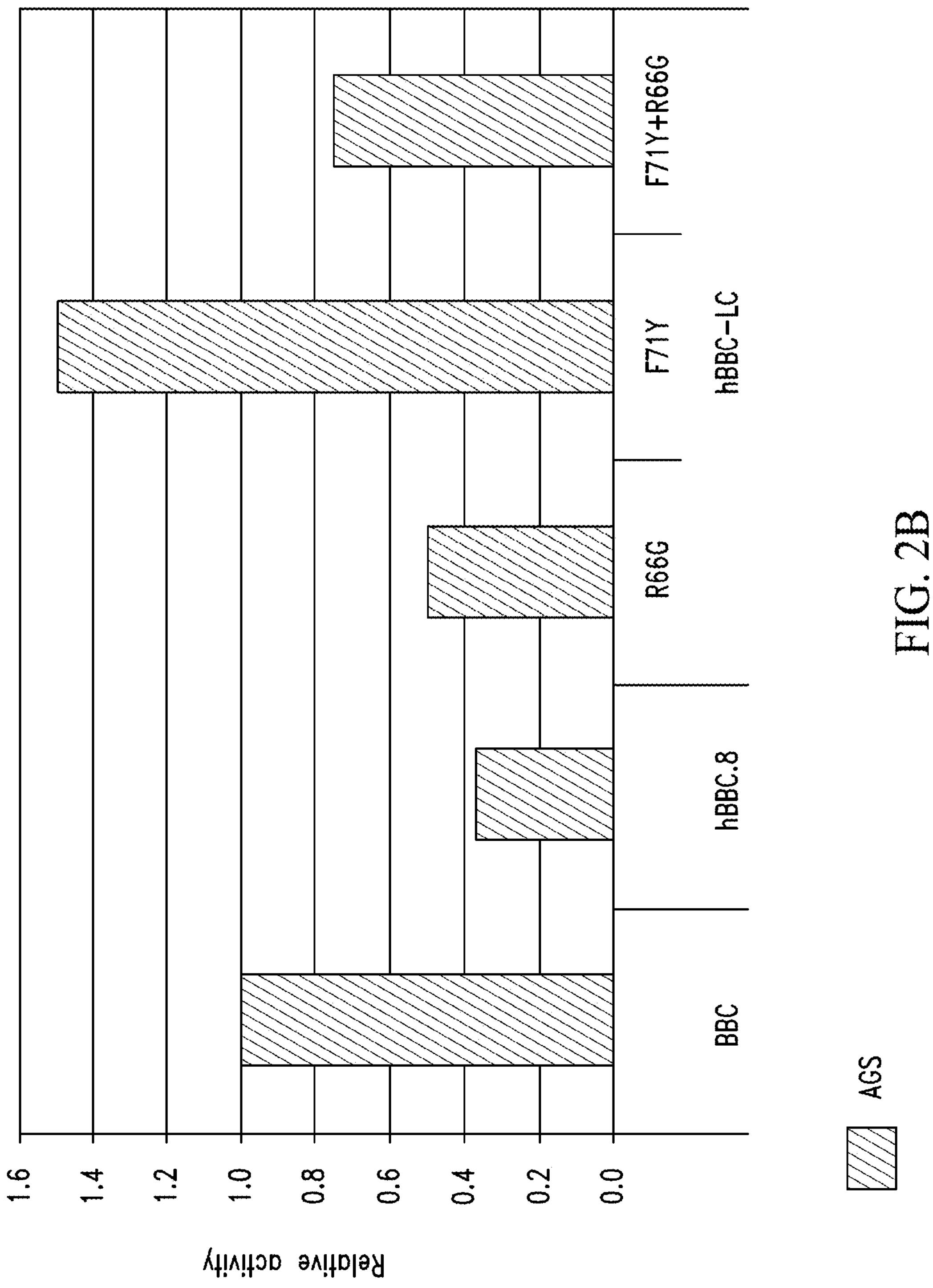
FIG. 2B shows relative activity of BBC, hBBC.8, hBBC.8 with R66G substitution mutation, hBBC.9, and hBBC.10 antibodies in an AGS cell binding assay. hBBC-LC with F71Y mutation represents hBBC.9. hBBC-LC with F71Y and R66G mutations represents hBBC.10.

SEQ ID NO:1 is the amino acid sequence of the heavy chain variable (VH) domain of antibody hBBC.10.1FQ:

QVQLQESGPGLVKPSQTLSLTCTVSGYSITSGYTWHWIRQHPGKGLEWL
GYIHYTGNTKYSPSLKSRLSISRDTSKNTFYLQMNSLTTEDTAVYYCGR
EALRGYDAGFWFTYWGQGTLVTV.

SEQ ID NO:2 is the amino acid sequence of the heavy chain complementarity determining region 1 (VH CDR1) of antibody IMH2/BBC, antibody hBBC.8, antibody hBBC.9, antibody hBBC.9.1, antibody hBBC.10, antibody hBBC.10.1, and antibody hBBC.10.1FQ:

SGYTWH.

SEQ ID NO:3 is the amino acid sequence of the VH CDR2 of antibody hBBC.9.1, antibody hBBC.10.1, and antibody hBBC.10.1FQ:

YIHYTGNTKYSPSLKS.

SEQ ID NO:4 is the amino acid sequence of the VH CDR3 of antibody hBBC.10.1, and antibody hBBC.10.1FQ:

EALRGYDAGFWFTY.

SEQ ID NO:5 is the amino acid sequence of the light chain variable (VL) domain of antibody hBBC.10, antibody hBBC.10.1, and antibody hBBC.10.1FQ:

DIQMTQSPSSLSASVGDRVTITCTASEDIYNRLTWYQQKPGKVPRLL
ISGATSLDTGVPSRFSGSGSGTDYTLTISSLQPEDVATYYCQQYWTT
PWTFGQGTKLEIK.

SEQ ID NO:6 is the amino acid sequence of the light chain complementarity determining region 1 (VL CDR1) of antibody IMH2/BBC, antibody hBBC.8, antibody hBBC.9, antibody hBBC.9.1, antibody hBBC.10, antibody hBBC.10.1, and antibody hBBC.10.1FQ:

TASEDIYNRLT.

SEQ ID NO:7 is the amino acid sequence of the VL CDR2 of antibody IMH2/BBC, antibody hBBC.8, antibody hBBC.9, antibody hBBC.9.1, antibody hBBC.10, antibody hBBC.10.1, and antibody hBBC.10.1FQ:

GATSLDT.

SEQ ID NO:8 is the amino acid sequence of the VL CDR3 of antibody IMH2/BBC, antibody hBBC.8, antibody hBBC.9, antibody hBBC.9.1, antibody hBBC.10, antibody hBBC.10.1, and antibody hBBC.10.1FQ:

QQYWTTPWT.

SEQ ID NO:9 is the amino acid sequence of a single chain fragment variable (scFv) derived from antibody hBBC.10.1, in the [VL-VH]orientation:

DIQMTQSPSSL-SASVGDRVTITCTASEDIYNRLTWYQQKPG-KVPRLLIS GAT-SLDTGVPSRFSGSGSGTDYTLTISSLQPEDV-ATYYCQQYWTTPWTFGQ GTKLEIK(GGGGS)$_x$ QVQLQESGPGLVKPSQTLSLTCTVSGYSITSGY TWHWIRQHPGKGLEWLGYIHYTGNT-KYSPSLKSRLSISRDTSKNQFFLKLSSV TTED-TAVYYCGREALRGYDAGFWFTYWGQGTLVTV, wherein “x” can be 1, or 2, 3, 4, 5, 6, 7, 8, 9, 10, or more repeats, of the sequence GGGGS shown in parentheses.

SEQ ID NO:10 is the amino acid sequence the full-length heavy chain (HC) of antibody hBBC.10.1:

QVQLQESGPGLVKPSQTLSLTCTVSGYSITSGYTWHWIRQHPGKGLE
WLGYIHYTGNTKYSPSLKSRLSISRDTSKNQFFLKLSSVTTEDTAVY
YCGREALRGYDAGFWFTYWGQGTLVTVSSASTKGPSVFPLAPSSKST
SGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKV
SNKALPAPIEKTISKAKGQPREPQVYTLPPSRDELTKNQVSLTCLVK
GFYPSDIAVEWESNGQPENNYKTTPPVLDSDGSFFLYSKLTVDKSRW
QQGNVFSCSVMHEALHNHYTQKSLSLSPGK.

SEQ ID NO:11 is the amino acid sequence the full-length light chain (LC) of antibody hBBC.10, antibody hBBC.10.1, and antibody hBBC.10.1FQ:

DIQMTQSPSSLSASVGDRVTITCTASEDIYNRLTWYQQKPGKVPRLL
ISGATSLDTGVPSRFSGSGSGTDYTLTISSLQPEDVATYYCQQYWTT
PWTFGQGTKLEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC.

SEQ ID NO:12 is a nucleotide sequence encoding the heavy chain variable (VH) domain of antibody hBBC.10.1:

Caggtgcagctgcaggaaagcggcccgggcctggtgaaaccgagcca
gaccctgagcctgacctgcaccgtgagcggctatagcattaccagcg
gctatacctggcattggattcgccagcatccgggcaaaggcctggaa
tggctgggctatattcattataccggcaacaccaaatatagcccgag
cctgaaaagccgcctgagcattagccgcgataccagcaaaaaccagt
tcttcctgaaactgagcagcgtgaccaccgaagataccgcggtgtat
tattgcggccgcgaagcgctgcgcggctatgatgctggcttctggtt
tacctattggggccaaggcaccctggtgaccgtg.

SEQ ID NO:13 is a nucleotide sequence encoding the heavy chain complementarity determining region 1 (VH CDR1) of antibody IMH2/BBC, antibody hBBC.8, antibody hBBC.9, antibody hBBC.9.1, antibody hBBC.10, hBBC.10.1, and antibody hBBC.10.1FQ:

agcggctatacctggcat.

SEQ ID NO:14 is a nucleotide sequence encoding the VH CDR2 of antibody hBBC.9.1, antibody hBBC.10, and antibody hBBC.10.1FQ:

tatattcattataccggcaacaccaaatatagcccgagcctgaaaagc.

SEQ ID NO:15 is a nucleotide sequence encoding the VH CDR3 of antibody hBBC.10.1 and antibody hBBC.10.1 FQ:

gaagcgctgcgcggctatgatgctggcttctggtttacctat.

SEQ ID NO:16 is a nucleotide sequence encoding the light chain variable (VL) domain of antibody hBBC.10, antibody hBBC.10.1, and antibody hBBC.10.1 FQ:

gatattcagatgacccagagcccgagcagcctgagcgcgagcgtgggcg
atcgcgtgaccattacctgcaccgcgagcgaagatatttataaccgcct
gacctggtatcagcagaaaccgggcaaagtgccgcgtctgctgatttct
ggcgcgaccagcctggataccggcgtgccgagccgctttagcggcagcg
gcagcggcaccgattacaccctgaccattagcagcctgcagccggaaga
tgtggcgacctattattgccagcagtattggaccaccccgtggaccttt
ggccagggcaccaaactggaaattaaa.

SEQ ID NO:17 is a nucleotide sequence encoding the light chain complementarity determining region 1 (VL CDR1) of antibody IMH2/BBC, antibody hBBC.8, antibody hBBC.9, antibody hBBC.9.1, antibody hBBC.10, antibody hBBC.10.1, and antibody antibody hBBC.10.1FQ:

accgcgagcgaagatatttataaccgcctgacc.

SEQ ID NO:18 is a nucleotide sequence encoding the VL CDR2 of antibody IMH2/BBC, antibody hBBC.8, antibody hBBC.9, antibody hBBC.9.1, antibody hBBC.10, antibody hBBC.10.1, and antibody hBBC.10.1FQ:

ggcgcgaccagcctggatacc.

SEQ ID NO:19 is a nucleotide sequence encoding the VL CDR3 of antibody antibody IMH2/BBC, antibody hBBC.8, antibody hBBC.9, antibody hBBC.9.1, antibody hBBC.10, antibody hBBC.10.1, and antibody hBBC.10.1FQ:

cagcagtattggaccaccccgtggacc.

SEQ ID NO:20 is a nucleotide sequence encoding a single chain fragment variable (scFv) in the [VL-(L)-VH] orientation derived from antibody hBBC.10.1:

gatattcagatgacccagagcccgagcagcctgagcgcgagcgtgggcg
atcgcgtgaccattacctgcaccgcgagcgaagatatttataaccgcct
gacctggtatcagcagaaaccgggcaaagtgccgcgtctgctgatttct -continued ggcgcgaccagcctggataccggcgtgccgagccgctttagcggcagcg
gcagcggcaccgattacaccctgaccattagcagcctgcagccggaaga
tgtggcgacctattattgccagcagtattggaccaccccgtggaccttt
ggccagggcaccaaactggaaattaaa(ggtggaggcggttct)$_x$cagg
tgcagctgcaggaaagcggcccgggcctggtgaaaccgagccagaccct
gagcctgacctgcaccgtgagcggctatagcattaccagcggctatacc
tggcattggattcgccagcatccgggcaaaggcctggaatggctgggct
atattcattataccggcaacaccaaatatagcccgagcctgaaaagccg
cctgagcattagccgcgataccagcaaaaaccagttcttcctgaaactg
agcagcgtgaccaccgaagataccgcggtgtattattgcggccgcgaag
cgctgcgcggctatgatgctggcttctggtttacctattggggccaagg
caccctggtgaccgtg, wherein "x" can be 1, or 2, 3, 4, 5, 6, 7, 8, 9, 10, or more repeats of the sequence ggtggaggcggttct shown in parentheses.

SEQ ID NO:21 is a nucleotide sequence encoding the full-length heavy chain (HC) of antibody hBBC.10.1:

caggtgcagctgcaggaaagcggcccgggcctggtgaaaccgagccaga
ccctgagcctgacctgcaccgtgagcggctatagcattaccagcggcta
tacctggcattggattcgccagcatccgggcaaaggcctggaatggctg
ggctatattcattataccggcaacaccaaatatagcccgagcctgaaaa
gccgcctgagcattagccgcgataccagcaaaaaccagttcttcctgaa
actgagcagcgtgaccaccgaagataccgcggtgtattattgcggccgc
gaagcgctgcgcggctatgatgctggcttctggtttacctattggggcc
aaggcaccctggtgaccgtgtcgagcgcttccaccaagggcccatcggt
cttccccctggcaccctcctccaagagcacctctgggggcacagcggcc
ctgggctgcctggtcaaggactacttccccgaaccggtgacggtgtcgt
ggaactcaggcgccctgaccagcggcgtgcacaccttcccggctgtcct
acagtcctcaggactctactccctcagcagcgtggtgaccgtgccctcc
agcagcttgggcacccagacctacatctgcaacgtgaatcacaagccca
gcaacaccaaggtggacaagaaagttgagcccaaatcttgtgacaaaac
tcacacatgcccaccgtgcccagcacctgaactcctggggggaccgtca
gtcttcctcttccccccaaaacccaaggacaccctcatgatctcccgga
cccctgaggtcacatgcgtggtggtggacgtgagccacgaagaccctga
ggtcaagttcaactggtacgtggacggcgtggaggtgcataatgccaag
acaaagccgcgggaggagcagtacaacagcacgtaccgtgtggtcagcg
tcctcaccgtcctgcaccaggactggctgaatggcaaggagtacaagtg
caaggtctccaacaaagccctcccagcccccatcgagaaaaccatctcc
aaagccaaagggcagccccgagaaccacaggtgtacaccctgcccccat
cccgggatgagctgaccaagaaccaggtcagcctgacctgcctggtcaa
aggcttctatcccagcgacatcgccgtggagtgggagagcaatgggcag -continued ccggagaacaactacaagaccacgcctcccgtgctggactccgacggct
ccttcttcctctacagcaagctcaccgtggacaagagcaggtggcagca
ggggaacgtcttctcatgctccgtgatgcatgaggctctgcacaaccac
tacacgcagaagagcctctccctgtctccgggtaaatga.

SEQ ID NO:22 is a nucleotide sequence encoding the full-length light chain (LC) of antibody hBBC.10.1 and antibody hBBC.10.1FQ:

gatattcagatgacccagagcccgagcagcctgagcgcgagcgtgggcg
atcgcgtgaccattacctgcaccgcgagcgaagatatttataaccgcct
gacctggtatcagcagaaaccgggcaaagtgccgcgtctgctgatttct
ggcgcgaccagcctggataccggcgtgccgagccgctttagcggcagcg
gcagcggcaccgattacaccctgaccattagcagcctgcagccggaaga
tgtggcgacctattattgccagcagtattggaccaccccgtggaccttt
ggccagggcaccaaactggaaattaaacgtacggtggctgcaccatctg
tcttcatcttcccgccatctgatgagcagttgaaatctggaactgcctc
tgttgtgtgcctgctgaataacttctatcccagagaggccaaagtacag
tggaaggtggataacgccctccaatcgggtaactcccaggagagtgtca
cagagcaggacagcaaggacagcacctacagcctcagcagcaccctgac
gctgagcaaagcagactacgagaaacacaaagtctacgcctgcgaagtc
acccatcagggcctgagctcgcccgtcacaaagagcttcaacaggggag
agtgttaa SEQ ID NO: 23 is the illustrative spacer amino acid sequence EGKSSGSGSESKVD.

SEQ ID NO: 24 is the illustrative spacer amino acid sequence KESGSVSSEQLAQFRSLD.

SEQ ID NO: 25 is the flexible polylinker amino acid sequence GGGGS.

SEQ ID NO: 26 is the flexible polylinker amino acid sequence GGGGSGGGGSGGGGS.

SEQ ID NO: 27 is the amino acid sequence of the VL domain of antibody IMH2/BBC:

DIQMTQSSSSFSVSLGDRVTITCTASEDIYNRLTWYQQKPGNVPRLLISG
ATSLDTGVPSRFSGSRSGKDYALSITSLQTEDVATYYCQQYWTTPWTFGG
GTRLEIK.

SEQ ID NO: 28 is the amino acid sequence of the VH domain of antibody IMH2/BBC:

DVQLQESGPDLVKPSQSLSLTCTVTGYSITSGYTWHWIRQFPGNTLEWLG
YIHYSGNTKYSPSLKSRLSVTRDTSKNQFFLQLNSVTTEDTATYYCGREA
LRGYDHGFWFTYWGQGTLVTV.

SEQ ID NO: 29 is the amino acid sequence of the VL domain of human acceptor framework AAS01771.1:

DIQMTQSPSSLSASVGDRVTITCRASQGISNYLAWYQQKPGKVPKLLIYA
ASTLQSGVPSRFSGSGSGTDFTLTISSLQPEDVATYYCQKYNSAPYTFGQ
GTKLEIK.

SEQ ID NO: 30 is the amino acid sequence of the VH domain of human acceptor framework CAD89404.1:

QVQLQESGPGLVKPSQTLSLTCTVSGGSISSGAYYWSWIRQHPGKGLEWI
GYIYYSGTTYYNPSLKSRLSMSRDTSKNQFSLKLSSVTAADTAVYYCARG
PYYDSPRPFDPWGQGTLVTV.

SEQ ID NO: 31 is the amino acid sequence of the VL domain of antibody hBBC.8:

DIQMTQSPSSLSASVGDRVTITCTASEDIYNRLTWYQQKPGKVPRLLISG
ATSLDTGVPSRFSGSRSGTDFTLTISSLQPEDVATYYCQQYWTTPWTFGQ
GTKLEIK.

SEQ ID NO: 32 is the amino acid sequence of the VH domain of antibody hBBC.8, antibody hBBC.9, and antibody hBBC.10:

QVQLQESGPGLVKPSQTLSLTCTVSGYSITSGYTWHWIRQHPGKGLEWLG
YIHYSGNTKYSPSLKSRLSISRDTSKNQFFLKLSSVTTEDTAVYYCGREA
LRGYDHGFWFTYWGQGTLVTV.

SEQ ID NO: 33 is the amino acid sequence of the VL domain of antibody hBBC.9 and antibody hBBC.9.1:

DIQMTQSPSSLSASVGDRVTITCTASEDIYNRLTWYQQKPGKVPRLLISG
ATSLDTGVPSRFSGSRSGTDYTLTISSLQPEDVATYYCQQYWTTPWTFGQ
GTKLEIK.

SEQ ID NO: 34 is the amino acid sequence of the VH domain of antibody hBBC.9.1:

QVQLQESGPGLVKPSQTLSLTCTVSGYSITSGYTWHWIRQHPGKGLEWLG
YIHYTGNTKYSPSLKSRLSISRDTSKNQFFLKLSSVTTEDTAVYYCGREA
LRGADHGFWFTYWGQGTLVTV.

SEQ ID NO: 35 is the amino acid sequence of the VH domain of antibody hBBC.10.1:

QVQLQESGPGLVKPSQTLSLTCTVSGYSITSGYTWHWIRQHPGKGLEWLG
YIHYTGNTKYSPSLKSRLSISRDTSKNQFFLKLSSVTTEDTAVYYCGREA
LRGYDAGFWFTYWGQGTLVTV.

SEQ ID NO: 36 is the amino acid sequence of a single chain fragment variable (scFv) derived from antibody hBBC.10.1 in the [VH-VL]orientation:

QVQLQESGPGLVKPSQTLSLTCTVSGYSITSGYT-WHWIRQHPGKGLE WLGYIHYTGNT-KYSPSLKSRLSISRDTSKNQFFLKLSSVTTED-TAVYYCGREA LRGYDAGFWFTYWGQGTLVTV $(GGGGS)_x$DIQMTQSPSSLSASVGDRVTITC TASEDIYNRLTWYQQKPGKVPRLLISGAT-

SLDTGVPSRFSGSGSGTDYTLTIS SL QPED-VATYYCQQYWTTPWTFGQGTKLEIK, wherein "x" can be 1, or 2, 3, 4, 5, 6, 7, 8, 9, 10, or more repeats of the sequence GGGGS shown in parentheses.

SEQ ID NO: 37 is a nucleotide sequence encoding a single chain fragment variable (scFv) in the [VH-(L)-VL]orientation derived from antibody hBBC.10.1:

```
caggtgcagctgcaggaaagcggcccgggcctggtgaaaccgagccagac
cctgagcctgacctgcaccgtgagcggctatagcattaccagcggctata
cctggcattggattcgccagcatccgggcaaaggcctggaatggctgggc
tatattcattataccggcaacaccaaatatagcccgagcctgaaaagccg
cctgagcattagccgcgataccagcaaaaaccagttcttcctgaaactga
gcagcgtgaccaccgaagataccgcggtgtattattgcggccgcgaagcg
ctgcgcggctatgatgctggcttctggtttacctattggggccaaggcac
cctggtgaccgtg(ggtggaggcggttct)xgatattcagatgacccaga
gcccgagcagcctgagcgcgagcgtgggcgatcgcgtgaccattacctgc
caccgcgagcgaagatatttataaccgcctgacctggtatcagagaaacc
gggcaaagtgccgcgtctgctgatttctggcgcgaccagcctggataccg
gcgtgccgagccgctttagcggcagcggcagcggcaccgattacaccctg
accattagcagcctgcagccggaagatgtggcgacctattattgccagca
gtattggaccaccccgtggacctttggccagggcaccaaactggaaatta
aa,
```

wherein "x" can be 1, or 2, 3, 4, 5, 6, 7, 8, 9, 10, or more repeats of the sequence ggtggaggcggttct shown in parentheses.

These and other sequences are provided in the accompanying Sequence Listing.

DETAILED DESCRIPTION

The present disclosure relates to humanized antibodies and antigen-binding fragments thereof, which are capable of specifically binding to certain Lewis antigens expressed on a variety of cancers. More specifically, as described herein for the first time and presented in greater detail below, the present chimeric, humanized antibodies unexpectedly bind with exquisite specificity to certain biantennary Lewis$^{B/Y}$ antigens that are expressed on cancer cells, and have robust antitumor activity in vivo. Additionally, the presently disclosed antibodies advantageously have surprisingly reduced (e.g., decreased in a statistically significant manner) binding to the monoantennary Lewis B antigen (which is expressed on healthy tissues) as compared to a BBC antibody which comprises a VL domain having the amino acid sequence set forth in SEQ ID NO: 27 and a VH domain having the amino acid sequence set forth in SEQ ID NO:28. The antibodies disclosed herein bind antigens that are distinct from the monoantennary Le$^{Y}$ antigen recognized by antibody BR96 and, without wishing to be bound by theory, the present antibodies may allow for safer and more specific targeting of cancer cells in therapeutic applications as compared to BR96. Furthermore, the antibodies and antigen-binding fragments of the present disclosure also bind to antigen-expressing cancer cells, efficiently and stably internalize into lysosomes of such cells, and are safely tolerated at therapeutic doses in a non-human primate model.

According to certain preferred embodiments and further according to non-limiting theory, beneficial uses of the presently disclosed antibodies and antigen-binding fragments thereof relate to methods of diagnosing and/or treating cancers, such as, for example, various gastric cancers, ovarian cancer, lung cancer, prostate cancer, pancreatic cancer, and other cancers. These and related embodiments are disclosed in greater detail herein.

Polypeptides and Proteins

The terms "polypeptide" "protein" and "peptide" and "glycoprotein" are used interchangeably and refer to a polymer of amino acids not limited to any particular length. The term does not exclude modifications such as myristylation, sulfation, glycosylation, phosphorylation and addition or deletion of signal sequences. The terms "polypeptide" or "protein" may mean one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically engineered or recombinant cells, and comprise molecules having the amino acid sequence of the native protein, or molecules having deletions from, additions to, and/or substitutions of one or more amino acids of the native sequence. Thus, a "polypeptide" or a "protein" can comprise one (termed "a monomer") or a plurality (termed "a multimer") of amino acid chains. The terms "peptide," "polypeptide" and "protein" specifically encompass the antibodies and antigen-binding fragments of the present disclosure, or sequences that have deletions from, additions to, and/or substitutions of one or more amino acid of an antibody or antigen-binding fragment thereof.

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s).

The term "polypeptide fragment" refers to a polypeptide (which can be monomeric or multimeric), that has an amino-terminal deletion, a carboxyl-terminal deletion, and/or an internal deletion or substitution of a naturally-occurring or recombinantly produced polypeptide. As used herein, "contiguous amino acids" refers to covalently linked amino acids corresponding to an uninterrupted linear portion of a disclosed amino acid sequence. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The terms "isolated protein" and "isolated polypeptide" referred to herein means that a subject protein or polypeptide (1) is free of at least some other proteins or polypeptides with which it would typically be found in nature, (2) is essentially free of other proteins or polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein or polypeptide with which the "isolated protein" or "isolated polypeptide" may be associated in nature, (6) is operably associated (by covalent or noncovalent interaction) with a polypeptide with which it is not associated in nature, or (7) does not occur in nature. Such an isolated protein or polypeptide can be encoded by genomic DNA, cDNA, mRNA or other RNA, of may be of synthetic origin according to any of a number of well-known chemistries for artificial peptide and protein synthesis, or any combination thereof. In certain embodiments, the isolated protein or polypeptide is substantially free from proteins or polypeptides or other contaminants that are found in its natural environment that would interfere with its use (therapeutic, diagnostic, prophylactic, research or otherwise).

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support. As used herein, "fusion protein" or "fusion polypeptide" refers to a protein that, in a single chain, has at least two distinct domains, wherein the domains are not naturally found together in a protein. A polynucleotide encoding a fusion protein may be constructed using PCR, recombinantly engineered, or the like, or such fusion proteins can be synthesized. A fusion protein may further contain other components, such as a tag, a linker, or a transduction marker. Fusion domain polypeptides may be joined to a polypeptide at the N-terminus and/or at the C-terminus, and may include as non-limiting examples, immunoglobulin-derived sequences such as Ig constant region sequences or portions thereof, affinity tags such as His tag (e.g., hexahistidine or other polyhistidine), FLAG™ or myc or other peptide affinity tags, detectable polypeptide moieties such as green fluorescent protein (GFP) or variants thereof (e.g., yellow fluorescent protein (YFP), blue fluorescent protein (BFP), other aequorins or derivatives thereof, etc.) or other detectable polypeptide fusion domains, enzymes or portions thereof such as glutathione-S-transferase (GST) or other known enzymatic detection and/or reporter fusion domains, and the like, as will be familiar to the skilled artisan. Additional detectable moieties are discussed herein.

Cysteine-containing peptides may be used as fusion peptides that can be joined to the N- and/or C-terminus of a polypeptide, such as an antibody or antigen-binding fragment thereof of the present disclosure to permit ready assembly of such polypeptides into disulfide-crosslinked dimers, trimers, tetramers or higher multimers according to established methodologies. For example, fusion polypeptides containing immunoglobulin gene superfamily member-derived sequences that include cysteine residues capable of forming interchain disulfide bridges are well known, as also are other strategies for engineering S—S linked multimers (e.g., Reiter et al., 1994 *Prot. Eng.* 7:697; Zhu et al., 1997 *Prot. Sci.* 6:781; Mabry et al., 2010 *Mabs* 2:20; Gao et al., 1999 *Proc. Nat. Acad. Sci. USA* 96:6025; Lim et al., 2010 *Biotechnol. Bioeng.* 106:27) Alternative approaches are also contemplated for grafting peptide sequences that promote multimer assembly as fusion domains onto a desired polypeptide such as the herein described antibodies and antigen-binding fragments (e.g., Fan et al., 2008 *FASEB J.* 22:3795).

Polypeptide modifications may be effected biosynthetically and/or chemically according to a wide variety of well-known methodologies, and may also include conjugation to carrier proteins (e.g., keyhole limpet hemocyanin (KLH), bovine serum albumin (BSA), ovalbumin (OVA) or other molecules), and covalent or non-covalent immobilization on solid supports. Chemical or biosynthetic conjugation to a carrier is contemplated, according to certain embodiments, for generation of conjugates that are multivalent with respect to the herein described antibodies or antigen-binding fragments thereof.

Also contemplated is detectable labeling with detectable indicator moieties (sometimes referred to as reporter moieties) such as fluorophores (e.g., FITC, TRITC, Texas Red, etc.). Examples of a broad range of detectable indicators (including colorimetric indicators) that may be selected for specific purposes are described in Haugland, 2005 The *Handbook: A Guide to Fluorescent Probes and Labeling Technologies—Tenth Ed.*, Invitrogen Corp./Molecular Probes™, Eugene, OR; in Mohr, 1999 *J. Mater. Chem.*, 9: 2259-2264; in Suslick et al., 2004 *Tetrahedron* 60:11133-11138; and in U.S. Pat. No. 6,323,039. (See also, e.g., Fluka Laboratory Products Catalog, 2001 Fluka, Milwaukee, WI; and Sigma Life Sciences Research Catalog, 2000, Sigma, St. Louis, MO.) A detectable indicator may be a fluorescent indicator, a luminescent indicator, a phosphorescent indicator, a radiometric indicator, a dye, an enzyme, a substrate of an enzyme, an energy transfer molecule, or an affinity label.

Other detectable indicators for use in certain embodiments contemplated herein include affinity reagents such as antibodies, lectins, immunoglobulin Fc receptor proteins (e.g., *Staphylococcus aureus* protein A, protein G or other Fc receptors), avidin, biotin, other ligands, receptors or counterreceptors or their analogues or mimetics, and the like. For such affinity methodologies, reagents for immunometric measurements, such as suitably labeled antibodies or lectins, may be prepared including, for example, those labeled with radionuclides (e.g., $^{76}$Br, $^{78}$Zr, $^{18}$Fl), with fluorophores, with affinity tags, with biotin or biotin mimetic sequences or those prepared as antibody-enzyme conjugates (see, e.g., Weir, D. M., *Handbook of Experimental Immunology,* 1986, Blackwell Scientific, Boston; Scouten, W. H., 1987 *Methods in Enzymology* 135:30-65; Harlow and Lane, *Antibodies: A Laboratory Manual,* 1988 Cold Spring Harbor Laboratory, Cold Spring Harbor, NY; Haugland, *Guide to Fluorescent Probes and Labeling Technologies—Tenth Ed.,* 2005 Invitrogen Corp./Molecular Probes™, Eugene, OR; Scopes, R. K., *Protein Purification: Principles and Practice,* 1987, Springer-Verlag, NY; Hermanson, G. T. et al., *Immobilized*

*Affinity Ligand Techniques,* 1992, Academic Press, Inc., NY; Luo et al., 1998 *J. Biotechnol.* 65:225 and references cited therein).

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art.

Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes. In certain embodiments, peptide spacer sequences contain, for example, Gly, Asn and Ser residues. Other near neutral amino acids, such as Thr and Ala, may also be included in a spacer sequence. Other amino acid sequences which may be usefully employed as spacers include those disclosed in Maratea et al., *Gene* 40:39 46 (1985); Murphy et al., *Proc. Natl. Acad. Sci. USA* 83:8258 8262 (1986); U.S. Pat. Nos. 4,935,233, and 4,751,180. Other illustrative and non-limiting examples of spacers may include, for example, Glu-Gly-Lys-Ser-Ser-Gly-Ser-Gly-Ser-Glu-Ser-Lys-Val-Asp (SEQ ID NO: 23) (Chaudhary et al., *Proc. Natl. Acad. Sci. USA* 87:1066-1070 (1990)) and Lys-Glu-Ser-Gly-Ser-Val-Ser-Ser-Glu-Gln-Leu-Ala-Gln-Phe-Arg-Ser-Leu-Asp (SEQ ID NO: 24) (Bird et al., *Science* 242:423-426 (1988)).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser (SEQ ID NO: 25) when present in a single iteration or repeated 1 to 5 or more times, or more; see, e.g., SEQ ID NO: 26. In certain illustrative and non-limiting embodiments, a peptide spacer may be between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide spacer comprises about 1, 5, 10, 15, 20, 25, 30, 35, 40, 45, 50 or more amino acids in length.

Amino acid sequence modification(s) of the antibodies or antigen-binding fragments thereof described herein are also contemplated according to certain embodiments. Modifications include, for example, conservative and non-conservative amino acid substitutions. A "conservative substitution" refers to amino acid substitutions that do not significantly affect or alter a particular characteristic (e.g., a binding activity such as a specific binding activity) of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gin or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and lie. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, lie, Val, and Cys; and large aromatic residues: Phe, Tyr, and Trp. Additional information can be found in Creighton (1984) Proteins, W.H. Freeman and Company.

For example, it may be desirable to improve the binding affinity and/or other biological properties of an antibody or antigen-binding fragment thereof. Amino acid sequence variants may be prepared, for instance, by introducing appropriate nucleotide changes into a polynucleotide that encodes the or by peptide synthesis. Such modifications include, for example, deletions from, and/or insertions into and/or substitutions of, residues within the amino acid sequence of the antibody or antigen-binding fragment thereof. Any combination of deletion, insertion, and substitution may be made to arrive at the final antibody or antigen-binding fragment variant, provided that the final construct possesses the desired characteristics (e.g., retains specific binding to a biantennary Lewis antigen as described herein, whilst not binding detectably to, or showing statistically significant decreased binding to, a monoantennary $Le^X$ or $Le^A$ or H antigen as described elsewhere herein). The amino acid changes also may alter post-translational processes of the antibody or antigen-binding fragment thereof, such as changing the number or position of glycosylation sites.

Determination of the three-dimensional structures of representative antibodies or antigen-binding fragments thereof may be made through routine methodologies such that substitution, addition, deletion or insertion of one or more amino acids with selected natural or non-natural amino acids can be virtually modeled for purposes of determining whether a so-derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. *Science* 327:1014-1018 (2010); Marcos et al., 2017 *Science* 355:201, and references cited therein. Some additional non-limiting examples of computer algorithms that may be used for these and related embodiments, such as for rational design of antibodies and antigen-binding fragments as provided herein, include VMD, which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/).

Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

Antibodies

Certain preferred embodiments of the present invention relate to antibodies or antigen-binding fragments thereof that specifically bind:

- to a biantennary $Le^b/Le^b$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II],
- to a biantennary $Le^Y/Le^Y$ antigen comprising $Fuc_4(Gal\beta1\rightarrow4GlcNAc)_2$ [III] or $[Fuc\alpha1\text{-}2Gal\beta1\text{-}4(Fuc\alpha1\text{-}3)GlcNAc]_2$ [IV],
- to a biantennary $Le^B/Le^Y$ antigen comprising $Fuc_2(Gal\beta1\rightarrow3GlcNAc)[Fuc_2(Gal\beta1\rightarrow4GlcNAc)]$ [V], or [Fucα1-2Galβ1-3(Fucα1-4)GlcNAc][Fucα1-2Galβ1-4(Fucα1-3)GlcNAc] [VI],
- and to a biantennary $Le^Y/Le^B$ antigen comprising $Fuc_2(Gal\beta1\text{-}4GlcNAc)[Fuc_2(Gal\beta1\text{-}3GlcNAc)]$ [VII] or [Fucα1-2Galβ1-4(Fucα1-3)GlcNAc][Fucα1-2Galβ1-3(Fucα1-4)GlcNAc] [VIII],
- and wherein the antibody or antigen-binding fragment thereof does not bind specifically to a monoantennary $Le^x$ antigen that comprises Galβ1-4(Fucα1→3)GlcNAc [IX], or to a biantennary $Le^x$ antigen that comprises $[Gal\beta1\rightarrow4(Fuc\alpha1\rightarrow3)GlcNAc]_2$ [X], or to a monoantennary $Le^A$ antigen that comprises Galβ1-3(Fucα1-4)GlcNAc [XI], or to a monoantennary H antigen type 2 that comprises Fucα1-2Galβ1-4GlcNAc [XII], or to a biantennary H antigen type 2 that comprises $(Fuc\alpha1\text{-}2Gal\beta1\text{-}4GlcNAc)_2$ [XIII] or to a monoantennary H antigen type 1 that comprises Fucα1-2Galβ1-3GlcNAc [XIV], and that in certain further particularly preferred embodiments do not specifically bind to certain other biantennary or monoantennary Lewis antigens, as described herein.

The term "antibody" (Ab) as used herein includes monoclonal antibodies, polyclonal antibodies, multispecific antibodies (e.g., bispecific or trispecific antibodies), humanized antibodies, chimeric antibodies, heteroconjugate antibodies, and antibody fragments, so long as they exhibit the desired biological activity, e.g., retain the ability to specifically bind to the presently disclosed biantennary Lewis antigens. The term "immunoglobulin" (Ig) is used interchangeably with "antibody" herein.

The basic antibody unit is a heterotetrameric glycoprotein composed of two identical light (L) chains and two identical heavy (H) chains. Each L chain is linked to an H chain by at least one (and typically one) covalent disulfide bond, while the two H chains are linked to each other by one or more disulfide bonds depending on the H chain isotype. Each H and L chain also has regularly spaced intrachain disulfide bridges. Each H chain has at the N-terminus a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The VL is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. It will be appreciated that mammals encoding multiple Ig isotypes will be able to undergo isotype class switching.

An IgM antibody consists of five of the basic heterotetramer units along with an additional polypeptide called J chain, and therefore contains ten antigen binding sites, while secreted IgA antibodies can polymerize to form polyvalent assemblages comprising two to five of the basic four-chain units along with a J chain. In the case of IgG, the four-chain unit general has a molecular weight of about 150,000 daltons. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The variable (V) domain mediates antigen binding and defines specificity of a particular antibody for its particular antigen. The gene sequence encoding the $V_H$ domain has multiple copies of variable (V), diversity (D), and joining (J) segments. The gene sequence encoding the $V_L$ domain contains multiple copies of V and J segments. The $V_H$ and $V_L$ regions undergo gene rearrangement (i.e., somatic recombination) to develop diverse antigen specificity in antibodies. The term "variable" refers to the fact that certain segments of the V domains differ extensively in sequence among antibodies.

However, the variability is not evenly distributed across the 110-amino acid span of the variable domains. Instead, the V regions consist of relatively invariant stretches called framework regions (FRs) of 15-30 amino acids separated by short regions of extreme variability called "hypervariable regions." These hypervariable regions are the result of somatic hypermutation during the affinity maturation process, and they are typically each 9-18 amino acids long. However, they have been found to range from 4-28 amino acids in length depending upon the particular epitope. For example, CDR3 regions up to at least 22 or 23 amino acids in length have been described. See, e.g., Morea V, et al., *J Mol Biol.* 275(2):269-94 (1998) and Kabat, E. A., et al., Sequences of Proteins of Immunological Interest, Fifth Edition. NIH Publication No. 91-3242 (1991). Antibody amino acid positions (e.g., CDR sequences) may be determined according to known numbering schemes, such as the Kabat, Chothia, IMGT, and/or EU numbering schemes.

The variable domains of native heavy and light chains each comprise four framework regions (FRs), largely adopting a β-sheet configuration, connected by three hypervariable regions (also known as complementarity determining regions (CDR) and defined further below), which form loops connecting, and in some cases forming part of, the β-sheet structure. The hypervariable regions in each chain are held together in close proximity by the FRs and, in some cases with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding of an antibody to an antigen, but exhibit various effector functions, such as participation of the antibody in antibody dependent cellular cytotoxicity (ADCC) or other mechanisms that may involve interaction of a constant region domain with cell surface Fc receptors (FcR).

The term "hypervariable region" when used herein refers to the amino acid residues of an antibody that are responsible for antigen binding. The hypervariable region generally comprises amino acid residues from a "complementarity determining region" or "CDR" (e.g., as may be determined according to Kabat numbering, around about residues 24-34 (L1), 50-56 (L2) and 89-97 (L3) in the $V_L$, and around about 28-36 (H1), 50-65 (H2) and 95-102 (H3) in the $V_H$; see Kabat et al., *Sequences of Proteins of Immunological Interest,* 5th Ed. Public Health Service, National Institutes of Health, Bethesda, Md. (1991); and/or according to methodologies known in the art for identifying CDRs as defined by Kabat, such as those described by Martin, "Protein Sequence and Structure Analysis of Antibody Variable Domains", In *Antibody Engineerinq*, R. Kontermann and S. Dubel, 2001, Springer-Verlag, Berlin, Germany, pages 422-438) and/or those residues from a "hypervariable loop" (e.g., residues 26-32 (L1), 50-52 (L2) and 91-96 (L3) in the $V_L$, and 26-32 (H1), 53-55 (H2) and 96-101 (H3) in the $V_H$; Chothia and Lesk, *J. Mol. Biol.* 196:901-917 (1987)).

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Bradford method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

An "intact" antibody is one that comprises an antigen-binding site as well as a $C_L$ and at least heavy chain constant domains, $C_H$ 1, $C_H$ 2 and $C_H$ 3. The constant domains may be native sequence constant domains (e.g., human native sequence constant domains) or amino acid sequence variants thereof. Preferably, the intact antibody has one or more effector functions.

An "antibody fragment" is a polypeptide comprising or consisting of a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H$ 1). Each Fab fragment is monovalent with respect to antigen binding, i.e., it has a single antigen-binding site. Pepsin treatment of an antibody yields a single large $F(ab')_2$ fragment that roughly corresponds to two disulfide linked Fab fragments having divalent antigen-binding activity and is still capable of cross-linking antigen. Both the Fab and $F(ab')_2$ are examples of "antigen-binding fragments." Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. Other chemical couplings of antibody fragments are also known.

The "Fc" fragment comprises the carboxy-terminal portions (i.e., the CH2 and CH3 domains of IgG) of both H chains held together by disulfides. The effector functions of antibodies are determined by sequences in the Fc region. The Fc domain is the portion of the antibody recognized by cell receptors, such as the FcR, and to which the complement-activating protein, C1q, binds. As discussed herein, modifications (e.g., amino acid substitutions) may be made to an Fc domain in order to modify (e.g., improve, reduce, or ablate) one or more functionality of an Fc-containing polypeptide (e.g., an antibody of the present disclosure).

"Fv" is the minimum antibody fragment that contains a complete antigen-recognition and antigen-binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although typically at a lower affinity than the entire binding site.

"Single-chain Fv" also abbreviated as "sFv" or "scFv", are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993). Other antibody fragments and molecules comprising the same include, for example, linear antibodies, tandem scFv, scFv-Fc, tandem scFv-Fc, scFv dimer, scFv-zipper, diabody-Fc, diabody-CH3, scDiabodies, scDiabody-Fc, scDiabody-CH3, nanobodies, TandAbs, minibodies, miniantibodies, triabodies, tetrabodies, scFab, Fab-scFv, Fab-scFv-Fc, scFv-CH-CL-scFv, and F(ab')2-scFv2, all of which are also contemplated herein.

In certain embodiments, an antibody or antigen-binding fragment of the present disclosure is a multispecific antibody, such as a bispecific or trispecific antibody. Formats for bispecific antibodies are disclosed in, for example, Spiess et al., Mol. Immunol. 67(2):95 (2015), and in Brinkmann and Kontermann, *mAbs* 9(2):182-212 (2017), which bispecific formats and methods of making the same are incorporated herein by reference and include, for example, Bispecific T cell Engagers (BiTEs), DARTs, Knobs-Into-Holes (KIH) assemblies, scFv-CH3-KIH assemblies, KIH Common Light-Chain antibodies, TandAbs, Triple Bodies, TriBi Minibodies, Fab-scFv, scFv-CH-CL-scFv, F(ab')2-scFv2, tetravalent HCabs, Intrabodies, CrossMabs, Dual Action Fabs (DAFs) (two-in-one or four-in-one), DutaMabs, DT-IgG, Charge Pairs, Fab-arm Exchange, SEEDbodies, Triomabs, LUZ-Y assemblies, Fcabs, κλ-bodies, orthogonal Fabs, DVD-IgGs, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, Zybody, and DVI-IgG (four-in-one).

As used herein, the term "polyclonal antibody" refers to an antibody obtained from a population of antigen-specific antibodies that recognize more than one epitope of the specific antigen. "Antigen" or "immunogen" refers to a peptide, lipid, polysaccharide or polynucleotide which is recognized by the adaptive immune system. Antigens may be self or non-self molecules. Examples of antigens include, but are not limited to, bacterial cell wall components, pollen, and rh factor. The region of an antigen that is specifically recognized by a specific antibody is an "epitope" or "antigenic determinant." A single antigen may have multiple epitopes.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different epitopes, each monoclonal antibody is directed against a single epitope of the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein include "chimeric antibodies" in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, U.S. Pat. Nos. 4,816,567; 5,530,101 and 7,498,415; and Morrison et al., Proc. Natl. Acad. Sci. USA, 81:6851-6855 (1984)). For example, chimeric antibodies may comprise human and non-human residues. Furthermore, chimeric antibodies may comprise residues that are not found in the recipient antibody or in the donor antibody. These modifications are made to further refine antibody performance. For further details, see Jones et al., *Nature* 321:522-525 (1986); Riechmann et al., *Nature* 332:323-329 (1988); and Presta, *Curr. Op. Struct. Biol.* 2:593-596 (1992). Chimeric antibodies also include primatized and humanized antibodies.

A "humanized antibody" is generally considered to be a human antibody that has one or more amino acid residues introduced into it from a source that is non-human. These non-human amino acid residues are typically taken from a variable domain. Humanization is traditionally performed following the method of Winter and co-workers (Jones et al., *Nature,* 321:522-525 (1986); Reichmann et al., *Nature,* 332:323-327 (1988); Verhoeyen et al., *Science,* 239:1534-1536 (1988)), by substituting non-human variable sequences for the corresponding sequences of a human antibody. Accordingly, such "humanized" antibodies are chimeric antibodies (U.S. Pat. Nos. 4,816,567; 5,530,101 and 7,498,415) wherein substantially less than an intact human variable domain has been substituted by the corresponding sequence from a non-human species. In some instances, a "humanized" antibody is one which is produced by a non-human cell or animal and comprises human sequences, e.g., $H_C$ domains.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance. In some instances, human antibodies are produced by transgenic animals. For example, see U.S. Pat. Nos. 5,770,429; 6,596,541 and 7,049,426.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation. Amino acid modifications (e.g., substitutions) to modify (e.g., improve, reduce, or ablate) Fc functionalities include, for example, the T250Q/M428L, M252Y/S254T/T256E, H433K/N434F, M428L/N434S, E233P/L234V/L235A/G236+A327G/A330S/P331S, E333A, S239D/A330L/1332E, P2571/Q311, K326W/E333S, S239D/I332E/G236A, N297Q, K322A, S228P, L235E+E318A/K320A/K322A, L234A/L235A, and L234A/L235A/P329G mutations, which mutations are summarized and annotated in "Engineered Fc Regions", published by InvivoGen (2011) and available online at www-.invivogen.com/PDF/review/review-Engineered-Fc-Regions-invivogen.pdf?utm_source=review&utm_medium=pdf&utm_campaign=review&utm_content=Engineered-Fc-Regions, and are incorporated herein by reference.

The phrase "functional fragment or analog" of an antibody or antigen-binding fragment thereof is a compound having qualitative biological activity in common with a full-length antibody or antigen-binding fragment thereof.

An antibody or antigen-binding fragment thereof having a "biological characteristic" of a designated antibody or antigen-binding fragment thereof is one that possesses one or more of the biological characteristics of that antibody antigen-binding fragment thereof which distinguish it from other antibodies or antibody-derived binding fragments. For example, in certain embodiments, an antibody or antigen-binding fragment thereof with a biological characteristic of a designated antibody will bind the same epitope as that bound by the designated antibody and/or have a common effector function as the designated antibody.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant Ko, and in certain embodiments an antibody or antigen-binding fragment thereof specifically binds to a Lewis antigen of the present disclosure if it binds with a Ko of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies and antigen-binding fragments can be readily determined using conventional techniques, for example, those described by Scatchard et al. (*Ann. N.Y. Acad. Sci. USA* 51:660 (1949)), or by surface plasmon resonance (SPR) (e.g., Hearty et al., 2012 *Meths. Mol. Biol.* 907:411), by isothermal titration calorimetry (ITC) (e.g., Dam et al., 2008 *J. Biol. Chem.* 283: 31366), by enzyme-linked immunosorbent assay (ELISA) (e.g., Bobrovnik, 2003 *J. Biochem.* Biophys. Meths. 75(3): 213), or by other methodologies familiar to those skilled in the art.

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS). Other methods of determining binding of an antibody to an antigen include, for example, enzyme-linked immunosorbent assay (ELISA), isothermal titration calorimetry (ITC), and surface plasmon resonance (SPR) techniques.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

Polynucleotides, Vectors, and Host Cells

In further aspects, the present disclosure provides in certain embodiments isolated polynucleotides that encode antibodies and antigen-binding fragments thereof as described herein, and also provides vectors comprising the same. Nucleic acids comprising polynucleotides may comprise DNA or RNA and may be wholly or partially synthetic.

The term "polynucleotide" as referred to herein means a single-stranded or double-stranded nucleic acid polymer, and specifically includes single and double-stranded form of DNA. Polynucleotides can be generated, for example, by the polymerase chain reaction (PCR) or by in vitro translation, and fragments generated by any of ligation, scission, endonuclease action, or exonuclease action. In certain embodiments, the polynucleotides of the present disclosure are produced by PCR. Polynucleotides may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. In further embodiments, nucleotides comprising a polynucleotide can be ribonucleotides or deoxyribonucleotides or a modified form of either type of nucleotide.

The term "naturally occurring nucleotides" includes deoxyribonucleotides and ribonucleotides. The term "modified nucleotides" includes nucleotides with modified or substituted sugar groups and the like (e.g., modified with bromouridine, arabinoside, or 2'3'-dideoxyribose). The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986*, Nucl. Acids Res.,* 14:9081; Stec et al., 1984*, J. Am. Chem. Soc.,* 106:6077; Stein et al., 1988*, Nucl. Acids Res.,* 16:3209; Zon et al., 1991*, Anti-Cancer Drug Design,* 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990*, Chemical Reviews,* 90:543, the disclosures of which are hereby incorporated by reference for any purpose. An oligonucleotide can include a detectable label to enable detection of the oligonucleotide or hybridization thereof.

The term "isolated polynucleotide" as used herein shall mean a polynucleotide of genomic, cDNA, or synthetic origin or some combination thereof, wherein by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

Reference to a nucleotide sequence as set out herein encompasses a DNA molecule with the specified sequence, and encompasses a RNA molecule with the specified sequence in which U is substituted for T, unless context requires otherwise.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding an antibody or antigen-binding fragment thereof, as described herein.

In other related embodiments, polynucleotide variants may have substantial identity to a polynucleotide sequence encoding an antibody or antigen-binding fragment thereof described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an antibody or antigen-binding fragment thereof described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody or antigen-binding fragment thereof encoded by the variant polynucleotide is not substantially diminished relative to an antibody or antigen-binding fragment thereof encoded by a polynucleotide sequence specifically set forth herein (e.g., relative to the antibody referred to herein as hBBC.10.1, which comprises the immunoglobulin heavy chain having the amino acid sequence set forth in SEQ ID NO: 10 and the immunoglobulin light chain having the amino acid sequence set forth in SEQ ID NO: 11).

In certain other related embodiments, polynucleotide fragments may comprise or consist essentially of various lengths of contiguous stretches of sequence identical to or complementary to a sequence encoding an antibody or antigen-binding fragment thereof as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an antibody or antigen-binding fragment thereof, or variant thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an antibody or antigen-binding fragment thereof described herein or at both ends of a polynucleotide encoding an antibody or antigen-binding fragment thereof described herein.

In another embodiment, polynucleotides are provided that are capable of hybridizing under moderate to high stringency conditions to a polynucleotide sequence encoding an antibody or antigen-binding fragment thereof, or variant thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode antibodies or antigen-binding fragments thereof that bind to a biantennary Lewis antigen as described herein. In other embodiments, such polynucleotides encode antibodies or antigen-binding fragments thereof, or variants thereof, that bind to a presently disclosed Lewis antigen at least about 50%, at least about 70%, and in certain embodiments, at least about 90% as well as an antibody or antigen-binding fragment thereof specifically set forth herein (e.g., antibody hBBC.10.1). In further embodiments, such polynucleotides encode antibodies or antigen-binding fragments thereof, or variants thereof, that bind to a presently disclosed Lewis antigen with greater affinity than the antibodies or antigen-binding fragments thereof specifically set forth herein, for example, that bind quantitatively at least about 105%, 106%, 107%, 108%, 109%, or 110% as well as an antibody or antigen-binding fragment thereof specifically set forth herein.

As described elsewhere herein, determination of the three-dimensional structures of the presently disclosed antibodies or antigen-binding fragments thereof may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody or antigen-binding fragment thereof such that, for example, affinity is maintained or better affinity is achieved. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. *Science* 327:1014-1018 (2010); Marcos et al., 2017 *Science* 355:201, and references cited therein.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the DNASTAR® Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington DC Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, CA; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, CA (1973); Wilbur, W. J. and Lipman, D. J., *Proc. Nat. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody or antigen-binding fragment thereof as described herein. Some such polynucleotides bear minimal sequence identity to the nucleotide sequence of a native or original polynucleotide sequence that encodes an antibody or antigen-binding fragment thereof described herein. Nonetheless, polynucleotides that vary due to differences in codon usage are expressly contemplated by the present disclosure. In certain embodiments, sequences that have been codon-optimized for mammalian expression are specifically contemplated. Codon optimization can be performed using known techniques and tools, e.g., using the GenScript® OptimiumGene™ tool. Codon-optimized sequences include sequences that are partially codon-optimized (i.e., at least one codon is optimized for expression in the host cell) and those that are fully codon-optimized.

Therefore, in another embodiment, a mutagenesis approach, such as site-specific mutagenesis, may be employed for the preparation of variants and/or derivatives of the antibodies or antigen-binding fragments thereof described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the present inventors contemplate the mutagenesis of the polynucleotide sequences that encode an antibody or antigen-binding fragment thereof disclosed herein, or a variant thereof, to alter one or more properties of the encoded polypeptide, such as the binding affinity to a Lewis antigen according to the present disclosure. Techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially available. Double-stranded plasmids are also routinely employed in site-directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of a RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression vectors that encode antibodies or antigen-binding fragments thereof include viral vectors, such as lentiviral vectors or γ-retroviral vectors. Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

According to certain related embodiments, there is provided a recombinant host cell which comprises one or more constructs as described herein; a nucleic acid encoding an antibody or antigen-binding fragment thereof or variant thereof; and a method of producing of the encoded product; which method comprises expression of the nucleic acid encoding therefor. Expression may conveniently be achieved by culturing under appropriate conditions a recombinant host cell containing the nucleic acid (e.g., in a vector of the present disclosure). Following production by expression, an antibody or antigen-binding fragment thereof may be isolated and/or purified using any suitable technique, and then used as desired.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells (e.g., HEK cells, such as HEK293-c18 cells), NSO mouse melanoma cells and many others. A common, preferred bacterial host is *E. coli.*

The expression of peptides in prokaryotic cells such as *E. coli* is well established in the art. For a review, see for example Pluckthun, A. *Bio/Technology* 9: 545-551 (1991). Expression in eukaryotic cells in culture is also available to those skilled in the art as an option for production of antibodies or antigen-binding fragments thereof, see recent reviews, for example Ref, M. E. (1993) *Curr. Opinion Biotech.* 4: 573-576; Trill J. J. et al. (1995) *Curr. Opinion Biotech* 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, forexample in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies and antigen-binding fragments thereof, and which further expresses or is capable of expressing a selected gene of interest, such as a gene encoding any herein described antibody or antigen-binding fragment. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an antibody or antigen-binding fragment thereof as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

It will be appreciated that the practice of the several embodiments of the present invention will employ, unless indicated specifically to the contrary, conventional methods in virology, immunology, microbiology, molecular biology and recombinant DNA techniques that are within the skill of the art, and many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3rd ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Certain of the presently disclosed embodiments relate to detection and characterization of specific immunological binding activity (e.g., antibody binding activity) that is directed toward carbohydrate-defined antigenic structures. Persons familiar with the art will appreciate that there are various methodologies by which to generate and test carbohydrate-specific immunological reagents, including fine structural characterization of cognate carbohydrate antigens. Non-limiting examples of such technologies are described in Haji-Ghassemi et al., 2015 *Glybiol.* 25:920; Dingjan et al., 2015 *Mol. Immunol.* 67(2 Pt A):75-88; Soliman et al., 2017 *Curr. Opin. Struct. Biol.* 44:1-8; and Hakomori, 2001 *Adv. Exp. Med. Biol.* 491:369-402; and in references cited therein. There and elsewhere can also be found descriptions of sources of carbohydrate-defined antigens and methods for their preparation, isolation, and structural characterization. Disclosed herein are exemplary and non-limiting applications of such approaches, and the present disclosure is not intended to be so limited and also contemplates synthetic preparation of structurally defined carbohydrate antigens, including by exploitation of the exquisite specificity of the biosynthetic enzymes known in the art as glycosyltransferases. See, e.g., Wu et al., Universal phosphatase-coupled glycosyltransferase assay, *Glycobiology* 21(6): 727-733, 2011; Becker et al., Fucose: biosynthesis and biological function in mammals, *Glycobiology* 13(7): 41R-53R, 2003; de Vries et al., Fucosyltransferases: structure/function studies, *Glycobiology* 11(10): 119R-128R, 2001.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein.

These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients, described further herein.

Compositions

In certain aspects, the present disclosure provides antibodies and antigen-binding fragments thereof, as well as variants thereof, and compositions comprising the same. In certain embodiments, an isolated antibody is provided that comprises an immunoglobulin heavy chain having the amino acid sequence set forth in SEQ ID NO: 10 and an immunoglobulin light chain having the amino acid sequence set forth in SEQ ID NO: 11.

In certain embodiments, an isolated antibody or antigen-binding fragment thereof is provided that comprises: an immunoglobulin heavy chain variable region that comprises the amino acid sequence set forth in SEQ ID NO: 35; and an immunoglobulin light chain variable region that comprises the amino acid sequence set forth in SEQ ID NO: 5, wherein the antibody or antigen-binding fragment thereof is capable of binding specifically:

to a biantennary $Le^B/Le^B$ antigen comprising $Fuc_4$ $(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II], to a biantennary $Le^Y/Le^Y$ antigen comprising $Fuc_4$ $(Gal\beta1\rightarrow4GlcNAc)_2$ [I] or $[Fuc\alpha1\text{-}2Gal\beta1\text{-}4(Fuc\alpha1\text{-}3)GlcNAc]_2$ [IV], to a biantennary $Le^B/Le^Y$ antigen comprising $Fuc_2$ $(Gal\beta1\rightarrow3GlcNAc)[Fuc_2(Gal\beta1\rightarrow4GlcNAc)]$ [V], or $[Fuc\alpha1\text{-}2Gal\beta1\text{-}3(Fuc\alpha1\text{-}4)GlcNAc][Fuc\alpha1\text{-}2Gal\beta1\text{-}4(Fuc\alpha1\text{-}3)GlcNAc]$ [VI], and to a biantennary $Le^Y/Le^B$ antigen comprising $Fuc_2$ $(Gal\beta1\text{-}4GlcNAc)[Fuc_2(Gal\beta1\text{-}3GlcNAc)]$ [VII] or $[Fuc\alpha1\text{-}2Gal\beta1\text{-}4(Fuc\alpha1\text{-}3)GlcNAc][Fuc\alpha1\text{-}2Gal\beta1\text{-}3(Fuc\alpha1\text{-}4)GlcNAc]$ [VIII], and wherein the antibody or antigen-binding fragment thereof does not bind specifically to a monoantennary $Le^x$ antigen that comprises $Gal\beta1\rightarrow4(Fuc\alpha1\rightarrow3)GlcNAc$ [IX], or to a biantennary $Le^x$ antigen that comprises $[Gal\beta1\rightarrow4(Fuc\alpha1\rightarrow3)GlcNAc]_2$ [X], or to a monoantennary $Le^A$ antigen that comprises $Gal\beta1\text{-}3(Fuc\alpha1\text{-}4)GlcNAc$ [XI], or to a monoantennary H antigen type 2 that comprises $Fuc\alpha1\text{-}2Gal\beta1\text{-}4GlcNAc$ [XII], or to a biantennary H antigen type 2 that comprises $(Fuc\alpha1\text{-}2Gal\beta1\text{-}4GlcNAc)_2$ [XIII] or to a monoantennary H antigen type 1 that comprises $Fuc\alpha1\text{-}2Gal\beta1\text{-}3GlcNAc$ [XIV].

In other embodiments, an isolated antibody or antigen-binding fragment thereof comprises: (a) an immunoglobulin heavy chain variable region that comprises a heavy chain complementarity determining region 1 (VH CDR1) comprising the amino acid sequence set forth in SEQ ID NO: 2; a heavy chain complementarity determining region 2 (VH CDR2) comprising the amino acid sequence set forth in SEQ ID NO: 3; a heavy chain complementarity determining region 3 (VH CDR3) comprising the amino acid sequence set forth in SEQ ID NO: 4; and (b) an immunoglobulin light chain variable region that comprises a light chain complementarity determining region 1 (VL CDR1) comprising the amino acid sequence set forth in SEQ ID NO: 6; a light chain complementarity determining region 2 (VL CDR2) comprising the amino acid sequence set forth in SEQ ID NO: 7; and a light chain complementarity determining region 3 (VL CDR3) comprising the amino acid sequence set forth in SEQ ID NO: 8; wherein the antibody or antigen-binding fragment thereof is capable of binding specifically:

to a biantennary $Le^B/Le^B$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II], to a biantennary $Le^Y/Le^Y$ antigen comprising $Fuc_4(Gal\beta1\rightarrow4GlcNAc)_2$ [III] or $[Fuc\alpha1\text{-}2Gal\beta1\text{-}4(Fuc\alpha1\text{-}3)GlcNAc]_2$ [IV], to a biantennary $Le^B/Le^Y$ antigen comprising $Fuc_2(Gal\beta1\rightarrow3GlcNAc)[Fuc_2(Gal\beta1\rightarrow4GlcNAc)]$ [V], or $[Fuc\alpha1\text{-}2Gal\beta1\text{-}3(Fuc\alpha1\text{-}4)GlcNAc][Fuc\alpha1\text{-}2Gal\beta1\text{-}4(Fuc\alpha1\text{-}3)GlcNAc]$ [VI], and to a biantennary $Le^Y/Le^B$ antigen comprising $Fuc_2(Gal\beta1\text{-}4GlcNAc)[Fuc_2(Gal\beta1\text{-}3GlcNAc)]$ [VII] or $[Fuc\alpha1\text{-}2Gal\beta1\text{-}4(Fuc\alpha1\text{-}3)GlcNAc][Fuc\alpha1\text{-}2Gal\beta1\text{-}3(Fuc\alpha1\text{-}4)GlcNAc]$ [VIII], and wherein the antibody or antigen-binding fragment thereof does not bind specifically to a monoantennary $Le^x$ antigen that comprises $Gal\beta1\rightarrow4(Fuc\alpha1\rightarrow3)GlcNAc$ [IX], or to a biantennary $Le^x$ antigen that comprises $[Gal\beta1\rightarrow4(Fuc\alpha1\rightarrow3)GlcNAc]_2$ [X], or to a monoantennary $Le^A$ antigen that comprises $Gal\beta1\text{-}3(Fuc\alpha1\text{-}4)GlcNAc$ [XI], or to a monoantennary H antigen type 2 that comprises $Fuc\alpha1\text{-}2Gal\beta1\text{-}4GlcNAc$ [XII], or to a biantennary H antigen type 2 that comprises $(Fuc\alpha1\text{-}2Gal\beta1\text{-}4GlcNAc)_2$ [XIII] or to a monoantennary H antigen type 1 that comprises $Fuc\alpha1\text{-}2Gal\beta1\text{-}3GlcNAc$ [XIV].

In certain presently disclosed embodiments, an isolated antibody, or antigen-binding fragment thereof, is monoclonal.

In certain presently disclosed embodiments, an isolated antibody, or antigen-binding fragment thereof, is humanized.

In certain embodiments, an isolated antibody, or antigen-binding fragment thereof, is selected from a Fab fragment, an F(ab')2 fragment, an Fv fragment, a single chain Fv (ScFv) antibody, and a diabody.

In certain still other embodiments, an isolated antibody or an antigen-binding fragment thereof is provided, comprising an immunoglobulin heavy chain variable region that comprises an amino acid sequence that has at least 90, 91, 92, 93, 94, 95, 96, 97, 98 or 99 percent identity to the amino acid sequence set forth in SEQ ID NO: 35; and an immunoglobulin light chain variable region that comprises an amino acid sequence that has at least 90, 91, 92, 93, 94, 95, 96, 97, 98 or 99 percent identity to the amino acid sequence set forth in SEQ ID NO: 5, wherein the antibody or antigen-binding fragment thereof is capable of binding specifically:

to a biantennary $Le^B/Le^B$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II], to a biantennary $Le^Y/Le^Y$ antigen comprising $Fuc_4(Gal\beta1\rightarrow4GlcNAc)_2$ [III] or [Fucα1-2Galβ1-4(Fucα1-3)GlcNAc]2 [IV], to a biantennary $Le^B/Le^Y$ antigen comprising $Fuc_2(Gal\beta1\rightarrow3GlcNAc)[Fuc_2(Gal\beta1\rightarrow4GlcNAc)]$ [V], or $[Fuc\alpha1\text{-}2Gal\beta1\text{-}3(Fuc\alpha1\text{-}4)GlcNAc][Fuc\alpha1\text{-}2Gal\beta1\text{-}4(Fuc\alpha1\text{-}3)GlcNAc]$ [VI], and to a biantennary $Le^Y/Le^B$ antigen comprising $Fuc_2(Gal\beta\beta1\text{-}4GlcNAc)[Fuc_2(Gal\beta1\text{-}3GlcNAc)]$ [VII] or $[Fuc\alpha1\text{-}2Gal\beta1\text{-}4(Fuc\alpha1\text{-}3)GlcNAc][Fuc\alpha1\text{-}2Gal\beta1\text{-}3(Fuc\alpha1\text{-}4)GlcNAc]$ [VIII], and wherein the antibody or antigen-binding fragment thereof does not bind specifically to a monoantennary $Le^x$ antigen that comprises $Gal\beta1\rightarrow4(Fuc\alpha1\rightarrow3)GlcNAc$ [IX], or to a biantennary $Le^x$ antigen that comprises $[Gal\beta1\rightarrow4(Fuc\alpha1\rightarrow3)GlcNAc]_2$ [X], or to a monoantennary $Le^A$ antigen that comprises $Gal\beta1\text{-}3(Fuc\alpha1\text{-}4)GlcNAc$ [XI], or to a monoantennary H antigen type 2 that comprises $Fuc\alpha1\text{-}2Gal\beta1\text{-}4GlcNAc$ [XII], or to a biantennary H antigen type 2 that comprises $(Fuc\alpha1\text{-}2Gal\beta1\text{-}4GlcNAc)_2$ [XIII] or to a monoantennary H antigen type 1 that comprises $Fuc\alpha1\text{-}2Gal\beta1\text{-}3GlcNAc$ [XIV].

In certain embodiments, an isolated antibody or antigen-binding fragment thereof comprises: (a) an immunoglobulin heavy chain variable region that comprises a heavy chain complementarity determining region 1 (VH CDR1) comprising the amino acid sequence set forth in SEQ ID NO: 2 or an amino acid sequence that has at least 90, 91, 92, 93, 94, 95, 96, 97, 98 or 99 percent identity to the amino acid sequence set forth in SEQ ID NO:2; a heavy chain complementarity determining region 2 (VH CDR2) comprising the amino acid sequence set forth in SEQ ID NO: 3 or an amino acid sequence that has at least 90, 91, 92, 93, 94, 95, 96, 97, 98 or 99 percent identity to the amino acid sequence set forth in SEQ ID NO:3; a heavy chain complementarity determining region 3 (VH CDR3) comprising the amino acid sequence set forth in SEQ ID NO: 4 or an amino acid sequence that has at least 90, 91, 92, 93, 94, 95, 96, 97, 98 or 99 percent identity to the amino acid sequence set forth in SEQ ID NO:4; and (b) an immunoglobulin light chain variable region that comprises a light chain complementarity determining region 1 (VL CDR1) comprising the amino acid sequence set forth in SEQ ID NO: 6 or an amino acid sequence that has at least 90, 91, 92, 93, 94, 95, 96, 97, 98 or 99 percent identity to the amino acid sequence set forth in SEQ ID NO:6; a light chain complementarity determining region 2 (VL CDR2) comprising the amino acid sequence set forth in SEQ ID NO: 7 or an amino acid sequence that has at least 90, 91, 92, 93, 94, 95, 96, 97, 98 or 99 percent identity to the amino acid sequence set forth in SEQ ID NO: 7; and a light chain complementarity determining region 3 (VL CDR3) comprising the amino acid sequence set forth in SEQ ID NO: 8 or an amino acid sequence that has at least 90, 91, 92, 93, 94, 95, 96, 97, 98 or 99 percent identity to the amino acid sequence set forth in SEQ ID NO: 8.

In other embodiments, an isolated antibody or antigen-binding fragment thereof comprises (i), (ii), (iii), (iv), (v), or (vi) as follows, or any combination thereof: (i) a VH CDR1 comprising a variant of the amino acid sequence set forth in SEQ ID NO: 2, wherein the variation consists of a Y→A substitution at position 33 according to Kabat numbering; (ii) a VH CDR3 comprising a variant of the amino acid sequence set forth in set forth in SEQ ID NO: 4, wherein the variation consists of a Y→A substitution at position 104 according to Kabat numbering; (iii) a VH CDR3 comprising a variant of the amino acid sequence set forth in set forth in SEQ ID NO: 4, wherein the variation consists of a H→A substitution at position 106 according to Kabat numbering; (iv) a VL CDR1 comprising a variant of the amino acid sequence set forth in SEQ ID NO: 6, wherein the variation consists of a Y→A substitution at position 30 according to Kabat numbering; (v) a VL CDR2 comprising a variant of the amino acid sequence set forth in SEQ ID NO: 7, wherein the variant consists of a G→A substitution at position 50 according to Kabat numbering; or (vi) a VL CDR3 comprising a variant of the amino acid sequence set forth in SEQ ID NO: 8, wherein the variation consists of a T→S substitution at position 93 according to Kabat numbering.

In any of the herein described embodiments, an isolated antibody or an antigen-binding fragment thereof may have reduced (e.g., decreased in a statistically significant manner) binding to a monoantennary Lewis B antigen or a monoantennary Lewis Y as compared to BBC antibody, which comprises a VL domain having the amino acid sequence set forth in SEQ ID NO: 27 and a VH domain having the amino acid sequence set forth in SEQ ID NO:28.

In certain further embodiments, an isolated antibody or antigen-binding fragment is provided that comprises CDRs as described herein (i.e., CDRs having at least 90% identity to SEQ ID NOs:2, 3, 4, 6, 7, and 8, respectively, including those CDR variants with the herein described amino acid substitutions), and comprises an immunoglobulin heavy chain variable region comprising or consisting of an amino acid sequence that has at least 90, 91, 92, 93, 94, 95, 96, 97, 98 or 99 percent identity to the amino acid sequence set forth in SEQ ID NO: 35; and an immunoglobulin light chain variable region that comprises or consists of an amino acid sequence that has at least 90, 91, 92, 93, 94, 95, 96, 97, 98 or 99 percent identity to the amino acid sequence set forth in SEQ ID NO:5.

Antibodies or antigen-binding fragments thereof such as those described herein, including but not limited to scFv, may, in certain embodiments, be comprised in a fusion protein that is capable of specific binding to a Lewis antigen as described herein. In some embodiments, a fusion protein is capable of expression at a surface of a host cell, e.g., a T cell, NK cell, or NK-T cell, and comprises an extracellular component comprising an antibody or antigen-binding fragment thereof as disclosed herein, and an intracellular component comprising an effector domain that is capable of directly or indirectly promoting an immunological response in a cell (e.g., immune system cell, such as a T cell) when receiving an appropriate signal (e.g., an effector domain from CD27, CD28, 4-1BB (CD137), OX40 (CD134), CD3ε, CD3δ, CD3ζ, CD25, CD27, CD28, CD79A, CD79B, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, Wnt, ROR2, Ryk, SLAMF1, SIp76, pTα, TCRα, TCRβ, TRIM, Zap70, PTCH2, or any combination thereof), wherein the extracellular component and the intracellular component are connected by a transmembrane domain (e.g., a CD8 transmembrane domain, a CD4 transmembrane domain, a CD27 transmembrane domain, or a CD28 transmembrane domain) and the intracellular component optionally comprises a costimulatory domain or portion thereof selected from CD27, CD28, 4-1BB (CD137), OX40 (CD134), or a combination thereof. In certain embodiments, an extracellular component of a fusion protein comprising an antibody or antigen-binding fragment of the present disclosure comprises a polypeptide derived from an immunoglobulin protein; e.g., an IgG4 hinge-CH2-CH3.

In these and related embodiments, an antigen-binding fragment may comprise a herein described antigen-binding fragment such as a scFv, and the extracellular component may further comprise a connector region comprising a hinge; e.g., in a chimeric antigen receptor molecule (CAR), which may be expressed on a cell surface of a host cell such as a T cell, a NK cell, or a NK-T cell for use in a cellular immunotherapy. CAR molecules and principles of design are described in, for example: Sadelain et al., *Cancer Discov.,* 3(4):388 (2013); Harris and Kranz, *Trends Pharmacol. Sci.,* 37(3):220 (2016); Stone et al., *Cancer Immunol. Immunother.,* 63(11):1163 (2014); Xu et al., 2018 Oncotarget 9:13991; Androulla et al., 2018 *Curr. Pharm. Biotechnol.* Volume 19 (April 2018); Wu et al., 2016 *Expert Opin. Biol. Ther.* 16:1469; Ren et al., 2017 *Protein Cell* 8:634; which CAR molecules, CAR designs, and CAR design principles are herein incorporated by reference in their entirety.

Also provided herein are antibody conjugates that comprise an antibody or antigen-binding fragment thereof of the present disclosure; and a payload molecule linked thereto. By way of background, monoclonal antibodies that specifically target antigens may be used as carrier molecules to deliver a therapeutic or detectable payload molecule to a site of antigen expression, e.g., a tumor cell that expresses the antigen. Binding by an antibody conjugate to the antigen can allow, for example, targeted delivery of a cytotoxic payload or a detectable moiety to a diseased cell or tissue for treatment, or detection, imaging, or monitoring of a disease, e.g., a cancer. In certain embodiments, an antibody conjugate is internalized by a target cell that expresses the antigen following or upon binding by the antibody conjugate. Internalization to the cytosol or to a lysosomal compartment of the target cell can permit selective release of a payload molecule to, for example, cause cytotoxic damage to the target cell.

Various techniques may be used to couple a payload molecule to an antibody or antigen-binding fragment thereof to form an antibody conjugate of the present disclosure. In some embodiments, an antibody conjugate comprises payload molecule that is covalently linked by a linker to the antibody or antigen-binding fragment thereof. Linkers used in antibody conjugates comprising cytotoxic or anti-proliferative agents (e.g., antibody drug conjugates) are typically organic compounds that fall into one of two groups, organized according to the mechanism by which the payload molecule is released from the carrier molecule. Cleavable linkers are designed to be selectively degraded or cleaved according to an inherent property of the target cell: three types of cleavable linkers are protease-sensitive linkers (whereby cleavage of the linker, e.g., a linker comprising a valine-citrulline or phenylalanine-lysine dipeptide or a tetrapeptide (e.g., GFLG or ALAL), by proteases present in a tumor cell lysosome releases the payload molecule); pH-sensitive linkers, containing an acid labile group that is selectively hydrolyzed by the lower pH of endosomal and lysosomal compartments, relative to cytosolic pH; and glutathione-sensitive linkers, which comprise a disulfide bridge that is reduced by intracellular glutathione. Non-cleavable linkers rely on non-specific degradation of the antibody conjugate to release the payload molecule.

Specific linkers, payloads, linker chemistries, and related mechanisms and methods are disclosed in Nareshkumar et al., *Pharm. Res.* 32:3526-3540 (2015), which compositions, methods, and techniques are herein incorporated by reference in their entirety. In certain embodiments, an antibody conjugate comprises a linker is selected from a cleavable linker and a non-cleavable linker. In further embodiments, the linker is a cleavable linker selected from a protease-sensitive linker, a pH-sensitive linker, or a glutathione-sensitive linker. In specific embodiments, a cleavable linker is a protease-sensitive linker comprising a valine-citrulline dipeptide.

A linker may be connected or coupled to the antibody or antigen-binding fragment thereof using any appropriate technique or mechanism. In some embodiments, a linker comprises a maleimide group (optionally PEGylated) capable of reacting with a reduced disulfide bridge in a hinge region of the antibody or antigen-binding fragment thereof. Other sites on the carrier molecule (i.e., the antibody or antigen-binding fragment thereof) suitable for conjugation to a linker may be introduced or engineered using recombinant techniques, such as introducing cysteine residues or non-natural amino acids for site-specific conjugation. Methods for introducing such modifications include, for example, the method described in Examples 6.3-7 of PCT Publication No. WO 2012/032181.

In some embodiments, a linker further comprises a self-demolishing group, also referred to as a self-immolative group or a self-immolative spacer, to assist in a selective cleavage reaction. In certain embodiments, the self-demolishing group is para-amino benzyl alcohol (PABC).

Click chemistries useful for generating antibody conjugates include those described in Meyer et al., *Bioconjug. Chem.* 27(12):2791-2807 (2016), and are herein incorporated by reference in their entirety.

In any of the antibody conjugates described herein, the payload molecule may be selected from a therapeutic agent and a detectable indicator. Therapeutic agents suitable for cancer therapy include those disclosed in Parslow et al., Biomedicines 4:14 (2016), which payloads and ADC design principles are hereby incorporated by reference. In certain embodiments, the payload molecule is a therapeutic agent selected from a tubulin-targeting antimitotic agent, a peptide-based toxin, a pyrrolobenzodiazepine (PBD) dimer, an antibiotic (e.g., calicheamicin), a pyrimidine synthesis inhibitor (e.g., 5-fluorouracil), an antimetabolite (e.g., methotrexate), a DNA alkylating agent, and a topoisomerase inhibitor (e.g., doxorubicin). In further embodiments, the payload molecule is selected from a maytansinoid, an auristatin, monomethylauristatin E (MMAE), and monomethylauristatin F (MMAF).

In other embodiments, the payload molecule is a detectable indicator. Detectable indicators suitable for use in antibody conjugates, as well as related labeling strategies and imaging techniques (e.g., PET, MRI, NIR), include those disclosed in Friese and Wu, *Mol. Immunol.* 67(200): 142-152 (2015) and Moek et al., *J. Nucl. Med.* 58:83S-90S (2017), all of which are hereby incorporated by reference. In certain embodiments, the detectable indicator is selected from a radionuclide, a dye, a radiometal, a fluorescent moiety, an MRI contrast agent, a microbubble, a carbon nanotube, a gold particle, fluorodeoxyglucose, an enzyme, a chromophore, and a radio-opaque marker. In specific embodiments, the detectable indicator is a radionuclide selected from $^{68}$Ga, $^{64}$Cu, $^{86}$Y, $^{89}$Zr, $^{124}$I, $^{99m}$Tc, $^{123}$I, $^{111}$In, $^{177}$Lu, $^{131}$I, $^{76}$Br, $^{78}$Zr, $^{18}$F, and $^{124}$T. In certain such embodiments, an antibody conjugate further comprises a radionuclide chelator selected from maleimide-labeled DOTA, N-hydroxysuccinimide-DOTA, and desferrioxamine (DFO).

Also provided herein are pharmaceutical compositions that comprise an antibody, antigen-binding fragment thereof, or antibody conjugate of the present disclosure; and a pharmaceutical carrier.

In another aspect, the present disclosure provides isolated polynucleotides that encode an antibody or antigen-binding fragment as described herein, which polynucleotides include sequence variants having at least 75%, at least 80%, at least 85%, at least 90%, at least 91%, at least 92%, at least 93%, at least 94%, at least 95%, at least 96%, at least 97%, at least 98%, or at least 99% sequence identity as compared to a specific nucleotide sequence disclosed herein. In certain embodiments, a polynucleotide that encodes an antibody or antigen-binding fragment (e.g., including a scFv, a Fab, a F(ab'2) fragment, a Fv fragment, or a diabody) of the present disclosure, or that encodes a portion of an antibody or antigen-binding fragment (e.g., a heavy chain, a light chain, VH, a VL, or a CDR), has at least 75%, at least 80%, at least 85%, at least 90%, at least 91%, at least 92%, at least 93%, at least 94%, at least 95%, at least 96%, at least 97%, at least 98%, or at least 99% sequence identity as compared to any one of SEQ ID NOs:12-22 or 37. In certain embodiments, the polynucleotide is codon-optimized for expression in a host cell, e.g., a mammalian cell. In any of the aforementioned embodiments, a polynucleotide may be provided in a recombinant vector. In certain embodiments, a vector comprises an expression control sequence operably linked to the polynucleotide encoding the antibody or antigen-binding fragment thereof. In certain such embodiments, the vector (e.g., recombinant vector) is an expression vector in which the expression control sequence comprises a promoter.

In another aspect, host cells are provided that comprise a recombinant vector or an expression vector as described herein. In a related aspect, methods are provided for producing an antibody or an antigen-binding fragment thereof that is capable of binding specifically:

to a biantennary $Le^B/Le^B$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II], to a biantennary $Le^Y/Le^Y$ antigen comprising $Fuc_4(Gal\beta1\rightarrow4GlcNAc)_2$ [III] or $[Fuc\alpha1\text{-}2Gal\beta1\text{-}4(Fuc\alpha1\text{-}3)GlcNAc]_2$ [IV], to a biantennary $Le^B/Le^Y$ antigen comprising $Fuc_2(Gal\beta1\rightarrow3GlcNAc)[Fuc_2(Gal\beta1\rightarrow4GlcNAc)]$ [V], or $[Fuc\alpha1\text{-}2Gal\beta1\text{-}3(Fuc\alpha1\text{-}4)GlcNAc][Fuc\alpha1\text{-}2Gal\beta1\text{-}4(Fuc\alpha1\text{-}3)GlcNAc]$ [VI], and to a biantennary $Le^Y/Le^B$ antigen comprising $Fuc_2(Gal\beta1\text{-}4GlcNAc)[Fuc_2(Gal\beta1\text{-}3GlcNAc)]$ [VII] or $[Fuc\alpha1\text{-}2Gal\beta1\text{-}4(Fuc\alpha1\text{-}3)GlcNAc][Fuc\alpha1\text{-}2Gal\beta1\text{-}3(Fuc\alpha1\text{-}4)GlcNAc]$ [VIII], and wherein the antibody or antigen-binding fragment thereof does not bind specifically to a monoantennary $Le^x$ antigen that comprises $Gal\beta1\rightarrow4(Fuc\alpha1\rightarrow3)GlcNAc$ [IX], or to a biantennary $Le^x$ antigen that comprises $[Gal\beta1\rightarrow4(Fuc\alpha1\rightarrow3)GlcNAc]_2$ [X], or to a monoantennary $Le^A$ antigen that comprises $Gal\beta1\text{-}3(Fuc\alpha1\text{-}4)GlcNAc$ [XI], or to a monoantennary H antigen type 2 that comprises $Fuc\alpha1\text{-}2Gal\beta1\text{-}4GlcNAc$ [XII], or to a biantennary H antigen type 2 that comprises $(Fuc\alpha1\text{-}2Gal\beta1\text{-}4GlcNAc)_2$ [XIII] or to a monoantennary H antigen type 1 that comprises $Fuc\alpha1\text{-}2Gal\beta1\text{-}3GlcNAc$ [XIV], wherein the methods comprise culturing a host cell of the present disclosure under conditions and for a time sufficient for expression by the host cell of the polynucleotide encoding the antibody or antigen-binding fragment thereof, thereby to obtain a culture comprising the antibody or antigen-binding fragment thereof; and recovering the antibody or antigen-binding fragment thereof from the culture.

Methods and Uses for Detecting and Treating Disease

In certain embodiments, the presently disclosed antibodies, antigen-binding fragments thereof, and antibody conjugates are useful in methods of detecting or treating a disease characterized by expression (e.g., overexpression) of a Lewis antigen as described herein.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of an antibody, antigen-binding fragment thereof, or antibody conjugate in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated with the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of treatment to reduce the likelihood of occurrence or recurrence of the disease or disorder or in need of prophylactic treatment may include subjects in whom the disease, condition, or disorder is to be reduced in severity or partially or fully avoided or incompletely or completely prevented (e.g., decreasing the likelihood of occurrence or recurrence of the disease or disorder, which may include but does not necessarily require absolute prevention). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

For example, in certain embodiments, methods are provided for treating or detecting cancer (i.e., a cancer expressing a Lewis antigen as described herein), wherein the methods comprise administering a pharmaceutical composition of the present disclosure to a subject in need thereof. As used herein, "cancer" refers to a condition characterized by aberrant or uncontrolled proliferation (e.g., hyperproliferation) of diseased cells, which may be characterized by malignant spread from a first tissue or site to an adjacent or distant tissue or tissues or sites within the body.

In particular embodiments of the methods, the subject has or is suspected of having a cancer that is selected from gastric cancer, colon cancer, breast cancer, lung cancer, lymphatic cancer, liver cancer, ovarian cancer, pancreatic prostate cancer, uterine cancer, and squamous cell carcinoma. In further embodiments, the cancer is selected from a stomach adenocarcinoma, a mucinous stomach adenocarcinoma, an undifferentiated stomach adenocarcinoma, a signet-ring cell stomach carcinoma, a colon adenocarcinoma, an invasive breast ductal carcinoma, a hepatocellular carcinoma, a lung adenocarcinoma, a squamous cell carcinoma, a metastatic lymph node adenocarcinoma, a mucinous ovarian adenocarcinoma, a pancreatic ductal adenocarcinoma, a pancreatic papillary adenocarcinoma, a prostate adenocarcinoma, and an endometrioid carcinoma. Administration of the antibodies, antigen-binding fragments, or antibody conjugates described herein, in pure form or in an appropriate pharmaceutical composition, can be carried out via any of the accepted modes of administration of agents for serving similar utilities. The pharmaceutical compositions can be prepared by combining an antibody, antigen-binding fragment, or antibody conjugate with an appropriate physiologically acceptable carrier, diluent or excipient, and may be formulated into preparations in solid, semi-solid, liquid or microparticle—(e.g., microdroplet) containing gaseous forms, such as tablets, capsules, powders, granules, ointments, solutions, suppositories, injections, inhalants, gels, microspheres, and aerosols. In addition, other pharmaceutically active ingredients (including other immunosuppressive agents as described elsewhere herein) and/or suitable excipients such as salts, buffers and stabilizers may, but need not, be present within the composition.

The precise dosage and duration of treatment may be a function of the condition or disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

An "effective amount" of a composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administering an effective amount to a subject that is susceptible to or at risk of developing a disease or disease-state (e.g., recurrence) as a beneficial and/or protective course of reducing (e.g., in a statistically significant manner relative to an untreated state) the likelihood of occurrence and/or severity of the disease or disease-state.

In various embodiments, an antibody conjugate of the present disclosure comprises a detectable payload as described herein and may be used to detect a disease such as a cancer either in vivo, in vitro, or ex vivo. In certain of these and other embodiments, the antibodies (i.e., one or more antibody) or antigen-binding fragments thereof described herein are conjugated (e.g., covalently) to a detectable label that may be detected directly or indirectly. In the present disclosure, any of the disclosed monoclonal antibodies, antigen-binding fragments thereof, and antibody conjugates may be linked to a detectable label (e.g., in addition to a detectable or therapeutic payload molecule of an antibody conjugate). In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to a peptide, the detectable label can be used to locate and/or quantify the target to which the specific peptide is bound. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies, antigen-binding fragments, and antibody conjugates used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include microparticles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosphate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to antibodies, antigen-binding fragments, and antibody conjugates described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

In certain embodiments, an antibody, antigen-binding fragment, or antibody conjugate of the present disclosure is used in a method of detecting or diagnosing a disease associated with expression of a Lewis antigen as described herein, wherein the method comprises contacting the antibody, antigen-binding fragment, or antibody conjugate with a sample from a subject suspected of having, or at risk for having, the disease, and detecting formation of an antibody: antigen complex and/or detecting specific binding of the antibody, antigen-binding fragment, or antibody conjugate in the sample. In certain embodiments, the sample comprises blood (e.g., peripheral blood), a tissue, a tumor, or any combination thereof. In certain embodiments, the diagnostic or detection method is performed ex vivo or in vitro.

Methods for in vivo detection of antibody conjugates with detectable payloads or detectable labels include those described in include those disclosed in Friese and Wu, Mol. Immunol. 67(200):142-152 (2015) and Moek et al., J. Nucl.

Med. 58:83S-90S (2017), all of which are hereby incorporated by reference. In certain embodiments, detecting an antibody, antigen-binding fragment, or antibody conjugate comprises performing Positron Emission Tomography (PET), Magnetic Resonance Imaging (MRI), Near Infrared Imaging (NRI), x-ray computed tomography (CT), single photon emission computed tomorgraphy (SPECT), optical imaging, ultrasonography, or any combination thereof.

Preferred modes of administration depend upon the nature of the condition to be treated, which in certain embodiments will refer to a deleterious or clinically undesirable condition the extent, severity, likelihood of occurrence and/or duration of which may be decreased (e.g., reduced in a statistically significant manner relative to an appropriate control situation such as an untreated control) according to certain methods provided herein. An amount that, following administration, detectably reduces, inhibits, at least partially prevents, decreases the severity or likelihood of occurrence of, or delays such a condition, for instance, the partial or complete reduction of a tumor burden or partial or complete reduction of metastatic spread, is considered effective. Persons skilled in the relevant arts will be familiar with any number of diagnostic, surgical and/or other clinical criteria that may indicate the clinical appropriateness of, and/or to which can be adapted, administration of the compositions described herein. See, e.g., Hanahan and Weinberg, 2011 *Cell* 144:646; Hanahan and Weinberg 2000 *Cell* 100:57; Cavallo et al., 2011 *Canc. Immunol. Immunother.* 60:319; Kyrigideis et al., 2010 *J. Carcinog.* 9:3; Park et al. 2009 *Molec. Therap.* 17:219; Cheever et al., 2009 *Clin Cancer Res* 15 (17):5323-5337; Lu et al., 2013 *Curr. Pharm. Biotechnol.* 14:714-22; Layke et al., 2004 *Am. Fam. Physician* 69:1133049; Bunn, 2012 *Arch. Pathol. Lab. Med.* 136:1478-81; Manne et al., 2005 *Drug Discov. Today* 10:965; Schmoll et al. (Eds.), 2009 *ESMO Handbook of Cancer Diagnosis and Treatment Evaluation*, CRC Press, Boca Raton, FL; Faix, 2013 *Crit. Rev. Clin. Lab. Sci.* 50(1):23-36 ("Biomarkers of Sepsis"); Wiersinga et al., 2014 *Virulence* 5(1):36-44 ("Host innate immune responses to sepsis"); Hotchkiss et al., 2013 *Nat. Rev. Immunol.* 13:862; Aziz et al., 2013 *J. Leukoc. Biol.* 93(3):329; Beyrau et al., 2012 *Open Biol.* 2:120134; Fry, 2012 *Amer. Surg.* 78:1; Kellum et al., 2007 *Arch. Intern. Med.* 167(15):1655; Remick, 2007 *Am. J. Pathol.* 170(5):1435; Hotchkiss et al., 2003 *New Engl. J. Med.* 348:138-150; Humar et al., Atlas of Organ Transplantation, 2006, Springer; Kuo et al., Comprehensive Atlas of Transplantation, 2004 Lippincott, Williams & Wilkins; Gruessner et al., Living Donor Organ Transplantation, 2007 McGraw-Hill Professional; Antin et al., Manual of Stem Cell and Bone Marrow Transplantation, 2009 Cambridge University Press; Wingard et al. (Ed.), Hematopoietic Stem Cell Transplantation: A Handbook for Clinicians, 2009 American Association of Blood Banks; and references cited therein.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described an antibodies, antigen-binding fragments thereof, or antibody conjugates in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of an antibody, antigen-binding fragment thereof, or antibody conjugate of the present disclosure, for treatment of a disease or condition of interest in accordance with teachings herein. In certain embodiments, administering comprises administering by a route that is selected from intravenous, parenteral, intragastric, intrapleural, intrapulmonary, intrarectal, intradermal, intraperitoneal, intratumoral, subcutaneous, oral, topical, transdermal, intracisternal, intrathecal, intranasal, and intramuscular.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an antibody, antigen-binding fragment thereof, or antibody conjugate as herein disclosed such that a suitable dosage will be obtained. Typically, this amount is at least 0.01% of the antibody or antigen-binding fragment in the composition. When intended for oral administration, this amount may be varied to be between 0.1 and about 70% of the weight of the composition. Certain oral pharmaceutical compositions contain between about 4% and about 75% of the antibody, antigen-binding fragment thereof, or antibody conjugate. In certain embodiments, pharmaceutical compositions and preparations according to the present invention are prepared so that a parenteral dosage unit contains between 0.01 to 10% by weight of antibody, antigen-binding fragment thereof, or antibody conjugate prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody, antigen-binding fragment thereof, or antibody conjugate of the invention and thereby assists in the delivery of the compound. Suitable agents that may act in this capacity include monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliverthe active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an antibody, antigen-binding fragment thereof, or antibody conjugate as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the peptide composition so as to facilitate dissolution or homogeneous suspension of the antibody, antigen-binding fragment thereof, or antibody conjugate in the aqueous delivery system.

The compositions are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the antibodies, antigen-binding fragments thereof, or antibody conjugates of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies, antigen-binding fragments thereof, or antibody conjugates of the invention and each active agent in its own separate pharmaceutical dosage formulation. For example, an antibody, antigen-binding fragment thereof, or antibody conjugate as described herein and the other active agent can be administered to the patient together in a single oral dosage composition such as a tablet or capsule, or each agent administered in separate oral dosage formulations. Similarly, an antibody, antigen-binding fragment thereof, or antibody conjugate as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of antibodies, antigen-binding fragments thereof, or antibody conjugates of this disclosure in combination with one or more other therapeutic agents. Such therapeutic agents may be accepted in the art as a standard treatment for a particular disease state as described herein, such as a cancer. Exemplary therapeutic agents contemplated include cytokines, growth factors, steroids, NSAIDs, DMARDs, anti-inflammatories, chemotherapeutics, immune checkpoint inhibitors, interfering RNAs, agonists of stimulatory immune checkpoint molecule, another antibody, antigen-binding fragment, or antibody conjugate that targets the cancer, or other active and ancillary agents.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/2B4, HVEM, BTLA, CD160, TIM3, GAL9, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise administering an antibody, antigen-binding fragment, or antibody conjugate of the present disclosure with one or more inhibitor of any one of the following immune suppression components, singly or in any combination.

In certain embodiments, an antibody, antigen-binding fragment, or antibody conjugate of the present disclosure is used in combination with a PD-1 inhibitor, for example a PD-1-specific antibody such as pidilizumab, nivolumab, pembrolizumab, MEDI0680 (formerly AMP-514), AMP-224, BMS-936558, or an antigen-binding fragment thereof, or any combination thereof. In further embodiments, an antibody, antigen-binding fragment, or antibody conjugate of the present disclosure is used in combination with a PD-L1 specific antibody, such as BMS-936559, durvalumab (MED14736), atezolizumab (RG7446), avelumab (MSB0010718C), MPDL3280A, or an antigen-binding fragment thereof, or any combination thereof.

In certain embodiments, an antibody, antigen-binding fragment, or antibody conjugate of the present disclosure is used in combination with a LAG3 inhibitor, such as LAG525, IMP321, IMP701, 9H12, BMS-986016, or any combination thereof.

In certain embodiments, an antibody, antigen-binding fragment, or antibody conjugate of the present disclosure is used in combination with an inhibitor of CTLA4. In particular embodiments, an antibody, antigen-binding fragment, or antibody conjugate of the present disclosure is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, an antibody, antigen-binding fragment, or antibody conjugate of the present disclosure is used in combination with a B7-H3 specific antibody or antigen-binding fragment thereof, such as enoblituzumab (MGA271), 376.96, or both. A B7-H4 antibody binding fragment may be a scFv or fusion protein thereof, as described in, for example, Dangaj et al., *Cancer Res.* 73:4820, 2013, as well as those described in U.S. Pat. No. 9,574,000 and PCT Patent Publication Nos. WO 2016/40724A1 and WO 2013/025779A1.

In certain embodiments, an antibody, antigen-binding fragment, or antibody conjugate of the present disclosure is used in combination with an inhibitor of CD244. In certain embodiments, an antibody, antigen-binding fragment, or antibody conjugate of the present disclosure is used in combination with an inhibitor of BLTA, HVEM, CD160, or any combination thereof. Anti-CD160 antibodies are described in, for example, PCT Publication No. WO 2010/084158.

In certain embodiments, an antibody, antigen-binding fragment, or antibody conjugate of the present disclosure is used in combination with an inhibitor of TIM3. In certain embodiments, an antibody, antigen-binding fragment, or antibody conjugate of the present disclosure is used in combination with an inhibitor of Gal9.

In certain embodiments, an antibody, antigen-binding fragment, or antibody conjugate of the present disclosure is used in combination with an inhibitor of adenosine signaling, such as a decoy adenosine receptor. In certain embodiments, an antibody, antigen-binding fragment, or antibody conjugate of the present disclosure is used in combination with an inhibitor of A2aR.

In certain embodiments, an antibody, antigen-binding fragment, or antibody conjugate of the present disclosure is used in combination with an inhibitor of KIR, such as lirilumab (BMS-986015). In certain embodiments, an antibody, antigen-binding fragment, or antibody conjugate of the present disclosure is used in combination with an inhibitor of an inhibitory cytokine (typically, a cytokine other than TGFβ) or Treg development or activity.

In certain embodiments, an antibody, antigen-binding fragment, or antibody conjugate of the present disclosure is used in combination with an IDO inhibitor, such as levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, an antibody, antigen-binding fragment, or antibody conjugate of the present disclosure is used in combination with an arginase inhibitor, such as N(omega)-Nitro-L-arginine methyl ester (L-NAME), N-omega-hydroxy-nor-I-arginine (nor-NOHA), L-NOHA, 2(S)-amino-6-boronohexanoic acid (ABH), S-(2-boronoethyl)-L-cysteine (BEC), or any combination thereof.

In certain embodiments, an antibody, antigen-binding fragment, or antibody conjugate of the present disclosure is used in combination with an inhibitor of VISTA, such as CA-170 (Curis, Lexington, Mass.).

In certain embodiments, an antibody, antigen-binding fragment, or antibody conjugate of the present disclosure is used in combination with an inhibitor of TIGIT such as, for example, COM902 (Compugen, Toronto, Ontario Canada), an inhibitor of CD155, such as, for example, COM701 (Compugen), or both.

In certain embodiments, an antibody, antigen-binding fragment, or antibody conjugate of the present disclosure is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, an antibody, antigen-binding fragment, or antibody conjugate of the present disclosure is used in combination with a LAIR1 inhibitor.

In certain embodiments, an antibody, antigen-binding fragment, or antibody conjugate of the present disclosure is used in combination with an inhibitor of CEACAM-1, CEACAM-3, CEACAM-5, or any combination thereof.

In certain embodiments, an antibody, antigen-binding fragment, or antibody conjugate of the present disclosure is used in combination with an agent that increases the activity (i.e., is an agonist) of a stimulatory immune checkpoint molecule. For example, an antibody, antigen-binding fragment, or antibody conjugate of the present disclosure can be used in combination with a CD137 (4-1BB) agonist (such as, for example, urelumab), a CD134 (OX-40) agonist (such as, for example, MED16469, MED16383, or MED10562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering an antibody, antigen-binding fragment, or antibody conjugate of the present disclosure with one or more agonist of a stimulatory immune checkpoint molecule, including any of the foregoing, singly or in any combination.

In certain embodiments, a combination therapy comprises an antibody, antigen-binding fragment, or antibody conjugate of the present disclosure and a secondary therapy comprising one or more of: another antibody, antigen binding-fragment thereof, or antibody conjugate that is specific for a cancer antigen expressed by the cancer (i.e., the same or a different antigen), a radiation treatment, a surgery, a chemotherapeutic agent, a cytokine, RNAi, or any combination thereof.

In certain embodiments, a combination therapy method comprises administering an antibody, antigen-binding fragment, or antibody conjugate of the present disclosure and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art. Proton therapies are reviewed in Thariat et al., *Bull. Cancer* pii: S0007-4551(1)300001-8 (2018).

In certain embodiments, a combination therapy method comprises administering an antibody, antigen-binding fragment, or antibody conjugate of the present disclosure and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines may be used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with an antibody, antigen-binding fragment, or antibody conjugate of the present disclosure of this disclosure.

Cell immunotherapies, including those involving T cells, NK cells, or NK-T cells expressing natural or recombinant TCRs and CARs specific for cancer antigens, and including adoptive transfer of such cells to a recipient, are an emerging therapeutic modality for cancer (see, e.g., Bonini and Mondino, Eur. *J. Immunol.* 45(9):2457-69 (2015) and Metha and Rezvani, *Front. Immunol.* 9:283 (2018)). In certain embodiments, a subject receiving an antibody, antigen-binding fragment, or antibody conjugate (or pharmaceutical composition) of the present disclosure has or is (i.e., concurrently, simultaneously, or sequentially) receiving a cell immunotherapy that targets the cancer.

Also provided herein are any of the presently disclosed antibodies, antigen-binding fragments, antibody conjugates, polynucleotides, vectors, host cells, and compositions for use in treating, detecting, or diagnosing a disease characterized by expression (e.g., overexpression) of a Lewis antigen as described herein. In certain embodiments, the disease is a cancer, such as any cancer as disclosed herein. In certain embodiments, the antibody, antigen-binding fragment, antibody conjugate, or composition is used in any combination therapy as described herein.

Also provided herein are any of the presently disclosed antibodies, antigen-binding fragments, antibody conjugates, polynucleotides, vectors, host cells, and compositions for use in the preparation of a medicament for the treatment of a disease characterized by expression (e.g., overexpression) of a Lewis antigen as described herein. In certain embodiments, the disease is a cancer, such as any cancer as disclosed herein. In certain embodiments, the medicament comprises or is used in any combination therapy as described herein.

As used in this specification and the appended claims, the singular forms "a," "an" and "the" include plural references unless the content-clearly dictates otherwise. Further, the use of the alternative (e.g., "or") should be understood to mean either one, both, or any combination thereof of the alternatives.

Throughout this specification, unless the context requires otherwise, the words "comprise", "have", or variations such as "has", "having", "comprises" or "comprising", will be understood to imply the inclusion of a stated element or integer or group of elements or integers but not the exclusion of any other element or integer or group of elements or integers. In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

As used herein, the term "about" means±no more than 20% of the indicated range, value, or structure, unless otherwise indicated, or in certain embodiments ±no more than 50, 45, 40, 35, 30, 25, 20, 19, 18, 17, 16, 15, 14, 13, 12, 10, 9, 8, 7, 6, or 5% of the indicated range, value, or structure, unless otherwise indicated.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" is not equivalent to "comprising" and refers to the specified materials or steps of a claim, or to those that do not materially affect the basic characteristics of a claimed subject matter Each embodiment in this specification is to be applied mutatis mutandis to every other embodiment unless expressly stated otherwise.

EXAMPLES

Example 1

Generation of Chimeric BBC Antibody

Isolation of Antibody Variable Region cDNAs

Hybridoma cells expressing murine IMH2/BBC antibody, which comprises a VL domain having the amino acid sequence set forth in SEQ ID NO: 27 and a VH domain having the amino acid sequence set forth in SEQ ID NO:28, were obtained from Dr. S. Hakomori (*Cancer Research* 52:3739-3745 (1992)). To prepare RNA for cDNA synthesis, $9\times10^6$ hybridoma cells were first harvested by low speed centrifugation (300 g for 5 min) followed by RNA isolation using a "total RNA miniprep purification kit" ™ (GeneMark™, GMbiolab Co. Ltd., Taichung City, Taiwan, ROC) according to the manufacturer's protocol. Antibody genes encoding IMH2 were then cloned from the purified RNA using the SMART RACE cDNA Amplification Kit™ (Takara/BD Biosciences-Clontech, Palo Alto, CA) with minor modifications compared to the supplier's recommended protocol.

Briefly, after the first strand cDNA synthesis and dC-tailing, cDNA specifically encoding light chain variable regions of IMH2 was isolated by two rounds of PCR using kit-supplied primers and specific primers designed based on known mouse kappa chain sequence in the constant region. The first PCR was carried out for 5 cycles of 30 seconds at 94° C. and 1 minute at 72° C.; followed by 5 cycles of 30 seconds at 94° C., 30 seconds at 67° C. and 1 minute at 72° C. Twenty-seven (27) additional cycles of PCR reaction comprising 30 seconds at 94° C., 30 seconds at 62° C. and 1 minute at 72° C. were added to ensure successful amplification. A second nested PCR including a preheating step at 94° C. for 5 minutes, followed by 35 cycles of 30 seconds at 94° C., 30 seconds at 54° C. and 1 minute at 72° C. and a final extension step at 72° C. for 3 minutes was then executed to further improve fidelity.

The cloning strategy for the heavy chain gene was slightly different. First, the single-stranded cDNA template used for PCR reaction was prepared from RNA with a mouse IgG3-specific primer to the constant domain 1 (CH1). Gene isolation was then performed by a single round PCR as follows: preheat at 94° C. for 5 minutes, 35 cycles of PCR reaction comprising 30 seconds at 94° C., 30 seconds at 62° C., 1 minute at 72° C., followed by a final extension step at 72° C. for 5 minutes in the presence of NUP primer (SMART™ RACE amplification kit, Clontech, Palo Alto, CA) and a nested primer to the mouse CH1 domain. cDNA encoding the variable region of both light and heavy chain fragments was then purified using a PCR purification kit (GeneMark™ GMbiolab Co. Ltd., ROC) and introduced into yT&A cloning vector (Yeastern Biotech™, Taipei, Taiwan, ROC) for positive clone identification and sequence determination.

Construction of Antibody Expression Plasmids

To build expression plasmids for producing the antibody referred to herein as "BBC" antibody, PCR primers and the antibody genes cloned in yT&A vector described above were used to prepare only the cDNAs encoding the mature (without leader peptide) heavy chain and light chain variable regions. PCR was performed as follows: preheating at 94° C. for 5 minutes, 35 cycles of PCR reaction comprising 30 seconds at 94° C., 30 seconds at 65° C. and 60 seconds at 72° C., and a final extension step at 72° C. for 3 minutes. Restriction enzyme recognition sequences were incorporated during PCR reaction at the 5' (NheI) and 3' (ApaI) ends of VH cDNA and at the 5' (NheI) and 3' (BsiWI) ends of VL cDNA to facilitate subsequent expression plasmids engineering. The amplified cDNA fragments were then sequentially digested with restriction enzymes ApaI/NheI for heavy chain and NheI/BsiWI for light chain genes. After gel purification, the recovered VH and VL cDNA were ligated to the pGNX-RhcG1 (VH) or pGNX-Rhck vector (VL) at the same restriction enzyme cloning sites to obtain the expression vectors pGNX-RhcG1-BBC and pGNX-Rhck-BBC, respectively. Inserted cDNA sequences were confirmed using a primer upstream to the multiple cloning site.

Transient Production of Antibody

For transient production of the chimeric BBC antibody, HEK293-c18 cells were co-transfected with heavy and light chain-encoding pGNX-RhcG1-BBC and pGNX-Rhck-BBC expression plasmids in the presence of polyethylenimine. Culture supernatant was harvested at the end of day 7 post-transfection for analysis.

Example 2

Generation of Humanized Bbc Antibodies

To produce humanized forms of the BBC antibody (described above in Ex. 1), homologous human antibody sequences (human acceptor) were selected to perform CDR grafting. Briefly, potential human acceptor sequences were identified by searching the NCBI protein database to locate the sequences exhibiting the highest homology to the heavy (SEQ ID NO: 28) and light (SEQ ID NO: 27) chain variable regions of the BBC antibody. The human acceptor frameworks CAD89404.1 (Vh) and AAS01771.1 (Vl) were chosen (FIG. 1). However, directly inserting non-human CDR sequences into human acceptor frameworks may result in the loss of binding affinity. Binding affinity may be restored after transferring framework residues from human acceptor back to the non-human donor sequence. Preferred back mutations restore the binding affinity by maintaining original CDR conformations.

To restore binding affinity post-CDR grafting, a 3-D model of the antibody was first built based on BBC crystal structure data, using the Accelrys Discovery Studio™ (BIOVIA, San Diego, CA) software. Critical amino acids were then predicted for back mutation by examining the structure as follows:

1. The mutation energy (for stability) of changed residues on the humanized framework was calculated. Positive values of mutation energy corresponded to a destabilizing effect of the mutation and vice versa.
2. The spatial distances between the framework residues and CDR regions were examined. The residues closest to CDRs were taken into consideration (within 4 Å).
3. The residues located on the interface of heavy chain variable region and light chain variable region were examined. These residues contributed to the assembling of the heavy chain and light chain, and therefore, could have a significant impact on the antibody structure.

Ten (10) influential positions (3 in the light chain and 7 in the heavy chain) based on the prediction criteria were initially chosen for back mutation. In addition, the methionine (M) residue at position 70 (according to Kabat numbering) of the selected human heavy chain template appeared to be an infrequent motif, and therefore was replaced with the highly conserved isoleucine (I) at that site (FIG. 1; back mutated residues (Human acceptor→hBBC.8) are underlined in Table 3 below; the Met→Ile residue is shown underlined with bold italics in Table 3 and boxed in FIG. 1). These amino acid conversions produced the "hBBC.8" humanized antibody.

Additional changes were introduced to further improve the antibody. First, two positions in the hBBC.8 light chain (R66 and F71) that vary between the mouse and human sequences were mutated to produce "hBBC.9" (containing F71Y mutation) and "hBBC.10" (containing F71Y and R66G mutations) (FIG. 2A; residues bolded and italicized, with no underlining, in Table 3). Binding of BBC and the generated humanized variants hBBC.9 and hBBC.10 to AGS cells is shown in FIG. 2B. Briefly, AGS human gastric cancer cell line (ATCC CRL-1739; ATCC, Manassas, VA) was regularly maintained in F12 medium and supplemented with 10% dialyzed fetal bovine serum. To perform cell binding studies, roughly $3\times10^5$ cells in 100 μl of PBS were mixed with an equal volume of diluted antibody. After 1 hour incubation at room temperature, 2 ml PBS was added to each sample to rinse off unbound antibody. Subsequent to centrifugation, the recovered cell pellet was re-suspended directly in 200 μl of Fluorescein (FITC)-AffiniPure™ Goat Anti-Human IgG, Fcγ Fragment Specific (Jackson ImmunoResearch, West Grove, PA, Cat. 109-095-098) diluted 1:200 in PBS. Following room temperature incubation for 30 minutes, the PBS wash was repeated to eliminate unbound secondary antibody. Collected cells were re-suspended in 200 ul PBS and analyzed on a BD FACSCanto™ flow cytometer system (BD Biosciences, San Jose, CA). Further analysis was performed to identify potentially immunogenic sequences.

Additional mutations in heavy or light chain produced the further variants "hBBC.9.1" and "hBBC.10.1" (residues bolded and underlined, no italics, in Table 3 below). Specifically, crystal structures of the BBC and hBBC.8 antibodies, and of simulated antigen/antibody complexes, were analyzed. Several residues in the light and heavy chain CDR regions (positions specified according to Kabat numbering) were identified for single site amino acid replacement. Amino acid switching at designated position(s) of antibody light or heavy chain gene was performed by two rounds of PCR reaction with specifically designed primers. To facilitate insertion of mutated antibody cDNA fragments into expression vectors, a restriction site was incorporated at each end (5'NheI and 3'ApaI for the cDNA chain, 5'NheI and 3'BsiWI for light chain cDNA) during PCR reaction. DNA fragments were produced after a second PCR reaction, cut with NheI/ApaI or NheI/BsiWI, and ligated to the same sites of pGNX-RhcG1 and pGNX-Rhck vectors for heavy chain and light chain gene construction, respectively. Mutated sites and changes are shown in Table 1.

TABLE 1

| Single site mutations of hBBC.8 | | |
|---|---|---|
| | Position and original amino acid | Changed amino acids |
| Light chain location | | |
| CDR1 | E27 | A |
| | Y30 | A |
| | N31 | A |
| | T34 | S, V |
| CDR2 | G50 | A |
| | S53 | A |
| CDR3 | Q89 | A |
| | T93 | A, S, V, D |
| Heavy chain location | | |
| CDR1 | S31 | A |
| | Y33 | A |
| CDR2 | Y54 | A |
| | S55 | T |
| | N57 | A, D, Q, Y, W |
| | S61 | A |
| CDR3 | Y104 | A |
| | D105 | A |
| | H106 | A |

Figure 2C:
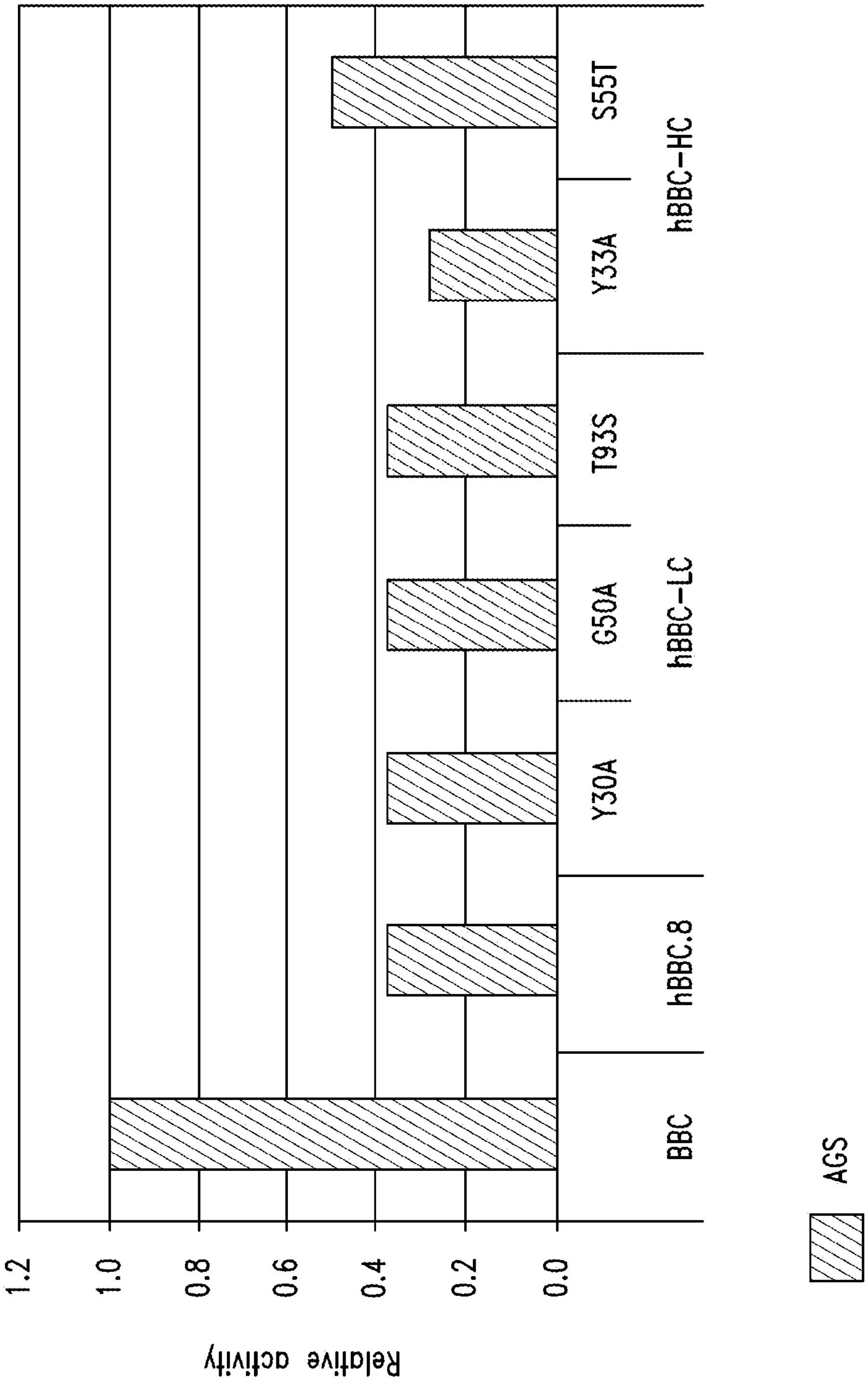
FIGS. 2C-2E show binding specificity of further generated variant antibodies (2C) for AGS cells and (2D, 2E) for AGS cells compared to synthetic monoantennary $Le^B$ antigen.

A number of the mutants exhibited in vitro binding activities equal to or greater than ½ activity of the chimeric antibody (BBC) in AGS cell binding assay (FIG. 2C, see also Table 2). In addition, some mutants also displayed specificity improvement by reduced cross-reactivity with a monovalent Lewis B structure (equal to or less than ⅛ strength compared to BBC) in an ELISA assay, as shown in Table 2. Monovalent Lewis B is a blood group antigen that is expressed in normal human tissues.

TABLE 2

| Binding Activity of BBC CDR Mutants | | | | |
|---|---|---|---|---|
| Light chain location | Original amino acid and position | Mutated amino acids | AGS Binding Activity | $Le^B$ ELISA |
| CDR1 | Y30 | A | = | |
| | R32 | A | − | |
| CDR2 | G50 | A | = | − |
| CDR3 | W92 | A | − | − |
| | T93 | S | = | − |

TABLE 2-continued

| Binding Activity of BBC CDR Mutants | | | | |
|---|---|---|---|---|
| Heavy chain location | Original amino acid and position | Changed amino acids | AGS Binding Activity | $Le^B$ ELISA |
| CDR1 | Y33 | A | = | |
| | T34 | A | − | |
| CDR2 | S55 | T | + | − |
| CDR3 | Y104 | A | = | − |
| | H106 | A | = | − |

Figure 2D:
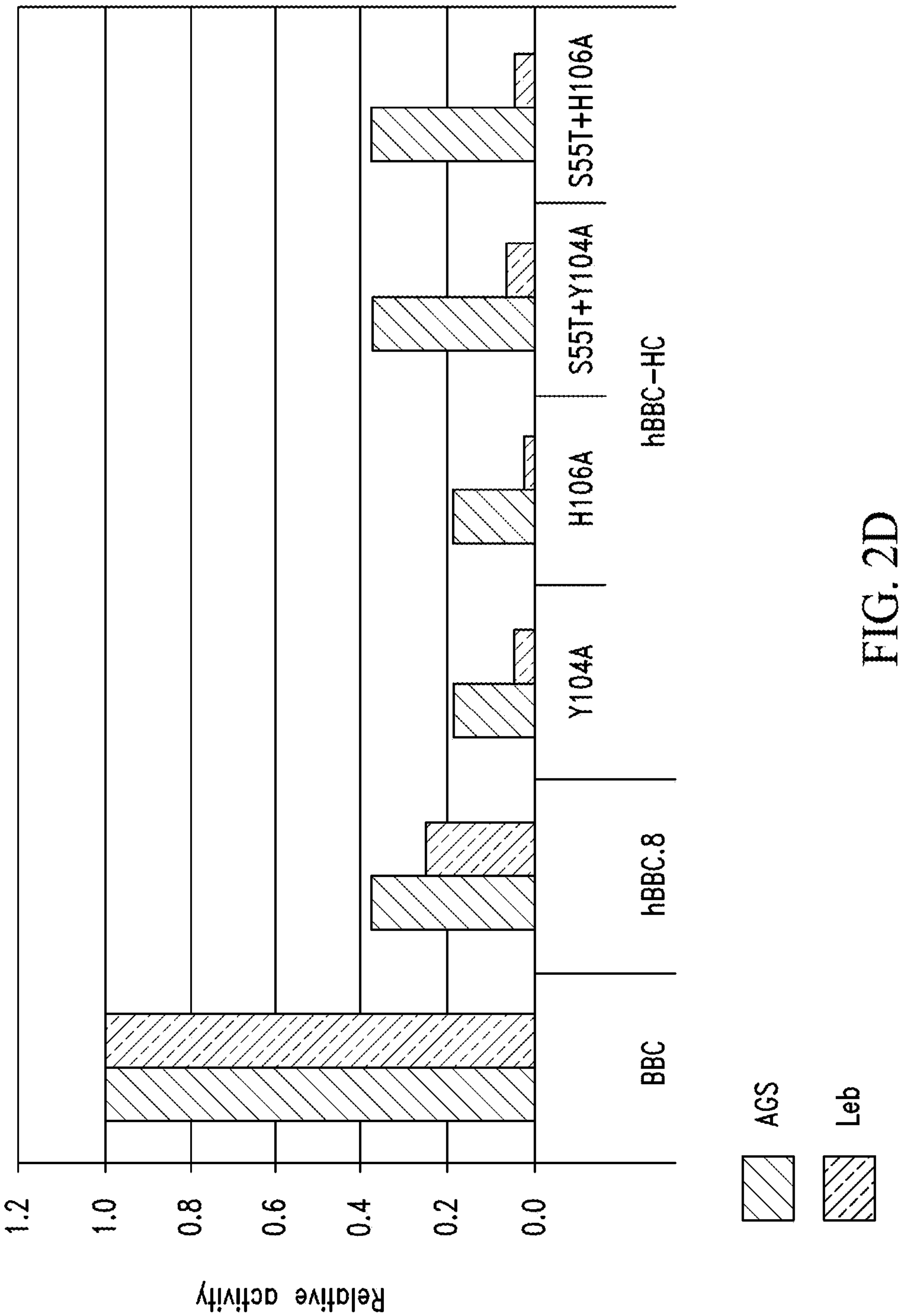

(=) no change in binding activity relative to BBC
(−) decrease in binding activity relative to BBC
(+) increased binding activity relative to BBC Since hBBC.8 which showed approximately ⅓ AGS cell binding activity compared to BBC (FIG. 2B), and exhibited very good tumor inhibition in the xenograft mouse model (see Example 6), these single amino acid-replaced antibody mutants have the potential to display anti-tumor activity. The positions and amino acid replacements of these analyzed clones are summarized in Table 1. To further confirm their capability for affinity and/or specificity improvement, a total of seven (7) single mutation sites (Table 2) were selected to evaluate in a humanized antibody template. These included five single-residue substitutions (three in the light chain and two in the heavy chain) that were tested for their effects on antibody binding to AGS cells (FIG. 2C), two heavy chain single-residue substitutions that were tested for their effects on antibody binding specificity (to AGS cells compared to purified $Le^B$, and two heavy chain double-residue replacements that were similarly analyzed (FIG. 2D).

Figure 2E:
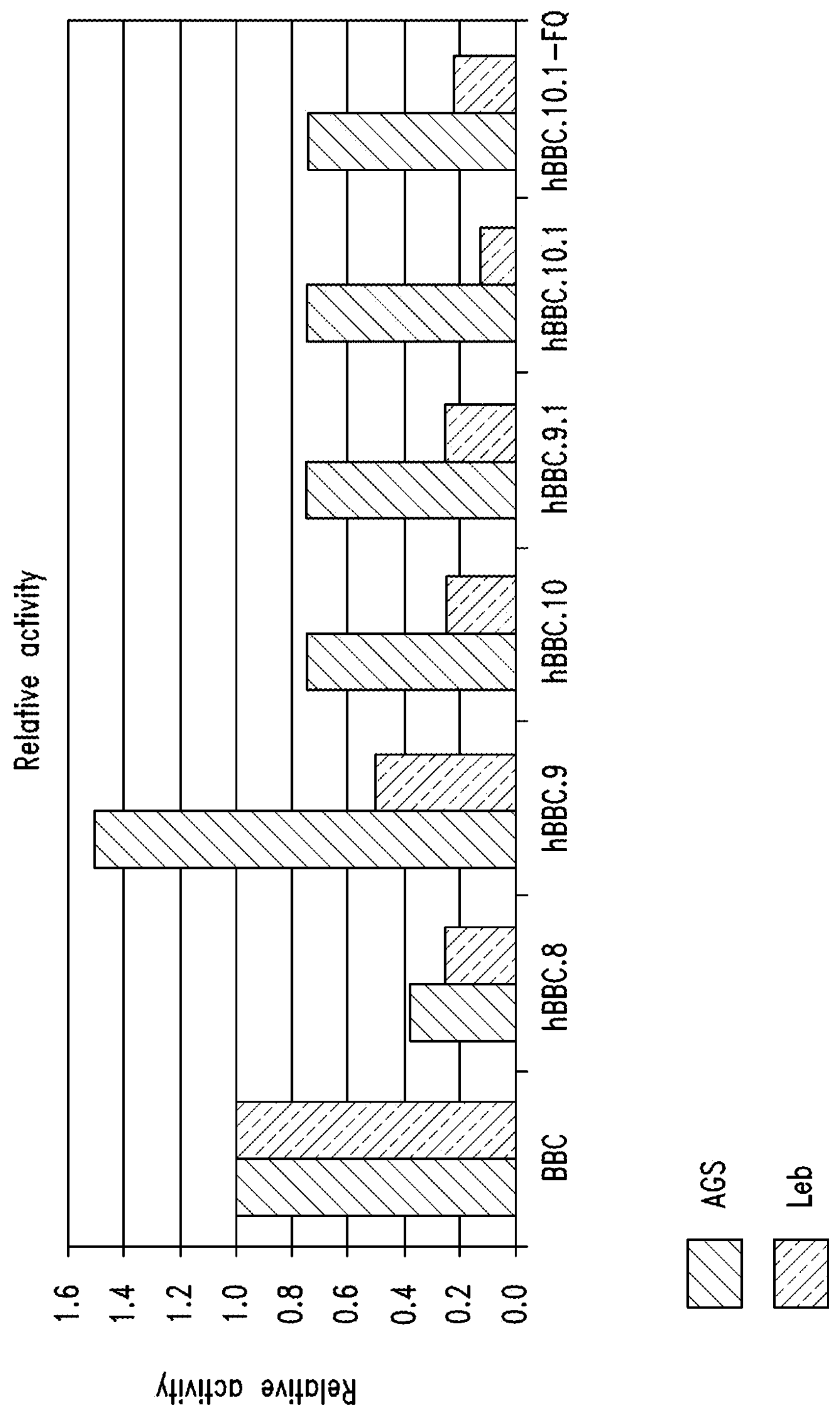

A further comparison of various humanized BBC versions constructed to the original chimeric form in terms of affinity (AGS cell binding assay) and specificity (Lewis b ELISA assay) is shown in FIG. 2E.

Epibase analysis of hBBC.9 (Applied Protein Services, Lonza Biologics, Cambridge, UK) predicted a region in the heavy chain region with a strong immunogenicity risk. To minimize the potential immunogenicity problem, 6 additional amino acid changes in the framework 3 region of heavy chain (positions 78, 80, 82-84, and 86) were included to match reference humanized antibodies at these locations (FIG. 3). These conversions gave the heavy chain framework for "hBBC.10.1FQ". The amino acid sequences of the various heavy and light chain variable regions described in this Example are summarized in Table 3.

TABLE 3

| Amino Acid Sequences of Antibody VH and VL Regions | | |
|---|---|---|
| Antibody | Light chain variable region | Heavy chain variable region |
| IMH2/BBC | DIQMTQSSSSFSVSLGDRV<br>TITC**TASEDIYNRLT**WYQQ<br>KPGNVPRLLIS**GATSLDT**G<br>VPSRFSGSRSGKDYALSIT<br>SLQTEDVATYYC**QQYWTT**<br>**PWT**FGGGTRLEIK<br>(SEQ ID NO: 27) | DVQLQESGPDLVKPSQSLSL<br>TCTVTGYSIT**SGYTWH**WIRQ<br>FPGNTLEWLG**YIHYSGNTKY**<br>**SPSLKS**RLSVTRDTSKNQFF<br>LQLNSVTTEDTATYYCGR**EA**<br>**LRGYDHGFWFTY**WGQGTLV<br>TV<br>(SEQ ID NO: 28) |
| Human acceptor | DIQMTQSPSSLSASVGDRV<br>TITC**RASQGISNYLA**WYQQ<br>KPGKVPKLLIY**AASTLQS**G<br>VPSRFSGSGSGTDFTLTIS<br>SLQPEDVATYYC**QKYNSA**<br>**PYT**FGQGTKLEIK<br>(SEQ ID NO: 29) | QVQLQESGPGLVKPSQTLSL<br>TCTVSGGSIS**SGAYYWS**WIR<br>QHPGKGLEWIG**YIYYSGTTY**<br>**YNPSLKS**RLS*M*SRDTSKNQF<br>SLKLSSVTAADTAVYYCAR**G**<br>**PYYDSPRPFDP**WGQGTLVTV<br>(SEQ ID NO: 30) |

TABLE 3-continued

| Amino Acid Sequences of Antibody VH and VL Regions | | |
|---|---|---|
| Antibody | Light chain variable region | Heavy chain variable region |
| hBBC.8 | DIQMTQSPSSLSASVGDRV<br>TITC**TASEDIYNRLT**WYQQ<br>KPGKVPRLLIS**GATSLDT**G<br>VPSRFSGSRSGTDFTLTISS<br>LQPEDVATYYC**QQYWTTP**<br>**WT**FGQGTKLEIK<br>(SEQ ID NO: 31) | QVQLQESGPGLVKPSQTLSL<br>TCTVSGYSIT**SGYTWH**WIRQ<br>HPGKGLEWLG**YIHYSGNTKY**<br>**SPSLKS**RLSISRDTSKNQFFL<br>KLSSVTTEDTAVYYCGR**EAL**<br>**RGYDHGFWFTY**WGQGTLVTV<br>(SEQ ID NO: 32) |
| hBBC.9 | DIQMTQSPSSLSASVGDRV<br>TITC**TASEDIYNRLT**WYQQ<br>KPGKVPRLLIS**GATSLDTG**<br>VPSRFSGSRSGTD*Y*TLTIS<br>SLQPEDVATYYC**QQYWTT**<br>**PWT**FGQGTKLEIK<br>(SEQ ID NO: 33) | (hBBC.8 heavy chain variable region<br>(SEQ ID NO: 32)) |
| hBBC.9.1 | (hBBC.9 light chain variable region (SEQ ID NO: 33)) | QVQLQESGPGLVKPSQTLSL<br>TCTVSGYSIT**SGYTWH**WIRQ<br>HPGKGLEWLG**YIHYTGNTKY**<br>**SPSLKS**RLS*I*SRDTSKNQFFL<br>KLSSVTTEDTAVYYCGR**EAL**<br>**RGADHGFWFTY**WGQGTLVTV<br>(SEQ ID NO: 34) |
| hBBC.10 | DIQMTQSPSSLSASVGDRV<br>TITC**TASEDIYNRLT**WYQQ<br>KPGKVPRLLIS**GATSLDTG**<br>VPSRFSGS*G*SGTD*Y*TLTIS<br>SLQPEDVATYYC**QQYWTT**<br>**PWT**FGQGTKLEIK<br>(SEQ ID NO: 5) | (hBBC.8 heavy chain variable region (SEQ ID NO: 32)) |
| hBBC.10.1 | (hBBC.10 light chain variable region<br>(SEQ ID NO: 5)) | QVQLQESGPGLVKPSQTLSL<br>TCTVSGYSIT**SGYTWH**WIRQ<br>HPGKGLEWLG**YIHYTGNTKY**<br>**SPSLKS**RLS*I*SRDTSKNQFFL<br>KLSSVTTEDTAVYYCGR**EAL**<br>**RGYDAGFWFTY**WGQGTLVTV<br>(SEQ ID NO: 35) |
| hBBC.10.1FQ | (hBBC.10 light chain variable region<br>(SEQ ID NO: 5)) | QVQLQESGPGLVKPSQTLSL<br>TCTVSGYSIT**SGYTWH**WIRQ<br>HPGKGLEWLG**YIHYTGNTKY**<br>**SPSLKS**RLS*I*SRDTSKN*TFY*L<br>*QMNSL*TTEDTAVYYCGR**EAL**<br>**RGYDAGFWFTY**WGQGTLVTV<br>(SEQ ID NO: 1) |

Example 3

Characterization of HBBC Epitope

BBC and the herein described variants were designed as glycan-binding monoclonal antibodies. Based on published specificity data of the parent IMH2 (BBC) antibody (Ito et al., *Cancer Res.* 52:3739, 1992), the target epitope of the generated BBC antibodies was hypothesized to be related to $Le^B$ and $Le^Y$ antigens. The following epitope characterization studies were performed using hBBC.10.1, also referred to in the following examples and referenced figures as "hBBC".

Immunopurification

Figure 4A:
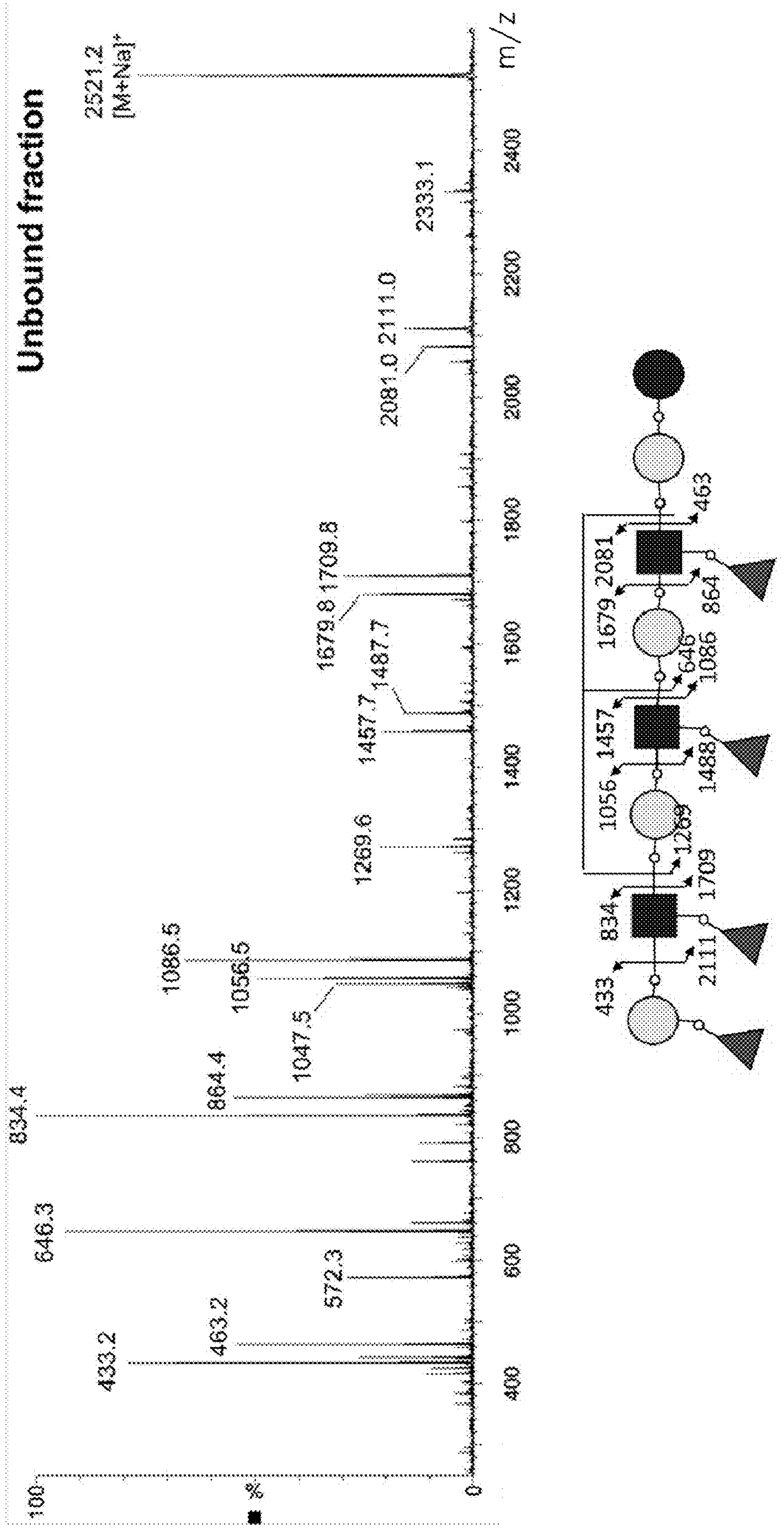
FIGS. 4A and 4B show MALDI-MSMS sequencing of $Fuc_4(LacNAc)_3Lac$ of COLO 205 GSL cells at m/z 2521 in unbound (4A) and BBC-bound (eluted) fractions (4B).
Figure 4B:
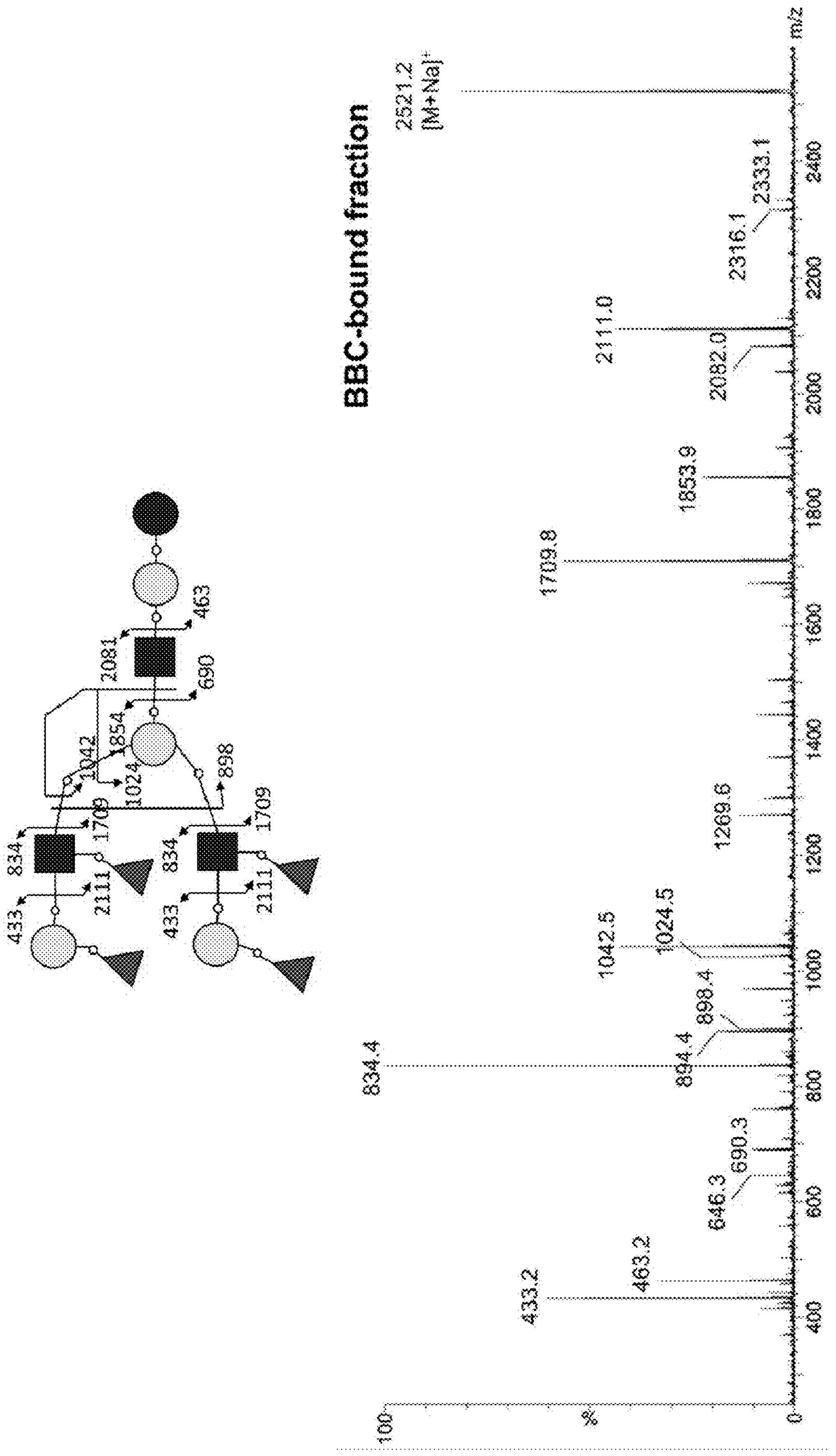

GSL-derived glycans from the colorectal cell cancer line Colo-205 were isolated and immunopurified using BBC. The glycans in unbound and eluted fractions were permethylated and profiled with MALDI-MS analysis, as shown in FIGS. 4A and 4B. The glycan profile of the unbound fraction was similar to the input glycan profile, indicating that most GSL-derived glycans from COLO 205 did not bind to BBC. In the eluted (BBC-bound) fraction, however, $Fuc_4$(LacNAc)$_3$Lac glycan was exclusively purified by BBC. Specifically, it was surprisingly found that the hBBC-purified glycan carried a biantennary $Le^{B/Y}$(i.e., $Le^B$/$Le^B$, $Le^B$/$Le^Y$, or $Le^Y$/$Le^Y$, based on the observation of both $Le^B$ and $Le^Y$ fingerprint fragments in the MS/MS experiment on I-branching antigens, whereas the glycan in unbound fraction was a linear structure, potentially $Le^B$-$Le^A$-$Le^A$-Lac. This result indicated that biantennary $Le^{B/Y}$ on I antigens is the epitope of BBC.

Figure 5A:
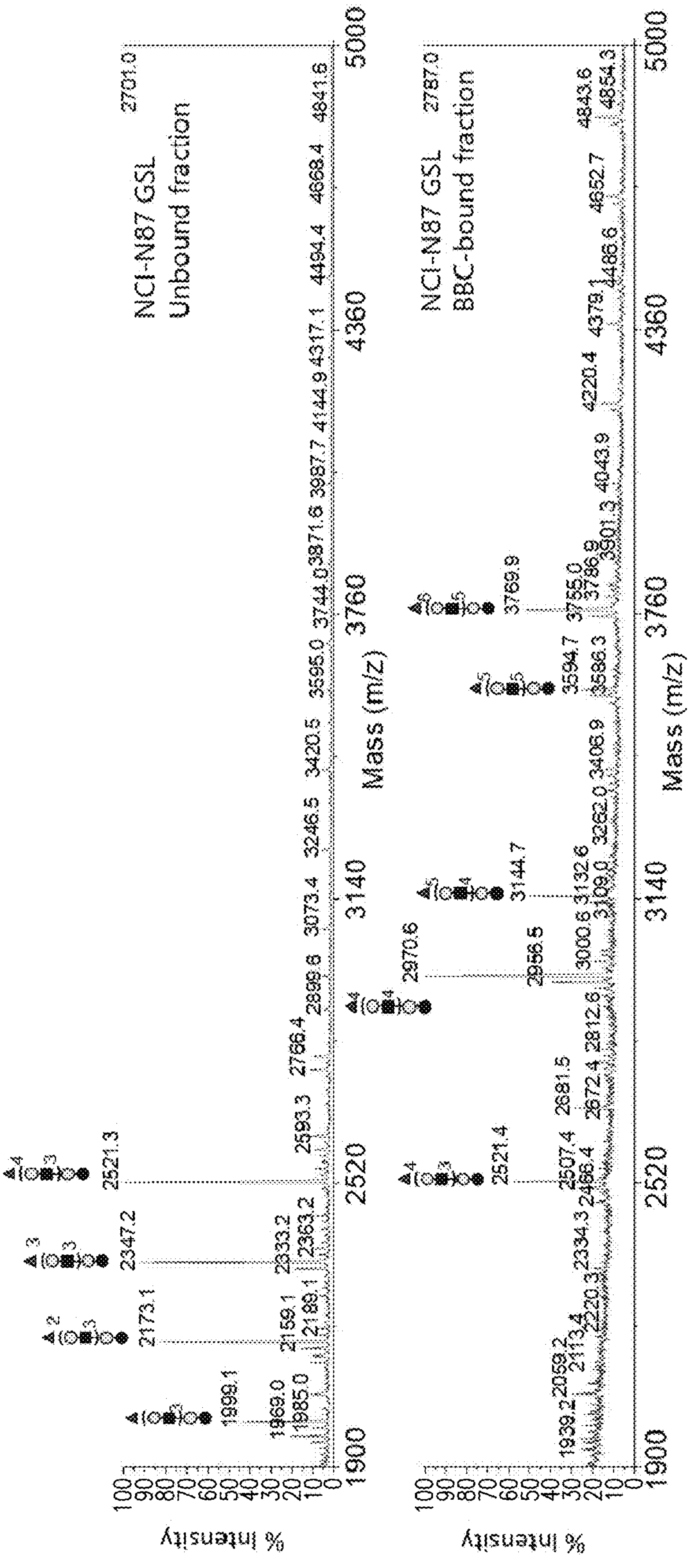
FIGS. 5A and 5B show, respectively, MALDI-MS profiles of BBC-binding (bottom) and non-binding (top) glycans of (A) NCI-N87 and (B) SW1116 GSL cells.
Figure 5B:
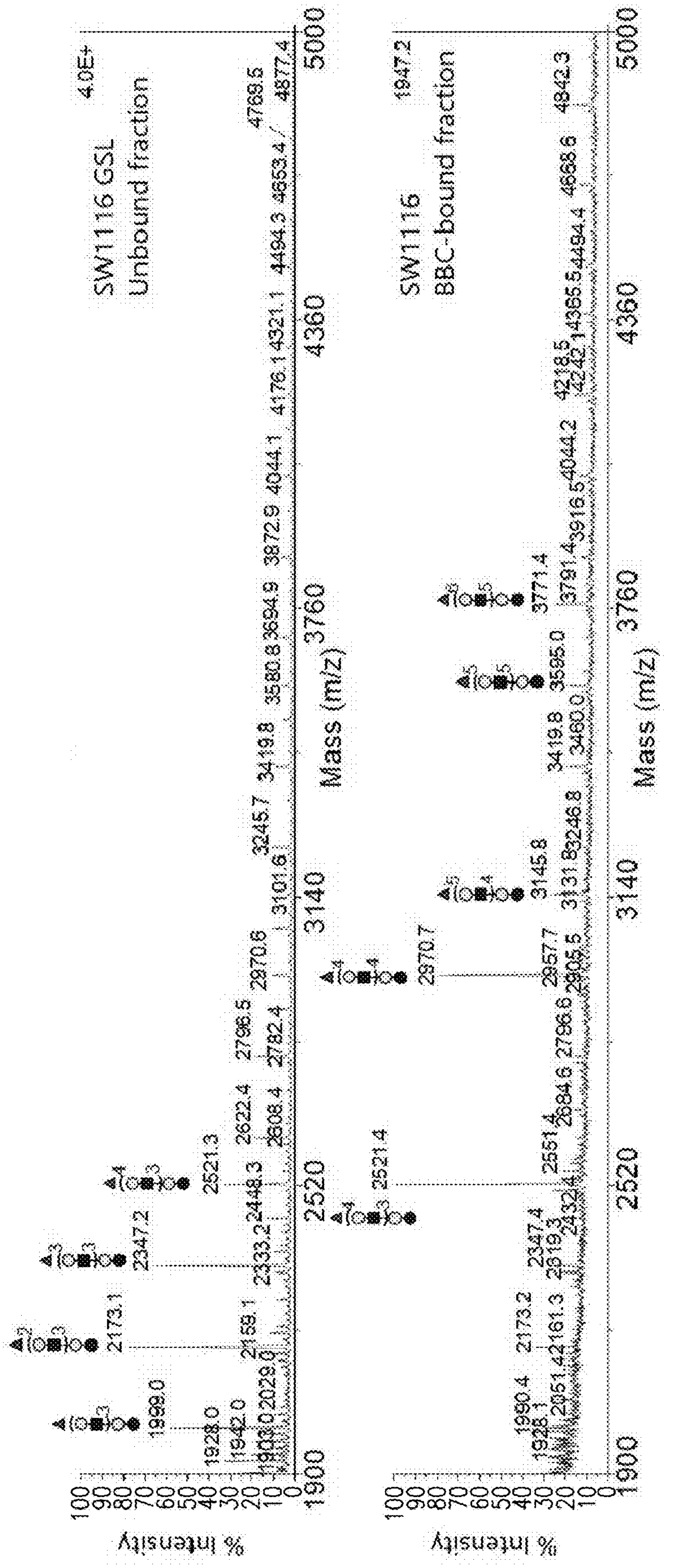
Figure 6A:
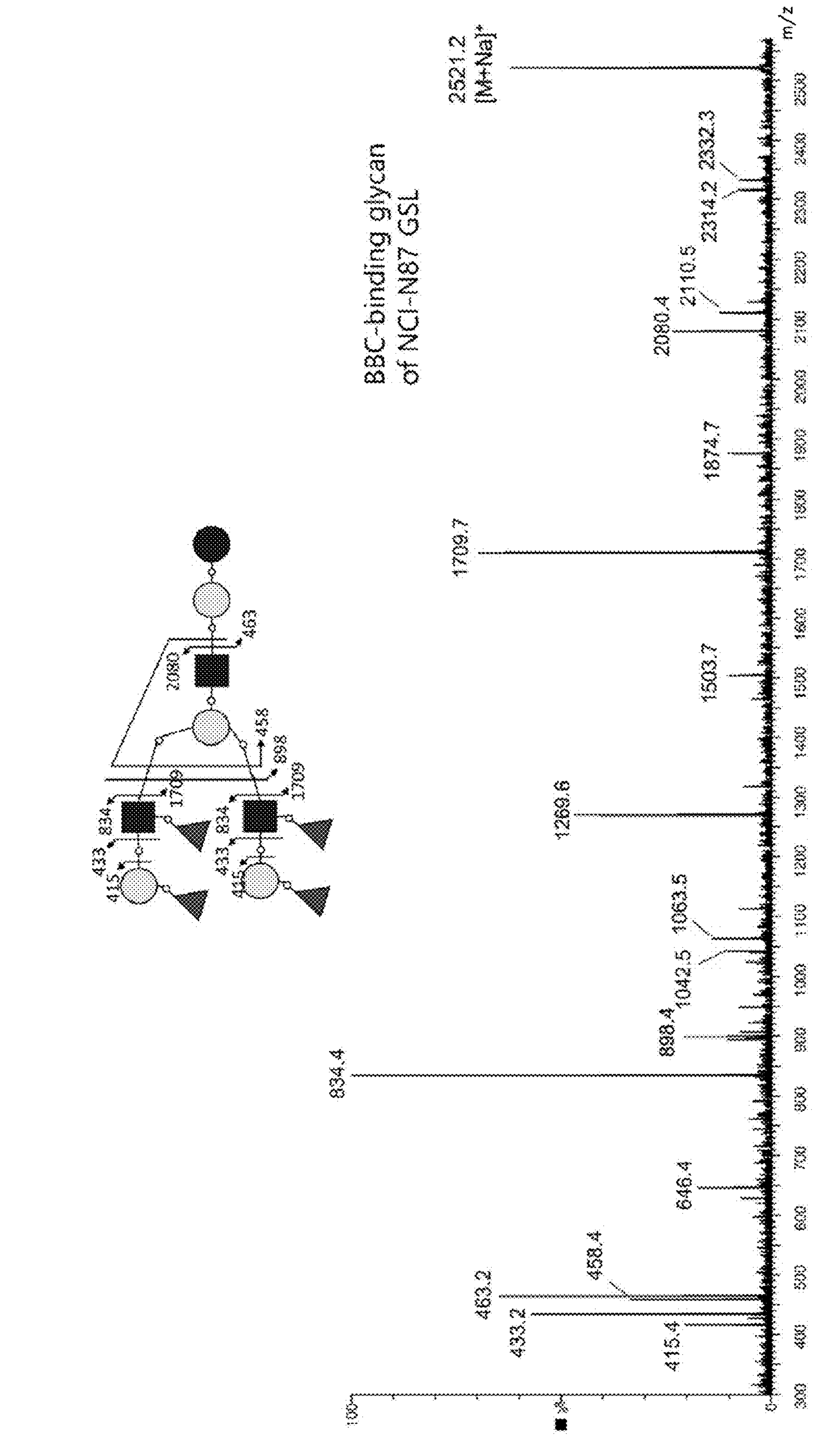
FIGS. 6A and 6B show MALDI-MSMS sequencing of $Fuc_4(LacNAc)_3Lac$ of NCI-N87 (6A) and SW1116 GSL cells (6B) at m/z 2521 in BBC-bound (eluted) fraction.
Figure 6B:
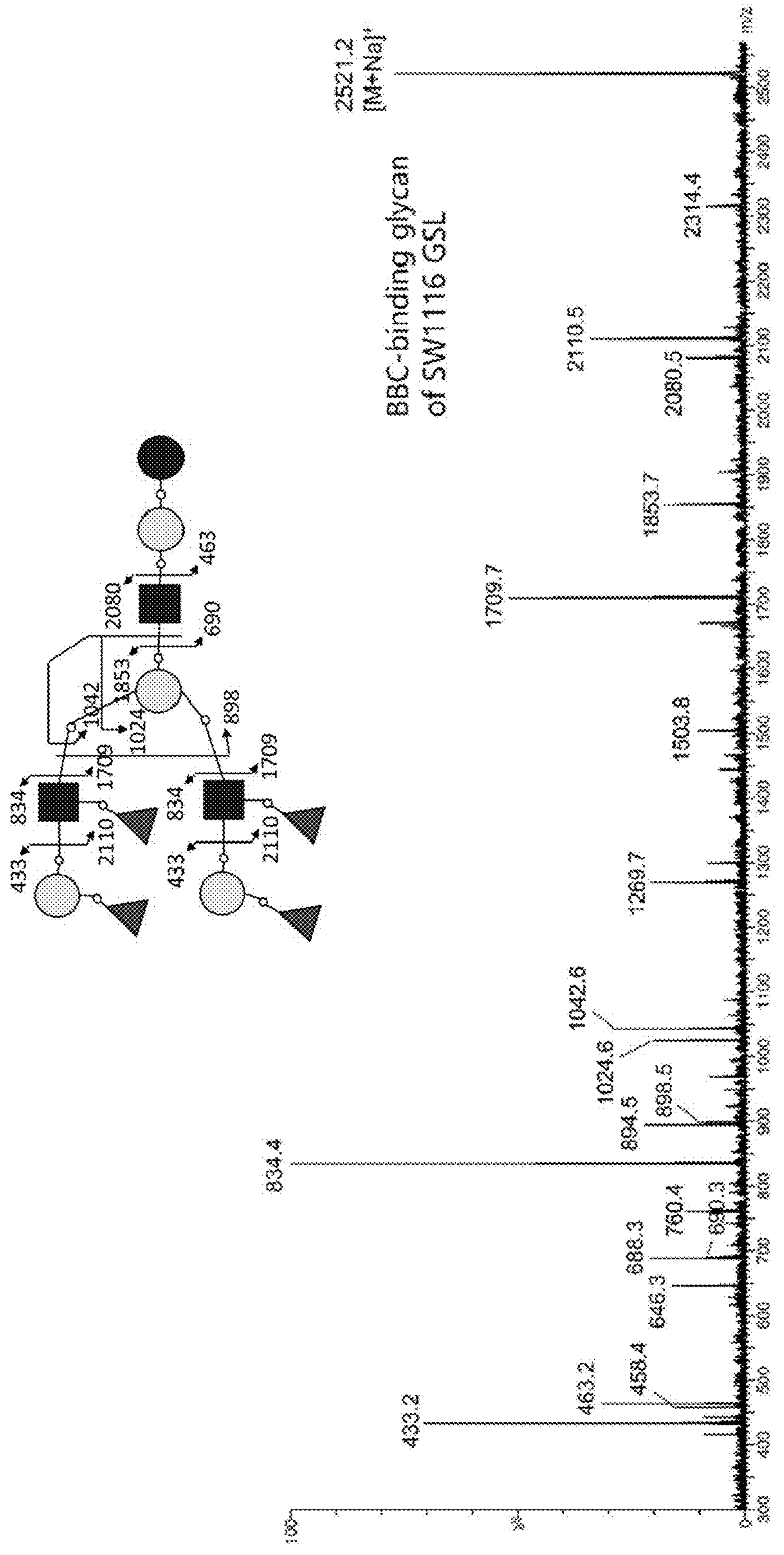

This result was further supported by immunopurification of BBC-binding glycans from GSL-derived glycans of the cell lines NCI-N87 and SW1116, which were selected for glycolipid expression of biantennary $Le^B$/on I antigen. As expected, BBC bound to the tetra-fucosylated GSL-derived glycan $Fuc_4$(LacNAc)$_3$Lac, rather than mono-, bi-, and tri-fucosylated glycans (FIGS. 5A-5B). Through MSMS sequencing, the BBC-binding glycan of NCI-N87 and SW1116 GSLs was confirmed to be the I antigen-carrying biantennary $Le^{B/Y}$ (FIGS. 6A and 6B).

Figure 7A:
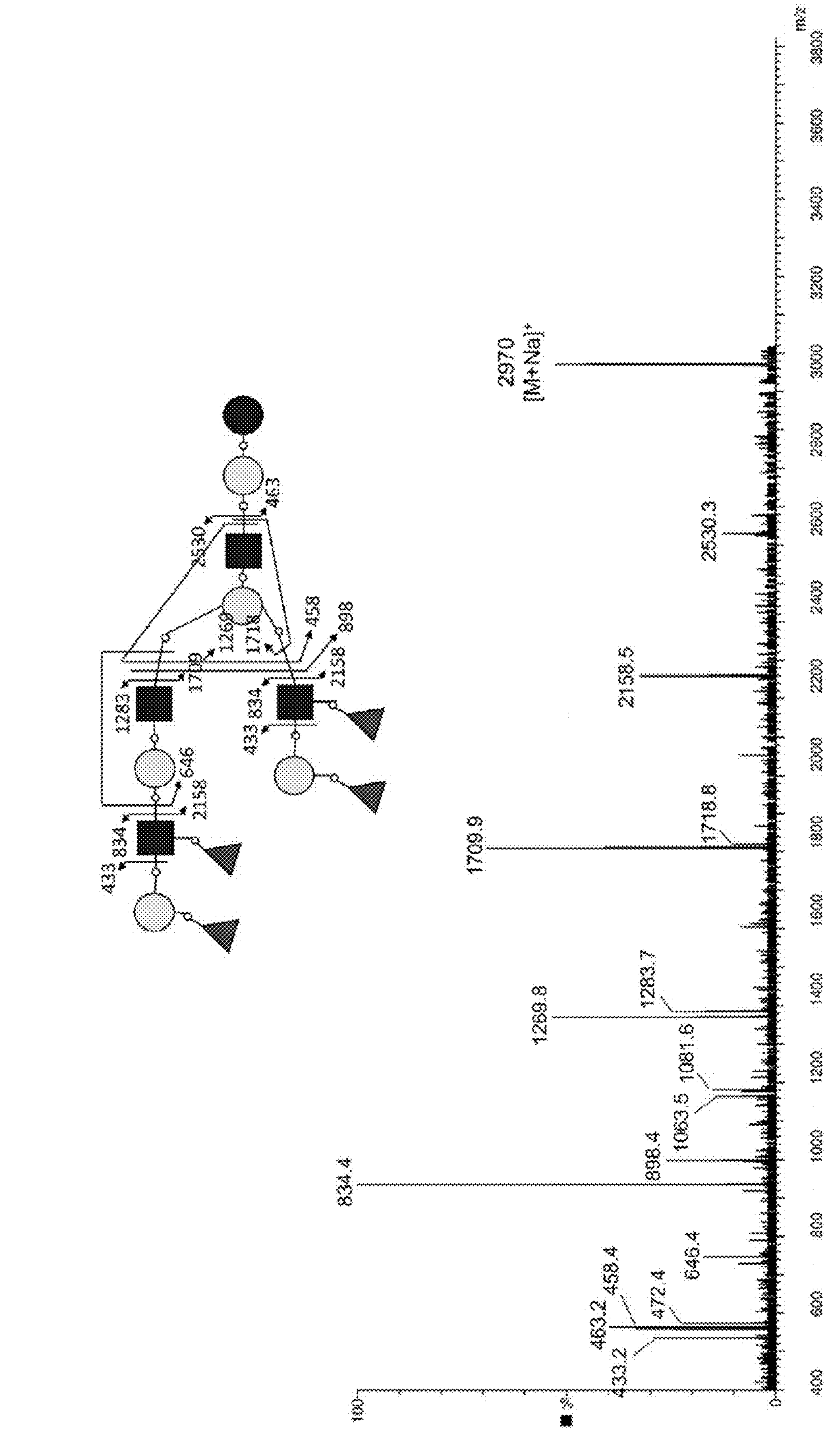
Figure 7B:
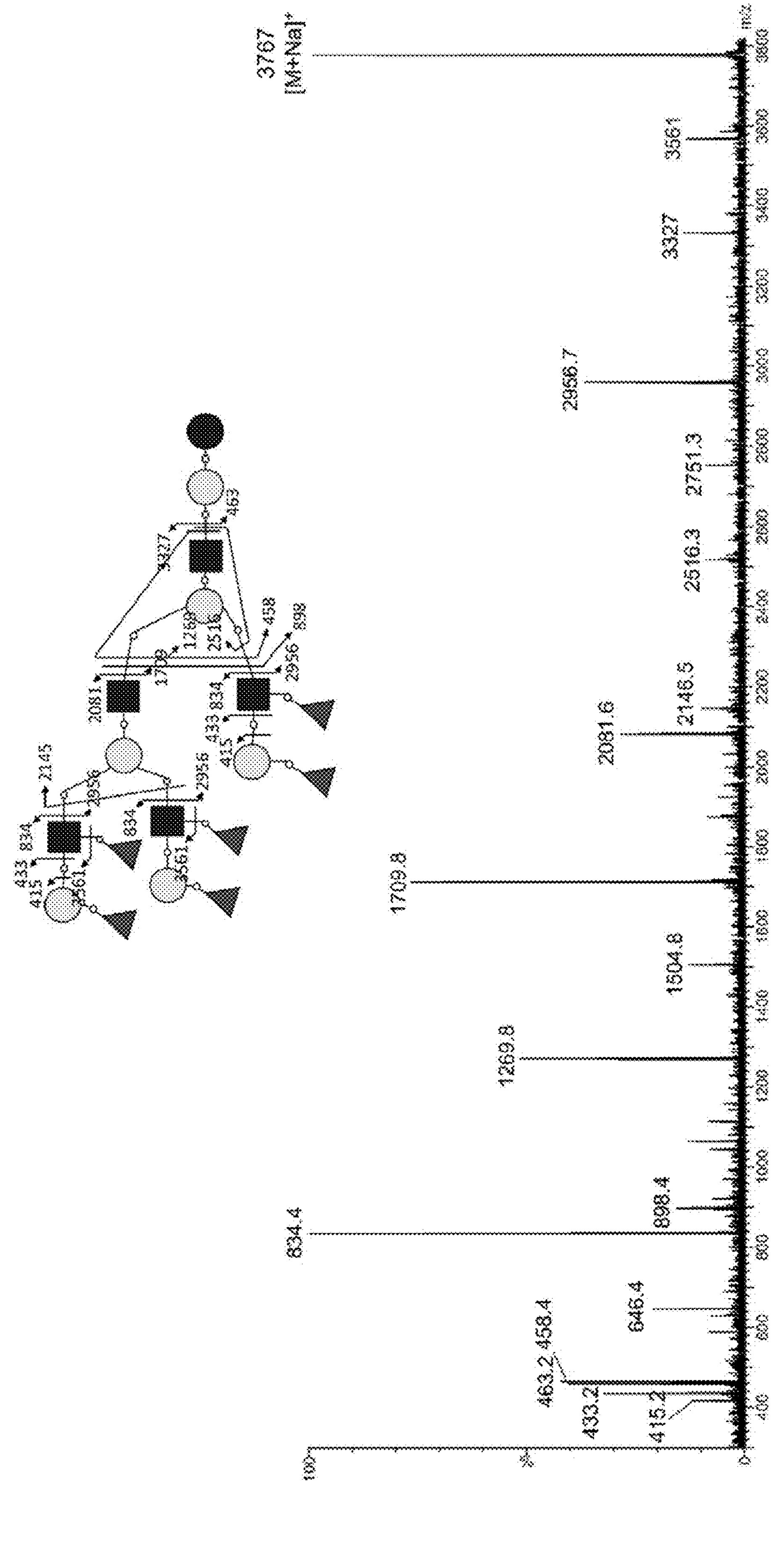
Figure 8A:
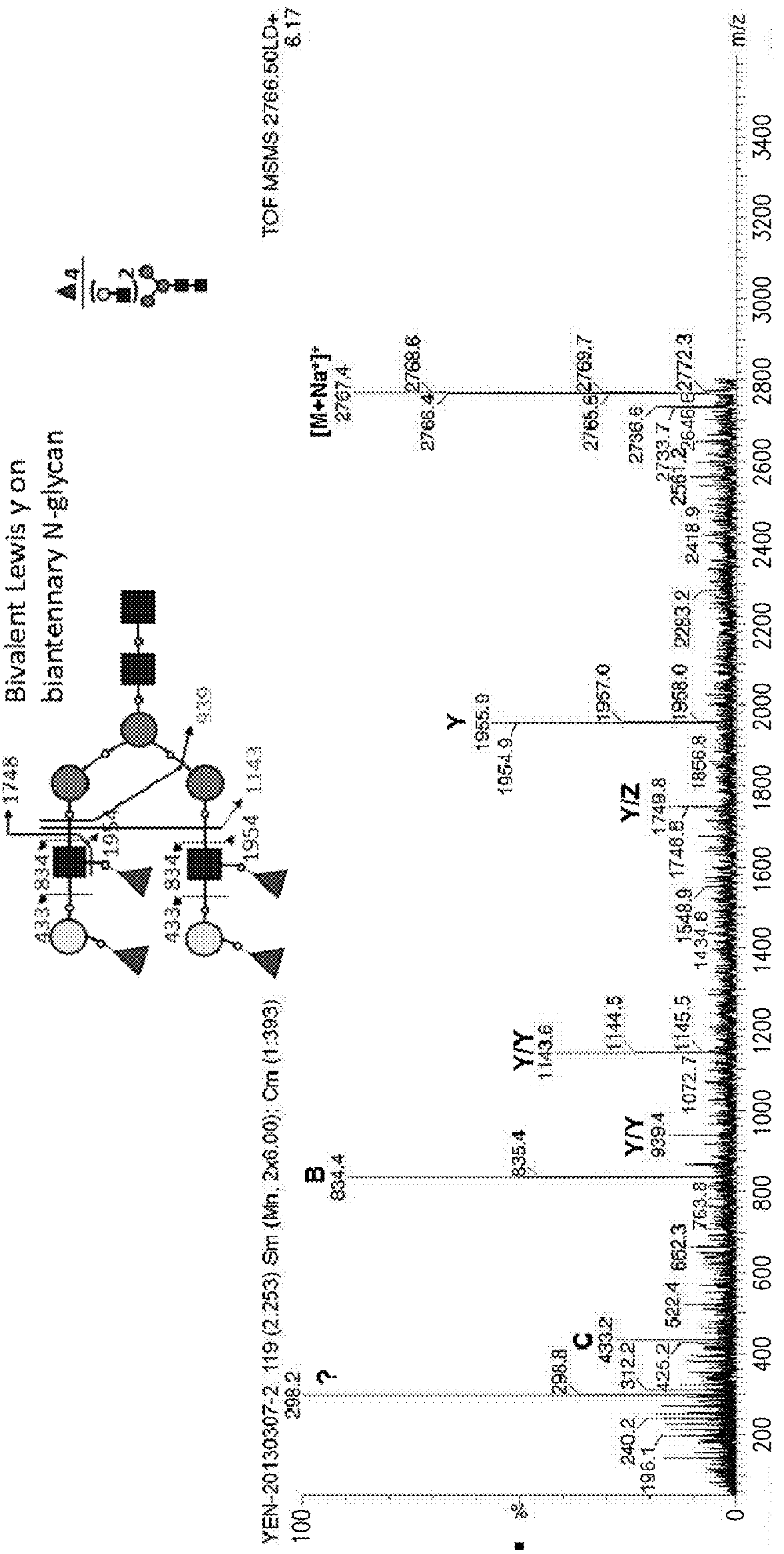
FIGS. 8A and 8B show MALDI-Q/TOF MS/MS sequencing of BBC-enriched AGS N-glycan.
Figure 8B:
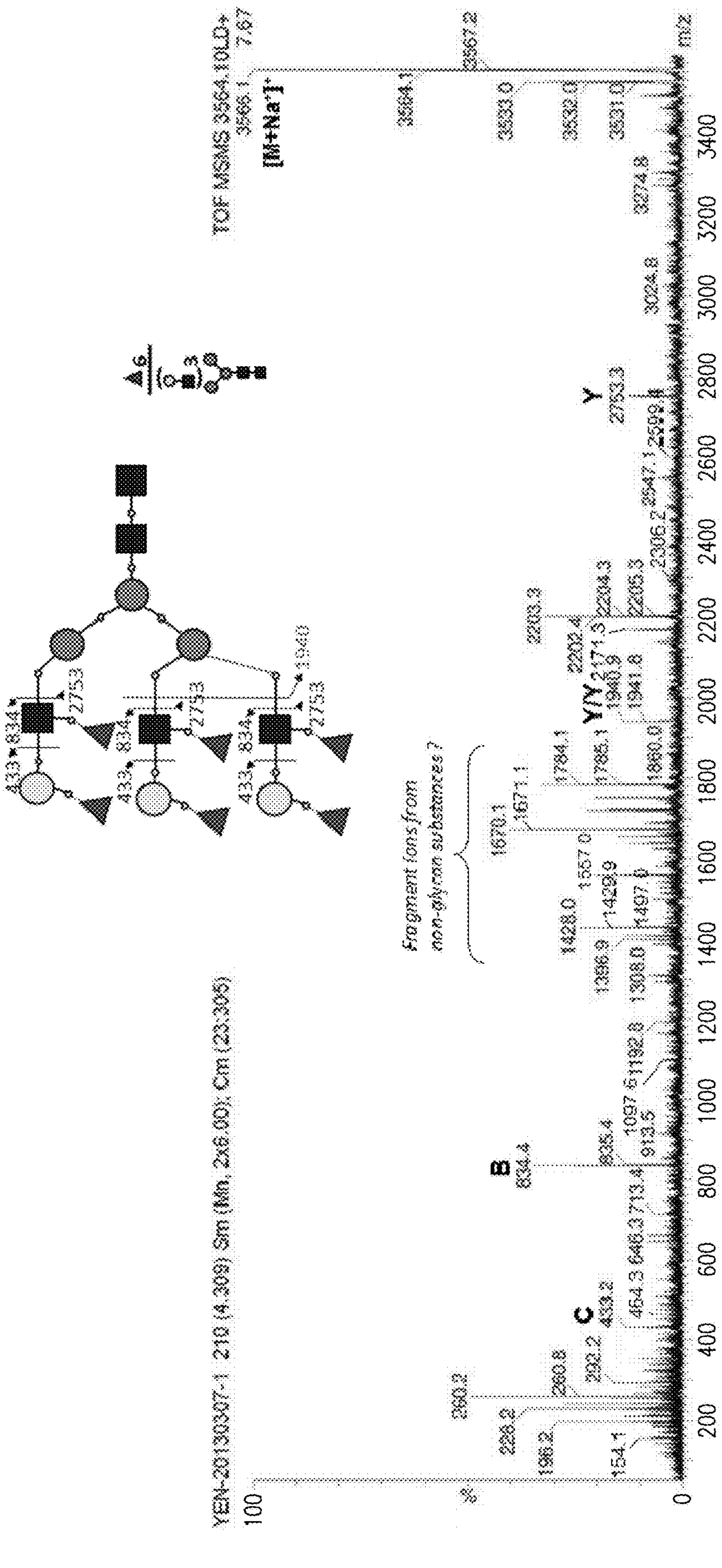
Figure 9A:
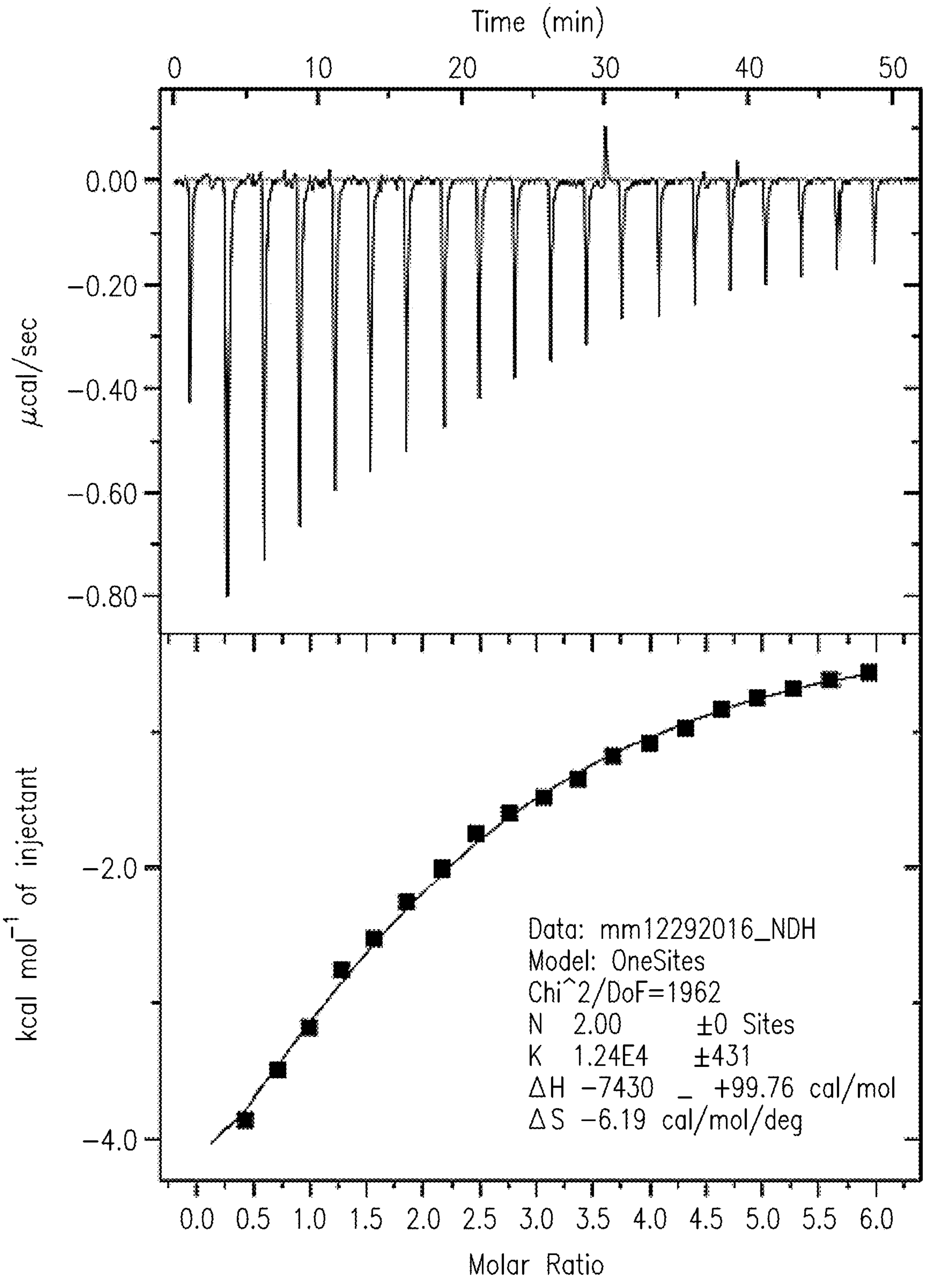
FIGS. 9A and 9B show, respectively, ITC titration graphs of glycan antigens (A) $Le^Y$-pentaose and (B) $Le^B$-pentaose with hBBC.10.1 antibody.
Figure 9B:
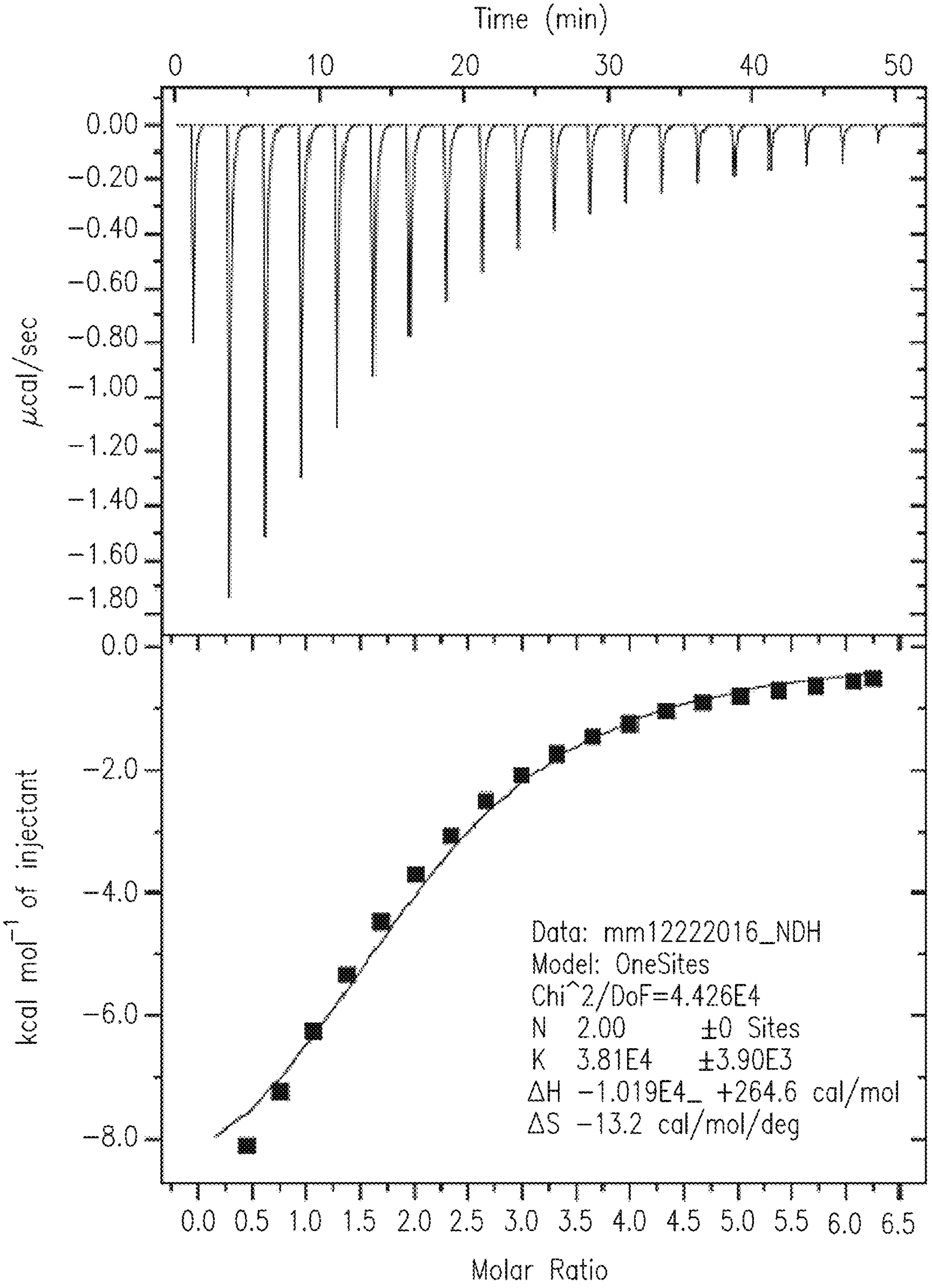
Figure 10A:
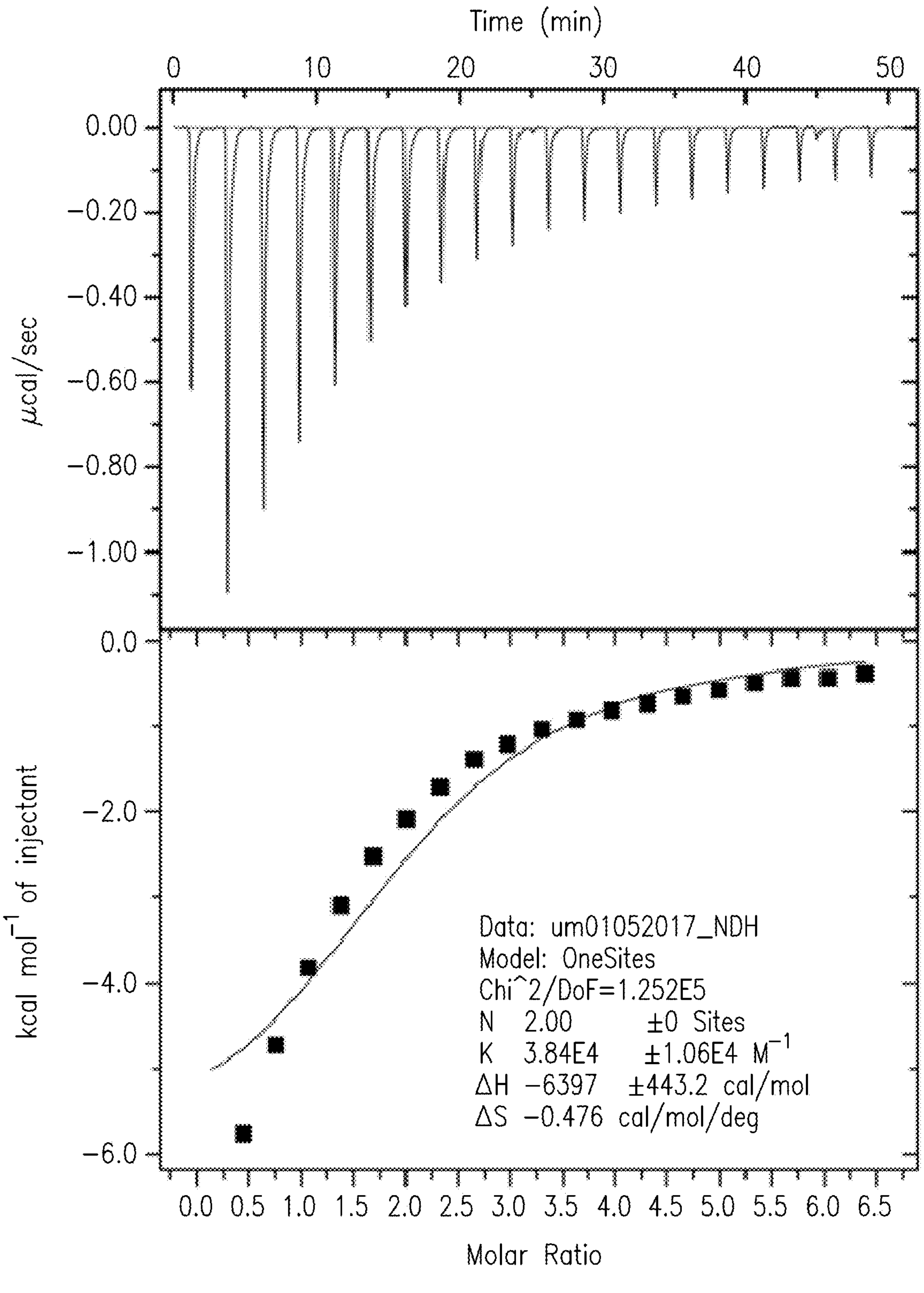
FIGS. 10A-10C show ITC titration graphs of additional glycan antigens with hBBC.10.1 antibody: (A) $Le^Y/Le^Y$-ASGA; (B) $Le^Y/Le^Y$-I antigen; (C) $Le^Y/Le^B$-I antigen.
Figure 10B:
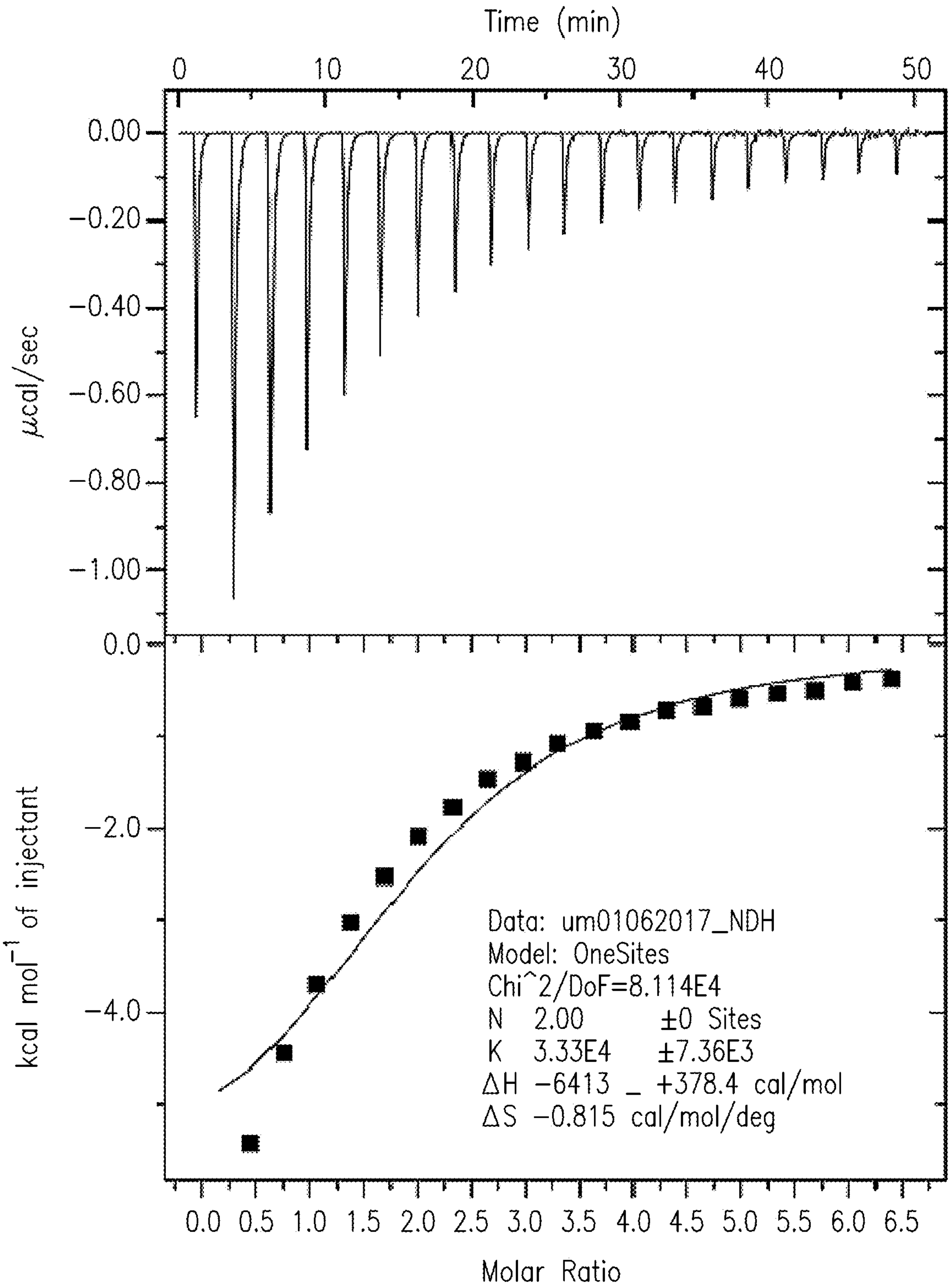
Figure 10C:
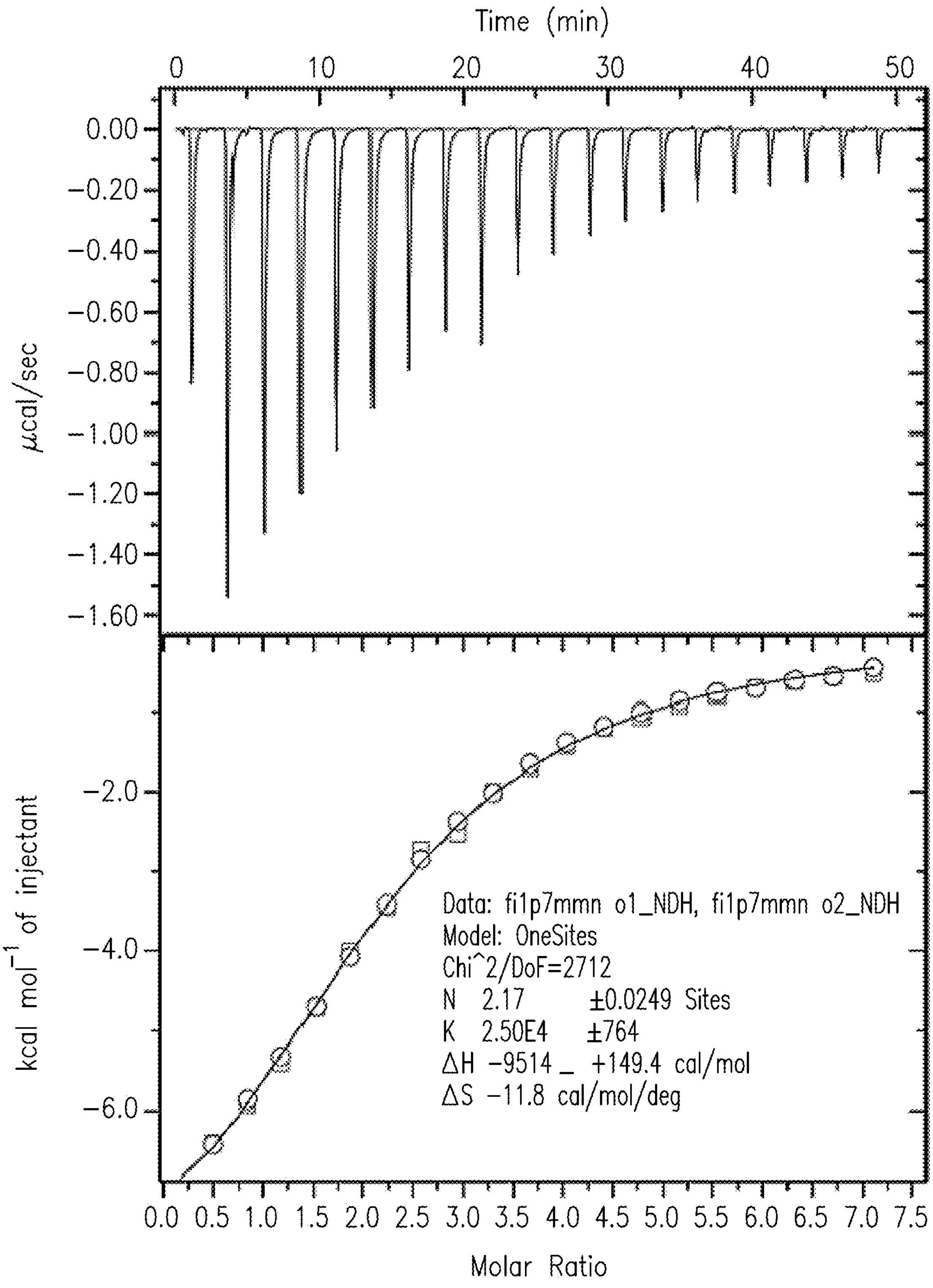
Figure 11A:
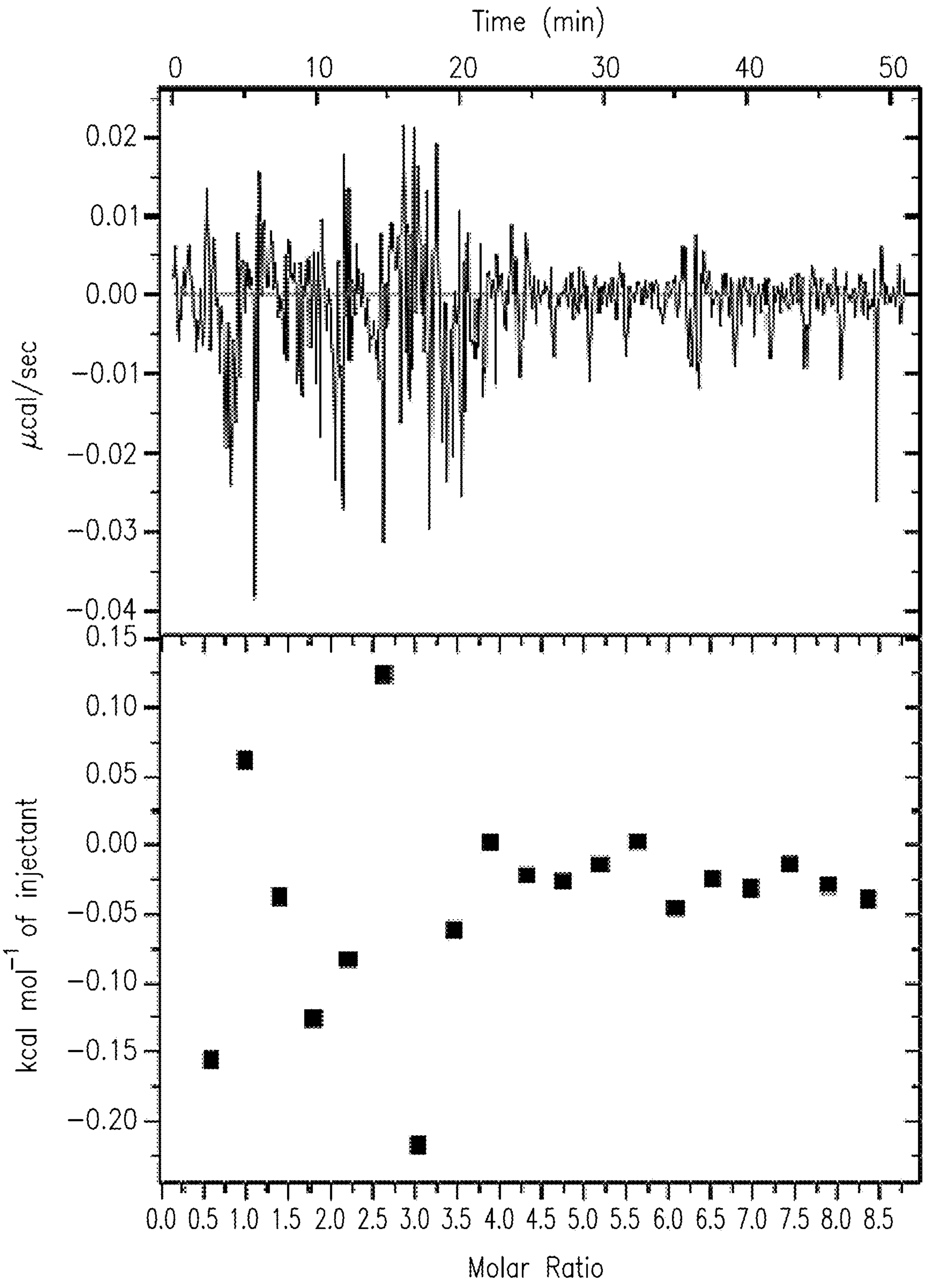
FIGS. 11A-11F show ITC titration graphs of other glycan antigens with hBBC.10.1 antibody: (A) $Le^X$-tetraose; (B) $Le^A$-tetraose; (C) H-antigen type I; (D) H-antigen type II; (E) H-ASGP; (F) $Le^X/Le^X$-ASGP.
Figure 11B:
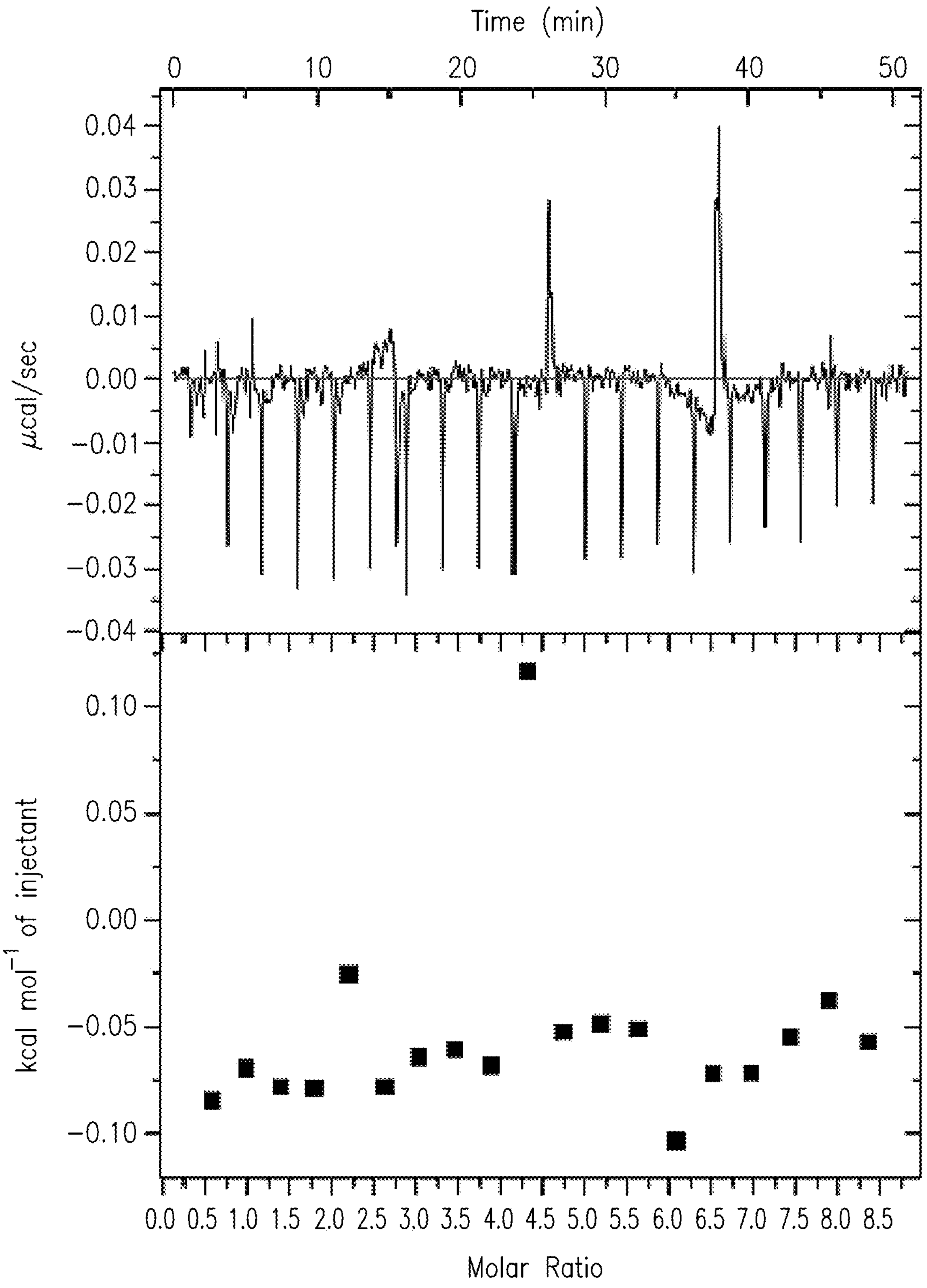
Figure 11C:
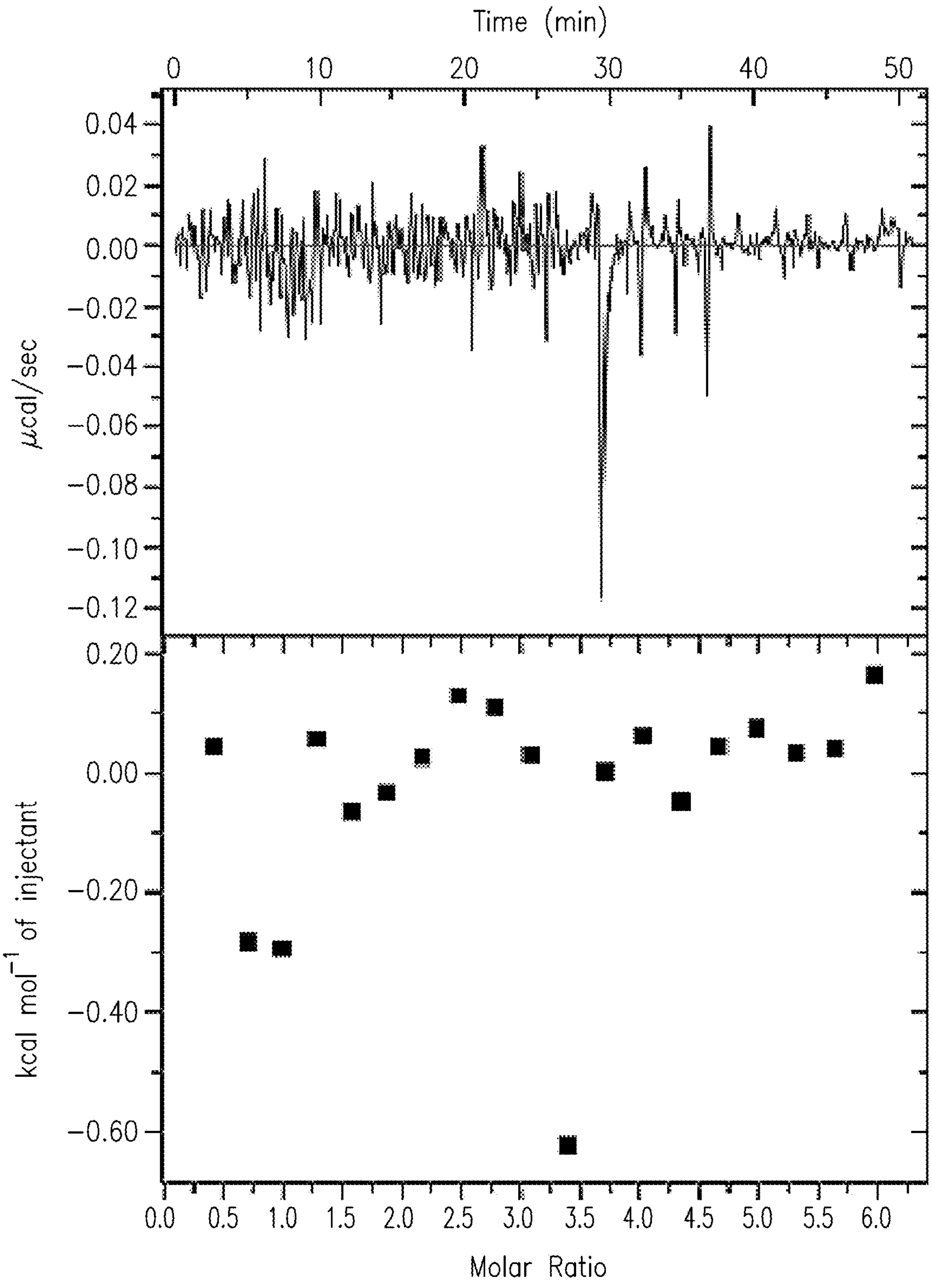
Figure 11D:
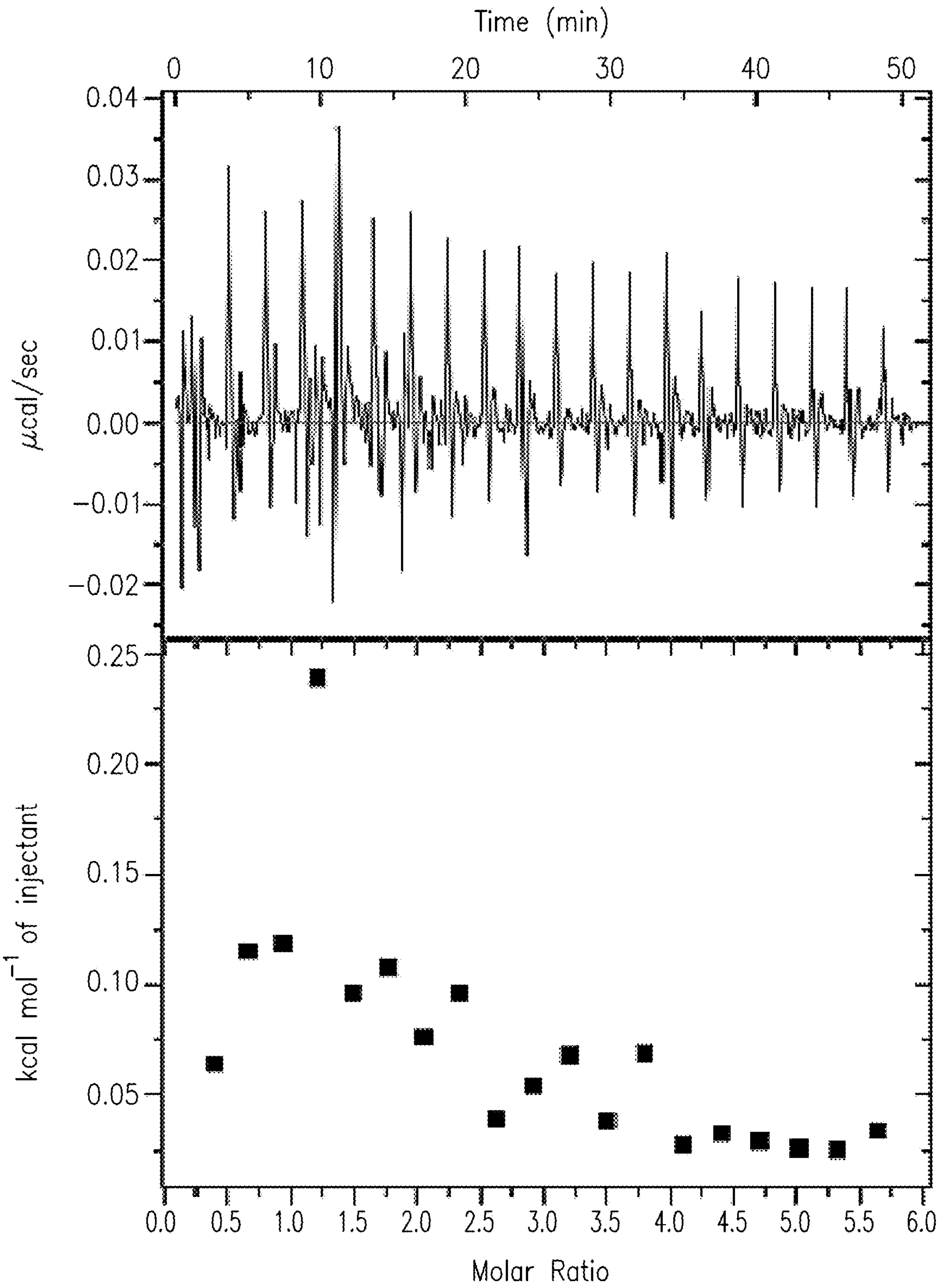
Figure 11E:
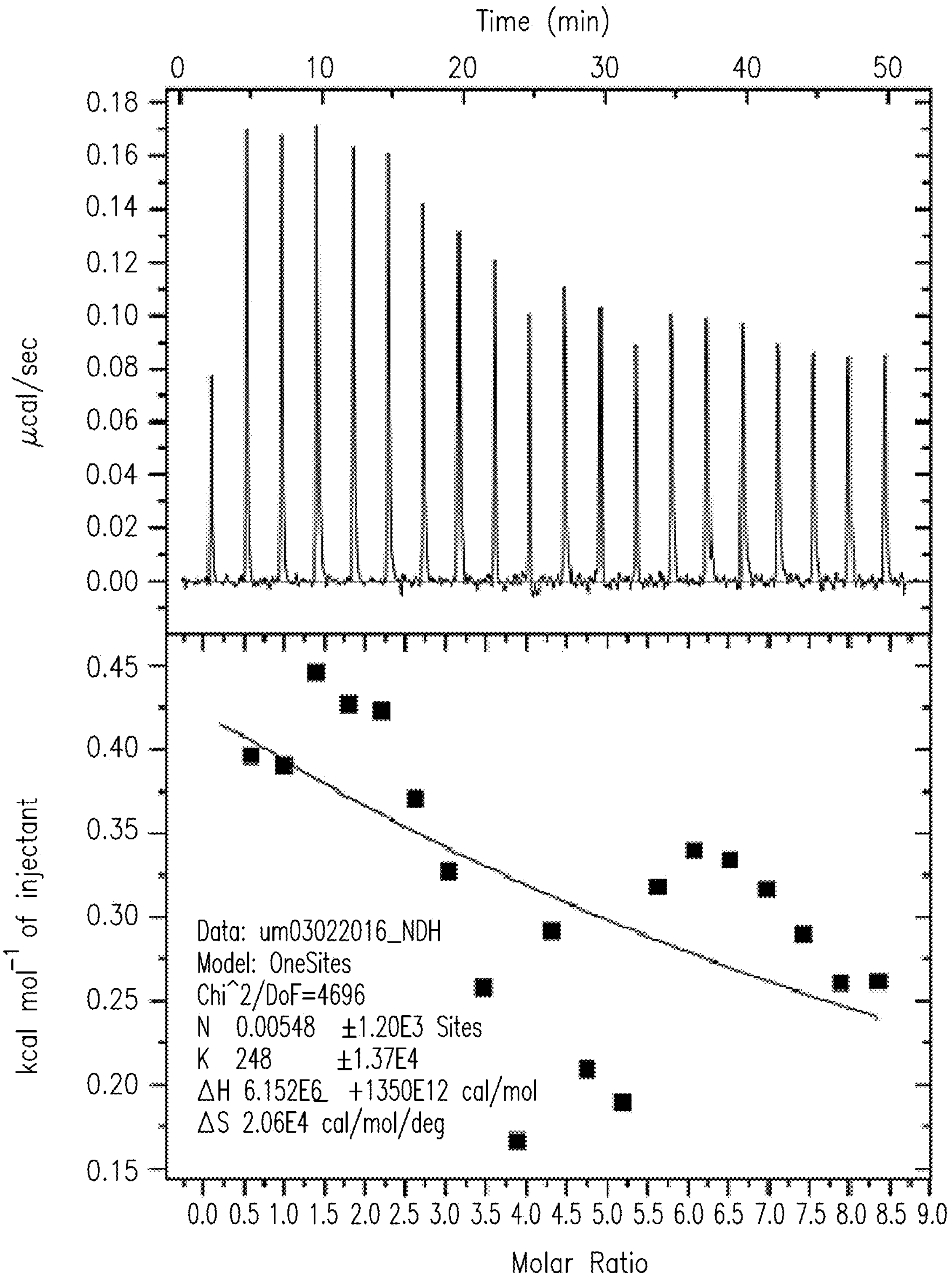
Figure 11F:
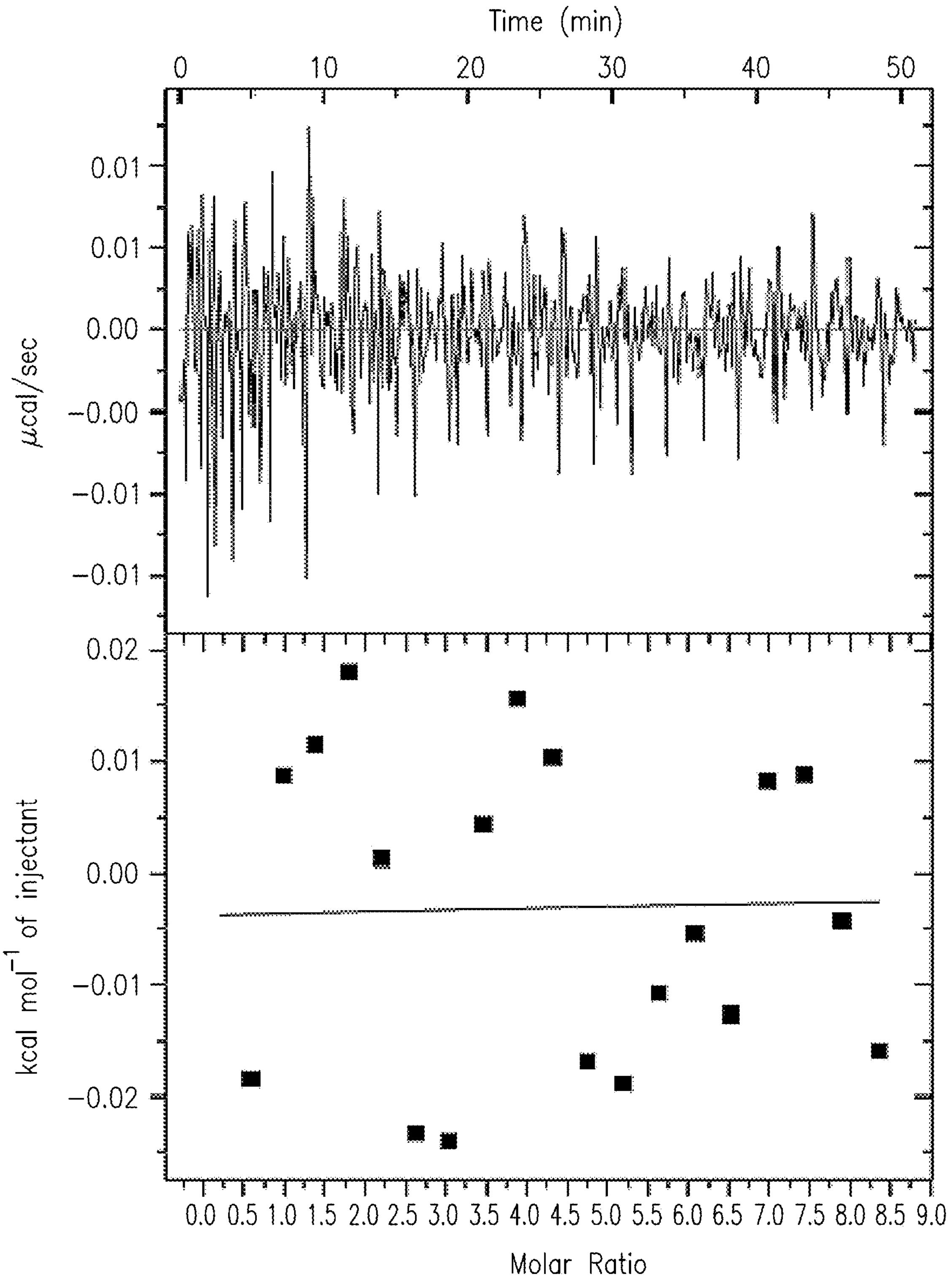

In addition to $Fuc_4$(LacNAc)$_3$Lac, a group of GSL-derived glycans from NCI-N87 and SW1116 was purified that featured multiple fucosylation (four fucose residues being the minimal requirement for binding by BBC). Two dominant BBC-binding glycans of NCI-N87 GSLs, $Fuc_4(LacNAc)_4Lac$ and $Fuc_6(LacNAc)_{4\rightarrow 5}Lac$, were sequenced using MSMS and determined to be I antigen-carrying glycan with bi- or tri-antennary $Le^Y$ (FIGS. 7A and 7B). Furthermore, when released N-glycans derived from the AGS cell line were immunopurified with BBC, the enriched N-glycans were found to be structures with bi- or tri-antennary $Le^Y$ (FIGS. 8A and 8B). This result is consistent with the enriched I antigen.

These data show that $Le^B$/Y is the binding unit of BBC. However, a monoantennary $Lewis^B$/Y is not sufficient to afford a strong binding with BBC. The unique I antigens and N-glycans with fully terminal fucoyslation provided multivalent LeBN, which is indicated to be the strong-binding epitope of BBC. Comparable immunopurification studies were also performed on hBBC and showed similar glycan enrichment specificity as BBC (data not shown), which indicated that hBBC and BBC share similar epitopes.

Isothermal Titration Calorimetry

Isothermal titration calorimetry (ITC) was performed to analyze the binding affinity between hBBC and a set of linear glycans of $Le^Y$-Gal, $Le^B$-Gal, $Le^A$-Gal, and $Le^X$-Gal, and branched glycans of $Le^Y/Le^Y$-ASGP, $Le^X/Le^X$-ASGP, H-ASGP, $Le^Y/Le^Y$-I antigen, and $Le^Y/Le^B$-I antigen. BR96 antibody (described in U.S. Pat. No. 5,491,088 A; variants described in U.S. Pat. No. 5,792,456 A) was included as a control. Because the glycans characterized from the hBBC immunopurification experiments were present in limited amounts, various $Le^B$ and $Le^Y$-related glycans were obtained from a commercial source (Elycityl S A, Crolles, France) or were enzymatically synthesized in-house according to art-established methodologies (e.g., Wu et al., 2011 *Glycobiology* 21(6): 727-733; Becker et al., 2003 *Glycobiology* 13(7): 41R-53R; de Vries et. al., 2001 *Glycobiology* 11(10): 119R-128R.

Briefly, for isothermal titration calorimetry (ITC), filtered PBS pH 7.2 was prepared in-house and the same batch of the buffer was used within one ITC injection round. mAb was pre-exchanged in filtered PBS pH 7.2 buffer with a protein concentration of 50 μM. The amount of glycan antigen was quantified by high-performance anion exchange with pulsed amperometric detection (HPAEC-PAD, e.g., Rothenhofer et al., 2015 *J. Chromatogr. B Analyt. Technol. Biomed. Life Sci.* 988:106) monosaccharide analysis with galactose as calculation standard. The quantified glycan antigen was dissolved in filtered PBS pH 7.2 (same batch as the one for mAb solution preparation) and 60 μL of solution was used for each injection.

The ITC experiment was performed on a MicroCal iTC200 system (Malvern Instruments Ltd, Malvern, UK). After loading of mAb solution (50 μM) into the sample cell of iTC200, the system temperature was set to 25° C. After the system temperature reached 25° C., the syringe was loaded with glycan antigen solution and slowly lowered into the mAb-filled sample cell. The experiment parameters were as follows: #of injections: 20; cell temperature: 25° C.; reference power: 6 μcal/s; initial delay: 60 s; sample cell concentration: 50 μM; stirring speed: 750 rpm with syringe concentration input with measured glycan antigen concentration. The injection parameters were as follows: injection volume: 2 μL; duration: 4 s; spacing: 150 s; filler period: 5 s; and the first injection volume was adjusted to 1 μL. When all settings were confirmed, the experiment was started, and the resulted data was processed by Origin for iTC200. The titration curve was fitted with One Set of Sites fitting model with repetition of 100 iterations to obtain the best fitting result. The K and $K_D$ were therefore calculated.

Figure 12A:
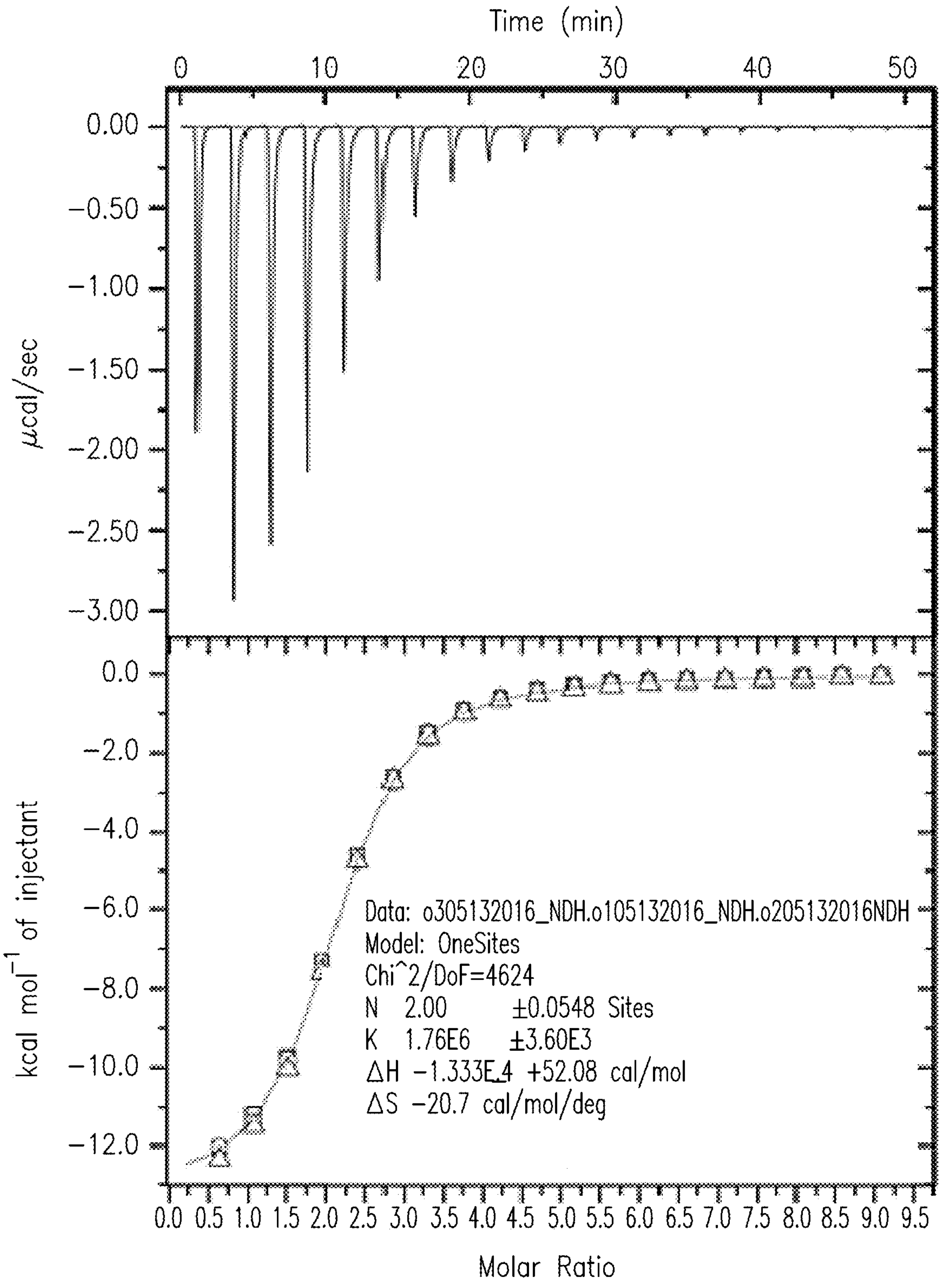
FIGS. 12A-12C provide ITC titration graphs of glycan antigens with a reference antibody "BR96": (A) $Le^Y$-pentaose; (B) $Le^Y/Le^Y$-I antigen, and C) $Le^Y/Le^Y$-ASGP.
Figure 12B:
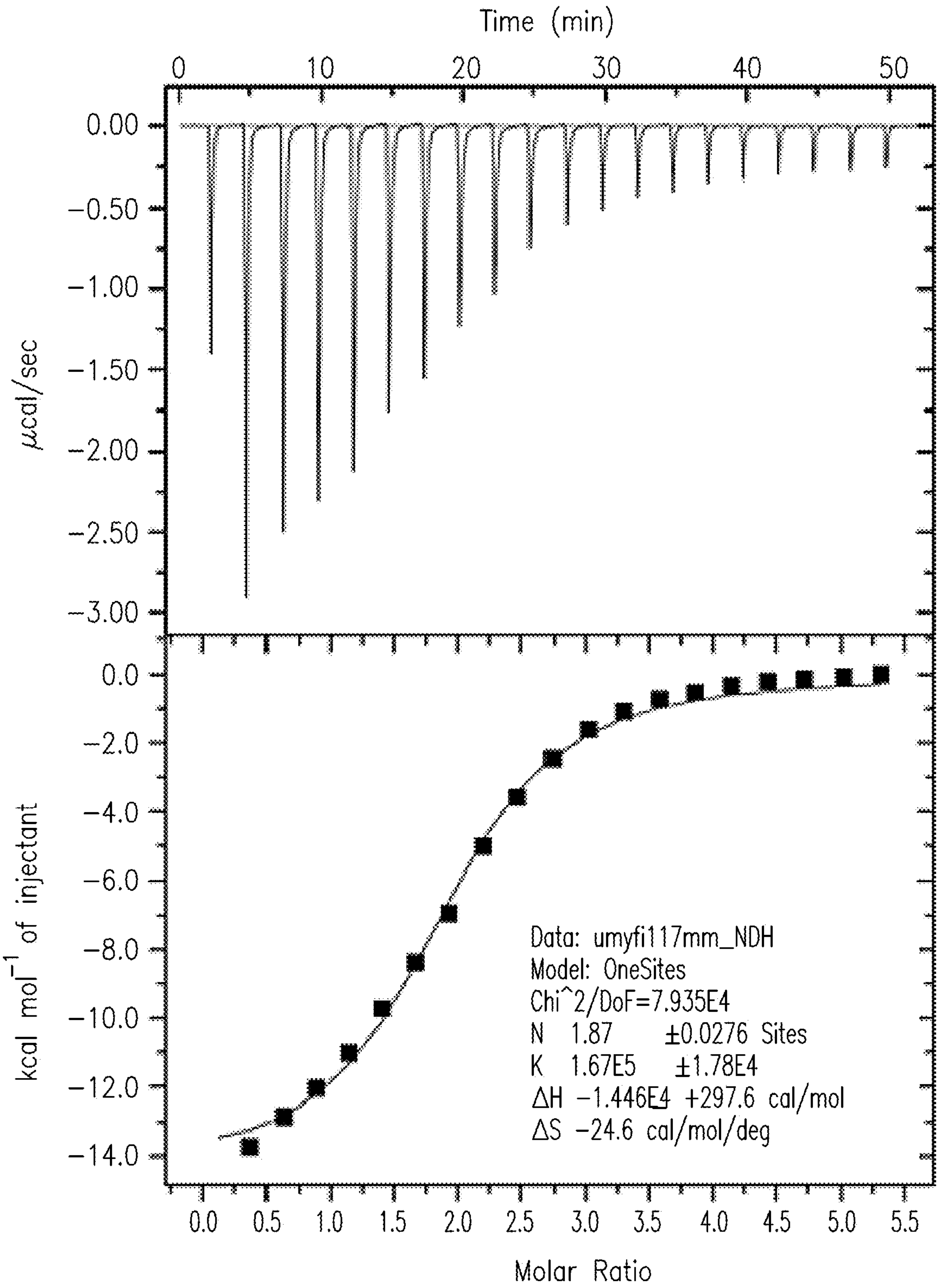
Figure 12C:
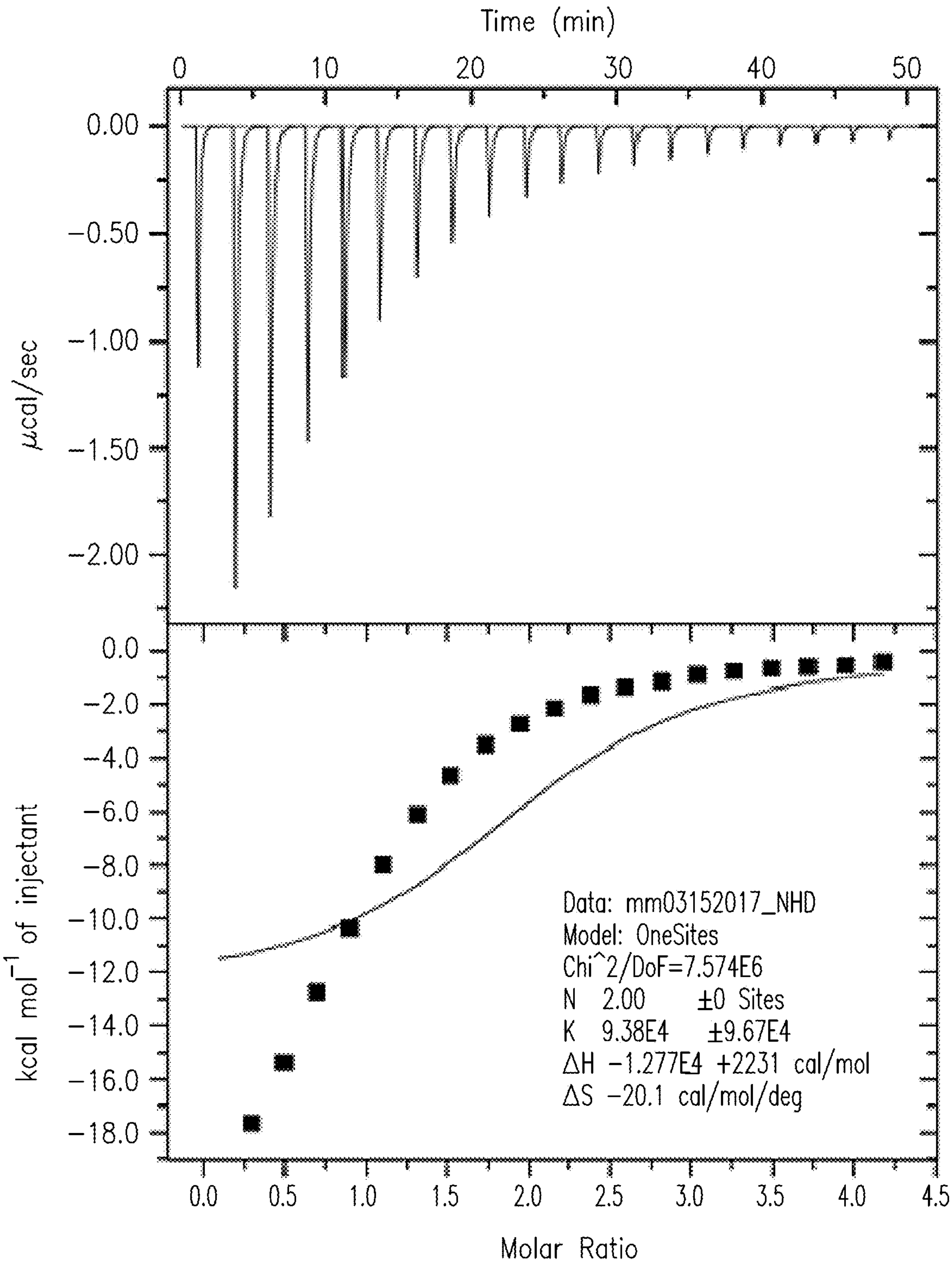

ITC titration graphs of various glycan antigens with hBBC antibody are shown in FIGS. 9A, 9B, 10A-10C, and 11A-11F. ITC titration graphs of various glycan antigens with BR96 antibody are shown in FIGS. 12A-12C. Briefly, the ITC analysis showed that hBBC has higher specific binding affinity against $Le^B$-Gal (KD=26.2 μM) than $Le^Y$-Gal (KD=80.6 μM). Furthermore, hBBC showed stronger binding affinity for biantennary structures ($Le^Y/Le^Y$-ASGP, $Le^Y/Le^Y$-I antigen, and $Le^Y/Le^B$-I antigen) than for single chain $Le^Y$-Gal antigens. The binding affinity of hBBC towards $Le^Y/Le^Y$-ASGP, $Le^Y/Le^Y$-I antigen and $Le^B/Le^Y$-I antigen appeared similar, suggesting that for biantennary glycan epitopes, $Le^Y$ and $Le^B$ side chains have comparable contributions to specific binding. Furthermore, as shown in FIGS. 11A-F, glycan antigens lacking tetra-fucosylated LacNAc moiety(s), whether in single chain or biantennary form ($Le^X$-Gal, $Le^A$-Gal, H-antigen type I, H antigen type II, H-ASGP, and $Le^X/Le^X$-ASGP), showed no specific binding with hBBC. These results indicate that tetra-fucosylated LacNAc with either type I or II linkage is necessary for specific binding by hBBC. In summary, consistent with the immunopurification data, ITC results showed that hBBC binds an epitope that includes structures containing $Le^Y$ and/or $Le^B$ (Table 4 and the Figures referenced therein). The BR96 control showed similar to slightly higher binding affinity for single chain $Le^Y$-Gal as compared to the biantennary $Le^Y/Le^Y$-I antigen and biantennary $Le^Y/Le^Y$-ASGP (FIGS. 12A-12C), suggesting that BR96 has no specific selectivity between single chain and biantennary $Le^Y$ glycans. Thus, hBBC possesses unique epitope specificity as compared to BR96.

TABLE 4

Isothermal Titration Calorimetry Results

| Antigen structure | Antigen name | hBBC | BR96 |
|---|---|---|---|
| FIG. 25A | $Le^Y$-Gal | $K_D$ = 80.6 μM | $K_D$ = 5.68 μM |
| FIG. 25B | $Le^B$-Gal | $K_D$ = 26.2 μM | n/a |
| FIG. 25C | $Le^Y/Le^Y$-ASGP | $K_D$ = 25.9 μM | $K_D$ = 10.66 μM |
| FIG. 25D | H-ASGP | No specific binding detected | n/a |
| FIG. 25E | $Le^X/Le^X$-ASGP | No specific binding detected | n/a |
| FIG. 25F | $Le^Y/Le^Y$-I antigen | $K_D$ = 30.0 μM | $K_D$ = 5.99 μM |
| FIG. 25G | $Le^Y/Le^B$-1 antigen | $K_D$ = 40 μM | n/a |
| FIG. 25H | $Le^A$-Gal | No specific binding detected | n/a |
| FIG. 25I | $Le^X$-Gal | No specific binding detected | n/a |
| FIG. 25J | H antigen type I | No specific binding detected | n/a |
| FIG. 25K | H antigen type II | No specific binding detected | n/a |

These results partially characterize the hBBC epitopes. However, the interaction between free-flowing hBBC and immobilized glycans provides additional information about the epitope; therefore, hBBC was tested with a series of immobilized glycans in surface plasmon resonance (SPR) and ELISA experiments. Streptavidin-coated analytical surfaces and biotin-conjugated glycans ($Le^Y$-Gal-biotin, $Le^B$-Gal-biotin, $Le^Y/Le^Y$-ASGA-biotin, and $Le^B/Le^B$ ASGA-biotin for SPR; $Le^Y$-Gal-biotin, $Le^B$-Gal-biotin, $Le^Y/Le^Y$-ASGA-biotin, $Le^B/Le^B$-ASGA-biotin, 3-$Le^Y$/6-$Le^B$-ASGA- Biotin, and 3-$Le^B$/6-$Le^Y$-ASGA-Biotin for ELISA) were utilized, as shown in Table 5 (with reference to the Figures noted therein).

TABLE 5

Structure and MW of glycan antigens used for SPR and ELISA

Figure 26A:
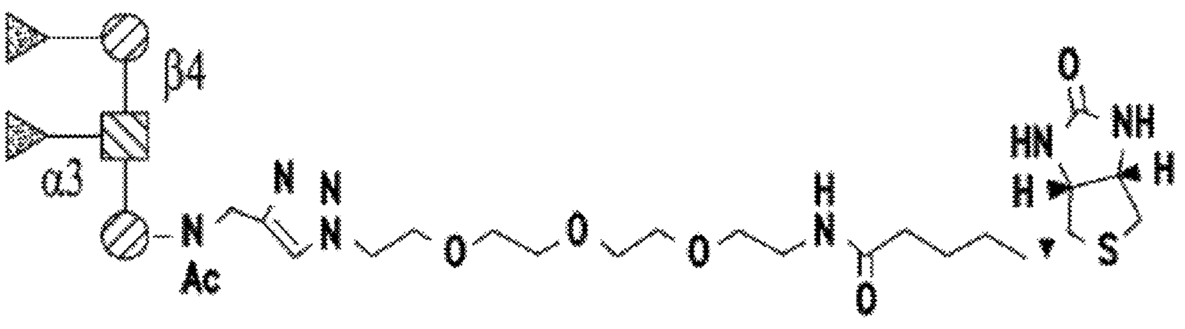
FIG. 26A illustrates the structure of antigen $Le^Y$-Gal-sp3-biotin.
Figure 26B:
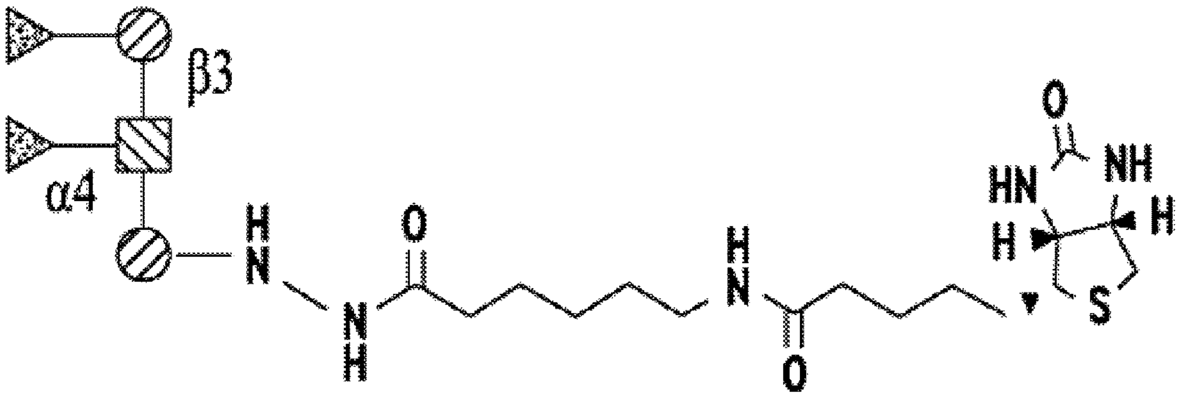
FIG. 26B illustrates the structure of antigen $Le^B$-Gal-LC-biotin.
Figure 26C:
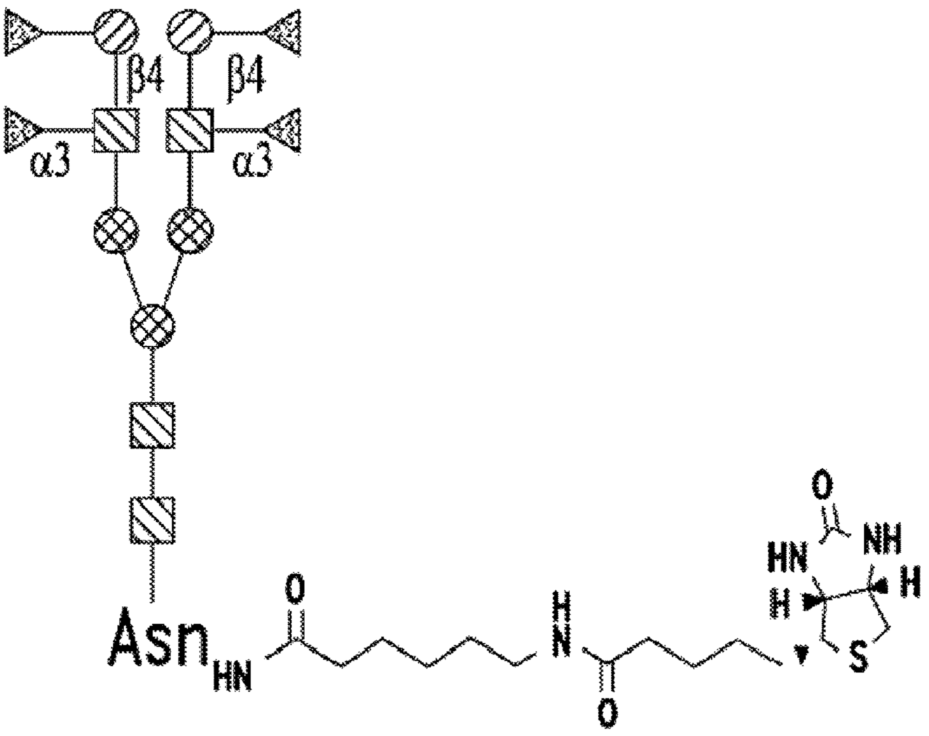
FIG. 26C illustrates the structure of antigen $Le^Y/Le^Y$-ASGA-biotin.
Figure 26D:
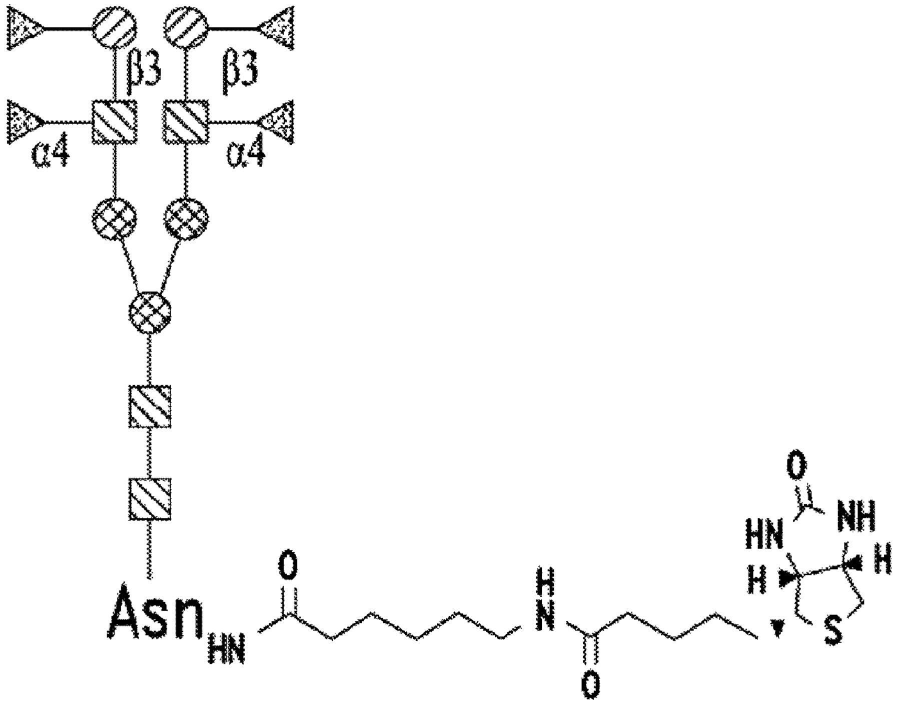
FIG. 26D illustrates the structure of antigen $Le^B$/$Le^B$-ASGA-biotin

| Antigen | Structure | Molecular weight |
|---|---|---|
| $Le^Y$-Gal-sp3-biotin | FIG. 26A | 1361.4 |
| $Le^B$-Gal-LC-biotin | FIG. 26B | 1191.25 |
| $Le^Y$/$Le^Y$-ASGA-biotin | FIG. 26C | 2679.61 |
| $Le^B$/$Le^B$-ASGA-biotin | FIG. 26D | 2679.61 |
| 3-$Le^Y$/6-$Le^B$-ASGA-biotin | FIG. 26E | 2679.61 |
| 3-$Le^B$/6-$Le^Y$-ASGA-biotin | FIG. 26F | 2679.61 |

Surface Plasmon Resonance

Figure 13A:
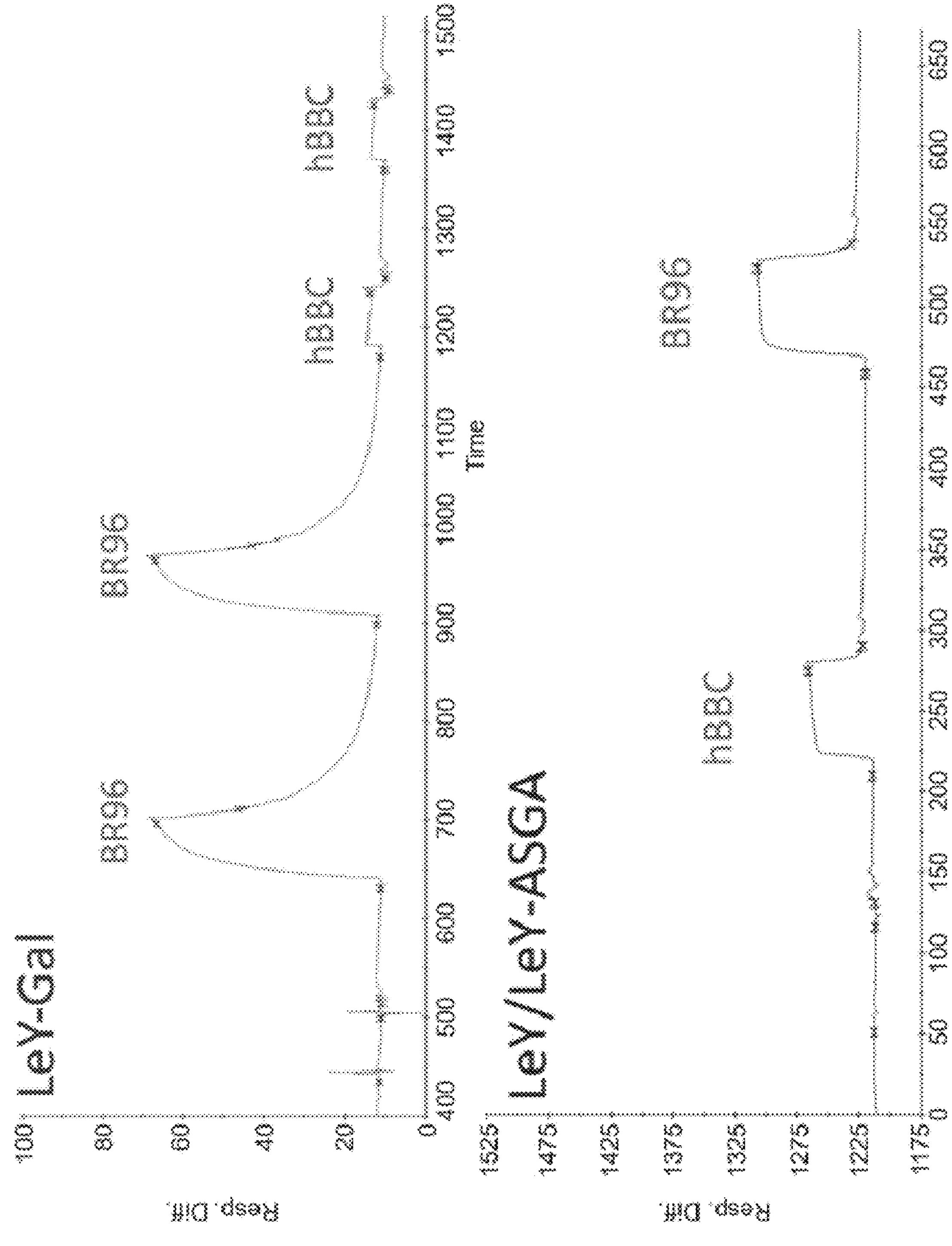
FIGS. 13A and 13B show surface plasmon resonance (SPR) sensorgrams of hBBC.10.1 and BR96 against the indicated glycan antigens: (A) $Le^Y$-Gal and $Le^Y/Le^Y$-ASGA; (B) $Le^B$-Gal and $Le^B/Le^B$-ASGA.
Figure 13B:
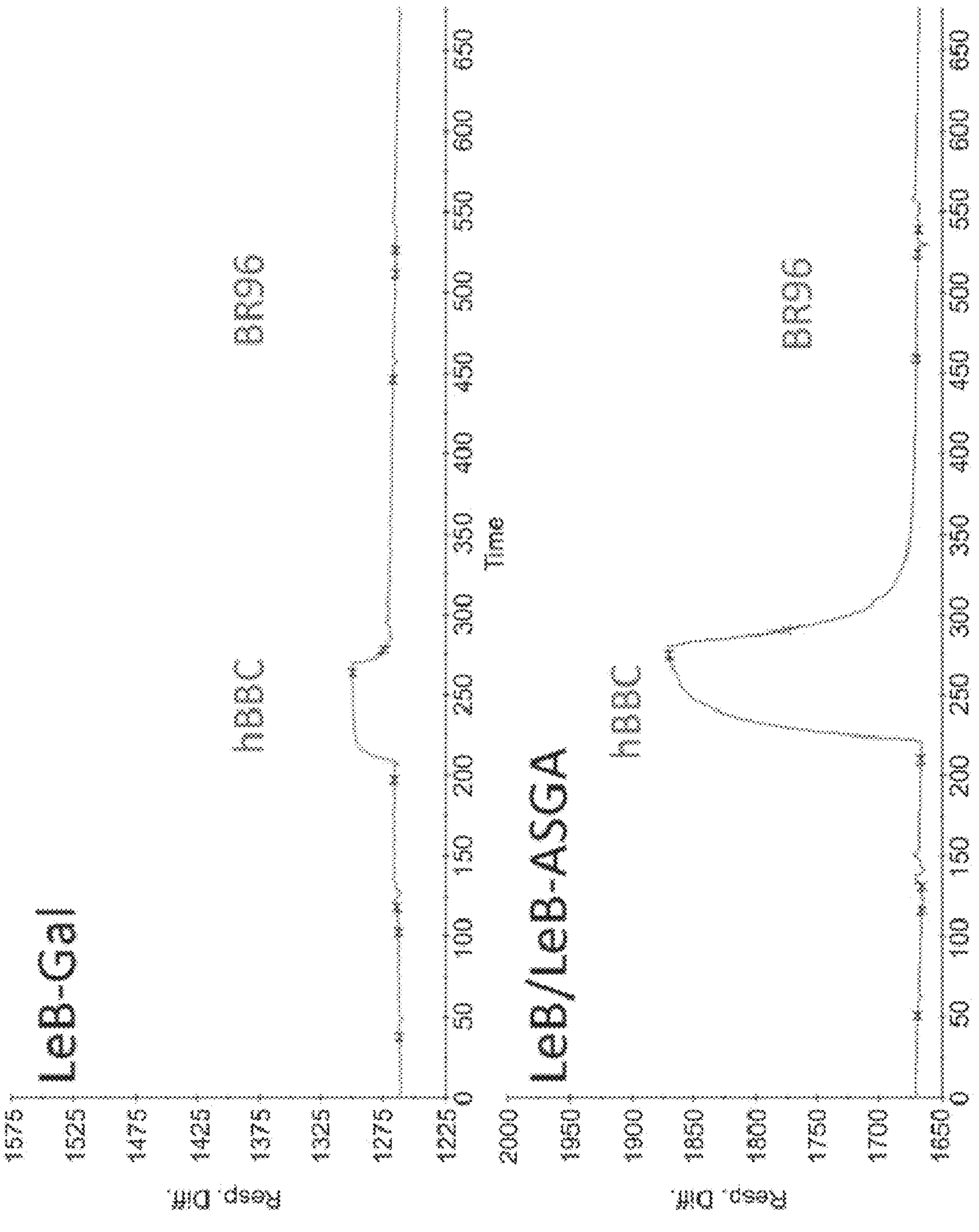

The binding affinity of hBBC for $Le^Y$-Gal-Biotin, $Le^B$-Gal-Biotin and $Le^Y$/$Le^Y$-ASGA-Biotin was analyzed by surface plasmon resonance (SPR) on streptavidin coated chips. Briefly, Biacore T100 was used with HBS-EP+ buffer (GE Healthcare) used as running buffer. Biotinylated glycan was diluted to 10 μM and immobilized to the sensor chip SA (GE Healthcare) according to the standard procedure. The glycans were immobilized at a flow rate of 10 μL/min for 60 s. hBBC or BR96 was buffer-exchanged to the HBS-EP+ buffer with Zeba desalting spin column (7K MWCO, 0.5 mL, ThermoFisher) and serially diluted to 480, 240, 120, 60, and 30 nM with HBS-EP+ buffer. Single-cycle kinetic analysis was performed. Antibody was associated to the glycans at the flow rate of 30 μL/min for 150 s and dissociated for 300 s. The chip was regenerated with 2 M $MgCl_2$ at the flow rate of 50 μL/min for 120 s. Data was evaluated with Biacore T200 Evaluation software (GE Healthcare). Two-state reaction was used for the curve-fitting and best-fit values of ka, kd and KD were obtained (Table 6). SPR sensorgrams showing binding of hBBC and BR96 against various glycan antigens are provided in FIGS. 13A and 13B.

TABLE 6

Summary of SPR Results

| Antigen name | hBBC | BR96 |
|---|---|---|
| $Le^Y$-Gal-Biotin | 40~59 μM | 270 nM |
| $Le^B$-Gal-Biotin | 2.3~3.1 μM | n/a |
| $Le^Y$/$Le^Y$-ASGA-Biotin | 2~3 μM | 1 μM |
| $Le^B$/$Le^B$-ASGA-Biotin | 1 μM | n/a |

SPR showed that the biantennary $Le^Y$/$Le^Y$-ASGA-Biotin presented higher affinity towards hBBC compared to single chain $Le^Y$-Gal-Biotin, which was consistent with the ITC result. In addition, the biantennary $Le^B$/$Le^B$-ASGA-Biotin presented higher affinity towards hBBC compared to single chain $Le^B$-Gal-Biotin, which is also in agreement with the observed trend for $Le^Y$ antigens. hBBC presented higher affinity towards $Le^B$-Gal-Biotin versus $Le^Y$-Gal-Biotin, which is comparable with the ITC result. The SPR also showed that hBBC has higher binding affinity towards $Le^B$/$Le^B$-ASGA-Biotin than $Le^Y$/$Le^Y$-ASGA-Biotin, which was consistent with the observation that hBBC has higher affinity towards $Le^B$-based antigen than $Le^Y$-based antigen. The comparable KD values of hBBC obtained from $Le^B$/$Le^B$-ASGA and $Le^Y$/$Le^Y$-ASGA further indicate that hBBC specifically associates with multi-fucosylated, namely bivalent Lewis B or Lewis Y structures. Notably, hBBC response to $Le^B$/$Le^B$-ASGA was stronger (sensorgram) than response to $Le^B$-Gal, though similar KD values were obtained from two antigens. $Le^B$/$Le^B$-ASGA appears to be the structure of highest affinity to hBBC.

By comparison, BR96 showed slightly higher affinity towards $Le^Y$-Gal-Biotin and $Le^Y$/$Le^Y$-ASGA-Biotin, which is comparable to the result from ITC when it comes to the structurally similar antigen $Le^Y$/$Le^Y$-ASGP. In summary, the SPR data was highly consistent with data from the ITC experiment.

Indirect ELISA

To evaluate antibody binding affinity by ELISA, the biotinylated glycan antigens were diluted to the adequate concentration in PBS buffer. 100 μL diluted antigen solution was applied to a streptavidin-coated 96-well assay plate and incubated in a shaker at 37° C. for 3.5 hours. The plate was washed with PBST (0.05% Tween-20 in PBS buffer) to remove excess glycan antigens. Primary antibodies serially titrated in diluent (0.1% BSA in PBS buffer) were applied to the assay plate and incubated in a shaker at 37° C. for 1 hour. Followed by PBST washing, 100 μL HRP-conjugated anti-human IgG antibody solution (SouthernBiotech, 1:15,000 dilution in diluent) was incubated in the assay plate in a shaker at 37° C. for 1 hour. After washing out the excess secondary antibody, 100 μL TMB reagent was applied and incubated at 37° C. for 15 min followed by quenching with 50 μL of 0.5 N HCl. The OD value was detected at 450 nm and subtracted by the value at 650 nm in a VERSA max microplate reader (Molecular Devices). The data was processed in Softmax Pro (Molecular Devices)

$Le^Y$/$Le^Y$-ASGA vs $Le^Y$-Gal

Figure 14A:
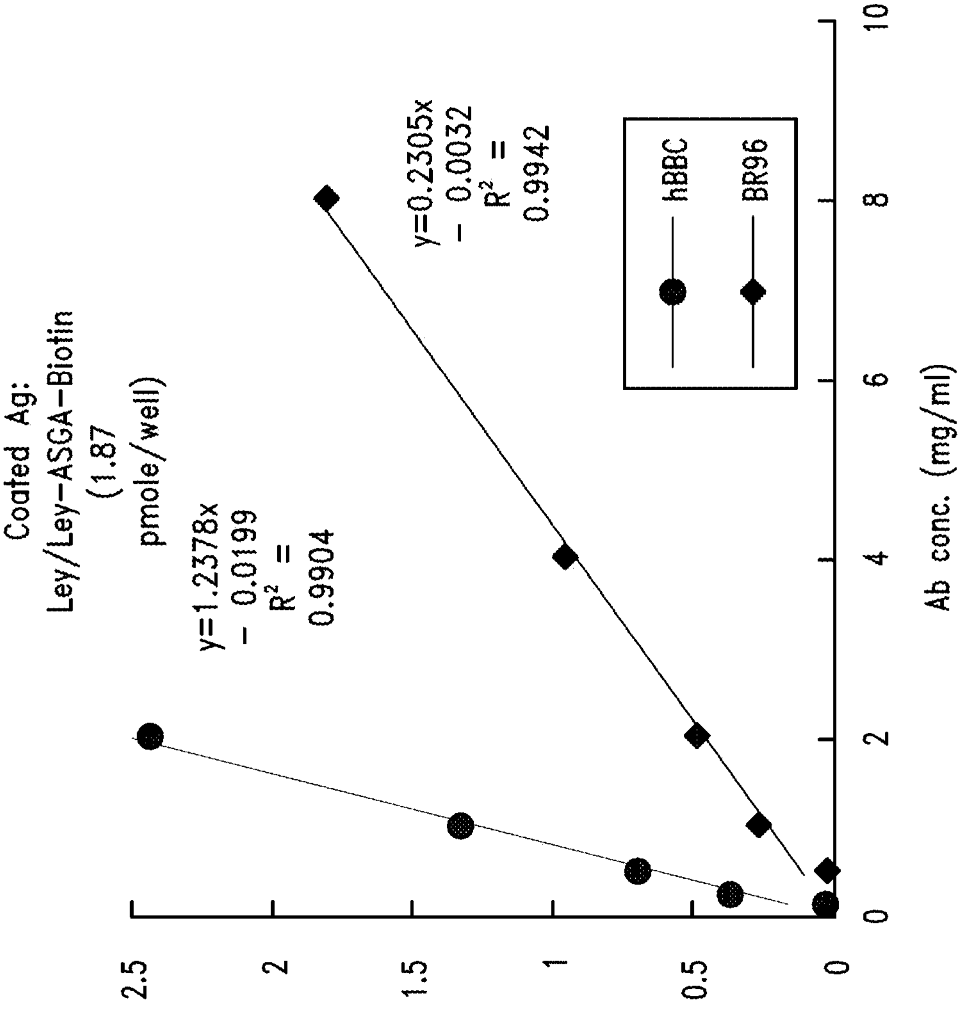
FIGS. 14A and 14B show results from an indirect ELISA of hBBC.10.1 binding to coated Lewis antigens at the indicated concentrations: (A) $Le^Y/Le^Y$-ASGA-Biotin; (B) $Le^Y$-Gal-Biotin.
Figure 14B:
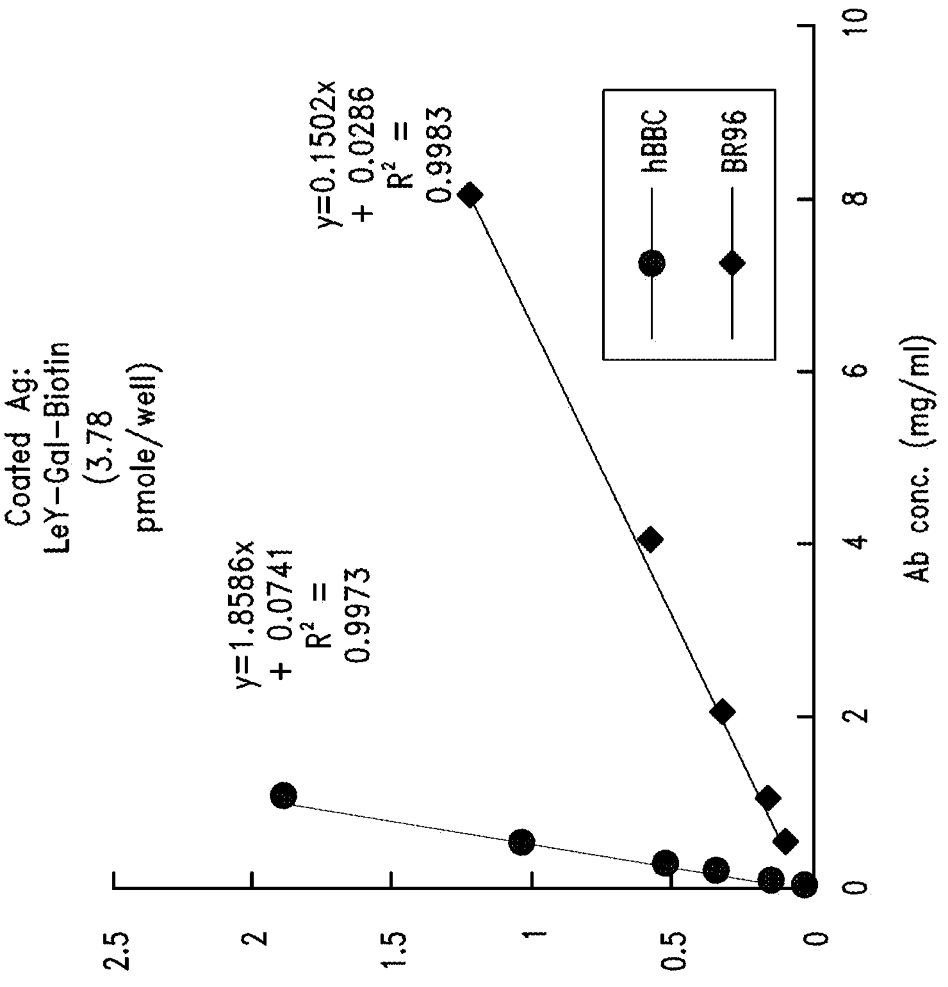

Binding activities of hBBC and the BR96 were tested on $Le^Y$-Gal-Biotin coated and $Le^Y$/$Le^Y$-ASGA-Biotin coated streptavidin-coated ELISA plates. The amount of coated antigen was as indicated in FIGS. 14A and 14B. hBBC showed much stronger binding to $Le^Y$/$Le^Y$-ASGA than to $Le^Y$-Gal. BR96 showed a contrary pattern to hBBC in that it bound $Le^Y$-Gal much better than $Le^Y$/$Le^Y$-ASGA. In sum, the indirect ELISA provided similar binding affinity results as the ITC and SPR experiments.

$Le^B$/$Le^B$-ASGA vs $Le^Y$/$Le^Y$-ASGA and $Le^B$-Gal

Figure 15:
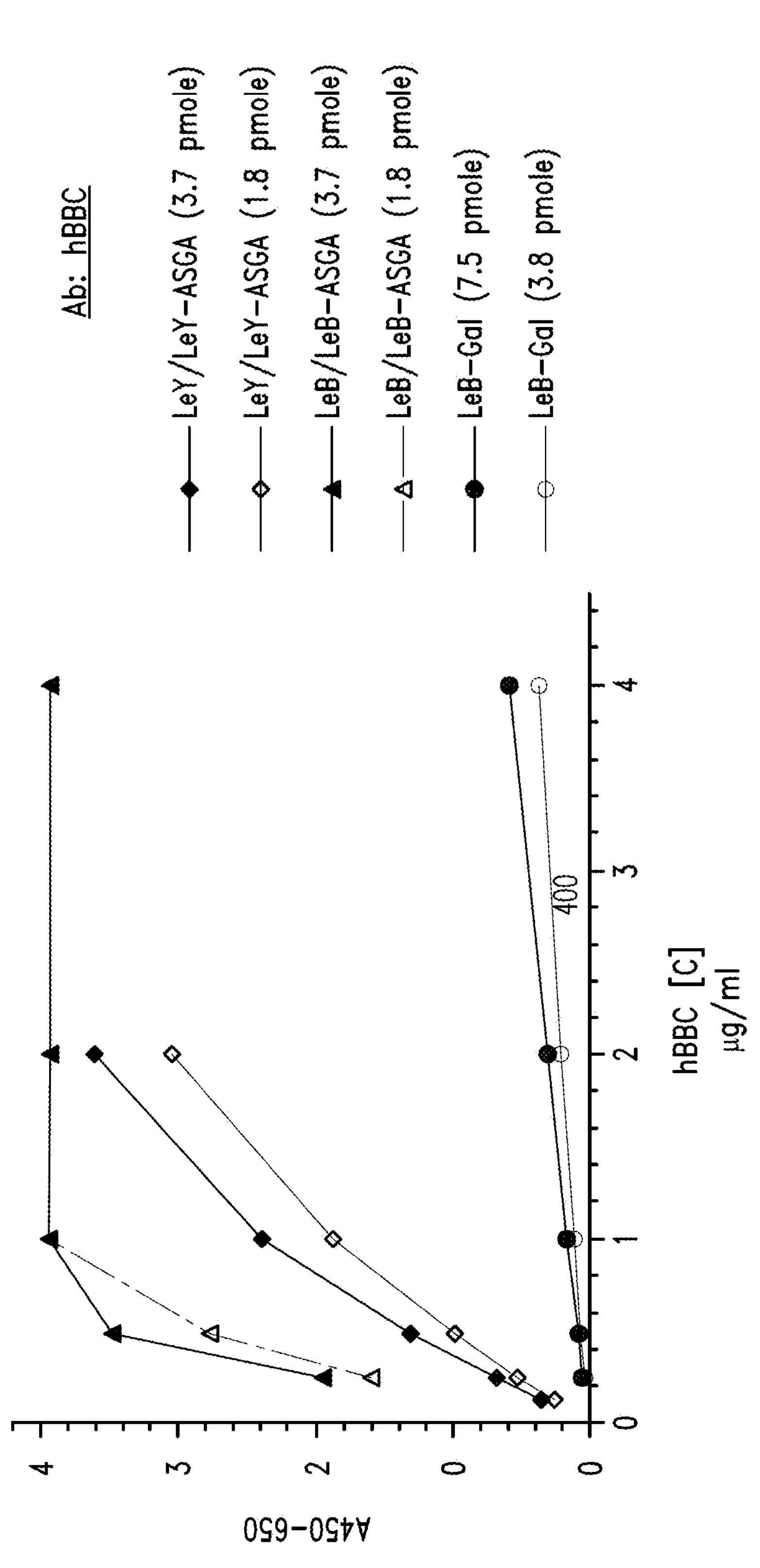
FIG. 15 shows results from indirect ELISA of hBBC.10.1 binding to coated Lewis antigens ($Le^B/Le^B$-ASGA vs $Le^Y/Le^Y$-ASGA and $Le^B$-Gal) at the indicated concentrations.

Next, hBBC was tested for binding on $Le^B$/$Le^B$-ASGA-Biotin, $Le^Y$/$Le^Y$-ASGA-Biotin, and $Le^B$-Gal-Biotin-coated streptavidin-coated ELISA plates. The amount of coating antigen was as indicated in FIG. 15. The result of the indirect ELISA was that hBBC showed significantly stronger binding to $Le^B$/$Le^B$-ASGA than to $Le^Y$/$Le^Y$-Gal and $Le^B$-Gal.

Antigen-Binding ELISA

An antigen-binding ELISA was developed to evaluate the relative binding affinity of hBBC to different glycan antigens. Briefly, hBBC was serially titrated and applied to a streptavidin-functionalized 96-well assay plate which had been coated with different glycan antigens. Binding of hBBC to glycan antigens was detected with a human IgG-specific antibody conjugated with horseradish peroxidase (HRP) followed by color development in TMB reagent. The absorbance at 450 nm using microplate reader was proportional to the amount of hBBC bound to its antigens. Relative affinity was determined by plotting the OD as a function of hBBC concentration.

Antigen Preparation

A biotinylated Lewis Y pentaose, $Le^Y$-Gal-sp3-biotin, was purchased from Elicityl (Crolles, France). Lewis B pentaose was purchased from Elicityl and further in-house biotinylated ($Le^B$-Gal-LC-biotin). The other four biotinylated glycans: $Le^Y$/$Le^Y$-ASGA-biotin, $Le^B$/$Le^B$-ASGA-biotin 3-$Le^Y$/6-$Le^B$-ASGA-Biotin ($Le^Y$/$Le^B$-ASGA-Biotin), and 3-$Le^B$/6-$Le^Y$-ASGA-Biotin ($Le^B$/$Le^Y$-ASGA-Biotin), were synthesized through a series of enzymatic glycosylation followed by chemical biotinylation (Table 5). The biotinylated glycan was analyzed by thin layer chromatography (TLC) and electrospray ionization-mass spectrometry (ESI-MS) to make sure the purity reached at least 95% and was free of unconjugated biotin. The HPAEC-PAD monosaccharide analysis was applied for the quantification of the biotinylated glycan.

Antibody hBBC was used in the antigen-binding ELISA.

ELISA

Biotinylated glycan antigens were diluted to 18.7 nM in PBS buffer. 100 μL diluted antigen solution was applied to a streptavidin-coated 96-well assay plate and incubated in a shaker at 37° C. for 3.5 hours. The plate was washed with PBST (0.05% Tween-20 in PBS buffer) to remove excess glycan antigens. Primary antibodies serially titrated in diluent (0.1% BSA in PBS buffer) were applied to the assay plate and incubated in a shaker at 37° C. for 1 hour. Followed by PBST washing, 100 μL HRP-conjugated anti-human IgG antibody solution (SouthernBiotech, 1:10,000 dilution in diluent) was incubated in the assay plate in a shaker at 37° C. for 1 hour. After washing out the excess secondary antibody, 100 μL TMB reagent was applied and incubated at 37° C. for 15 min followed by quenching with 50 μL of 0.5 N HCl. The OD value was detected at 450 nm and subtracted by the value at 650 nm in a VERSA max microplate reader (Molecular Devices). The data was processed in Softmax Pro (Molecular Devices).

Results

Figure 16A:
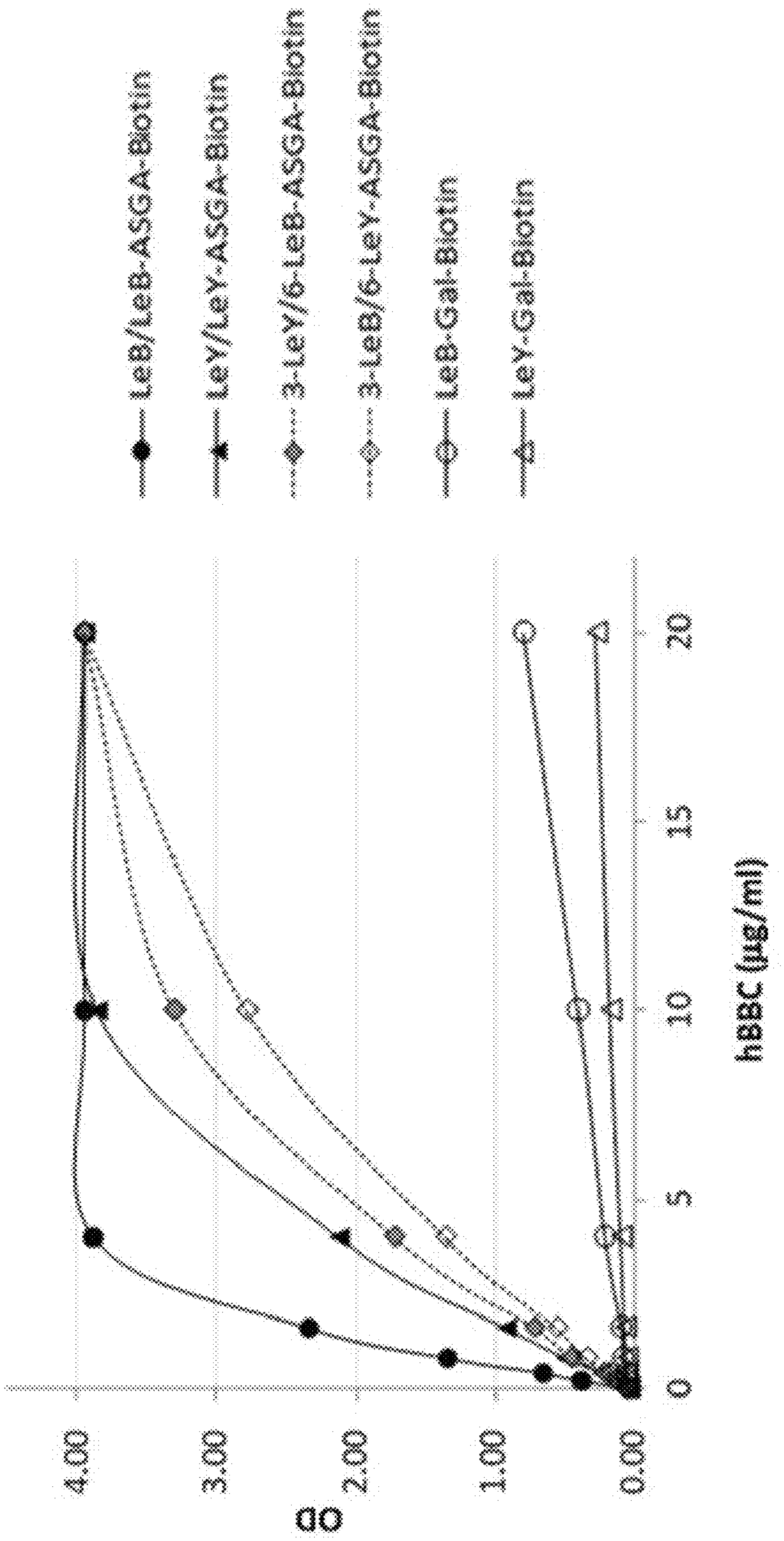
FIG. 16A shows results from an antigen-binding ELISA of hBBC.10.1 to glycan antigens including $Le^Y$-Gal-sp3-biotin ($Le^Y$-Gal), $Le^B$-Gal-LC-biotin ($Le^B$-Gal), $Le^Y/Le^Y$-ASGA-biotin ($Le^Y/Le^Y$-ASGA), $Le^B/Le^B$-ASGA-biotin ($Le^B/Le^B$-ASGA), 3-$Le^Y$/6-$Le^B$-ASGA-Biotin ($Le^Y/Le^B$-ASGA), and 3-$Le^B$/6-$Le^Y$-ASGA-Biotin ($Le^B/Le^Y$-ASGA). The coating amount of all antigens was the same (1.87 pmole)).

Data are shown in FIG. 16A. When hBBC bound to $Le^B$/$Le^B$-ASGA, $Le^Y$/$Le^Y$-ASGA, 3-$Le^Y$/6-$Le^B$-ASGA-Biotin, and 3-$Le^B$/6-$Le^Y$-ASGA-Biotin in an antigen-binding ELISA, the OD value increased within a narrow range of low antibody concentration (0.4-4 μg/mL), whereas the binding of hBBC was apparently weaker with $Le^Y$-Gal and $Le^B$-Gal, indicating a bivalent $Le^Y$, $Le^B$, $Le^B$/$Le^Y$, or $Le^Y$/$Le^B$ in one glycan provided a higher binding affinity to hBBC than did a single $Lewis^Y$/B moiety.

Direct Comparison of Antigen-Binding Affinity: hBBC.10.1 vs. BBC

The purpose of the experiment was to compare the antigen affinity of hBBC.10.1 to that of the ancestral BBC antibody by antigen-binding ELISA.

Antigen Preparation

A biotinylated Lewis Y pentaose, $Le^Y$-Gal-sp3-biotin, was purchased from Elicityl. Lewis B pentaose was purchased from Elicityl and further in-house biotinylated ($Le^B$-Gal-LC-biotin). The other four biotinylated glycans: $Le^Y$/$Le^Y$-ASGA-biotin, $Le^B$/$Le^B$-ASGA-biotin 3-$Le^Y$/6-$Le^B$-ASGA-Biotin ($Le^Y$/$Le^B$_ASGA-Biotin), and 3-$Le^B$/6-$Le^Y$-ASGA-Biotin ($Le^B$/$Le^Y$-ASGA-Biotin), were synthesized through a series of enzymatic glycosylation followed by chemical biotinylation (Table 5). The biotinylated glycan was analyzed by TLC and ESI-MS to make sure the purity reached at least 95% and was free of unconjugated biotin. The HPAEC-PAD monosaccharide analysis was applied for the quantification of the biotinylated glycan.

Antibody

BBC and hBBC.10.1 were used in antigen-binding ELISA.

Antigen-Binding ELISA 96-well EvenCoat™ Streptavidin microplates (R&D Biosystems, MN, Cat No. CP004) were incubated with various biotinylated glycans in PBS at an amount of 3.73 pmol/well at 4° C. overnight. After washing 3 times with PBS/0.05% Tween 20 (Sigma, Cat No. P1379-500 mL), 100 μL of diluted BBC or hBBC.10.1 antibodies were added into the antigen coated wells, and then incubated at 37° C. for 1 hr. The wells were washed 3 times with PBS/0.05% Tween 20, followed by incubation with 100 μL of 10000× diluted Mouse anti-Human IgG(Fc)-HRP (Southern Biotech, Cat No. 9040-05) at 37° C. for 1 hr. After washing, 100 μl of SureBlue™ Reverse TMB (KPL, Cat No. 53-00-03) was added for color development at 37° C. for 15 minutes. The reaction was stopped by adding 0.5N HCl. The absorbance was read at a wavelength of 450 nm with 650 nm reference on a VERSAMAX™ microplate reader (Molecular Devices, San Jose, CA), and the data was processed by the Softmax-Pro™ software (Molecular Devices).

Results

Figure 16B:
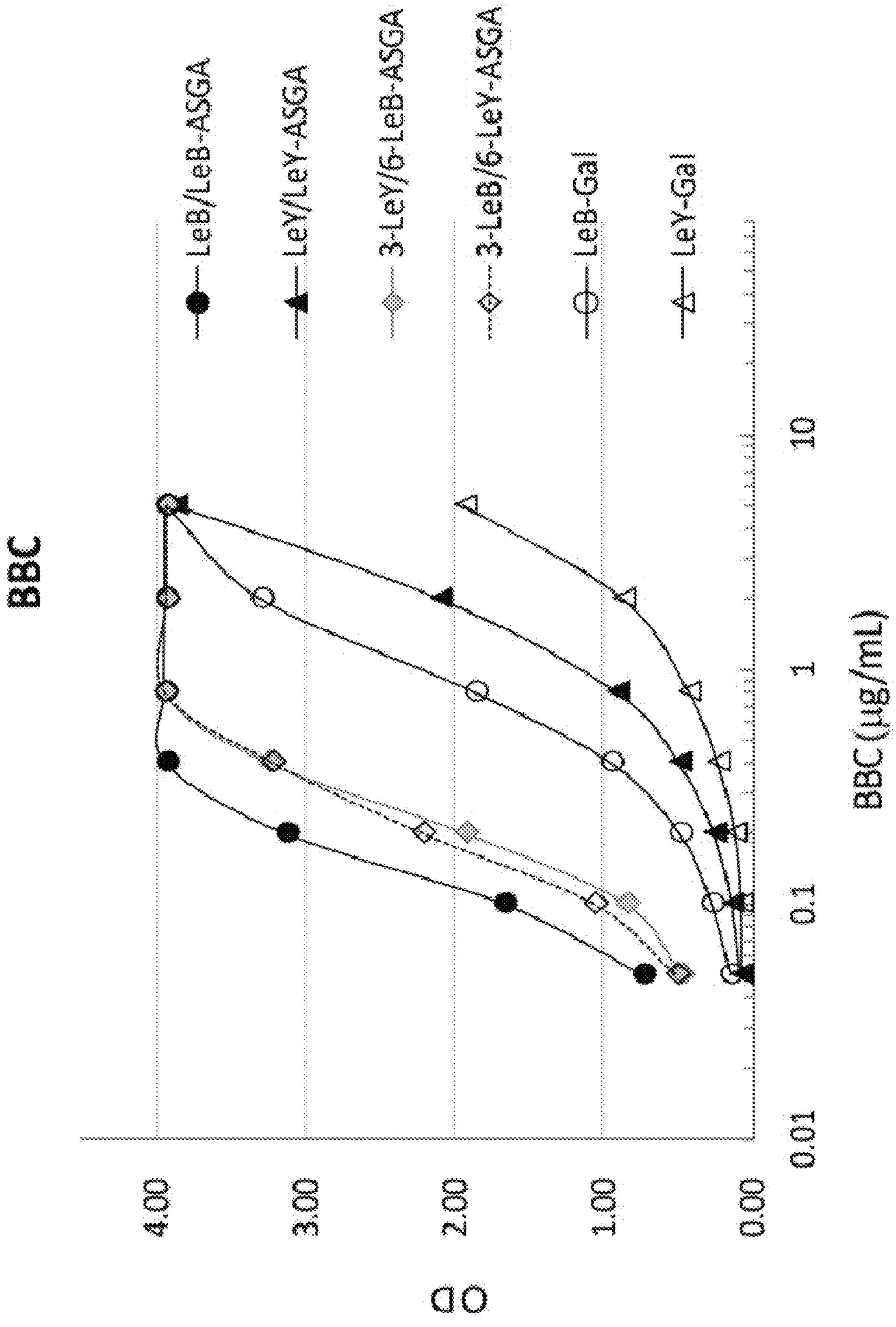
FIGS. 16B and 16C show, respectively, results from antigen-binding ELISA experiments comparing the affinity and selectivity of (16B) BBC antibody and (16C) hBBC.10.1 antibody for antigen.
Figure 16C:
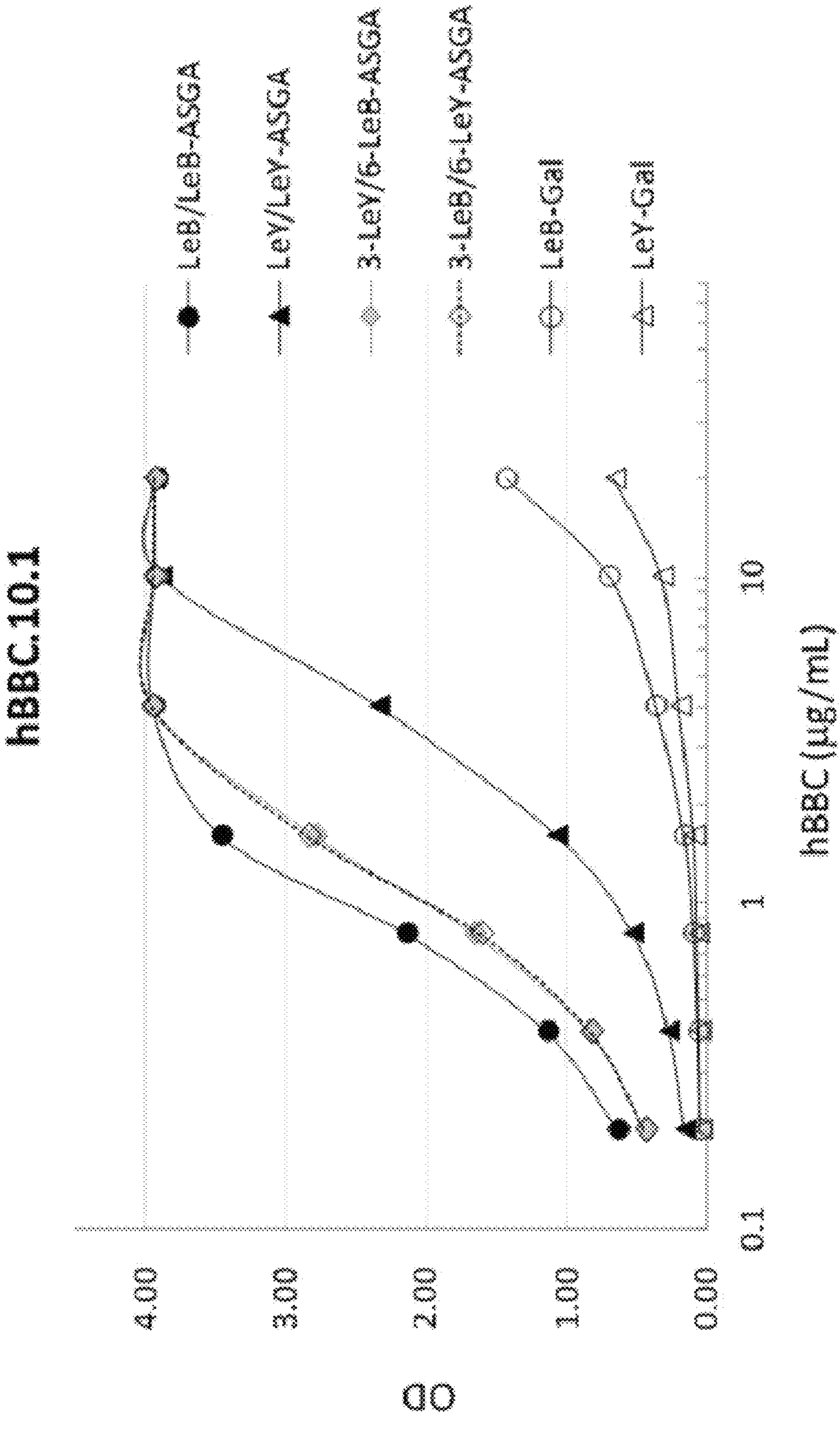

The antigen-binding ELISA of BBC (FIG. 16B) and hBBC.10.1 (FIG. 16C) showed that hBBC.10.1 had lower affinity towards single chain glycan antigens ($Le^B$-Gal and $Le^Y$-Gal) as compared to BBC, and both antibodies had high affinity towards the biantennary glycan antigens ($Le^B$/$Le^B$-ASGA, $Le^Y$/$Le^Y$-ASGA, 3-$Le^Y$/6-$Le^B$-ASGA, and 3-$Le^B$/6-$Le^Y$-ASGA). These data suggested that hBBC.10.1 had better binding selectivity between single chain and biantennary antigens than BBC.

SUMMARY

The epitope characterization experiments described in this Example indicated that hBBC specifically bound to cancer cell line-derived bi, and tri-antennary $Le^{Y/B}$ I antigen; and also to bi- and tri-antennary $Le^Y$ N-glycans. Furthermore, the epitope recognized by hBBC comprised di-fucosylated LacNAc backbone(s). Biantennary $Le^B$/$Le^B$-ASGA was the antigen with strongest binding affinity with hBBC. The biantennary $Le^Y$/$Le^Y$-ASGA, $Le^Y$/$Le^B$-ASGA, and $Le^B$/$Le^Y$-ASGA also showed high affinity towards hBBC compared to single-chain $Le^B$-Gal and $Le^Y$-Gal antigens. Also, whether the antigens were in single-chain or biantennary structures, solely $Le^B$-based antigens showed higher affinity towards hBBC than solely $Le^Y$-based antigens. Finally, the binding behavior (kinetics) and the epitopes of hBBC differed from that of BR96.

Example 4

Internalization of HBBC in Target Cells

Antibodies can be used as carriers to deliver a functional payload to a desired site. For example, some cancer therapies use antigen-specific antibodies to deliver cytotoxic drugs (i.e., antibody-drug conjugates or ADCs) into tumor cells via endocytosis, also known as internalization. Some current ADCs include cleavable linkers that are cleaved in the lysosomal compartment and thereby selectively release drug following internalization, with the added benefit of increasing stability of the drug in serum.

Figure 17:
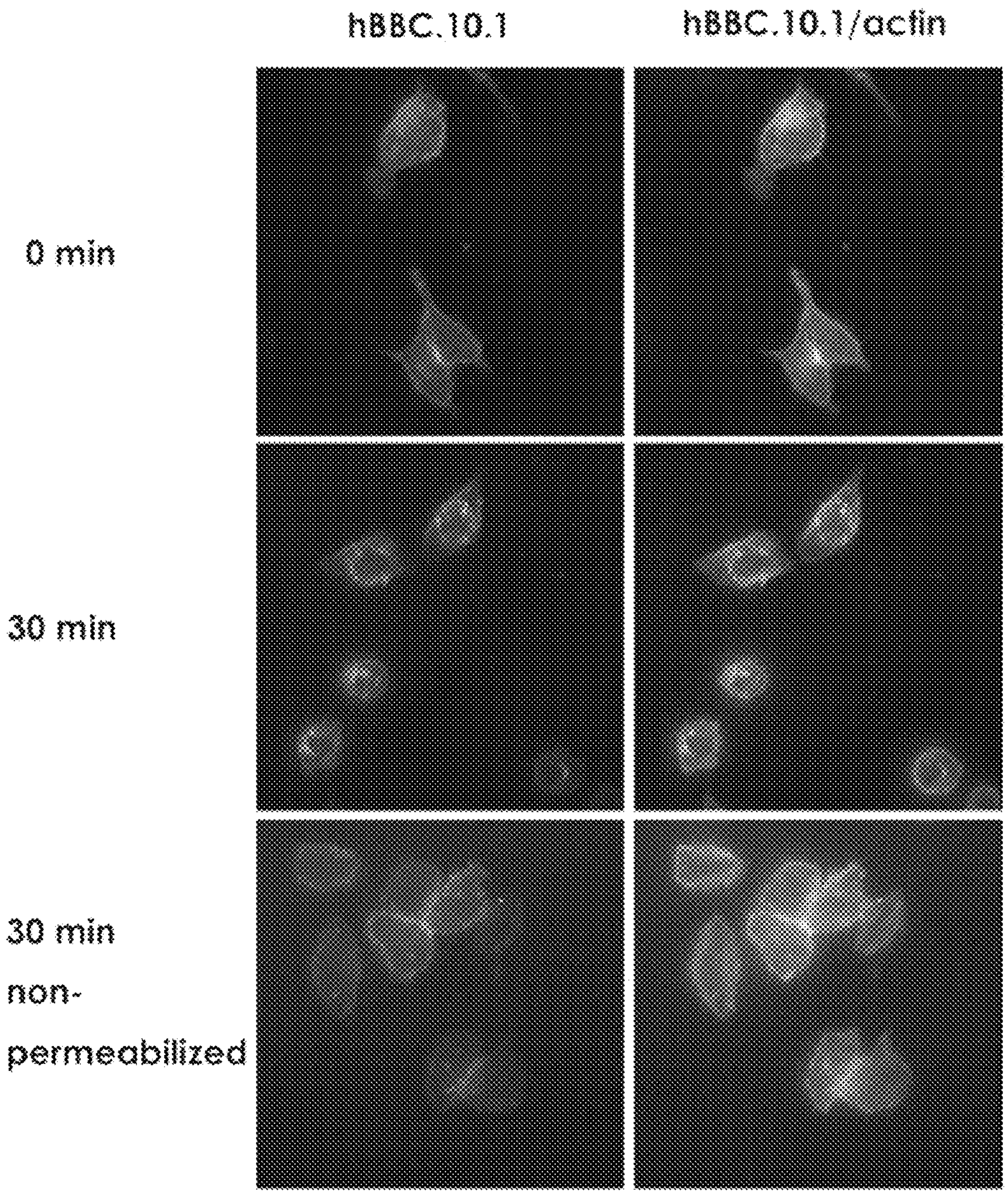
FIG. 17 provides fluorescence microscopy images showing endocytosis of hBBC.10.1 by AGS gastric cancer cells. Left panels: hBBC.10.1 stained by Alexa488-conjugated anti-human IgG (green channel). Right panels: overlay with F-actin staining labelled with phalloidin rhodamine (red channel). Regions in which the fluorescein and rhodamine co-distributed appeared as yellow under the microscope and appear as co-localized fluorescent signal in the merged image.

To test whether hBBC internalized effectively into cancer cells, the following experiments were performed. First, in a conventional internalization assay, hBBC antibody was added to AGS gastric cancer cells in culture and binding was performed at 4° C. for 1 hr to allow specific antibody/receptor interaction, but halt endocytosis. Then, non-specifically bound antibody was washed away and cells were shifted to 37° C. to allow normal endocytosis. At 0 min and 30 min, cells were fixed and hBBC was detected using Alexa488-conjugated anti-human IgG antibody (FIG. 17, left-hand panels). F-actin was labeled by phalloidin rhodamine (right-hand panels; co-distributed staining appeared as yellow fluorescent signal). As shown in FIG. 17, hBBC stained cell membrane at 0 min and then underwent internalization and localized to cytosolic vesicles around the nucleus after 37° C. incubation (30 min, permeabilized cells). Cytosolic signal was further demonstrated by non-permeabilized control in which only faint membranous signals can be detected (30 min, non-permeabilized cells). These data show that hBBC effectively internalizes into AGS cells within 30 minutes.

Figure 18:
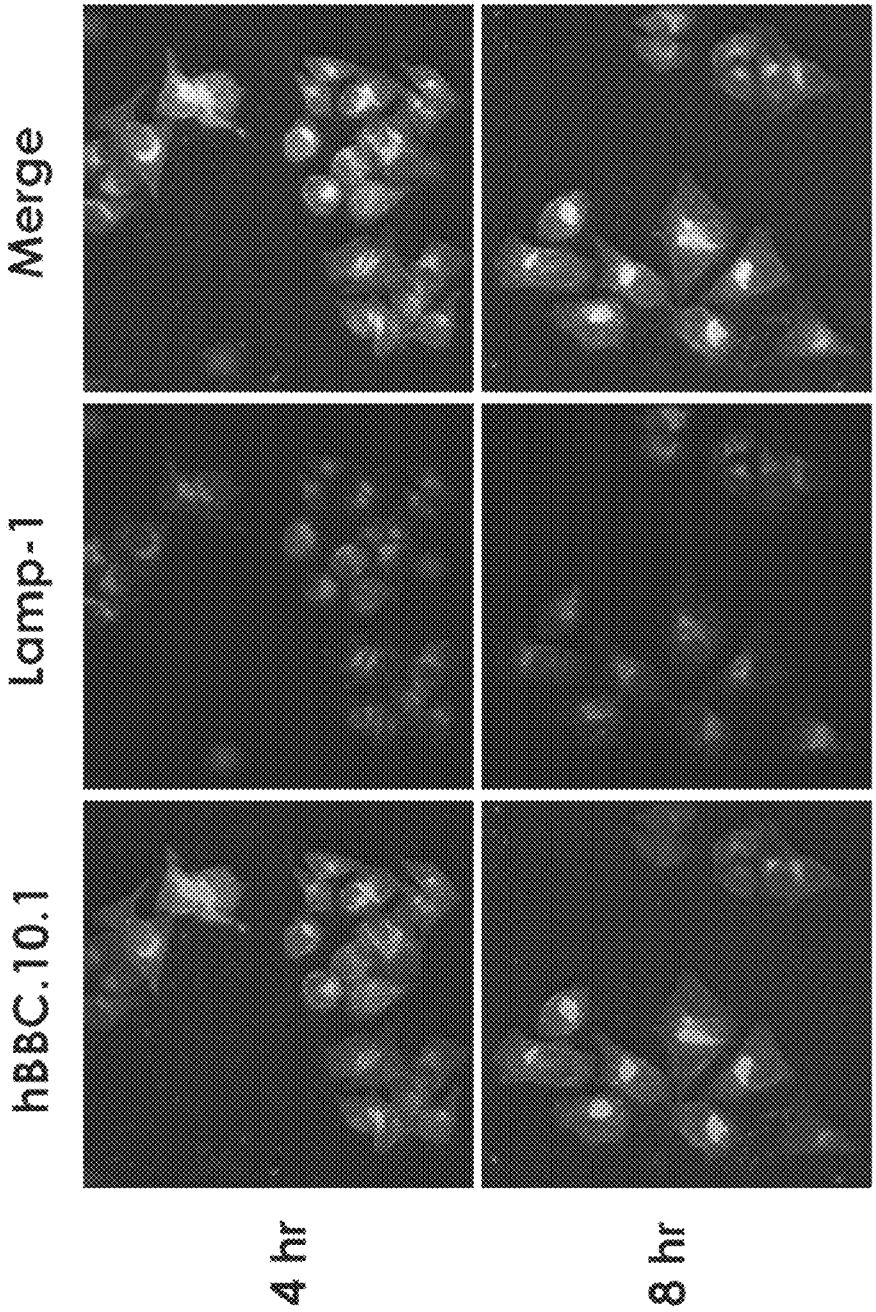
FIG. 18 provides fluorescence microscopy images showing lysosomal localization of hBBC.10.1 in AGS gastric cancer cells. Left panels: hBBC.10.1 stained by Alexa488-conjugated anti-human IgG (green channel). Middle panels: lysosome labeled with anti-Lamp-1 antibody followed by anti-rabbit IgG (red channel). Right panels: Merge.

In a second experiment, real-time intracellular localization of hBBC was examined. Briefly, hBBC antibody was added to AGS cells and incubated for 4 or 8 hour at 37° C. to facilitate internalization. Cells were then fixed and real-time localization of hBBC was examined using Alexa488-conjugated anti-human IgG antibody (FIG. 18, anti-human IgG shown in left panels). Lysosomes were labeled by anti-Lamp-1 antibody followed by labeled anti-rabbit IgG antibody (shown in middle panels). As shown in FIG. 18, hBBC is co-localized with Lamp-1 (Merge; right panels) after a 4 or 8 hour incubation, indicating that internalized hBBC is localized to the lysosomal compartment. Moreover, hBBC can be stabilized in the lysosomal compartment without apparent degradation for at least 8 hours. These results indicate that hBBC has utility for use as in antigen-targeting conjugates, such as ADCs.

Example 5

Immunostaining of HBBC in Human Tissue Samples

Healthy and cancerous tissue samples were obtained and immunostaining with hBBC 10.1 was performed on formalin-fixed paraffin-embedded tissue sections according to a standard protocol. Staining results for healthy and cancerous tissues are summarized in Tables 7 and 8, respectively.

TABLE 7 hBBC.10.1 immunostaining of various human normal tissues.

| Tissue | hBBC 10.1_2 µg/ml |
|---|---|
| Pancreas | ± (3/3) |
| Tongue (Salivary gland tissue) | + (3/3) |
| Larynx | ++ (3/3) |
| Esophagus | ± (3/3) |
| Stomach | + (3/3) |
| Small intestine | +++ (3/3) |
| Colon | – |
| Hypophysis | – |
| Breast | – |
| Cerebrum | – |
| Cerebellum | – |
| Adrenal gland | – |
| Parathyroid gland | – |
| Ovary | – |
| Testis | – |
| Spleen | – |
| Tonsil | – |
| Thymus gland | – |
| Bone marrow | – |
| Lung | – |
| Heart | – |
| Liver | – |
| Kidney | – |
| Prostate | – |
| Uterus | – |
| Uterine cervix | – |
| Striated muscle | – |
| Skin | – |
| Nerve | – |
| greater omentum | – |
| Endometrium | – |

TABLE 8 hBBC immunostaining in human cancerous tissues.

| Organ | Pathology diagnosis | Type | Positive rate | | |
|---|---|---|---|---|---|
| Stomach | Adenocarcinoma | Malignant | 57/175 | 32.6% | 33.2% |
| | Mucinous adenocarcinoma | | 6/17 | 35.3% | |
| | Undifferentiated adenocarcinoma | | 1/2 | 50.0% | |
| | Signet-ring cell carcinoma | | 1/2 | 50.0% | |
| Colon | Adenocarcinoma | Malignant | 11/23 | 47.8% | 44.0% |
| | Mucinous adenocarcinoma | | 0/2 | 0.0% | |
| Breast | Invasive ductal carcinoma | Malignant | 1/23 | 4.3% | 4.2% |
| | Mixed lobular and duct carcinoma | | 0/1 | 0.0% | |
| Liver | Hepatocellular carcinoma | Malignant | 1/40 | 2.5% | 2.5% |
| Lung | Adenocarcinoma | Malignant | 3/15 | 20.0% | 20.0% |
| | Squamous cell carcinoma | | 2/10 | 20.0% | |
| Lymph node | Metastatic adenocarcinoma | Metastasis | 13/40 | 32.5% | 32.5% |
| Ovary | Serous adenocarcinoma | Malignant | 0/33 | 0.0% | 5.0% |
| | Mucinous adenocarcinoma | | 2/6 | 33.3% | |
| | Endometrioid adenocarcinoma | | 0/1 | 0.0% | |

TABLE 8-continued hBBC immunostaining in human cancerous tissues.

| Organ | Pathology diagnosis | Type | Positive rate | | |
|---|---|---|---|---|---|
| Pancreas | Duct adenocarcinoma | Malignant | 11/24 | 45.8% | 48.0% |
| | Papillary adenocarcinoma | | 1/1 | 100.0% | |
| Prostate | Adenocarcinoma | Malignant | 1/25 | 4.0% | 4.0% |
| Uterus | Endometrioid adenocarcinoma | Malignant | 10/40 | 25.0% | 25.0% |
| Others | Squamous cell carcinoma | Malignant | 1/32 | 3.1% | 3.1% |

In addition, various human cancer cell lines were stained with hBBC.10.1 to determine epitope expression patterns. Results are summarized in Table 9.

TABLE 9 hBBC epitope expression on human cancer cell lines.

| Type | Cell line | hBBC.10.1 binding |
|---|---|---|
| Gastric cancer | AGS | +++ |
| | TSGH9201 | + |
| | NCI-N87 | ++ |
| | KATO III | − |
| | MKN45 | − |
| | MKN74 | − |
| | MKN7 | − |
| | LOVO | − |
| Colonic cancer | Colon 205 | − |
| | Colon 201 | + |
| | SW1116 | +++ |
| | DLD-1 | ++ |
| | LS 174T | + |
| | HT-29 | − |
| | T84 | − |
| Breast cancer | MCF-7 | ++ |
| | MDA-MB231 | − |
| | MDA-MB453 | − |
| | T47D | − |
| Ovary cancer | NIH OVCAR-3 | + |
| | SW626 | + |
| | SK-OV-3 | − |
| | ES-2 | − |
| Pancreatic cancer | SU.86.86 | − |
| | EBC-1 | − |
| | PABC-1 | − |
| Lung cancer | NCI-H146 | + |
| | NCI-H209 | − |
| Skin cancer | A431 | − |

Example 6

Antitumor Activity of HBBC in a Xenograft Model of Colon Cancer

A series of in vivo animal studies were conducted to evaluate the tumor inhibitory effect of hBBC in xenograft SCID models, which included introducing human cancer cells from the gastric cancer cell lines AGS, TSGH9201, and from the colon cancer cell lines COLO 201, COLO 205, DLD-1. hBBC.10.1 has shown strong to moderate binding level to all the cell lines except COLO 205 (Table 9 of Example 5). hBBC.10.1 was used for all xenograft studies, and BR96 was used as a control.

In Vivo Anti-Tumor Activity of hBBC.10.1 in DLD-1 and COLO 205 Xenograft Models

The objective of this study was to examine tumor inhibitory effects of a high dose of hBBC.10.1 in DLD-1 and COLO 205 xenograft models. Briefly, human colon cancer cell lines DLD-1 and COLO 205 were obtained from the American Type Culture Collection (ATCC, Manassas, VA, USA). Cells were grown in RPMI 1640 medium supplemented with 10% fetal bovine serum (FBS), and the cell culture was maintained in a humidified incubator under a 5% $CO_2$ atmosphere at 37° C. Cells at passage 5-8 were used for tumor inoculation.

Specific-pathogen-free (SPF) female CB17 severe combined immunodeficiency (SCID) mice were purchased from BioLASCO (Taiwan), and allowed to acclimate for at least one week before any experimental manipulation. Mice were housed in individually ventilated cages (IVC) in a temperature-controlled environment (22±2° C.) with 50±10% humidity under a 12:12 hour light-dark cycle. All experiments were performed following the regulations and animal protection law mandated by the Council of Agriculture, Taiwan.

Cancer cells were re-suspended at a cell density of $5\times10^6$/200 μL in ice cold serum free medium containing 50% of BD Matrigel (Cat. 354248), and injected subcutaneously into the flank region of SCID mice aged 6-8 weeks. Tumor size was measured weekly with a vernier caliper (Laser Tools and Technics (LTT), Hsin Chu City, Taiwan, 150×0.05 mm) and tumor weight was estimated as "weight in mg=(width$^2$×length) mm$^3$/2" (Ito et al. (1992) *Cancer Res.* 52:3739). When tumor weight reached 150-200 mg, the mice were randomly divided into 9 groups (n=6 per group) with each group having comparable tumor sizes, and antibody treatment was begun. Tumor-bearing SCID mice were intraperitoneally injected with hBBC.10.1 (lot: 17001) once per week at 50 mg/kg for six weeks. Tumor-bearing SCID mice intraperitoneally injected with saline served as negative controls.

Figure 19A:
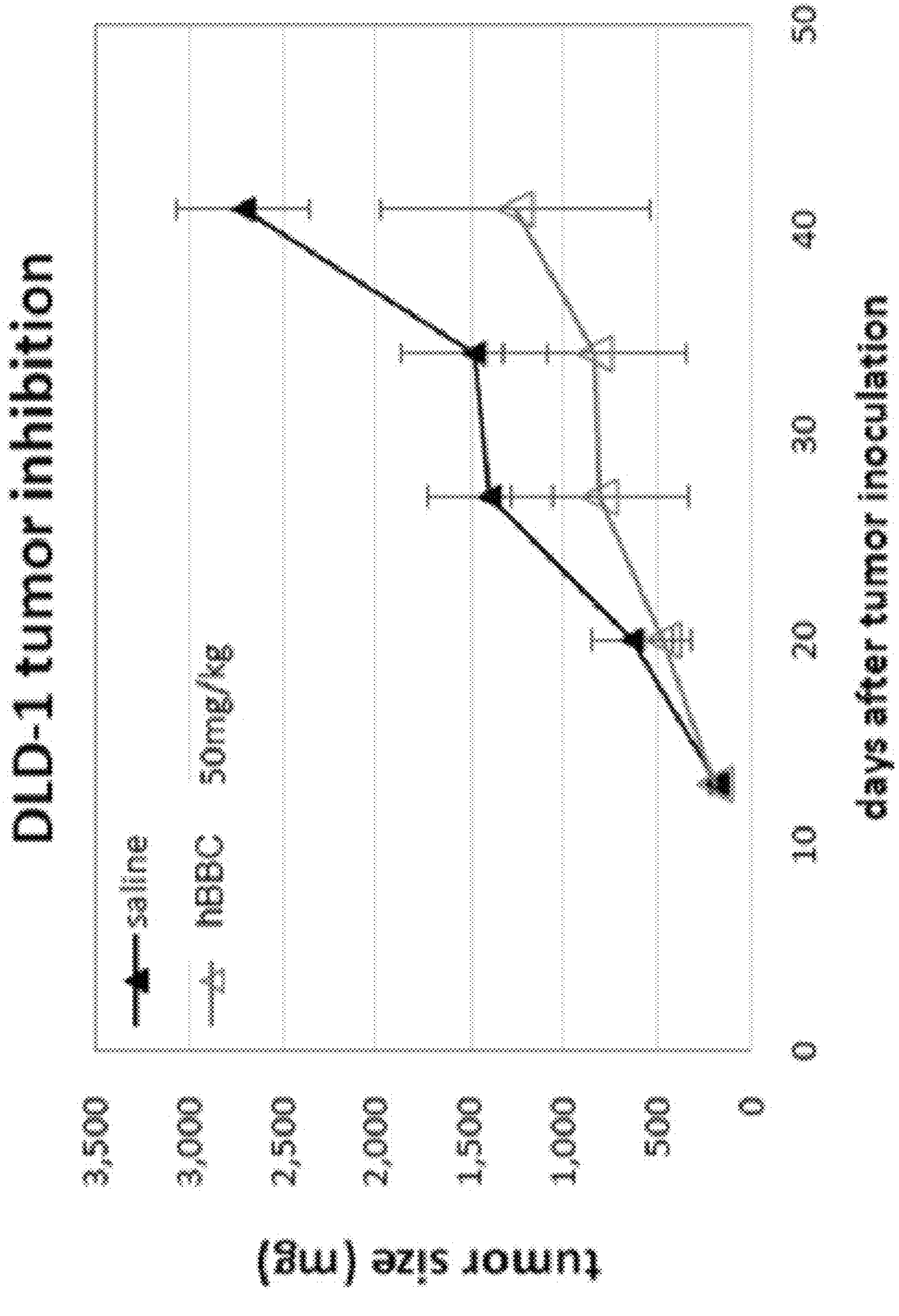
FIGS. 19A and 19B show antitumor activity of hBBC.10.1 in an in vivo xenograft experiment in which immunodeficient SCID mice were administered (A) human DLD-1 or (B) COLO 205 tumor cells followed by antibody once tumors developed.
Figure 19B:
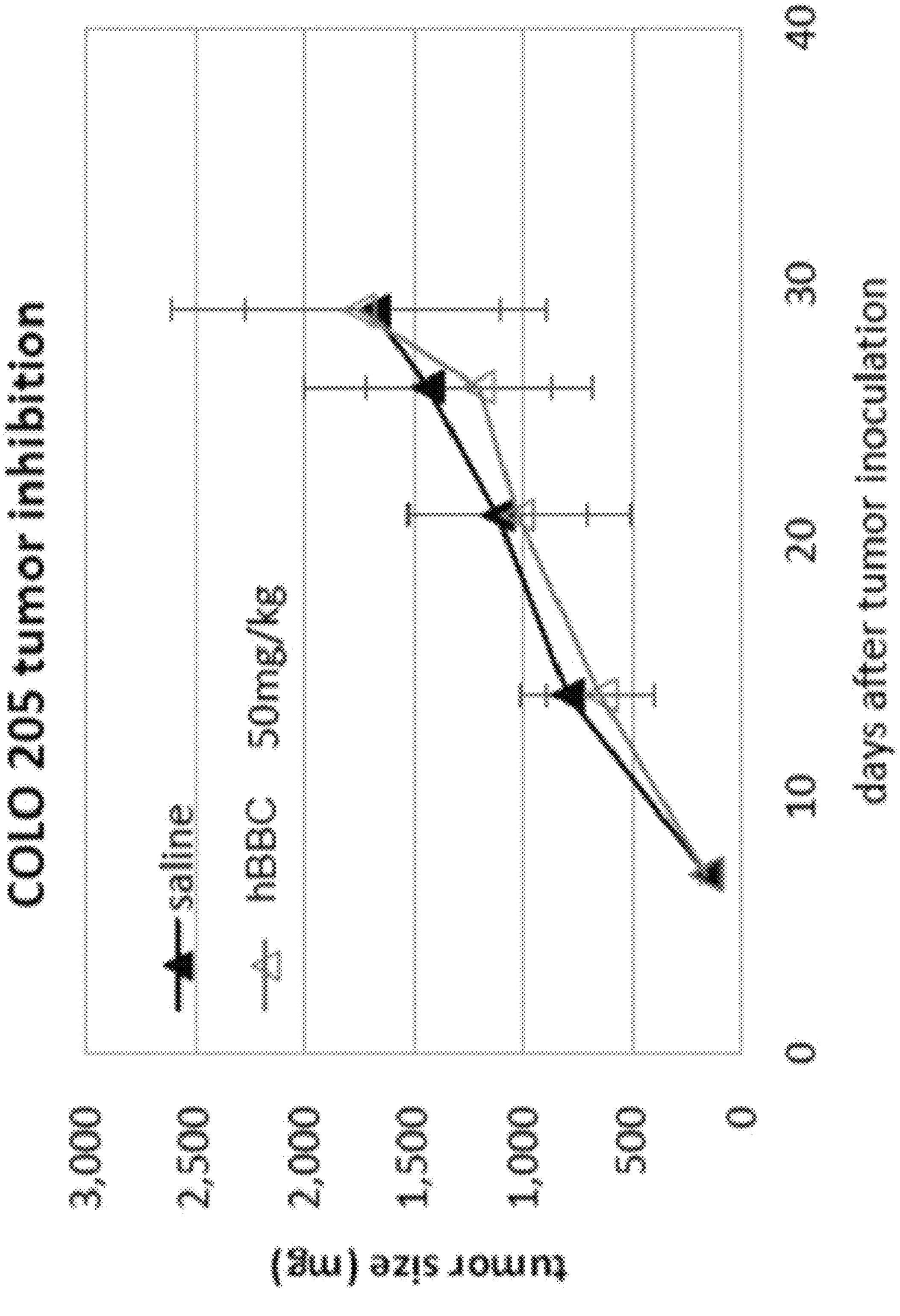

Results from the DLD-1 and COLO 205 xenograft experiments are shown in FIGS. 19A and 19B, respectively. hBBC.10.1 was able to effectively inhibit DLD-1 tumor growth, but not COLO 205 tumor growth, relative to control. These data are consistent with the observed ability of hBBC.10.1 to bind DLD-1 cells, but not COLO 205.

Anti-Tumor Activity of hBBC in a Xenograft Model of Gastric Adenocarcinoma

The objective of this study was to compare the anti-tumor efficacy of hBBC.10.1 and BR96 at low doses ranging from 0.008 to 1 mg/kg in the AGS xenograft model. Briefly, human gastric adenocarcinoma cell line AGS (CRL-1739) was obtained from the American Type Culture Collection (ATCC, Manassas, VA, USA). AGS cells were grown in Ham's F-12K medium supplemented with 10% fetal bovine serum (FBS), and the cell culture was maintained in a humidified incubator under a 5% $CO_2$ atmosphere at 37° C. AGS cells at passage 5-8 were used for tumor inoculation.

Specific-pathogen-free (SPF) female CB17 severe combined immunodeficiency (SCID) mice were purchased from BioLASCO (Taiwan), and allowed to acclimate for at least one week before any experimental manipulation. Mice were housed in individually ventilated cages (IVC) in a temperature-controlled environment (22±2° C.) with 50±10% humidity under a 12:12 hour light-dark cycle. All experiments were performed following the regulations and animal protection law mandated by the Council of Agriculture, Taiwan.

AGS cells were re-suspended at a cell density of $5\times10^6$/200 μL in ice-cold serum-free medium containing 50% of BD Matrigel (Cat. 354248), and injected subcutaneously into the flank region of SCID mice aged 6-8 weeks. Tumor size was measured weekly with a vernier caliper (Laser Tools and Technics (LTT), Hsin Chu City, Taiwan, 150×0.05 mm) and tumor weight was estimated as "weight in mg=(width$^2$×length) mm$^3$/2" [Ito et al. (1992) *Cancer Res.* 52:3739]. When tumor weight reached 150-200 mg, the mice were randomly divided into 9 groups (n=6 per group) with each group having comparable tumor sizes, and antibody treatment was begun. Tumor-bearing SCID mice were intraperitoneally injected with either hBBC.10.1 (lot: 17001) or BR96 (lot: 17001) once per week at 1, 0.2, 0.04, or 0.008 mg/kg for six weeks, with the first dose being given at 1.5-fold of the predetermined dose. Tumor-bearing SCID mice intraperitoneally injected with saline served as negative controls.

Figure 20A:
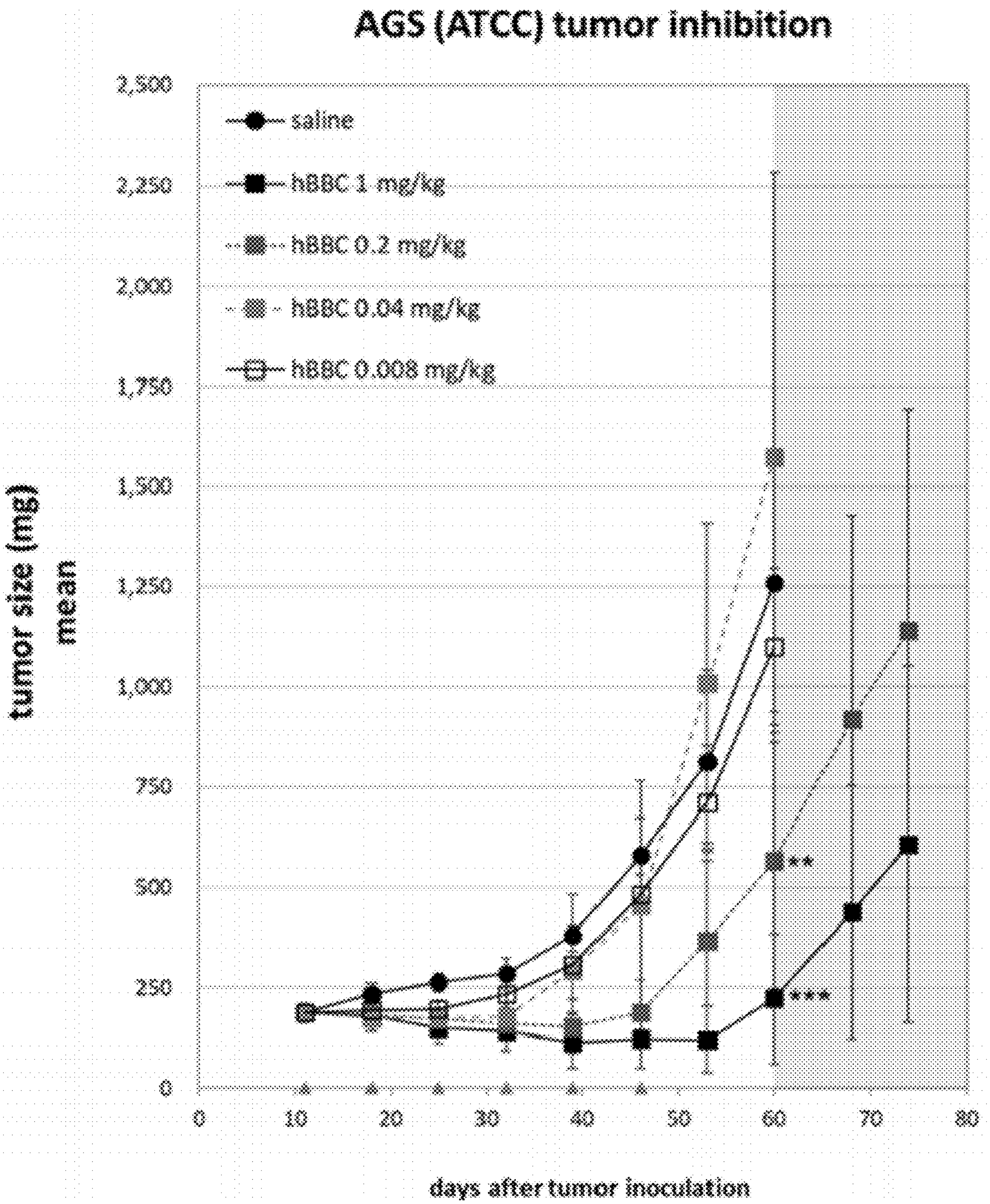
FIGS. 20A and 20B show, respectively, antitumor activity of various concentrations of (A) hBBC.10.1 and (B) BR96 in in vivo xenograft experiments in which immunodeficient SCID mice were administered human AGS gastric cancer adenocarcinoma cells followed by antibody once tumors developed.
Figure 20B:
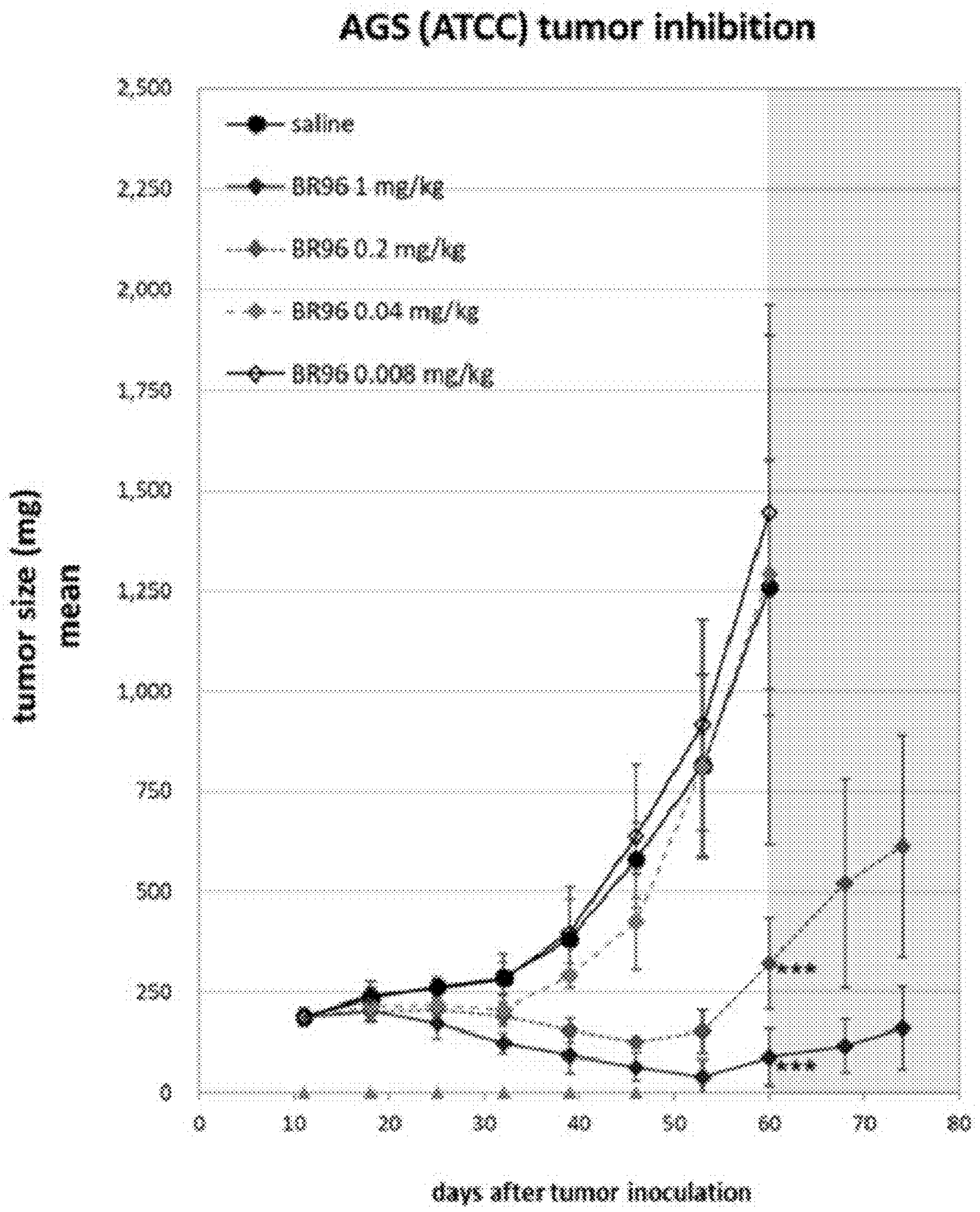

Results for hBBC.10.1-treated and BR96-treated mice are shown in FIGS. 20A and 20B, respectively. When administered at weekly doses of 1 and 0.2 mg/kg, both hBBC.10.1 and BR96 significantly inhibited tumor growth compared with control. However, both antibodies failed to show inhibitory effects at lower doses (0.04 and 0.008 mg/kg). Due to ethical considerations, mice were sacrificed when the tumor burden was greater than 10% of body weight. Some mice receiving saline or lower doses of antibody reached this endpoint at 60 days after inoculation; hence, statistical analysis was performed only on data generated up to day 60. In contrast, tumor growth to 10% of body weight was effectively delayed in AGS tumor-bearing mice administered higher doses (1 and 0.2 mg/kg) of hBBC.10.1 or BR96. This dose-response study indicates that hBBC.10.1 has comparable antitumor efficacy to BR96 in AGS tumor-bearing mice.

Figure 20C:
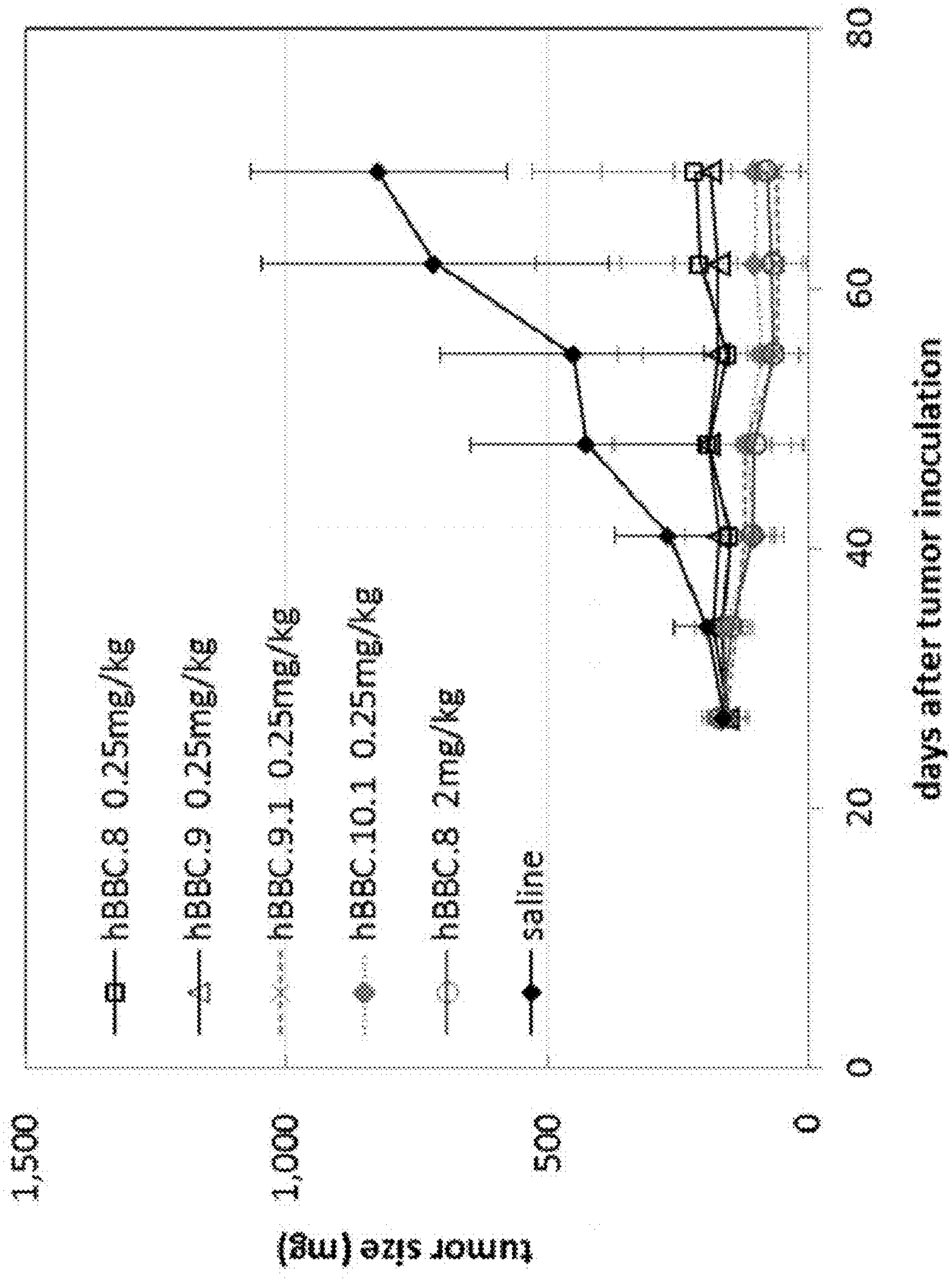
FIGS. 20C and 20D show antitumor activity of hBBC antibodies of the present disclosure in in vivo xenograft experiments.
Figure 20D:
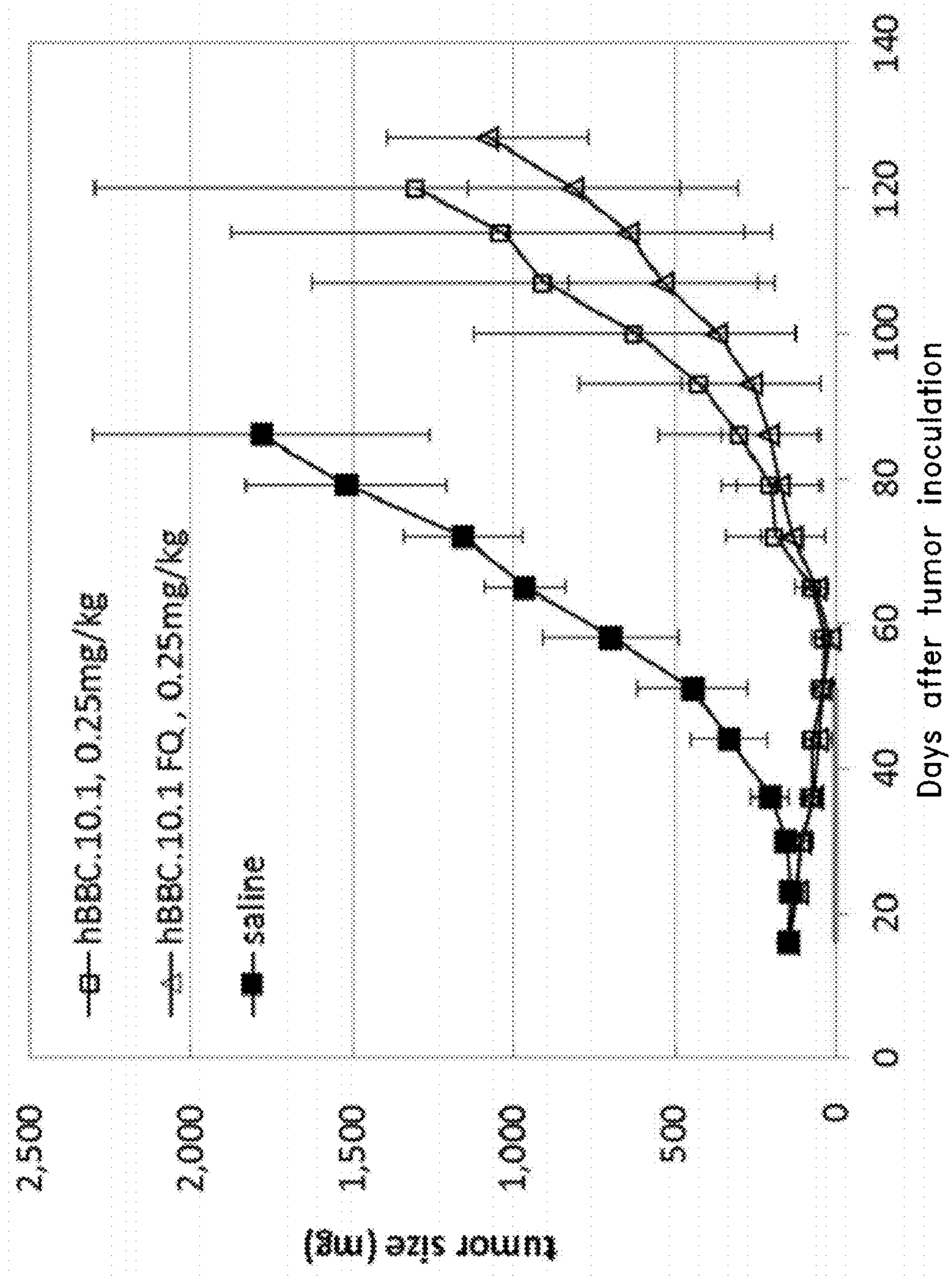

The antitumor efficacy of hBBC.10.1 was compared with that of other generated hBBC antibodies of the present disclosure. In one experiment, harvested AGS cells were washed with PBS twice and resuspended at a cell density of $5\times10^6$/200 μL in PBS containing 25% of BD Matrigel™ (BD Biosciences, Cat. 354248). Thereafter, 200 μL of the AGS cell suspension was injected subcutaneously ($5\times10^6$ cells/mouse) into female SCID mice (6-8 weeks of age) in the flank region. The tumor size was measured weekly with a vernier caliper (Laser 150×0.05 mm) and the tumor weight was estimated as "weight in mg=(width$^2$×length) mm$^3$/2" [Hisashi Ito et al. (1992)]. When the tumor weight reached 150-200 mg, the mice were randomly divided into 6 groups (n=6 per group) with each group having comparable tumor sizes, and started on antibody treatment. Tumor-bearing SCID mice were intraperitoneally injected with hBBC.8 or mutants (hBBC.9, hBBC.9.1, hBBC.10.1) twice per week at the dose of 0.25 mg/kg for six weeks. In addition, hBBC.8 was tested at a higher dose, at 2 mg/kg. Tumor-bearing SCID mice intraperitoneally injected with saline served as negative controls. Data are shown in FIG. 20C. Antitumor effects were observed with hBBC.8, hBBC.9, and hBBC.9.1, although the effect was somewhat weaker than hBBC.10.1. Comparable antitumor activity to hBBC.10.1 (0.25 mg/kg) was observed for hBBC.8 at a higher dose (2 mg/kg).

hBBC.10.1 was also compared to hBBC.10.1FQ for anti-tumor activity. Briefly, harvested AGS cells were washed with PBS twice and resuspended at a cell density of $5\times10^6$/200 μL in PBS containing 25% of BD Matrigel™ (Cat. 354248). Thereafter, 200 μL of the AGS cell suspension was injected subcutaneously ($5\times10^6$ cells/mouse) into female SCID mice (age 6-8 weeks) in the flank region. The tumor size was measured weekly with a vernier caliper (Laser 150×0.05 mm) and the tumor weight was estimated as "weight in mg=(width$^2$×length) mm$^3$/2" [Hisashi Ito et al. (1992)]. When the tumor weight reached 150-200 mg, the mice were randomly divided into 3 groups (n=8 per group) with each group having comparable tumor sizes, and started on antibody treatment. Tumor-bearing SCID mice were intraperitoneally injected with either hBBC.10.1 or hBBC.10.1 FQ once per week at the dose of 0.25 mg/kg for six weeks with the first dose being given at a 1.5-fold of the predetermined dose. Tumor-bearing SCID mice intraperitoneally injected with saline served as negative controls. The data (FIG. 20D) show that hBBC.10.1 FQ had slightly stronger antitumor activity.

Figure 21:
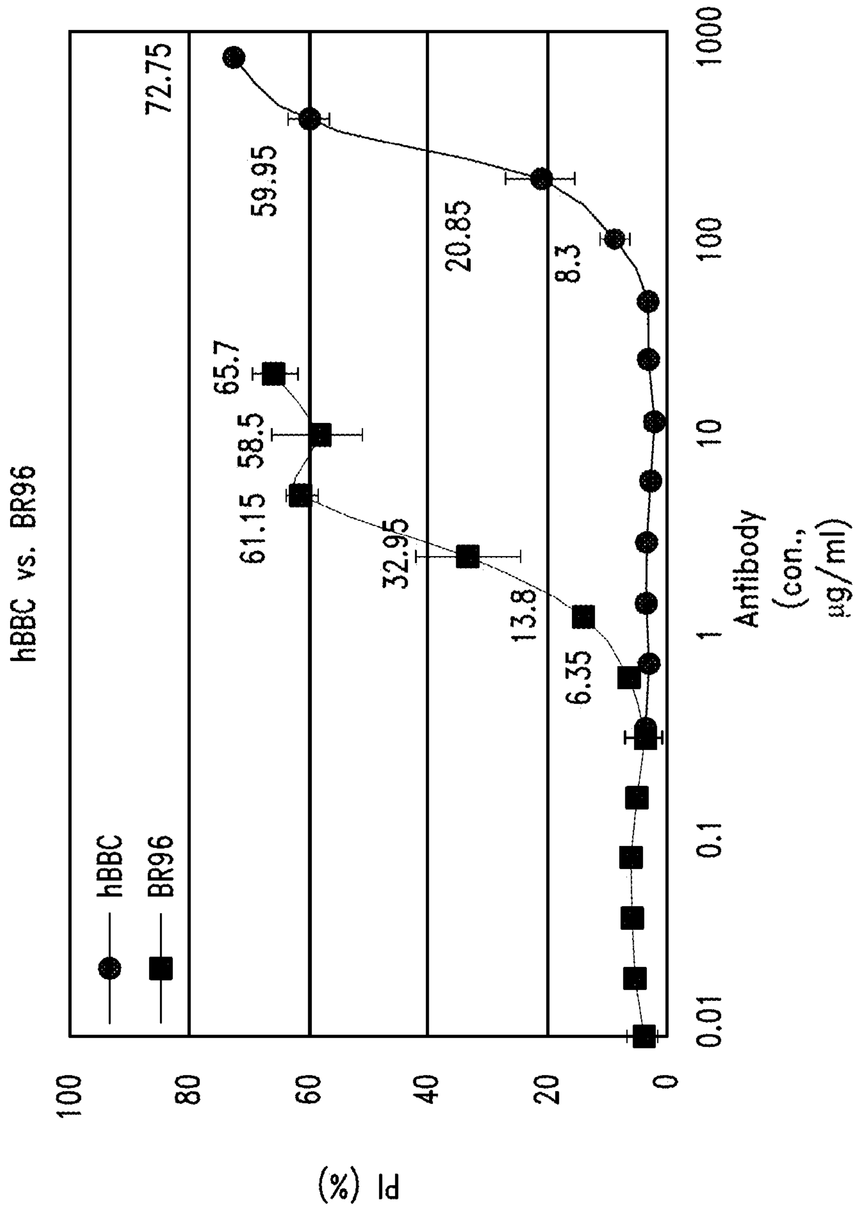
FIG. 21 shows direct killing of AGS tumor cells by hBBC.10.1 ("hBBC") and BR96 at various concentrations of antibody. Killing was measured as a percentage of target cells stained with propium iodide (PI).

In follow-on experiments, xenograft AGS (×AGS) cells isolated from AGS xenograft tumors were shown to express at least 2×hBBC epitope as compared to AGS cell line cells (data not shown). ×AGS cells also elicited more potent ADCC and CDC activity by hBBC as compared to parent cell line (data not shown). hBBC had a somewhat weaker direct killing effect on target ×AGS cells versus BR96 (PI staining), as shown in FIG. 21.

Anti-Tumor Activity of hBBC in a Xenograft Model of Gastric Carcinoma

The objective of this study was to compare the anti-tumor efficacy of hBBC.10.1 and BR96 at low doses ranging from 0.04 to 10 mg/kg in the TSGH 9201 xenograft model. Briefly, human gastric carcinoma cell line TSGH 9201 (Cat. 60146) was obtained from the Bioresource Collection and Research Center (BCRC) of the Food Industry Research and Development Institute (FIRDI, Hsinchu, Taiwan). TSGH 9201 cells with higher expression of the hBBC epitope were enriched by 2 rounds of fluorescent activated cell sorting (FACS) (BD FACSJAZZ™ cell sorter, BD Biosciences, Singapore, Cat. 655486) using a following staining with anti-hBBC (lot: B24) followed by 200-fold diluted Fluorescein (FITC)-AffiniPure™ Goat Anti-Human IgG, Fcγ Fragment Specific (Jackson ImmunoResearch Inc., West Grove, PA, Cat. 109-095-098). Compared with parental TSGH 9201 cells, the expression level of hBBC epitope was enhanced nearly 4-fold in the enriched cells, designated as TSGH 9201 (2s) (not shown) Both parental and enriched cells were grown in RPMI-1640 medium (Gibco) supplemented with 10% fetal bovine serum (FBS), and 1 mM sodium pyruvate. Cell culture was maintained in a humidified incubator under a 5% $CO_2$ atmosphere at 37° C. TSGH 9201 (2s) cells at passage 5-8 were used for tumor inoculation.

Specific-pathogen-free (SPF) female CB17 severe combined immunodeficiency (SCID) mice were purchased from BioLASCO (Taiwan), and allowed to acclimate for at least one week before any experimental manipulation. Mice were housed in individually ventilated cages (IVC) in a temperature-controlled environment (22±2° C.) with 50±10% humidity under a 12:12 hour light-dark cycle. All experiments were performed following the regulations and animal protection law mandated by the Council of Agriculture, Taiwan.

TSGH 9201 (2s) cells were re-suspended at a cell density of $5\times10^6$/200 μL in ice-cold serum-free medium containing 25% of BD Matrigel (Cat. 354248), and 200 μL of the cell suspension was injected subcutaneously into SCID mice at the age of 6-8 weeks in the flank region. Tumor size was measured weekly with a vernier caliper (Laser Tools and Technics (LTT), Hsin Chu City, Taiwan, 150×0.05 mm) and tumor weight was estimated as "weight in mg=(width$^2$× length) mm$^3$/2" [Ito et al. (1992) *Cancer Res.* 52:3739]. When tumor weight reached 150-200 mg, the mice were randomly divided into 3 groups (n=5 per group) with each group having comparable tumor sizes, and started antibody treatment. To evaluate the in vivo efficacy of hBBC.10.1 and BR96, tumor-bearing SCID mice were intraperitoneally injected with either hBBC.10.1 (lot: B24) or BR96 (lot: T05) at 10 mg/kg once per week for six weeks, with the first dose being given at 1.5-fold of the indicated dose. In a second study to compare the anti-tumor activity of hBBC.10.1 and BR96 at lower doses, tumor-bearing SCID mice were intraperitoneally injected with either hBBC.10.1 (lot: 17001) or BR96 (lot: 17001) once per week at 10, 1, 0.2, or 0.04 mg/kg for six weeks, with the first dose being given at 1.5-fold of the indicated dose. Tumor-bearing SCID mice intraperitoneally injected with saline served as negative controls.

Figure 22:
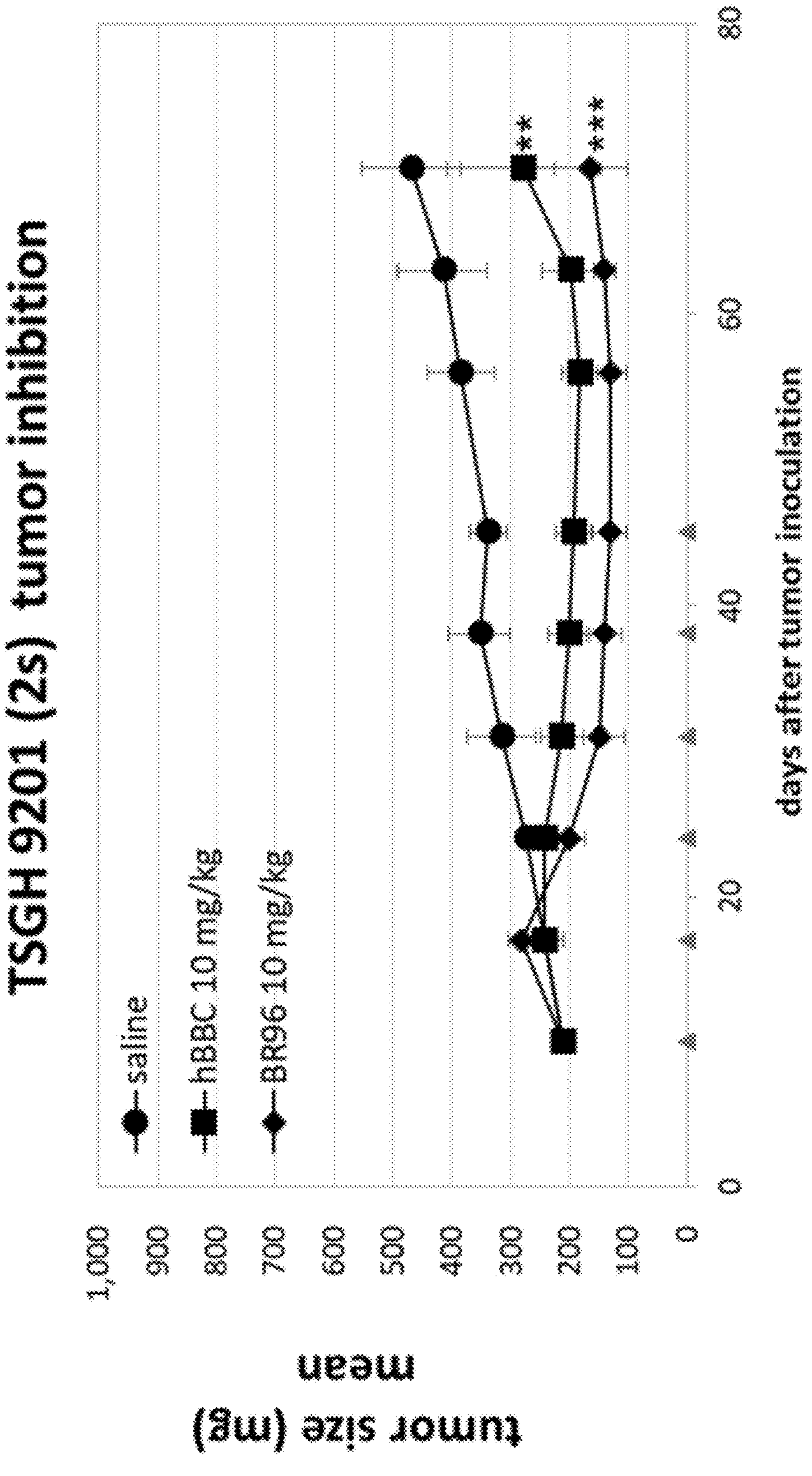
FIG. 22 shows antitumor activity of hBBC.10.1 ("hBBC") and BR96 in an in vivo xenograft experiment in which immunodeficient SCID-mice were administered human TSGH 9201 gastric carcinoma cells followed by antibody once tumors developed.

Results are shown in FIG. 22. Both hBBC.10.1 and BR96 significantly inhibited tumor growth at a weekly dose of 10 mg/kg, compared with saline group.

Anti-Tumor Activity of hBBC.10.1 in a Xenograft Model of Colorectal Adenocarcinoma The objectives of this study were: 1) to examine the ability of hBBC.10.1 to inhibit COLO 201 xenograft tumor growth; and 2) to compare the anti-tumor activities of hBBC and BR96 at doses ranging from 0.008 to 1 mg/kg in the COLO 201 xenograft model.

Briefly, the human colorectal adenocarcinoma cell line COLO 201 (CCL-224), derived from ascites fluid, was obtained from the American Type Culture Collection (ATCC, Manassas, VA, USA). COLO 201 cells were grown in RPMI-1640 medium (Gibco) supplemented with 10% fetal bovine serum (FBS), and 1 mM sodium pyruvate. Cell culture was maintained in a humidified incubator under a 5% $CO_2$ atmosphere at 37° C. COLO 201 cells at passage 5-8 were used for tumor inoculation.

Specific-pathogen-free (SPF) female CB17 severe combined immunodeficiency (SCID) mice were purchased from BioLASCO (Taiwan), and allowed to acclimate for at least one week before any experimental manipulation. Mice were housed in individually ventilated cages (IVC) in a temperature-controlled environment (22±2° C.) with 50±10% humidity under a 12:12 hour light-dark cycle. All experiments were performed following the regulations and animal protection law mandated by the Council of Agriculture, Taiwan.

COLO 201 cells were re-suspended at a cell density of 2×10$^6$/200 μL in ice-cold serum-free medium, and 200 μL of the cell suspension was injected subcutaneously into SCID mice at the age of 6-8 weeks in the flank region. Tumor size was measured weekly with a vernier caliper (Laser 150×0.05 mm) and tumor weight was estimated as "weight in mg=(width$^2$×length) mm$^3$/2" [Ito et al. (1992) *Cancer Res.* 52:3739]. When tumor weight reached 150-200 mg, the mice were randomly divided into control and treatment groups (n=6 per group) with each group having comparable tumor sizes, and antibody treatment was started. Two studies were executed to evaluate the in vivo efficacy of hBBC on inhibition of COLO 201 tumor growth.

Figure 23:
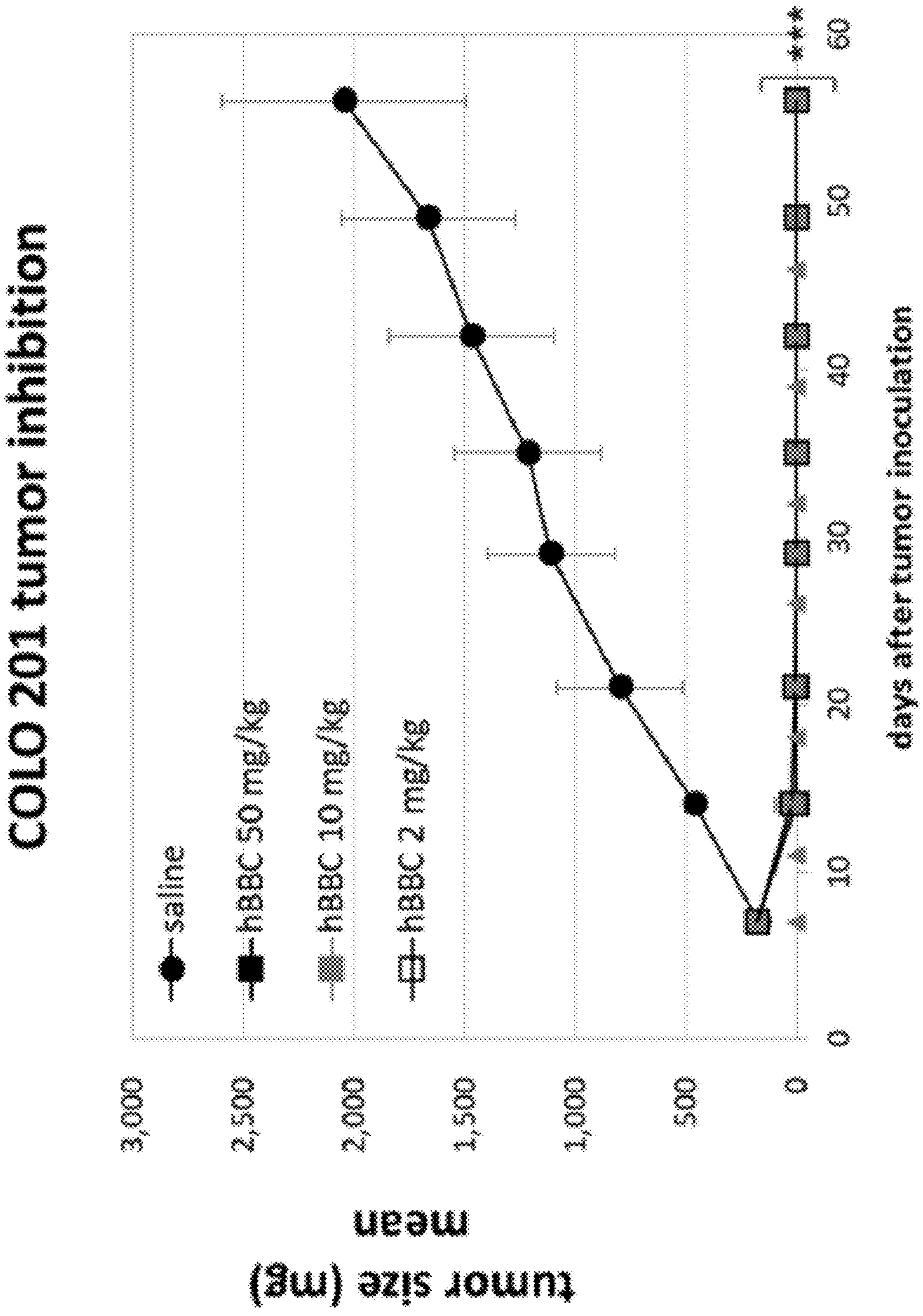
FIG. 23 shows antitumor activity of various concentrations of hBBC.10.1 ("hBBC") in an in vivo xenograft experiment in which immunodeficient SCID mice were administered human COLO 201 colorectal adenocarcinoma cells followed by antibody once tumors developed.

In the first study, the tumor-bearing SCID mice were intraperitoneally injected with hBBC.10.1 (lot: B26) at doses ranging from 2 to 50 mg/kg twice per week for six weeks with the first dose being given at a 1.5-fold of the indicated dose. Results from the first study are shown in FIG. 23. hBBC.10.1 treatment at 2-50 mg/kg significantly inhibited the growth of tumor compared with saline group. Tumors shrank rapidly and eventually disappeared at only one week after the administration of hBBC, i.e. two weeks after tumor inoculation.

Figure 24A:
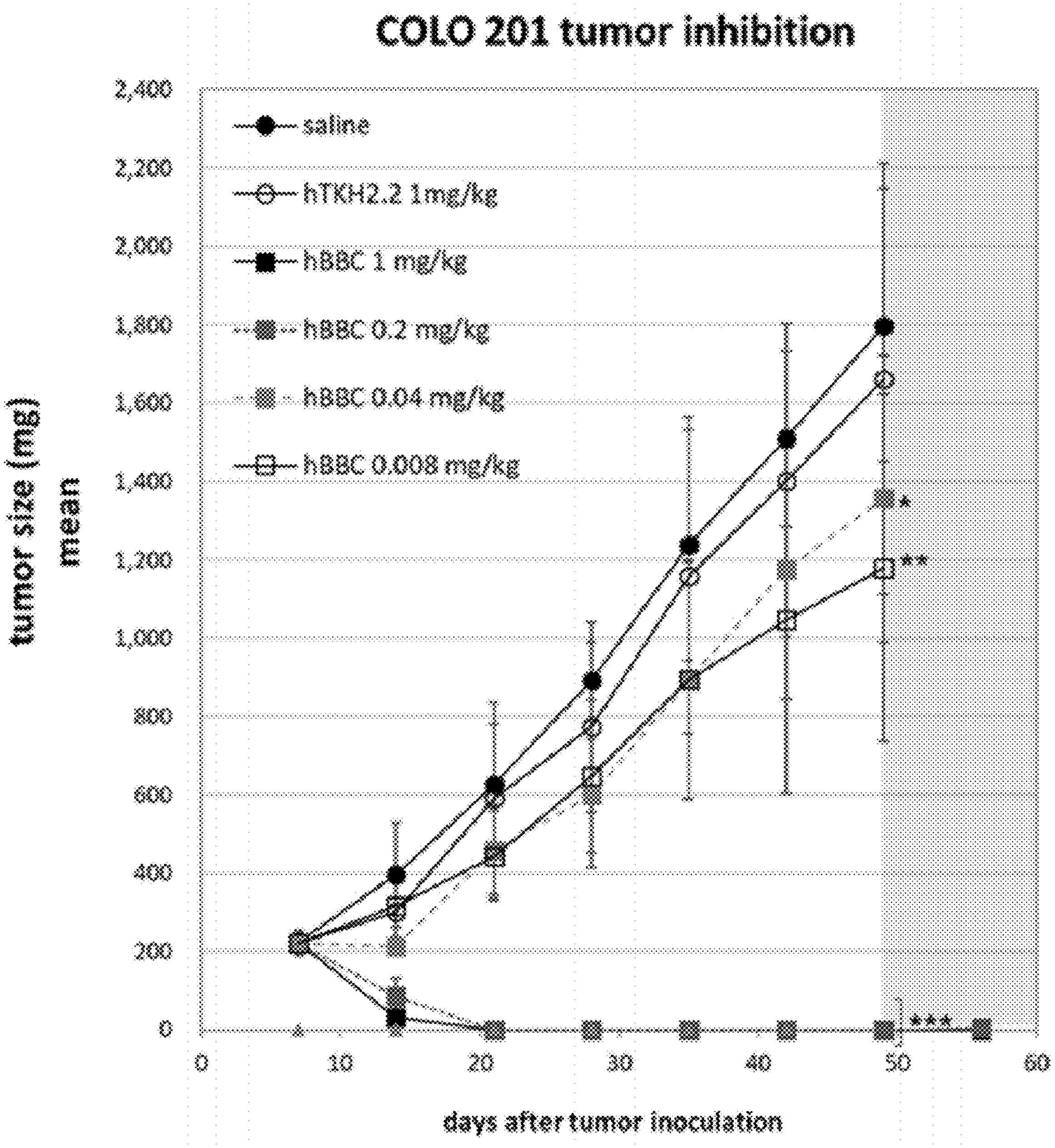
FIGS. 24A and 24B show antitumor activity of (A) hBBC.10.1 ("hBBC") and (B) BR96 in in vivo xenograft experiments in which immunodeficient SCID mice were administered human COLO 201 colorectal adenocarcinoma cells followed by antibody once tumors developed.
Figure 24B:
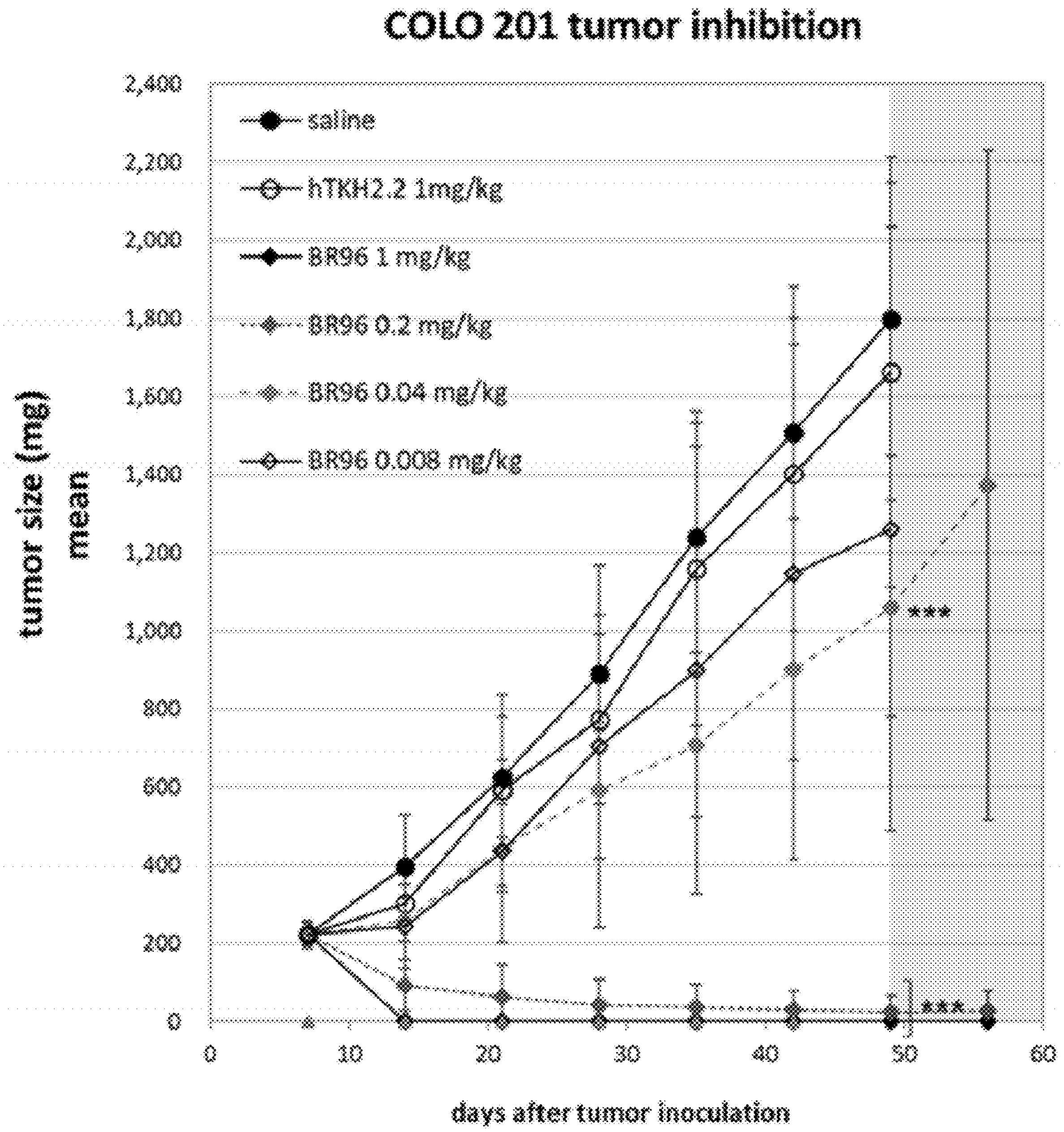

In the second study, further comparison on anti-tumor activity of hBBC.10.1 and BR96 at lower doses was conducted. Tumor-bearing SCID mice were intraperitoneally injected with either hBBC.10.1 (lot: 17001) or BR96 (lot: 17001) once per week (beginning day 7) at 1, 0.2, 0.04, and 0.008 mg/kg for six weeks with the first dose being given at a 1.5-fold of the indicated dose. Tumor-bearing SCID mice intraperitoneally injected with saline served as negative controls. Purified antibody hTKH2.2 (lot: 1020429) was included as a negative control antibody, which is a humanized anti-STn antibody produced in-house by transient expression in HEK293 cells. Results from the second study are shown in FIGS. 24A and 24B. Both hBBC.10.1 and BR96 at a weekly dose of 1 or 0.2 mg/kg significantly inhibited tumor growth compared with saline and hTKH2.2 control groups, while lower doses (0.04 and 0.008 mg/kg hBBC.10.1; 0.04 mg/kg BR96) showed effects on delaying of tumor growth. Due to ethical considerations, mice were sacrificed when the tumor burden was greater than 10% of body weight. Some mice receiving saline or lower doses of hBBC.10.1 or BR96 reached this endpoint at 49 days after inoculation; hence, statistical analysis was only performed on data obtained up until day 49.

This dose-response study shows that hBBC.10.1 has comparable anti-tumor efficacy to BR96 in COLO 201 tumor-bearing mice.

Example 7

Immunostaining of HBBC in Primate and Human Tissues hBBC.10.1 immunostaining was performed on corresponding healthy tissues from human and cynomolgus monkey (*Macaca fascicularis*). Briefly, staining was performed using formalin-fixed paraffin-embedded tissue sections with 2 μg/ml hBBC.10.1 according to a standard protocol. Results are summarized in Table 10 and showed similar staining patterns between human and cynomolgus tissues.

TABLE 10 hBBC.10.1 immunostaining of human and Cynomolgus tissues

| Tissue | Human | Cynomolgus |
|---|---|---|
| Pancreas | ± (3/3) | ± (3/3) |
| Tongue (Salivary gland tissue) | + (3/3) | − |
| Larynx | ++ (3/3) | + (3/3) |
| Esophagus | ± (3/3) | − |
| Stomach | + (3/3) | + (3/3) |
| Small intestine | +++ (3/3) | +++ (3/3) |
| Colon | − | − |
| Hypophysis | − | − |
| Breast | − | − |
| Cerebrum | − | − |
| Cerebellum | − | − |
| Adrenal gland | − | − |
| Parathyroid gland | − | − |
| Ovary | − | − |
| Testis | − | − |
| Spleen | − | − |
| Tonsil | − | − |

TABLE 10-continued hBBC.10.1 immunostaining of human and Cynomolgus tissues

| Tissue | Human | Cynomolgus |
|---|---|---|
| Thymus gland | – | – |
| Bone marrow | – | – |
| Lung | – | – |
| Heart | – | – |
| Liver | – | – |
| Kidney | – | – |
| Prostate | – | – |
| Uterus | – | – |
| Uterine cervix | – | – |
| Striated muscle | – | – |
| Skin | – | – |
| Nerve | – | – |
| greater omentum | – | – |
| endometrium | – | – |

Example 8

Safety and Tolerability Study of HBBC.10.1 in a Primate Model

To evaluate the tolerability and acceptable dose range of hbbc.10.1 in cynomolgus monkeys following a single intravenous (iv) bolus injection, a single-dose tolerability and dose-range-finding study was performed (non-glp). Briefly, male and female cynomolgus monkeys (*Macaca fascicularis*) were assigned to four groups of one male and one female in each group. The animals in groups 1 through 4 received dose levels of 0, 50, 200, and 300 mg/kg of hbbc.10.1, respectively. The animals in groups 2 and 3 were dosed once via slow i.v. Bolus injection over a duration of at least 5 minutes. The animals in groups 1 and 4 were dosed once by 20 minute (±1 minute) i.v. Infusion using a pump and primed infusion lines. Approximately 24 hours after dosing, necropsy was performed. During necropsy, gross observations and organ weights were recorded and tissues were collected for histopathology. Some of the collected tissues were processed to slides and examined microscopically.

The results indicated that hBBC.10.1 was well-tolerated in Cynomolgus monkeys from dose range 50-300 mg/kg. Minimal hemorrhage was observed in the cecum and/or colon in animals receiving 200 and 300 mg/kg and is likely test article-related. Other possible test article-related changes are chronic and acute inflammation in the stomach of one animal receiving 200 mg/kg, infiltration of neutrophils in the crypts of the duodenum in one animal receiving 200 mg/kg, and villous atrophy of the ileum in one animal receiving 300 mg/kg. No abnormal findings were observed in animals that received 50 mg/kg (Group 2).

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An antibody conjugate comprising an isolated antibody or antigen-binding fragment thereof, and a payload molecule covalently linked by a cleavable linker to the isolated antibody or antigen-binding fragment thereof, wherein the cleavable linker is a protease-sensitive linker comprising a valine-citrulline dipeptide, and the payload molecule is a therapeutic agent, a detectable indicator, or a combination thereof, wherein the isolated antibody or antigen-binding fragment thereof comprises:

(a) an immunoglobulin heavy chain variable region (VH) comprising a complementarity determining region 1 (VH CDR1) comprising the amino acid sequence set forth in SEQ ID NO: 2 or a variant thereof, wherein the variant consists of a Y to A substitution at position 33 of SEQ ID NO: 35, a complementarity determining region 2 (VH CDR2) comprising the amino acid sequence set forth in SEQ ID NO: 3 or a variant thereof, wherein the variant consists of a T to S substitution at position 55 of SEQ ID NO: 35, a complementarity determining region 3 (VH CDR3) comprising the amino acid sequence set forth in SEQ ID NO: 4 or a variant thereof, wherein the variant consists of a Y to A substitution at position 104 of SEQ ID NO: 35, a A to H substitution at position 106 of SEQ ID NO: 35, or both; and (b) an immunoglobulin light chain variable region (VL) comprising a complementarity determining region 1 (VL CDR1) comprising the amino acid sequence set forth in SEQ ID NO: 6 or a variant thereof, wherein the variant consists of a Y to A substitution at position 30 of SEQ ID NO: 5, a complementarity determining region 2 (VL CDR2) comprising the amino acid sequence set forth in SEQ ID NO: 7 or a variant thereof, wherein the variant consists of a G to A substitution at position 50 of SEQ ID NO: 5, and a complementarity determining region 3 (VL CDR3) comprising the amino acid sequence set forth in SEQ ID NO: 8 or a variant thereof, wherein the variant consists of a T to S substitution at position 93 of SEQ ID NO: 5.

2. The antibody conjugate of claim 1, wherein the isolated antibody or antigen-binding fragment thereof comprises: the VH CDR1 comprising the amino acid sequence set forth in SEQ ID NO: 2, the VH CDR2 comprising the amino acid sequence set forth in SEQ ID NO: 3, the VH CDR3 comprising the amino acid sequence set forth in SEQ ID NO: 4, the VL CDR1 comprising the amino acid sequence set forth in SEQ ID NO: 6, the VL CDR2 comprising the amino acid sequence set forth in SEQ ID NO: 7, and the VL CDR3 comprising the amino acid sequence set forth in SEQ ID NO: 8.

3. The antibody conjugate of claim 1, wherein the antibody or antigen-binding fragment thereof binds specifically to at least one of (a)-(d):

(a) a biantennary $Le^B/Le^B$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II], (b) a biantennary $Le^Y/Le^Y$ antigen comprising $Fuc_4(Gal\beta1\rightarrow4GlcNAc)_2$ [III] or $[Fuc\alpha1\text{-}2Gal\beta1\text{-}4(Fuc\alpha1\text{-}3)GlcNAc]_2$ [IV], (c) a biantennary $Le^B/Le^Y$ antigen comprising $Fuc_2(Gal\beta1\rightarrow3GlcNAc)[Fuc_2(Gal\beta1\rightarrow4GlcNAc)]$ [V], or $[Fuc\alpha1\text{-}2Gal\beta1\text{-}3(Fuc\alpha1\text{-}4)GlcNAc][Fuc\alpha1\text{-}2Gal\beta1\text{-}4(Fuc\alpha1\text{-}3)GlcNAc]$ [VI], and (d) a biantennary $Le^Y/Le^B$ antigen comprising $Fuc_2(Gal\beta1\text{-}4GlcNAc)[Fuc_2(Gal\beta1\text{-}3GlcNAc)]$ [VII] or $[Fuc\alpha1\text{-}2Gal\beta1\text{-}4(Fuc\alpha1\text{-}3)GlcNAc][Fuc\alpha1\text{-}2Gal\beta1\text{-}3(Fuc\alpha11\text{-}4)GlcNAc]$[VIII].

4. The antibody conjugate of claim 3, wherein the antibody or antigen-binding fragment thereof binds specifically to:

the biantennary $Le^B/Le^B$ antigen [I] or [II], the biantennary $Le^Y/Le^Y$ antigen [III] or [IV], the biantennary $Le^B/Le^Y$ antigen [V] or [VI], and the biantennary be $Le^Y/Le^B$ antigen [VII] or [VIII].

5. The antibody conjugate of claim 1, wherein the antibody or antigen-binding fragment thereof does not bind specifically to a monoantennary $Le^x$ antigen that comprises Galβ1→4(Fucα1→3)GlcNAc [IX], or to a biantennary $Le^x$ antigen that comprises $[Gal\beta1\rightarrow4(Fuc\alpha1\rightarrow3)GlcNAc]_2$ [X], or to a monoantennary $Le^A$ antigen that comprises Galβ1-3(Fucα1-4)GlcNAc [XI], or to a monoantennary H antigen type 2 that comprises Fucα1-2Gal31-4GlcNAc [XII], or to a biantennary H antigen type 2 that comprises $(Fuc\alpha1\text{-}2Gal\beta13\text{-}4GlcNAc)_2$ [XIII] or to a monoantennary H antigen type 1 that comprises Fucα1-2Galβ1-3GlcNAc [XIV].

6. The antibody conjugate of claim 1, wherein:

the VH comprises an amino acid sequence that has at least 90, 91, 92, 93, 94, 95, 96, 97, 98, or 99 percent identity to the amino acid sequence set forth in SEQ ID NO: 35, and the VL comprises an amino acid sequence that has at least 90, 91, 92, 93, 94, 95, 96, 97, 98, or 99 percent identity to the amino acid sequence set forth in SEQ ID NO: 5.

7. The antibody conjugate of claim 6, wherein the VH comprises an amino acid sequence that has at least 97 percent identity to the amino acid sequence set forth in SEQ ID NO: 35, and the VL comprises an amino acid sequence that has at least 97 percent identity to the amino acid sequence set forth in SEQ ID NO: 5.

8. The antibody conjugate of claim 6, wherein the VH comprises the amino acid sequence set forth in SEQ ID NO: 35, and the VL comprises the amino acid sequence set forth in SEQ ID NO: 5.

9. The antibody conjugate of claim 1, wherein the antibody or antigen-binding fragment thereof further comprises an Fc fragment comprising CH2 and CH3 domains of a human IgG1 subclass or CH2 and CH3 domains of a human IgG4 subclass.

10. The antibody conjugate of claim 9, wherein the Fc fragment comprises the CH2 and CH3 domains of human IgG1 subclass.

11. The antibody conjugate of claim 1, wherein the antibody comprises: an immunoglobulin heavy chain having the amino acid sequence set forth in SEQ ID NO: 10 and an immunoglobulin light chain having the amino acid sequence set forth in SEQ ID NO: 11.

12. An antibody conjugate comprising an isolated antibody or antigen-binding fragment thereof linked to a payload molecule by a cleavable linker, wherein:

(i) the isolated antibody or antigen-binding fragment thereof comprises:

(a) in an immunoglobulin heavy chain variable region, a complementarity determining region 1 (VH CDR1) comprising the amino acid sequence set forth in SEQ ID NO: 2 or a variant thereof, wherein the variant consists of a Y to A substitution at position 33 of SEQ ID NO: 35, a VH CDR2 comprising the amino acid sequence set forth in SEQ ID NO: 3 or a variant thereof, wherein the variant consists of a T to S substitution at position 55 of SEQ ID NO: 35, a VH CDR3 comprising the amino acid sequence set forth in SEQ ID NO: 4 or a variant thereof, wherein the variant consists of a Y to A substitution at position 104 of SEQ ID NO: 35, a A to H substitution at position 106 of SEQ ID NO: 35, or both;

(b) in an immunoglobulin light chain variable region (VL), a complementarity determining region 1 (VL CDR1) comprising the amino acid sequence set forth in SEQ ID NO: 6 or a variant thereof, wherein the variant consists of a Y to A substitution at position 30 of SEQ ID NO: 5, a VL CDR2 comprising the amino acid sequence set forth in SEQ ID NO: 7 or a variant thereof, wherein the variant consists of a G to A substitution at position 50 of SEQ ID NO: 5, and a VL CDR3 comprising the amino acid sequence set forth in SEQ ID NO: 8 or a variant thereof, wherein the variant consists of a T to S substitution at position 93 of SEQ ID NO: 5, and (c) means for coupling to the linker:

(ii) the cleavable linker is a protease-sensitive linker comprising a valine-citrulline dipeptide; and (iii) the payload molecule is a therapeutic agent.

13. The antibody conjugate of claim 1, wherein the therapeutic agent is selected from the group consisting of a maytansinoid, an auristatin, doxorubicin, calicheamicin, and a PBD dimer.

14. A pharmaceutical composition, comprising the antibody conjugate of claim 1 and a pharmaceutical carrier.

15. The pharmaceutical composition of claim 14 for treating a cancer that expresses one or more biantennary Lewis antigens selected from the group consisting of biantennary $Le^B/Le^B$, biantennary $Le^Y/Le^Y$, biantennary $Le^B/Le^Y$, and biantennary $Le^Y/Le^B$ in a subject in need thereof, wherein the payload molecule is a therapeutic agent.

16. The pharmaceutical composition of claim 15, wherein the cancer is colorectal adenocarcinoma, gastric adenocarcinoma, or lung cancer.

17. A method of detecting cancer, comprising administering the antibody conjugate of claim 1 to a subject in need thereof, wherein the payload molecule is a detectable indicator.

18. The antibody conjugate of claim 13, wherein the therapeutic agent is monomethylauristatin E (MMAE).

19. The antibody conjugate of claim 13, wherein the auristatin is monomethylauristatin E (MMAE) or monomethylauristatin F (MMAF).

20. The antibody conjugate of claim 1, wherein the payload molecule is selected from the group consisting of a tubulin-targeting anti-mitotic agent, a peptide-based toxin, a PBD dimer, an antibiotic, a pyrimidine synthesis inhibitor, an antimetabolite, a DNA alkylating agent, and a topoisomerase inhibitor.

21. The antibody conjugate of claim 1, wherein the payload molecule is a cytotoxic agent or an anti-proliferative agent.

22. The antibody conjugate of claim 12, wherein the payload molecule is a cytotoxic agent or an anti-proliferative agent.

23. The antibody conjugate of claim 12, wherein the payload molecule is selected from the group consisting of a tubulin-targeting anti-mitotic agent, a peptide-based toxin, a PBD dimer, an antibiotic, a pyrimidine synthesis inhibitor, an antimetabolite, a DNA alkylating agent, and a topoisomerase inhibitor.

24. The antibody conjugate of claim 12, wherein the antibody or antigen-binding fragment thereof binds specifically to at least one of (a)-(d):

(a) a biantennary $Le^B/Le^B$ antigen comprising $Fuc_4(Gal\beta1\rightarrow3GlcNAc)_2$ [I] or $[Fuc\alpha1\text{-}2Gal\beta1\text{-}3(Fuc\alpha1\text{-}4)GlcNAc]_2$ [II], (b) a biantennary $Le^Y/Le^Y$ antigen comprising $Fuc_4(Gal\beta1\rightarrow4GlcNAc)_2$ [III] or $[Fuc\alpha1\text{-}2Gal\beta1\text{-}4(Fuc\alpha1\text{-}3)GlcNAc]_2$ [IV], (c) a biantennary $Le^B/Le^Y$ antigen comprising $Fuc_2(Gal\beta1\rightarrow3GlcNAc)[Fuc_2(Gal\beta1\rightarrow4GlcNAc)]$ [V], or [Fucα1-2Galβ1-3(Fucα1-4)GlcNAc][Fucα1-2Galβ1-4(Fucα1-3)GlcNAc] [VI], and (d) a biantennary $Le^Y/Le^B$ antigen comprising $Fuc_2(Gal\beta1\text{-}4GlcNAc)[Fuc_2(Gal\beta1\text{-}3GlcNAc)]$ [VII] or

[Fucα1-2Galβ1-4(Fucα1-3)GlcNAc][Fucα1-2Galβ1-3(Fucα1-4)GlcNAc] [VIII].

25. The pharmaceutical composition of claim 15, wherein the payload molecule is a cytotoxic agent or an anti-proliferative agent.

26. The antibody conjugate of claim 12, wherein the isolated antibody or antigen-binding fragment thereof comprises: the VH CDR1 comprising the amino acid sequence set forth in SEQ ID NO: 2, the VH CDR2 comprising the amino acid sequence set forth in SEQ ID NO: 3, the VH CDR3 comprising the amino acid sequence set forth in SEQ ID NO: 4, the VL CDR1 comprising the amino acid sequence set forth in SEQ ID NO: 6, the VL CDR2 comprising the amino acid sequence set forth in SEQ ID NO: 7, and the VL CDR3 comprising the amino acid sequence set forth in SEQ ID NO: 8.

* * * * *

SEQUENCE LISTING

```
Sequence total quantity: 51
SEQ ID NO: 1            moltype = AA  length = 121
FEATURE                 Location/Qualifiers
REGION                  1..121
                        note = Synthetic sequence - heavy chain variable (VH)
                         domain of antibody hBBC.10.1FQ
source                  1..121
                        mol_type = protein
                        organism = synthetic construct
SEQUENCE: 1
QVQLQESGPG LVKPSQTLSL TCTVSGYSIT SGYTWHWIRQ HPGKGLEWLG YIHYTGNTKY  60
SPSLKSRLSI SRDTSKNTFY LQMNSLTTED TAVYYCGREA LRGYDAGFWF TYWGQGTLVT  120
V                                                                  121

SEQ ID NO: 2            moltype = AA  length = 6
FEATURE                 Location/Qualifiers
REGION                  1..6
                        note = Synthetic sequence - heavy chain complementarity
                         determining region 1 (VH CDR1) of antibody IMH2/BBC,
                         antibody hBBC.8, antibody hBBC.9,
source                  1..6
                        mol_type = protein
                        organism = synthetic construct
SEQUENCE: 2
SGYTWH                                                             6

SEQ ID NO: 3            moltype = AA  length = 16
FEATURE                 Location/Qualifiers
REGION                  1..16
                        note = Synthetic sequence - VH CDR2 of antibody hBBC.9.1,
                         antibody hBBC.10.1, and antibody hBBC.10.1FQ
source                  1..16
                        mol_type = protein
```

```
                        organism = synthetic construct
SEQUENCE: 3
YIHYTGNTKY SPSLKS                                              16

SEQ ID NO: 4            moltype = AA  length = 14
FEATURE                 Location/Qualifiers
REGION                  1..14
                        note = Synthetic sequence - VH CDR3 of antibody hBBC.10.1,
                         and antibody hBBC.10.1FQ
source                  1..14
                        mol_type = protein
                        organism = synthetic construct
SEQUENCE: 4
EALRGYDAGF WFTY                                                14

SEQ ID NO: 5            moltype = AA  length = 107
FEATURE                 Location/Qualifiers
REGION                  1..107
                        note = Synthetic sequence - light chain variable (VL)
                         domain of antibody hBBC.10, antibody hBBC.10.1, and
                         antibody hBBC.10.1FQ
source                  1..107
                        mol_type = protein
                        organism = synthetic construct
SEQUENCE: 5
DIQMTQSPSS LSASVGDRVT ITCTASEDIY NRLTWYQQKP GKVPRLLISG ATSLDTGVPS  60
RFSGSGSGTD YTLTISSLQP EDVATYYCQQ YWTTPWTFGQ GTKLEIK               107

SEQ ID NO: 6            moltype = AA  length = 11
FEATURE                 Location/Qualifiers
REGION                  1..11
                        note = Synthetic sequence - light chain complementarity
                         determining region 1 (VL CDR1) of antibody IMH2/BBC,
                         antibody hBBC.8, antibody hBBC.9,
source                  1..11
                        mol_type = protein
                        organism = synthetic construct
SEQUENCE: 6
TASEDIYNRL T                                                   11

SEQ ID NO: 7            moltype = AA  length = 7
FEATURE                 Location/Qualifiers
REGION                  1..7
                        note = Synthetic sequence - VL CDR2 of antibody IMH2/BBC,
                         antibody hBBC.8, antibody hBBC.9, antibody hBBC.9.1,
                         antibody hBBC.10, antibody hBBC.10.1, and antibody
                         hBBC.10.1FQ
source                  1..7
                        mol_type = protein
                        organism = synthetic construct
SEQUENCE: 7
GATSLDT                                                        7

SEQ ID NO: 8            moltype = AA  length = 9
FEATURE                 Location/Qualifiers
REGION                  1..9
                        note = Synthetic sequence - VL CDR3 of antibody IMH2/BBC,
                         antibody hBBC.8, antibody hBBC.9, antibody hBBC.9.1,
                         antibody hBBC.10, antibody hBBC.10.1, and antibody
                         hBBC.10.1FQ
source                  1..9
                        mol_type = protein
                        organism = synthetic construct
SEQUENCE: 8
QQYWTTPWT                                                      9

SEQ ID NO: 9            moltype = AA  length = 278
FEATURE                 Location/Qualifiers
REGION                  1..278
                        note = Synthetic sequence - single chain fragment variable
                         (scFv) derived from antibody hBBC.10.1, in the [VL-VH]
                         orientation
VARIANT                 113..157
                        note = Any one or all of amino acids 113-157 can either be
                         present or absent
source                  1..278
                        mol_type = protein
                        organism = synthetic construct
SEQUENCE: 9
```

```
DIQMTQSPSS LSASVGDRVT ITCTASEDIY NRLTWYQQKP GKVPRLLISG ATSLDTGVPS  60
RFSGSGSGTD YTLTISSLQP EDVATYYCQQ YWTTPWTFGQ GTKLEIKGGG GSGGGGSGGG  120
GSGGGGSGGG GSGGGGSGGG GSGGGGSGGG GSGGGGSQVQ LQESGPGLVK PSQTLSLTCT  180
VSGYSITSGY TWHWIRQHPG KGLEWLGYIH YTGNTKYSPS LKSRLSISRD TSKNQFFLKL  240
SSVTTEDTAV YYCGREALRG YDAGFWFTYW GQGTLVTV                          278

SEQ ID NO: 10          moltype = AA  length = 453
FEATURE                Location/Qualifiers
REGION                 1..453
                       note = Synthetic sequence - full-length heavy chain (HC) of
                        antibody hBBC.10.1
source                 1..453
                       mol_type = protein
                       organism = synthetic construct
SEQUENCE: 10
QVQLQESGPG LVKPSQTLSL TCTVSGYSIT SGYTWHWIRQ HPGKGLEWLG YIHYTGNTKY  60
SPSLKSRLSI SRDTSKNQFF LKLSSVTTED TAVYYCGREA LRGYDAGFWF TYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 11          moltype = AA  length = 214
FEATURE                Location/Qualifiers
REGION                 1..214
                       note = Synthetic sequence - full-length light chain (LC) of
                        antibody hBBC.10, antibody hBBC.10.1, and antibody
                        hBBC.10.1FQ
source                 1..214
                       mol_type = protein
                       organism = synthetic construct
SEQUENCE: 11
DIQMTQSPSS LSASVGDRVT ITCTASEDIY NRLTWYQQKP GKVPRLLISG ATSLDTGVPS  60
RFSGSGSGTD YTLTISSLQP EDVATYYCQQ YWTTPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 12          moltype = DNA  length = 363
FEATURE                Location/Qualifiers
misc_feature           1..363
                       note = Synthetic sequence - heavy chain variable (VH)
                        domain of antibody hBBC.10.1
source                 1..363
                       mol_type = other DNA
                       organism = synthetic construct
SEQUENCE: 12
caggtgcagc tgcaggaaag cggcccgggc ctggtgaaac cgagccagac cctgagcctg  60
acctgcaccg tgagcggcta tagcattacc agcggctata cctggcattg gattcgccag  120
catccgggca aaggcctgga atggctgggc tatattcatt ataccggcaa caccaaatat  180
agcccgagcc tgaaaagccg cctgagcatt agccgcgata ccagcaaaaa ccagttcttc  240
ctgaaactga gcagcgtgac caccgaagat accgcggtgt attattgcgg ccgcgaagcg  300
ctgcgcggct atgatgctgg cttctggttt acctattggg gccaaggcac cctggtgacc  360
gtg                                                                363

SEQ ID NO: 13          moltype = DNA  length = 18
FEATURE                Location/Qualifiers
misc_feature           1..18
                       note = Synthetic sequence - heavy chain complementarity
                        determining region 1 (VH CDR1) of antibody IMH2/BBC,
                        antibody hBBC.8, antibody hBBC.9
source                 1..18
                       mol_type = other DNA
                       organism = synthetic construct
SEQUENCE: 13
agcggctata cctggcat                                               18

SEQ ID NO: 14          moltype = DNA  length = 48
FEATURE                Location/Qualifiers
misc_feature           1..48
                       note = Synthetic sequence - VH CDR2 of antibody hBBC.9.1,
                        antibody hBBC.10, and antibody hBBC.10.1FQ
source                 1..48
                       mol_type = other DNA
                       organism = synthetic construct
SEQUENCE: 14
tatattcatt ataccggcaa caccaaatat agcccgagcc tgaaaagc              48
```

```
SEQ ID NO: 15           moltype = DNA  length = 42
FEATURE                 Location/Qualifiers
misc_feature            1..42
                        note = Synthetic sequence - VH CDR3 of antibody hBBC.10.1
                         and antibody hBBC.10.1FQ
source                  1..42
                        mol_type = other DNA
                        organism = synthetic construct
SEQUENCE: 15
gaagcgctgc gcggctatga tgctggcttc tggtttacct at                     42

SEQ ID NO: 16           moltype = DNA  length = 321
FEATURE                 Location/Qualifiers
misc_feature            1..321
                        note = Synthetic sequence - light chain variable (VL)
                         domain of antibody hBBC.10, antibody hBBC.10.1, and
                         antibody hBBC.10.1FQ
source                  1..321
                        mol_type = other DNA
                        organism = synthetic construct
SEQUENCE: 16
gatattcaga tgacccagag cccgagcagc ctgagcgcga gcgtgggcga tcgcgtgacc  60
attacctgca ccgcgagcga agatatttat aaccgcctga cctggtatca gcagaaaccg  120
ggcaaagtgc cgcgtctgct gatttctggc gcgaccagcc tggataccgg cgtgccgagc  180
cgctttagcg gcagcggcag cggcaccgat tacaccctga ccattagcag cctgcagccg  240
gaagatgtgg cgacctatta ttgccagcag tattggacca ccccgtggac ctttggccag  300
ggcaccaaac tggaaattaa a                                            321

SEQ ID NO: 17           moltype = DNA  length = 33
FEATURE                 Location/Qualifiers
misc_feature            1..33
                        note = Synthetic sequence - light chain complementarity
                         determining region 1 (VL CDR1) of antibody IMH2/BBC,
                         antibody hBBC.8, antibody hBBC.9
source                  1..33
                        mol_type = other DNA
                        organism = synthetic construct
SEQUENCE: 17
accgcgagcg aagatattta taaccgcctg acc                               33

SEQ ID NO: 18           moltype = DNA  length = 21
FEATURE                 Location/Qualifiers
misc_feature            1..21
                        note = Synthetic sequence - VL CDR2 of antibody IMH2/BBC,
                         antibody hBBC.8, antibody hBBC.9, antibody hBBC.9.1,
                         antibody hBBC.10, antibody hBBC.10.1, and antibody
                         hBBC.10.1FQ
source                  1..21
                        mol_type = other DNA
                        organism = synthetic construct
SEQUENCE: 18
ggcgcgacca gcctggatac c                                            21

SEQ ID NO: 19           moltype = DNA  length = 27
FEATURE                 Location/Qualifiers
misc_feature            1..27
                        note = Synthetic sequence - VL CDR3 of antibody antibody
                         IMH2/BBC, antibody hBBC.8, antibody hBBC.9, antibody
                         hBBC.9.1, antibody hBBC.10, antibody hBBC.10.1, and
                         antibody hBBC.10.1FQ
source                  1..27
                        mol_type = other DNA
                        organism = synthetic construct
SEQUENCE: 19
cagcagtatt ggaccacccc gtggacc                                      27

SEQ ID NO: 20           moltype = DNA  length = 834
FEATURE                 Location/Qualifiers
misc_feature            1..834
                        note = Synthetic sequence - single chain fragment variable
                         (scFv) in the [VL-(L)-VH] orientation derived from
                         antibody hBBC.10.1
misc_feature            337..471
                        note = Any one or all of nucleotides 337-471 can either be
                         present or absent.
source                  1..834
                        mol_type = other DNA
                        organism = synthetic construct
SEQUENCE: 20
```

```
gatattcaga tgacccagag cccgagcagc ctgagcgcga gcgtgggcga tcgcgtgacc  60
attacctgca ccgcgagcga agatatttat aaccgcctga cctggtatca gcagaaaccg  120
ggcaaagtgc cgcgtctgct gatttctggc gcgaccagcc tggataccgg cgtgccgagc  180
cgctttagcg gcagcggcag cggcaccgat tacaccctga ccattagcag cctgcagccg  240
gaagatgtgg cgacctatta ttgccagcag tattggacca ccccgtggac ctttggccag  300
ggcaccaaac tggaaattaa aggtggaggc ggttctggtg gaggcggttc tggtggaggc  360
ggttctggtg gaggcggttc tggtggaggc ggttctggtg gaggcggttc tggtggaggc  420
ggttctggtg gaggcggttc tggtggaggc ggttctggtg gaggcggttc tcaggtgcag  480
ctgcaggaaa gcggcccggg cctggtgaaa ccgagccaga ccctgagcct gacctgcacc  540
gtgagcggct atagcattac cagcggctat acctggcatt ggattcgcca gcatccgggc  600
aaaggcctgg aatggctggg ctatattcat tataccggca acaccaaata tagcccgagc  660
ctgaaaagcc gcctgagcat tagccgcgat accagcaaaa accagttctt cctgaaactg  720
agcagcgtga ccaccgaaga taccgcggtg tattattgcg gccgcgaagc gctgcgcggc  780
tatgatgctg gcttctggtt tacctattgg ggccaaggca ccctggtgac cgtg        834
```

```
SEQ ID NO: 21          moltype = DNA  length = 1362
FEATURE                Location/Qualifiers
misc_feature           1..1362
                       note = Synthetic sequence - full-length heavy chain (HC) of
                        antibody hBBC.10.1
source                 1..1362
                       mol_type = other DNA
                       organism = synthetic construct
SEQUENCE: 21
caggtgcagc tgcaggaaag cggcccgggc ctggtgaaac cgagccagac cctgagcctg  60
acctgcaccg tgagcggcta tagcattacc agcggctata cctggcattg gattcgccag  120
catccgggca aaggcctgga atggctgggc tatattcatt ataccggcaa caccaaatat  180
agcccgagcc tgaaaagccg cctgagcatt agccgcgata ccagcaaaaa ccagttcttc  240
ctgaaactga gcagcgtgac caccgaagat accgcggtgt attattgcgg ccgcgaagcg  300
ctgcgcggct atgatgctgg cttctggttt acctattggg gccaaggcac cctggtgacc  360
gtgtcgagcg cttccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaat ga                    1362
```

```
SEQ ID NO: 22          moltype = DNA  length = 645
FEATURE                Location/Qualifiers
misc_feature           1..645
                       note = Synthetic sequence - full-length light chain (LC) of
                        antibody hBBC.10.1 and antibody hBBC.10.1FQ
source                 1..645
                       mol_type = other DNA
                       organism = synthetic construct
SEQUENCE: 22
gatattcaga tgacccagag cccgagcagc ctgagcgcga gcgtgggcga tcgcgtgacc  60
attacctgca ccgcgagcga agatatttat aaccgcctga cctggtatca gcagaaaccg  120
ggcaaagtgc cgcgtctgct gatttctggc gcgaccagcc tggataccgg cgtgccgagc  180
cgctttagcg gcagcggcag cggcaccgat tacaccctga ccattagcag cctgcagccg  240
gaagatgtgg cgacctatta ttgccagcag tattggacca ccccgtggac ctttggccag  300
ggcaccaaac tggaaattaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttaa                 645
```

```
SEQ ID NO: 23          moltype = AA  length = 14
FEATURE                Location/Qualifiers
REGION                 1..14
                       note = Synthetic sequence - illustrative spacer amino acid
                        sequence
source                 1..14
                       mol_type = protein
                       organism = synthetic construct
SEQUENCE: 23
EGKSSGSGSE SKVD                                                   14
```

```
SEQ ID NO: 24           moltype = AA  length = 18
FEATURE                 Location/Qualifiers
REGION                  1..18
                        note = Synthetic sequence - illustrative spacer amino acid
                         sequence
source                  1..18
                        mol_type = protein
                        organism = synthetic construct
SEQUENCE: 24
KESGSVSSEQ LAQFRSLD                                                18

SEQ ID NO: 25           moltype = AA  length = 5
FEATURE                 Location/Qualifiers
REGION                  1..5
                        note = Synthetic sequence - flexible polylinker amino acid
                         sequence
source                  1..5
                        mol_type = protein
                        organism = synthetic construct
SEQUENCE: 25
GGGGS                                                              5

SEQ ID NO: 26           moltype = AA  length = 15
FEATURE                 Location/Qualifiers
REGION                  1..15
                        note = Synthetic sequence - flexible polylinker amino acid
                         sequence
source                  1..15
                        mol_type = protein
                        organism = synthetic construct
SEQUENCE: 26
GGGGSGGGGS GGGGS                                                   15

SEQ ID NO: 27           moltype = AA  length = 107
FEATURE                 Location/Qualifiers
REGION                  1..107
                        note = Synthetic sequence - VL domain of antibody IMH2/BBC
source                  1..107
                        mol_type = protein
                        organism = synthetic construct
SEQUENCE: 27
DIQMTQSSSS FSVSLGDRVT ITCTASEDIY NRLTWYQQKP GNVPRLLISG ATSLDTGVPS  60
RFSGSRSGKD YALSITSLQT EDVATYYCQQ YWTTPWTFGG GTRLEIK                107

SEQ ID NO: 28           moltype = AA  length = 121
FEATURE                 Location/Qualifiers
REGION                  1..121
                        note = Synthetic sequence - VH domain of antibody IMH2/BBC
source                  1..121
                        mol_type = protein
                        organism = synthetic construct
SEQUENCE: 28
DVQLQESGPD LVKPSQSLSL TCTVTGYSIT SGYTWHWIRQ FPGNTLEWLG YIHYSGNTKY  60
SPSLKSRLSV TRDTSKNQFF LQLNSVTTED TATYYCGREA LRGYDHGFWF TYWGQGTLVT  120
V                                                                  121

SEQ ID NO: 29           moltype = AA  length = 107
FEATURE                 Location/Qualifiers
REGION                  1..107
                        note = Synthetic sequence - VL domain of human acceptor
                         framework AAS01771.1
source                  1..107
                        mol_type = protein
                        organism = synthetic construct
SEQUENCE: 29
DIQMTQSPSS LSASVGDRVT ITCRASQGIS NYLAWYQQKP GKVPKLLIYA ASTLQSGVPS  60
RFSGSGSGTD FTLTISSLQP EDVATYYCQK YNSAPYTFGQ GTKLEIK                107

SEQ ID NO: 30           moltype = AA  length = 120
FEATURE                 Location/Qualifiers
REGION                  1..120
                        note = Synthetic sequence - VH domain of human acceptor
                         framework CAD89404.1
source                  1..120
                        mol_type = protein
                        organism = synthetic construct
SEQUENCE: 30
QVQLQESGPG LVKPSQTLSL TCTVSGGSIS SGAYYWSWIR QHPGKGLEWI GYIYYSGTTY  60
```

```
YNPSLKSRLS MSRDTSKNQF SLKLSSVTAA DTAVYYCARG PYYDSPRPFD PWGQGTLVTV  120

SEQ ID NO: 31           moltype = AA  length = 107
FEATURE                 Location/Qualifiers
REGION                  1..107
                        note = Synthetic sequence - VL domain of antibody hBBC.8
source                  1..107
                        mol_type = protein
                        organism = synthetic construct
SEQUENCE: 31
DIQMTQSPSS LSASVGDRVT ITCTASEDIY NRLTWYQQKP GKVPRLLISG ATSLDTGVPS  60
RFSGSRSGTD FTLTISSLQP EDVATYYCQQ YWTTPWTFGQ GTKLEIK                107

SEQ ID NO: 32           moltype = AA  length = 121
FEATURE                 Location/Qualifiers
REGION                  1..121
                        note = Synthetic sequence - VH domain of antibody hBBC.8,
                         antibody hBBC.9, and antibody hBBC.10
source                  1..121
                        mol_type = protein
                        organism = synthetic construct
SEQUENCE: 32
QVQLQESGPG LVKPSQTLSL TCTVSGYSIT SGYTWHWIRQ HPGKGLEWLG YIHYSGNTKY  60
SPSLKSRLSI SRDTSKNQFF LKLSSVTTED TAVYYCGREA LRGYDHGFWF TYWGQGTLVT  120
V                                                                  121

SEQ ID NO: 33           moltype = AA  length = 107
FEATURE                 Location/Qualifiers
REGION                  1..107
                        note = Synthetic sequence - VL domain of antibody hBBC.9
                         and antibody hBBC.9.1
source                  1..107
                        mol_type = protein
                        organism = synthetic construct
SEQUENCE: 33
DIQMTQSPSS LSASVGDRVT ITCTASEDIY NRLTWYQQKP GKVPRLLISG ATSLDTGVPS  60
RFSGSRSGTD YTLTISSLQP EDVATYYCQQ YWTTPWTFGQ GTKLEIK                107

SEQ ID NO: 34           moltype = AA  length = 121
FEATURE                 Location/Qualifiers
REGION                  1..121
                        note = Synthetic sequence - VH domain of antibody hBBC.9.1
source                  1..121
                        mol_type = protein
                        organism = synthetic construct
SEQUENCE: 34
QVQLQESGPG LVKPSQTLSL TCTVSGYSIT SGYTWHWIRQ HPGKGLEWLG YIHYTGNTKY  60
SPSLKSRLSI SRDTSKNQFF LKLSSVTTED TAVYYCGREA LRGADHGFWF TYWGQGTLVT  120
V                                                                  121

SEQ ID NO: 35           moltype = AA  length = 121
FEATURE                 Location/Qualifiers
REGION                  1..121
                        note = Synthetic sequence - VH domain of antibody hBBC.10.1
source                  1..121
                        mol_type = protein
                        organism = synthetic construct
SEQUENCE: 35
QVQLQESGPG LVKPSQTLSL TCTVSGYSIT SGYTWHWIRQ HPGKGLEWLG YIHYTGNTKY  60
SPSLKSRLSI SRDTSKNQFF LKLSSVTTED TAVYYCGREA LRGYDAGFWF TYWGQGTLVT  120
V                                                                  121

SEQ ID NO: 36           moltype = AA  length = 278
FEATURE                 Location/Qualifiers
REGION                  1..278
                        note = Synthetic sequence - single chain fragment variable
                         (scFv) derived from antibody hBBC.10.1 in the [VH-VL]
                         orientation
VARIANT                 127..171
                        note = Any one or all of amino acids 127-171 can either be
                         present or absent.
source                  1..278
                        mol_type = protein
                        organism = synthetic construct
SEQUENCE: 36
QVQLQESGPG LVKPSQTLSL TCTVSGYSIT SGYTWHWIRQ HPGKGLEWLG YIHYTGNTKY  60
SPSLKSRLSI SRDTSKNQFF LKLSSVTTED TAVYYCGREA LRGYDAGFWF TYWGQGTLVT  120
VGGGGSGGGG SGGGGSGGGG SGGGGSGGGG SGGGGSGGGG SGGGGSGGGG SDIQMTQSPS  180
SLSASVGDRV TITCTASEDI YNRLTWYQQK PGKVPRLLIS GATSLDTGVP SRFSGSGSGT  240
```

```
DYTLTISSLQ PEDVATYYCQ QYWTTPWTFG QGTKLEIK                   278

SEQ ID NO: 37          moltype = DNA  length = 834
FEATURE                Location/Qualifiers
misc_feature           1..834
                       note = Synthetic sequence - single chain fragment variable
                        (scFv) in the [VH-(L)-VL] orientation derived from
                        antibody hBBC.10.1
misc_feature           393..513
                       note = Any one or all of nucleotides 393-513 can either be
                        present or absent.
source                 1..834
                       mol_type = other DNA
                       organism = synthetic construct
SEQUENCE: 37
caggtgcagc tgcaggaaag cggcccgggc ctggtgaaac cgagccagac cctgagcctg  60
acctgcaccg tgagcggcta tagcattacc agcggctata cctggcattg gattcgccag  120
catccgggca aaggcctgga atggctgggc tatattcatt ataccggcaa caccaaatat  180
agcccgagcc tgaaaagccg cctgagcatt agccgcgata ccagcaaaaa ccagttcttc  240
ctgaaactga gcagcgtgac caccgaagat accgcggtgt attattgcgg ccgcgaagcg  300
ctgcgcggct atgatgctgg cttctggttt acctattggg gccaaggcac cctggtgacc  360
gtgggtggag gcggttctgg tggaggcggt tctggtggag gcggttctgg tggaggcggt  420
tctggtggag gcggttctgg tggaggcggt tctggtggag gcggttctgg tggaggcggt  480
tctggtggag gcggttctgg tggaggcggt tctgatattc agatgaccca gagcccgagc  540
agcctgagcg cgagcgtggg cgatcgcgtg accattacct gcaccgcgag cgaagatatt  600
tataaccgcc tgacctggta tcagcagaaa ccgggcaaag tgccgcgtct gctgatttct  660
ggcgcgacca gcctggatac cggcgtgccg agccgcttta gcggcagcgg cagcggcacc  720
gattacaccc tgaccattag cagcctgcag ccggaagatg tggcgaccta ttattgccag  780
cagtattgga ccaccccgtg gacctttggc cagggcacca aactggaaat taaa        834

SEQ ID NO: 38          moltype = AA  length = 32
FEATURE                Location/Qualifiers
REGION                 1..32
                       note = Synthetic sequence - heavy chain framework region 3
                        hBBC.10.1
source                 1..32
                       mol_type = protein
                       organism = synthetic construct
SEQUENCE: 38
RLSISRDTSK NQFFLKLSSV TTEDTAVYYC GR                         32

SEQ ID NO: 39          moltype = AA  length = 32
FEATURE                Location/Qualifiers
REGION                 1..32
                       note = Synthetic sequence - heavy chain framework region 3
                        hBBC.10.1FQ
source                 1..32
                       mol_type = protein
                       organism = synthetic construct
SEQUENCE: 39
RLSISRDTSK NTFYLQMNSL TTEDTAVYYC GR                         32

SEQ ID NO: 40          moltype = AA  length = 32
FEATURE                Location/Qualifiers
REGION                 1..32
                       note = Synthetic sequence - heavy chain framework region 3
                        reference 1
source                 1..32
                       mol_type = protein
                       organism = synthetic construct
SEQUENCE: 40
RFTISRDDSK NTFYLQMNSL RAEDTAVYYC AR                         32

SEQ ID NO: 41          moltype = AA  length = 32
FEATURE                Location/Qualifiers
REGION                 1..32
                       note = Synthetic sequence - heavy chain framework region 3
                        reference 2
source                 1..32
                       mol_type = protein
                       organism = synthetic construct
SEQUENCE: 41
RFTISADTSK NTAYLQMNSL RAEDTAVYYC SR                         32

SEQ ID NO: 42          moltype = AA  length = 16
FEATURE                Location/Qualifiers
REGION                 1..16
                       note = Synthetic sequence - of CDRH2 of IMH2/hBBC
source                 1..16
```

```
                        mol_type = protein
                        organism = synthetic construct
SEQUENCE: 42
YIHYSGNTKY SPSLKS                                                  16

SEQ ID NO: 43           moltype = AA  length = 13
FEATURE                 Location/Qualifiers
REGION                  1..13
                        note = Synthetic sequence - of CDRH2 of IMH2/hBBC
source                  1..13
                        mol_type = protein
                        organism = synthetic construct
SEQUENCE: 43
EALRGYDHGF WFT                                                     13

SEQ ID NO: 44           moltype = AA  length = 121
FEATURE                 Location/Qualifiers
REGION                  1..121
                        note = Synthetic sequence - Human Acceptor VH 1
source                  1..121
                        mol_type = protein
                        organism = synthetic construct
SEQUENCE: 44
VQLQEWGPGL VKPSQTLSLT CTVSGGSIYN FGHYWSWIRH YPGKGLEWIG YIYYSGSTYY  60
NPSLKSRLTI SADTSKNQFS LELNSMTAAD TAVYYCARAG GSAAGTHDAF DIWGQGTMVT  120
V                                                                  121

SEQ ID NO: 45           moltype = AA  length = 122
FEATURE                 Location/Qualifiers
REGION                  1..122
                        note = Synthetic sequence - Human Acceptor VH 2
source                  1..122
                        mol_type = protein
                        organism = synthetic construct
SEQUENCE: 45
QVQLQESGPG LVKPSQTLSL TCTVSGDSIN SSGFYWTWIR QHPGKGLEWI GSMFYGGSPY  60
NNPSLKSRLT ISVDTSKNQF SLYLNSVTAA DTAVYYCARA FDYSASGSFY FGSWGQGTLV  120
TV                                                                 122

SEQ ID NO: 46           moltype = AA  length = 120
FEATURE                 Location/Qualifiers
REGION                  1..120
                        note = Synthetic sequence - Human Acceptor VH 3
source                  1..120
                        mol_type = protein
                        organism = synthetic construct
SEQUENCE: 46
QVQLQESGPG LVKPSQTLSL TCTVSGGSIS SGAYYWSWIR QHPGKGLEWI GYIYYSGTTY  60
YNPSLKSRLS MSRDTSKNQF SLKLSSVTAA DTAVYYCARG PYYDSPRPFD PWGQGTLVTV  120

SEQ ID NO: 47           moltype = AA  length = 117
FEATURE                 Location/Qualifiers
REGION                  1..117
                        note = Synthetic sequence - Human Acceptor VH 4
source                  1..117
                        mol_type = protein
                        organism = synthetic construct
SEQUENCE: 47
QVQLQESGPG LVKPSETLSL TCTVSGDSIS SGGTHWSWIR QLPGQGLEWL GYLYNSRSTY  60
YNPSLESRLT ISADTSKNQF SLNLSTVTAA DTAVYYCARK SGFREFDLWG QGTLVTV     117

SEQ ID NO: 48           moltype = AA  length = 116
FEATURE                 Location/Qualifiers
REGION                  1..116
                        note = Synthetic sequence - Human Acceptor VH 5
source                  1..116
                        mol_type = protein
                        organism = synthetic construct
SEQUENCE: 48
QVQLQESGPG LVKPSQTLSL TCTVSGTSIS TGGYHWTWIR QQPGKGLEWL GYIYHSGSSY  60
YNPSLKSRLT ISVDTSKNQF SLNLNSVTAA DTAVYYCARN SGADFDYWGQ GTLVTV      116

SEQ ID NO: 49           moltype = AA  length = 120
FEATURE                 Location/Qualifiers
REGION                  1..120
                        note = Synthetic sequence - Human Acceptor VH 6
source                  1..120
                        mol_type = protein
                        organism = synthetic construct
```

-continued

```
SEQUENCE: 49
QLQLQESGPR LVKPSQTLSL TCSVSGGSIS GAYHWSWIRQ LPGKGLEWVG YIYYTGNTYF  60
NPSLKSRISI SVDTSKNQFS LKMNSVTVAD TAMYYCARDP IALPGRGVFD YWGQGTLVTV  120

SEQ ID NO: 50          moltype = AA  length = 113
FEATURE                Location/Qualifiers
REGION                 1..113
                       note = Synthetic sequence - Human Acceptor VH 7
source                 1..113
                       mol_type = protein
                       organism = synthetic construct
SEQUENCE: 50
LEQSGPSLVK PSQTLSLTCS VTGDSITSGY WNWIRKFPGN KLEYMGYISY SGSTYYNLSL  60
RSRISITRDT SKNQYYLQLN SVTTEDTATY YCALITTTTY AMDYWGQGTT VTV         113

SEQ ID NO: 51          moltype = AA  length = 118
FEATURE                Location/Qualifiers
REGION                 1..118
                       note = Synthetic sequence - Human Acceptor VH 8
source                 1..118
                       mol_type = protein
                       organism = synthetic construct
SEQUENCE: 51
EVQLQESGPS LVKPSQTLSL TCSVTGDSIT NGFWIWIRKF PGNKLEYMGY ISYSGSTYYN  60
PSLKSRISIT RDTSQNQFYL QLNSVTTEDT GTYYCACRSY GRTPYYFDFW GQGTTLTV    118
```